US010538786B2

(12) United States Patent
Kamrud et al.

(10) Patent No.: US 10,538,786 B2
(45) Date of Patent: Jan. 21, 2020

(54) RECOMBINANT ARTERIVIRUS REPLICON SYSTEMS AND USES THEREOF

(71) Applicant: Janssen Pharmaceuticals, Inc., Titusville, NJ (US)

(72) Inventors: Kurt Iver Kamrud, San Diego, CA (US); Nathaniel Stephen Wang, San Diego, CA (US); Martina Felderman, La Jolla, CA (US); Nancy C. Carrico, La Jolla, CA (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 0 days.

(21) Appl. No.: 15/486,131

(22) Filed: Apr. 12, 2017

(65) Prior Publication Data

US 2017/0314043 A1 Nov. 2, 2017

Related U.S. Application Data

(60) Provisional application No. 62/322,149, filed on Apr. 13, 2016.

(51) Int. Cl.
*C12N 15/86* (2006.01)
*C07K 16/32* (2006.01)
(Continued)

(52) U.S. Cl.
CPC ............ *C12N 15/86* (2013.01); *A61K 48/005* (2013.01); *C07K 14/005* (2013.01); *C07K 16/32* (2013.01);
(Continued)

(58) Field of Classification Search
None
See application file for complete search history.

(56) References Cited

U.S. PATENT DOCUMENTS 4,727,138 A 2/1988 Goeddel et al.
4,738,927 A 4/1988 Taniguchi et al.
(Continued)

FOREIGN PATENT DOCUMENTS

WO WO 1985/02862 7/1985
WO WO 1985/04188 9/1985
(Continued)

OTHER PUBLICATIONS

Tian et al. Arterivirus minor envelope proteins are a major determinant of viral tropism in cell culture. J Virol. Apr. 2012;86(7):3701-12. (Year: 2012).*
(Continued)

*Primary Examiner* — Michelle S Horning
(74) *Attorney, Agent, or Firm* — Panitch Schwarze Belisario & Nadel LLP

(57) ABSTRACT

The present disclosure generally relates to viral-based expression systems suitable for the production of molecule of interests in recombinant host cells. The disclosure particularly relates to nucleic acid constructs, such as expression vectors, containing a modified arterivirus genome or replicon RNA in which at least some of its original viral sequence has been deleted. Also included in the disclosure are viral-based expression vectors including one or more expression cassettes encoding heterologous polypeptides. In some embodiments, the expression cassettes are configured and positioned at defined locations on the viral genome so as to enable expression of the heterologous polypeptides in a tunable manner.

28 Claims, 46 Drawing Sheets

Specification includes a Sequence Listing.

(51) Int. Cl.
*A61K 48/00* (2006.01)
*C07K 14/005* (2006.01)
*C12P 21/00* (2006.01)

(52) U.S. Cl.
CPC .......... *C12P 21/00* (2013.01); *C07K 2317/51* (2013.01); *C07K 2317/515* (2013.01); *C07K 2319/00* (2013.01); *C12N 2760/16122* (2013.01); *C12N 2760/18522* (2013.01); *C12N 2770/10043* (2013.01)

(56) References Cited

U.S. PATENT DOCUMENTS

| | | | |
|---|---|---|---|
| 4,762,791 A | 4/1988 | Goeddel et al. | |
| 4,810,643 A | 3/1989 | Souza | |
| 4,892,743 A | 1/1990 | Leibowitz et al. | |
| 4,966,843 A | 10/1990 | McCormick et al. | |
| 4,999,291 A | 3/1991 | Souza | |
| 5,017,691 A | 5/1991 | Lee et al. | |
| 5,116,742 A | 5/1992 | Cech et al. | |
| 5,225,337 A | 7/1993 | Robertson et al. | |
| 5,246,921 A | 9/1993 | Reddy et al. | |
| 6,224,879 B1 | 5/2001 | Sjoberg et al. | |
| 6,982,087 B2 | 1/2006 | Johnston et al. | |
| 7,419,674 B2 | 9/2008 | Chulay et al. | |
| 8,080,255 B2 * | 12/2011 | Smith .................. | A61K 39/145 424/210.1 |
| 9,801,897 B2 | 10/2017 | Geall et al. | |
| 2005/0070700 A1 | 3/2005 | Giese | |
| 2009/0018031 A1 | 1/2009 | Trinklein et al. | |
| 2014/0079734 A1 | 3/2014 | Frolov et al. | |
| 2016/0166678 A1 | 6/2016 | Kallen et al. | |
| 2018/0104359 A1 | 4/2018 | Kamrud | |
| 2018/0171340 A1 | 6/2018 | Kamrud et al. | |

FOREIGN PATENT DOCUMENTS

| | | |
|---|---|---|
| WO | WO 1990/06370 | 6/1990 |
| WO | WO 1995/31565 A1 | 11/1995 |
| WO | WO 1996/37616 A1 | 11/1996 |
| WO | WO 2004/055161 A2 | 7/2004 |
| WO | WO 2012/087983 A1 | 6/2012 |
| WO | WO 2014/170493 A2 | 10/2014 |
| WO | WO 2016/184822 A1 | 9/2016 |
| WO | WO 2017/024000 A1 | 2/2017 |
| WO | WO 2017/180770 A1 | 10/2017 |
| WO | WO 2018/075235 A1 | 4/2018 |
| WO | WO 2018/106615 A1 | 6/2018 |

OTHER PUBLICATIONS

Huang et al. Development of a vaccine vector based on a subgenomic replicon of porcine reproductive and respiratory syndrome virus. J Virol Methods. Sep. 2009;160(1-2):22-8. (Year: 2009).*

Baker et al., Protein Structure Predication and Structural Genomics, Science (2001) vol. 294, No. 5540, pp. 93-96 (Year: 2001).*

Attwood, T. The Babel of Bioinformatics, Science (2000) vol. 290, No. 5491, pp. 471-473 (Year: 2000).*

Agapov et al., Noncytopathic Sindbis Virus RNA Vectors for Heterologous Gene Expression, Proc. Natl. Acad. Sci., 1998, pp. 12989-12994, vol. 95.

Altmann et al., Cotransfection of ICAM-1 and HLA-DR Reconstitutes Human Antigen-Presenting Cell Function in Mouse L Cells, Nature, 1989, pp. 512-514, vol. 338.

Barbieri et al., Purification and partial characterization of another form of the antiviral protein from the seeds of *Phytolacca americana* L. (pokeweed), Biochem. J., 1982, pp. 55-59, vol. 203.

Barrette-Ng et al., Structure of Arterivirus nsp-4, J. Biol. Chem., 2002, pp. 39960-39966, vol. 277, Issue 42.

Beerens & Snijder, An RNA Pseudoknot in the 3' End of the Arterivirus Genome Has a Critical Role in Regulating Viral RNA Synthesis, J. Virol., 2007, pp. 9426-9436, vol. 81, Issue 17.

Besnard et al., Selection against expression of the *Escherichia coli* gene gpt in hprt+ mouse teratocarcinoma and hybrid cells, Mol. Cell. Biol., 1987, pp. 4139-4141, vol. 7.

Brakenhof et al., Molecular cloning and expression of hybridoma growth factor in *Escherichia coli*, J. Immunol., Dec. 15, 1987, pp. 4116-4121, vol. 139, Issue 12.

Bzik et al., Molecular cloning and sequence analysis of the Plasmodium falciparum dihydrofolate reductase-thymidylate synthase gene, Proc. Natl. Acad. Sci. USA, Dec. 1987, pp. 8360-8364, vol. 84.

Calderwood et al., Nucleotide sequence of the Shiga-like toxin genes of *Escherichia coli*, Proc. Natl. Acad. Sci. USA, Jul. 1987, pp. 4364-4368, vol. 84.

Carroll and Collier, Active Site of Pseudomonas aeruginosa Exotoxin A, J. Biol. Chem., 1987, pp. 8707-8711, vol. 262.

Castillo-Olivares et al., Generation of a Candidate Live Marker Vaccine for Equine Arteritis Virus by Deletion of the Major Virus Neutralization Domain, J. Virol., 2003, pp. 8470-8480, vol. 77, Issue 15.

Chen et al., The complete primary structure of abrin-a B chain. FEBS Letters, 1992, pp. 115-118, vol. 309.

Chin et al., Tissue-specific Expression of Hepatic Functions Genetic Aspects, Ann. N.Y. Acad. Sci., Oct. 1986, pp. 120-130, vol. 478.

Collins et al., Primary Amino Acid Sequence of α-Trichosanthin and Molecular Models for Abrin A-chain and α-Trichosanthin, J. Biol. Chem., 1990, pp. 8665-8669, vol. 265.

Coussens et al., Tyrosine kinase receptor with extensive homology to EGF receptor shares chromosomal location with neu oncogene, Science, 1985, pp. 1132-1139, vol. 230.

De Vries et al., Genetic Manipulation of Equine Arteritis Virus Using Full-Length cDNA Clones: Separation of Overlapping Genes and Expression of a Foreign Epitope. Virology, 2000, pp. 84-97, vol. 270.

De Vries et al., Recombinant Equine Arteritis Virus Expression Vector, Virology, Jun. 5, 2001, pp. 259-276, vol. 284, Issue 2.

De Wilde et al., Cyclophilin Inhibitors Block Arterivirus Replication by Interfering with Viral RNA Synthesis, J. Virol., 2013, pp. 1454-1464, vol. 87, Issue 3.

Den Boon et al., Equine Arteritis Virus Subgenomic RNA Transcription: UV Inactivation and Translation Inhibition Studies, Virology, 1995, pp. 364-372, vol. 213.

Deng et al., Structural Basis for the Regulatory Function of a Complex Zinc-binding Domain in a Replicative Arterivirus Helicase Resembling a Nonsense-Mediated mRNA Decay Helicase, Nucl. Acids Res., 2013, pp. 3464-3477, vol. 42, Issue 5.

Ding et al., In Vivo Genome-Wide Profiling of RNA Secondary Structure Reveals Novel Regulatory Features, Nature, 2014, pp. 696-700 (and Methods), vol. 505.

Dowdy et al., Efficient Generation of Human iPSCs by a Synthetic Self-Replicative RNA, Cell Stem Cell, 2013, pp. 246-254, vol. 13.

Evensen et al., Direct Molecular Cloning and Expression of Two Distinct Abrin A-chains, J. Biol. Chem., Apr. 15, 1991, pp. 6848-6852, vol. 266, Issue 11.

Fainstein et al., Nucleotide sequence analysis of human abl and bcr-abl cDNAs, Oncogene, Dec. 1, 1989, pp. 1477-1481, vol. 4. Issue 12.

Faktor et al., The identification of hepatitis B virus X gene responsive elements reveals functional similarity of X and HTLV-I tax, Oncogene, Jun. 1, 1990, pp. 867-872, vol. 5, Issue 6.

Familletti et al., A convenient and rapid cytopathic effect inhibition assay for interferon, Methods in Enz., 1981, pp. 387-394, vol. 78.

Fang et al., Efficient-2 Frameshifting by Mammalian Ribosomes to Synthesize an Additional Arterivirus Protein, PNAS, 2012, pp. E2920-E2928.

Field et al., Isolation and Characterization of Acyclovir-Resistant Mutants of Herpes Simplex Virus, J. Genl. Virol., 1980, pp. 115-124, vol. 49.

Finter et al., The Use of Interferon-α in Virus Infections, Drugs, 1991, pp. 749-765, vol. 42.

Firth et al., Discovery of a Small Arterivirus Gene that Overlaps the GP5 Coding Sequence and is Important for Virus Production, J. Genl. Virol., 2011, pp. 1097-1106, vol. 92.

(56) References Cited

OTHER PUBLICATIONS

Gansbacher et al., Retroviral Vector-mediated γ-Interferon Gene Transfer into Tumor Cells Generates Potent and Long Lasting Antitumor Immunity, Cancer Res., Dec. 15, 1999, pp. 7820-7825, vol. 50.
Gansbacher et al., Interleukin 2 Gene Transfer into Tumor Cells Abrogates Tumorigenicity and Includes Protective Immunity, J. Ex. Med., The Rockefeller University Press, Oct. 1990, pp. 1217-1224, vol. 172.
Gibson et al., Enzymatic assembly of DNA molecules up to several hundred kilobases, Nature Methods, Apr. 12, 2009, pp. 343-345, vol. 6.
Glaser AL et al., An infectious cDNA clone of equine arteritis virus: a tool for future fundamental studies and vaccine development. Proceedings of the 8th International Conference on Equine Infectious Diseases, Dubai 1998; 1999, pp. 166-176.
Golumbek et al., Treatment of established renal cancer by tumor cells engineered to secrete interleukin-4, Science, Nov. 1, 1991, pp. 713-716, vol. 254.
Grabstein et al., Cloning of a T cell growth factor that interacts with the beta chain of the interleukin-2 receptor. Science, 1994, pp. 965-968, vol. 264.
Hooper et al., Molecular Smallpox Vaccine Delivered by Alphavirus Replicons Elicits Protective Immunity in Mice and Non-Human Primates, Vaccine, 2009, pp. 494-511, vol. 28, Issue 2.
Horikawa et al., Molecular cloning and nucleotide sequence of cDNA encoding the human liver S-adenosylmethionine synthetase, Biochem. Intl., Sep. 1, 1991, pp. 81-90, vol. 25, Issue 1.
Irvin JD, Purification and partial characterization of the antiviral protein from Phytolacca americana which inhibits eukaryotic protein synthesis, Arch. Biochem & Biophys, Aug. 1975, pp. 522-528, vol. 169, Issue 2.
Irvin JD, Pokeweed antiviral protein, Pharmac. Ther., 1983, pp. 371-387, vol. 21, Issue 3.
Irvin JD et al., Purification and properties of a second antiviral protein from Phytolacca americana which inactivates eukaryotic ribosomes, Arch. Biochem. & Biophys., Apr. 1, 1980, pp. 418-425, vol. 200, Issue 2.
Jackson et al., Nucleotide sequence analysis of the structural genes for Shiga-like toxin I encoded by bacteriophage 933J from *Escherichia coli*. Microb. Path., Feb. 1987, pp. 147-153, vol. 2, Issue 2.
Jayaraman et al., Enhancement of in vivo cell-mediated immune responses by three distinct cytokines, J. Immunol., 1990, pp. 942-951, vol. 144.
Kamrud et al., Alphavirus Replicon Approach to Promoterless Analysis of IRES Elements, Virology, 2007, pp. 376-387, vol. 360.
Karupiah et al., Elevated natural killer cell responses in mice infected with recombinant vaccinia virus encoding murine IL-2, J. Immunol., Jan. 1, 1990, pp. 290-298, vol. 144, Issue 1.
Kasteren PB et al., 2013. Deubiquitinase function of arterivirus papain-like protease 2 suppresses the innate immune response in infected host cells. Proc. Natl. Acad. Sci. USA, Feb. 2013, E838-E847.
Kerr et al., Anti-penicillin-V-amidase conjugates kill antigen-positive tumor cells when combined with doxorubicin phenoxyacetamide, Cancer. Immunol. Immunother.,1990, pp. 202-206, vol. 31, Issue 4.
Knoops et al., Ultrastructural Characterization of Arterivirus Replication Structures: Reshaping the Endoplasmic Reticulum to Accommodate Viral RNA Synthesis, J. Virol., 2011, pp. 2474-2487, vol. 86, Issue 5.
Lamb et al., Nucleotide sequence of cloned cDNA coding for preproricin, Eur. J. Biochem.,1985, pp. 265-270, vol. 148.
Lee et al., Multiagent Vaccines Vectored by Venezuelan Equine Encephalitis Virus Replicon Elicits Immune Responses to Marburg Virus and Protection against Anthrax and Botulinum Neurotoxin in Mice, Vaccine, 2006, pp. 6886-6892, vol. 24.
Lehmann et al., Arterivirus nsp12 Versus the Coronavirus nsp16 2'-O-Methyltransferase: Comparison of the C-terminal Cleavage Products of Two Nidovirus pp1ab Polyproteins, J. Genl. Virol., 2015, pp. 2643-2655, vol. 96.
Lehmann et al., Arterivirus RNA-Dependent RNA Polymerase: Vital Enzymatic Activity remains Elusive, Virology, 2016, pp. 68-74, vol. 487.
Linsley et al., Binding of the B Cell activation antigen B7 to CD28 costimulates T cell proliferation and Interleukin 2 mRNA accumulation, J. Exp. Med., Mar. 1991, pp. 721-730, vol. 173.
Linsley et al., CTLA-4 Is a second receptor for the B Cell activation antigen B7, J. Exp. Med., Sep. 1991, pp. 561-570, vol. 174.
Maher and Dolinick, Specific hybridization arrest of dihydrofolate reductase mRNA in vitro using anti-sense RNA or anti-sense oligonucleotides, Arch. Biochem & Biophys., Feb. 15, 1987, pp. 214-220, vol. 253, Issue 1.
Maio, et al., Modulation by cytokines of HLA antigens, intercellular adhesion molecule 1 and high molecular weight melanoma associated antigen expression and of immune lysis of clones derived from the melanoma cell line MeM 50-10. Can. Immunol. Immunother., Jan. 1989, pp. 34-42, vol. 30, Issue 1.
Manolaridis, et al., Structure and Genetic Analysis of the Arterivirus Nonstructural Protein 7α, J. Virol., 2011, pp. 7449-7453, vol. 85, Issue 14.
Mekalanos et al., Cholera toxin genes: nucleotide sequence, deletion analysis and vaccine development, Nature, 1983, pp. 551-557, vol. 306.
Molenkamp R et al., The arterivirus replicase is the only viral protein required for genome replication and subgenomic mRNA transcription, J. Genl. Virol., 2000, pp. 2491-2496, vol. 81.
Molenkamp et al., Isolation and Characterization of an Arterivirus Defective Interfering RNA Genome, J. Virol., 2000, pp. 3156-3165, vol. 74, Issue 7.
Molenkamp et al., Characterization of an Arterivirus Defective Interfering RNA, 2001, pp. 519-525. In the Nidoviruses (Coronaviruses and Arteriviruses), Ehud Lavi et al. (ed.), Kluwer Academic/Plenum Publishers.
Mullen, Transfer of the bacterial gene for cytosine deaminase to mammalian cells confers lethal sensitivity to 5-fluorocytosine: A negative selection system, Proc. Natl. Acad. Sci. USA, Jan. 1992, pp. 33-37, vol. 89.
Nagata, et al., Synthesis in *E. coli* of a polypeptide with human leukocyte interferon activity, Nature, 1980, pp. 316-320, vol. 284.
Nedialkova, et al., Biochemical Characterization of Arterivirus Nonstructural Protein 11 Reveals the Nidovirus-Wide Conservation of a Replicative Endoribonuclease, J. Virol., 2009, pp. 5671-5682, vol. 83, Issue 11.
Nedialkova et al., Arterivirus Nsp1 Modulates the Accumulation of Minus-Strand Templates to Control the Relative Abundance of Viral mRNAs, PLoS Pathogens, 2010, e1000772, pp. 1-15, vol. 6, Issue 2.
Pasternak, Genetic Manipulation of Arterivirus Alternative mRNA Leader-Body Junction Sites Reveals Tight Regulation of Structural Protein Expression, J. Virol., Dec. 2000, pp. 11642-11653, vol. 74, Issue 24.
Pasternak, Sequence requirements for RNA strand transfer during nidovirus discontinuous subgenomic RNA synthesis, EMBO J., 2001, pp. 7220-7228, vol. 20, Issue 24.
Pasternak, The stability of the duplex between sense and antisense transcription-regulating sequences is a crucial factor in arterivirus subgenomic mRNA synthesis, J. Virol., 2003, pp. 1175-1183, vol. 77, Issue 2.
Pasternak, Regulation of Relative Abundance of Arterivirus Subgenomic mRNAs, J. Virol., Aug. 2004, pp. 8102-8113, vol. 78, Issue 15.
Pedersen et al., Open Reading Frame 1a-Encoded Subunits of the Arterivirus Replicase induce Endoplasmic Reticulum-Derived Double-Membrane Vesicles which carry the Viral Replication Complex, J. Virol., 1999, pp. 2016-2026, vol. 73, Issue 3.
Perri et al., Replicon Vectors Derived from Sindbis Virus and Semliki Forest Virus that Establish Persistent Replication in Host Cells, J. Virol., 2000, pp. 9802-9807, vol. 74, Issue 20.

(56) References Cited

OTHER PUBLICATIONS

Posthuma et al., Site-Directed Mutagenesis of the Nidovirus Replicative Endoribonuclease NendoU Exerts Pleiotropic Effects on the Arterivirus Life Cycle, J. Virol., 2006, pp. 1653-1661, vol. 80, Issue 4.
Posthuma et al., Formation of the Arterivirus Replication/Transcription Complex: a Key Role for Nonstructural Protein 3 in the Remodeling of Intracellular Membranes, J. Virol., 2008, pp. 4480-4491, vol. 82, Issue 9.
Pushko et al., Individual and Bivalent Vaccines Based on Alphavirus Replicons Protect Guinea Pigs against Infection with Lassa and Ebola Viruses, J. Virol., 2001, pp. 11677-11685, vol. 75, Issue 23.
Pushko et al., Replicon-Helper Systems from Attenuated Venezuelan Equine Encephalitis Virus: Expression of Heterologous Genes In Vitro and Immunization against Heterologous Pathogens In Vivo, Virology, Dec. 22, 1997, pp. 389-401, vol. 239, Issue 2.
Radford et al., Cell-Type Specificity of Interferon-γ-Mediated HLA Class I Gene Transcription in Human Hematopoietic Tumor Cells. American Society of Hepatology, 1991, pp. 2008-2015.
Rogne et al., The isolation and characterisation of a cDNA clone for human lecithin:cholesterol acyl transferase and its use to analyze the genes in patients with LCAT deficiency and fish eye disease, Biochem, Biophys. Res. Commun., 1987, pp. 161-169, vol. 148, Issue 1.
Sanchez and Holmgren, Recombinant system for overexpression of cholera toxin B subunit in Vibrio cholerae as a basis for vaccine development, Proc. Natl. Acad. Sci. USA, Jan. 1989, pp. 481-485, vol. 86, Issue 2.
Seif et al., Stable Antiviral Expression in BALB/c 3T3 Cells Carrying a Beta Interferon Sequence behind a Major Histocompatibility Complex Promoter Fragment, J. Virol., Oct. 1991, pp. 664-671, vol. 65, Issue 2.
Seybert et al., Biochemical Characterization of the Equine Arteritis Virus Helicase Suggests a Close Functional Relationship Between Arterivirus and Coronavirus Helicases, J. Virol., 2000, pp. 9586-9593, vol. 74, Issue 20.
Snijder, E.J., The Arterivirus Replicase, The Road from RNA to Protein(s), and Back Again, 1998, pp. 97-108. In Coronaviruses and Arteriviruses, Enjuanes et al. (ed.), Plenum Press, NY.
Snijder, E.J., Arterivirus RNA Synthesis Dissected, 2001, pp. 241-253. In the Nidoviruses (Coronaviruses and Arteriviruses), Ehud Lavi et al. (ed.), Kluwer Academic/Plenum Publishers.
Snijder et al., Proteolytic Processing of the Arterivirus Replicase, 1995, pp. 443-451. In Corona-and Related Viruses, P.J. Talbot and G.A. Levy (ed.), Plenum Press, NY.
Snijder et al., The Arterivirus Nsp2 Protease, J. Biol. Chem., 1995, pp. 16671-16676, vol. 270, Issue 28.
Snijder et al., Heterodimerization of the Two Major Envelope Proteins is Essential for Arterivirus Infectivity, J. Virol., 2003, pp. 97-104, vol. 77, Issue 1.
Snijder et al., 2005. The order *Nidovirales*, pp. 390-404, In Topley and Wilson's microbiology and microbial infections, B. W. Mahy and V. ter Meulen (ed.), Hodder Arnold, London, United Kingdom.
Snijder EJ et al., "Identification of a Novel Structural Protein of Arteriviruses," J. Virol, Aug. 1999, pp. 6335-6345, vol. 37, Issue 8.
Stanton et al., Nucleotide sequence comparison of normal and translocated murine c-myc genes, Nature, Aug. 1984, pp. 423-425, vol. 310.
Stirpe et al., Gelonin, a New Inhibitor of Protein Synthesis, Nontoxic to Intact Cells, J. Biol. Chem., Jul. 25, 1980, pp. 6947-6953, vol. 255.
Te Velthuis, et al., $Zn^{2+}$ Inhibits Coronavirus and Arterivirus RNA Polymerase Activity In Vitro and Zinc Ionophores Block the Replication of these Viruses in Cell Culture, PLoS Pathogens, 2010, e1001176, pp. 1-10, vol. 6, Issue 11.
Tepper et al., Murine interleukin-4 displays potent anti-tumor activity in vivo, Cell, May 5, 1989, pp. 503-512, vol. 57.
Thaa et al., Myristoylation of the Arterivirus E Protein: The Fatty Acid Modification is not Essential for Membrane Association but Contributes Significantly to Virus Infectivity, J. Genl. Virol., 2009, pp. 2704-2712, vol. 90.
Tian et al., Arterivirus Minor Envelope Proteins Are a Major Determinant of Viral Tropism in Cell Culture, J. Virol., 2017, pp. 3701-3712, vol. 86, Issue 7.
Tijerina et al., DMS Footprinting of Structured RNAs and RNA-Protein Complexes, Nat. Protoc., 2007, pp. 2608-2623, vol. 2, Issue 10.
Tijms et al., A zinc finger-containing papain-like protease couples subgenomic mRNA synthesis to genome translation in a positive-stranded RNA virus, Proc. Natl. Acad. Sci. USA, 2001, pp. 1889-1894, vol. 98, Issue 4.
Tijms et al., Arterivirus Subgenomic mRNA Synthesis and Virion Biogenesis Depend on the Multifunctional nsp1 Autoprotease, J. Virol., Oct. 2007, pp. 10496-10505, vol. 81, Issue 19.
Tweten et al., Diphtheria toxin. Effect of substituting aspartic acid for glutamic acid 148 on ADP-ribosyltransferase activity., J. Biol. Chem., Jun. 3, 1985, pp. 10392-10394, vol. 260.
Twu et al., Hepatitis B virus X gene can transactivate heterologous viral sequences, Proc Natl. Acad. Sci. USA, Mar. 1989, pp. 2046-2050, vol. 86.
Van Aken et al., Expression, Purification, and In Vitro Activity of an Arterivirus Main Proteinase, Virus Res., 2006, pp. 97-106, vol. 120.
Van Aken et al., Mutagenesis Analysis of the nsp4 Main Proteinase Reveals Determinants of Arterivirus Replicase Polyprotein Autoprocessing, J. Virol., 2006, pp. 3428-3437, vol. 80, Issue 7.
Van Den Born et al., Discontinuous Subgenomic RNA Synthesis in Arteriviruses is Guided by an RNA Hairpin Structure Located in the Genomic Leader Region, J. Virol., 2005, pp. 6312-6324, vol. 79, Issue 10.
Van Den Born, Value of routine funduscopy in patients with hypertension: systematic review, BMJ, Jul. 9, 2005, pp. 1-5, vol. 331.
Van Den Born, et al., "An infectious recombinant equine arteritis virus expressing green fluorescent protein from its replicase gene," J. Genl. Virol., Apr. 2007, pp. 1196-1205, vol. 88.
Van Der Meer et al., ORF1a-Encoded Replicase Subunits are Involved in the Membrane Association of the Arterivirus Replication Complex, J. Virol., 1998, pp. 6689-6698, vol. 72, Issue 8.
Van Dinten, An infectious arterivirus cDNA clone: Identification of a replicase point mutation that abolishes discontinuous mRNA transcription, Proc. Natl. Acad. Sci. USA, Feb. 1997, pp. 991-996, vol. 94, Issue 3.
Van Dinten et al., Proteolytic Processing of the Open Reading Framer 1b-Encoded Part of Arterivirus Replicase is Mediated by nsp4 Serine Protease and is Essential for Virus Replication, J. Virol., 1999, pp. 2027-2037, vol. 73, Issue 3.
Van Dinten et al., The Predicted Metal-Binding Region of the Arterivirus Helicase Protein is Involved in Subgenomic mRNA Synthesis, Genome Replication, and Virion Biogenesis, J. Virol., 2000, pp. 5213-5223, vol. 74, Issue 11.
Van Hemert et al., The In Vitro RNA Synthesizing Activity of the Isolated Arterivirus Replication/Transcription Complex is Dependent on a Host Factor, J. Biol. Chem., 2008, pp. 16525-16536, vol. 283, Issue 24.
Van Kasteren et al., Arterivirus and Nairovirus Ovarian Tumor Domain-Containing Deubiquitinases Target Activated RIG-I to Control Innate Immune Signaling, J. Virol., 2011, pp. 773-785, vol. 82, Issue 2.
Van Kasteren et al., Deubiquitinase Function of Arterivirus Papain-Like Protease 2 Suppresses the Innate Immune Response in Infected Host Cells, PNAS, 2013, pp. E838-E847.
Van Marle, et al., Characterization of an Equine Arteritis Virus Replicase Mutant Defective in Subgenomic mRNA Synthesis, J. Virol., 1999, pp. 5274-5281, vol. 73, Issue 7.
Van Marle et al., Arterivirus discontinuous mRNA transcription is guided by base pairing between sense and antisense transcription-regulating sequences, Pro. Natl. Acad. Sci. USA, Aug. 6, 1999, pp. 12056-12061, vol. 96, Issue 21.

(56) References Cited

OTHER PUBLICATIONS

Vrudhula et al., Prodrugs of doxorubicin and melphalan and their activation by a monoclonal antibody-penicillin-G amidase conjugate, J. Med. Chem., 1993, pp. 919-923, vol. 36, Issue 7.
Wassenaar, et al., Alternative Proteolytic Processing of the Arterivirus Replicase ORF1a Polyprotein: Evidence that NSP2 Acts as a Cofactor for the NSP4 Serine Protease, J. Virol., 1997, pp. 9313-9322, vol. 71, Issue 12.
Watanabe, et al., Exogenous expression of mouse interferon gamma cDNA in mouse neuroblastoma C1300 cells results in reduced tumorigenicity by augmented anti-tumor immunity, Proc. Natl. Acad. Sci. USA, Dec. 1989, pp. 9456-9460, vol. 86.
Weber et al., Immunotherapy of a murine tumor with interleukin 2. J. Exp. Med., 1987, pp. 1716-1733, vol. 166.
Wilson et al., Prospects for gene therapy of familial hypercholesterolemia, Mol. Biol. Med., Jun. 1, 1990, pp. 223-232, vol. 7, Issue 3.
Wood et al., Preproabrin: genomic cloning, characterisation and the expression of the A-chain in *Escherichia coli*, Eur. J. Biochem., 1991, pp. 723-732, vol. 198.
Yamamoto et al., The human LDL receptor: a cysteine-rich protein with multiple Alu sequences in its mRNA, Cell, Nov. 1984, pp. 27-38, vol. 39, Issue 1.
International Search Report and Written Opinion, dated Jul. 10, 2017, in International Patent Application No. PCT/US2017/027249, filed Apr. 12, 2017.
Altschul SF et al., “Basic Local Alignment Search Tool”; J. Mol. Biol. 215:403-410 (1990).
Atkins, G, et al. Therapeutic and Prophylactic Applications of Alphavirus Vectors, Expert Reviews in Molecular Medicine, Cambridge University Press, vol. 10, No. 1, pp. 1-18 (2008).
Berglund, P. et al., Enhancing Immune Response Using Suicidal DNA Vaccines,, Nature Biotechnology, vol. 16, pp. 562-565 (1998).
Cheng, W. et al. Enhancement of Sindbis Virus Self-Replicating RNA Vaccine Potency by Linkage of *Mycobacterium tuberculosis* Heat Shock Protein 70 Gene to an Antigen Gene, Journal of Immunology, vol. 166, pp. 6218-6226 (2001).
Davis, N. et al., In Vitro Synthesis of Infectious Venezuelan Equine Encephalitis Virus RNA from a cDNA Clone: Analysis of a Viable Deletion Mutant’ Virology, vol. 171, pp. 189-204 (1989).
Dubensky, T. et al. Sindbis Virus DNA-Based Expression Vectors: Utility for In Vitro and In Vivo Gene Transfer, Journal of Virology, vol. 70, No, 1, pp. 508-519 (1996).
Frolov, I. et al. Cis-acting RNA elements at the 5' end of Sindbis virus genome RNA regulate minus-and plus-strand RNA synthesis, RNO, vol. 7, pp. 1638-1651 (2001).
Frolov, I et al., Translation of Sindbis Virus mRNA: Effects of Sequences Downstream of the Initiating Codon Journal of Virology, vol. 70, No. 2, pp. 1182-1190 (1996).
Frolov, I et al. Translation of Sindbis Virus mRNA: Effects of Sequences Downstream of the Initiating Codon, Journal of Virology, vol. 68, No. 12, pp. 8111-8117 (1994).
GenBank/NCBI accession No. J02363.
GenBank accession # JX473847.
GenBank/NCBI accession No. L01443.1.
GenBank/NCBI accession No. L04653.
GenBank/NCBI accession No. NC_001449.
GenBank/NCBI accession No. NC_003215.
GenBank/NCBI accession No. U38304.
GenBank/NCBI accession No. U38305.
GenBank/NCBI accession No. X04129.
Giulietta et al., Engineered alphavirus replicon vaccines based on known attenuated viral mutants show limited effects on immunogenicity. Virology, 447(1):254-264 (2013).
Gorchakov, R. et al., Selection of Functional 5 cis-Acting Elements Promoting Efficient Sindbis Virus Genome Replication, Journal of Virology, vol. 78, No. 1, pp. 61-75 (2004).
Hardy, R. et al Requirements at the 3 End of the Sindbis Virus Genome for Efficient Synthesis of Minus-Strand RNA, Journal of Virology, pp. 4630-4639 (2005).
Hyde, J. et al., The 5' and 3' ends of alphavirus RNAs—non-coding is not non-functional, Virus Res., vol. 206, pp. 99-107 (2015).
Karlin & Altschul, Applications and statistics for multiple high-scoring segments in molecular sequences Proc. Nat'l. Acad. Sci. USA 90:5873-87 (1993).
Kelley, B. et al. Potential of Alphavirus Vectors in the Treatment of Advanced Solid Tumors, Recent Patents on Anti-Drug Discovery, vol. 2, No. 2, pp. 159-166 (2007).
Kim, D. et al. Enhancement of Protein Expression by Alphavirus Replicons by Designing Self-Replication Subgenomic RNAs, PNAS, vol. 111, No. 29 (2016).
Klimstra et al., Adaptation of Sindbis Virus to BHK Cells Selects for Use of Heparan Sulfate as an Attachment Receptor. J. Virol. 72: pp. 7357 (1988).
Kinney, R. et al., Attenuation of Venezuelan Equine Encephalitis Virus Strain TC-83 Is Encoded by the 5'-Noncoding Region and the E2 Envelope Glycoprotein, Journal of Virology, vol. 67, No. 3, pp. 1269-1277, (1993).
Kofler R. et al., Mimicking live flavivirus immunization with a noninfectious RNA vaccine, PNAS, vol. 101, No. 7, pp. 1951-1956, (2004).
Kulasegaran-Shylini et al., Structural and Functional Elements of Promoter Encoded by the 5' Untranslated Region of the Venezuelan Equine Encephalitis Virus Genome J. Virol. 83:17 p. 8327-8339 (2009).
Kulasegaran-Shylini et al., The 5'UTR-specific mutation in VEEV TC-83 genome has a strong effect on RNA replication and subgenomic RNA synthesis, but not on translation of the encoded proteins. Virology, 387(1): 211-221 (2009).
Luo, R., et al., Antiviral activity of type I and type III interferons against porcine reproductive and respiratory syndrome virus (PRRSV), Antiviral Research, vol. 91, pp. 99-101 (2011).
McKnight et al., Deduced consensus sequence of Sindbis virus strain AR339: mutations contained in laboratory strains which affect cell culture and in vivo phenotypes. Virol. 70:1981 (1996).
McLoughlin, M. et al. Alphavirus infections in salmonids—a review, Journal of Fish Diseases, vol. 30, pp. 511-531 (2007).
Mogler, M. et al., RNA-based viral vectors, Expert Rev. Vaccines, pp. 1-30 (2014).
Muraggi, G et al. Engineered Alphavirus Replicon Vaccines Based on Known Attenuated Viral Mutants Show Limited Effects on Immunogenicity, Virology, vol. 44, pp. 254-264 (2013).
Needleman, S. et al., A general method applicable to the search for similarities in the amino acid sequence of two proteins J. Mol. Biol. 48:443-53 (1970).
Nolz, J et al. Strategies and Implications for Prime-Boost Vaccination to Generate Memory CD8 T Cells, Advances in Experimental Medicine and Biology, pp. 69-83, (2011).
Pearson, W. et al., Improved tools for biological sequence comparison, Proc. Natl. Acad. Sci. US, vol. 85, pp. 2444-2448 (1988).
Pijlman, G. et al., Kunjin virus replicons: an RNA-based, noncytopathic viral vector system for protein production, vaccine and gene therapy applications, Expert Opin. Biol. Ther, vol. 6, No. 2, pp. 135-145 (2006).
Rice, C. et al., Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants, Journal of Virology, vol. 61, No. 12, pp. 3809-3819 (1987).
Sjoberg,E et al., A Significantly Improved Semliki Forest Virus Expression System Based on Translation Enhancer Segments from the Viral Capsid Gene, Biotechnology, Vo,. 12, pp. 1127-1131, (1994).
Smith et all, Comparison of Biosequences, Adv. Appl. Math., 2:482-89 (1981).
Strauss et al., The AlpahViruses: Gene Expression, Replication and Evolution, Microbiological Reviews, pp. 491-562 (1994).
Toribio et al., Inhibition of host translation by virus infection in vivo, PNAS, vol. 107, No. 21, pp. 9837-9842 (2010).
Toribio et al., An RNA Trapping Mechanism in Alphavirus MRNA Promotes Translation and Initiation Nucleic Acids Res. 19, 44(9): pp. 4368-4380 (2016).

(56) References Cited

OTHER PUBLICATIONS

Ventoso, I., Adaptive Changes in Alphavirus mRNA Translation Allowed Colonization of Vertebrate Hosts, Journal of Virology, vol. 86, No. 17, pp. 9484-9494 (2012).
Ventoso, I. et al. Translational resistance of late alphavirus mRNA to elF2 phosphorylation: a strategy to overcome the antiviral effect of protein kinase PKR, Genes and Development, vol. 20, pp. 87-100 (2006).
Ward, S. et al., Generation of CTL responses using Kunjin replicon RNA, Immunology and Cell Biology, vol. 81, pp. 73-78 (2003).
White, L. et al., Role of Alpha/Beta Interferon in Venezuelan Equine Encephalitis Virus Pathogenesis: Effect of an Attenuating Mutation in the 59 Untranslated Region, Journal of Virology, vol. 75, No. 8, pp. 3706-3718 (2001).
Zhou, X. et al. Self-replicating Semliki Forest virus RNA as recombinant vaccine, Vaccine, vol. 12, No. 16, pp. 1510-1514 (1994).
International Search Report and Written Opinion, dated Dec. 1, 2017, in International Application No. PCT/US2017/054928.
International Search Report and Written Opinion, dated Jul. 3, 2018, in International Application No. PCT/US2017/064561.
Shylini, R Structure-Function Studies of the Venezuelanequine Encephalitis Virus 5'utr Promoter Element and Its Role in Attenuation of the Virus, Dissertation for Doctor of Philosophy, The University of Texas Medical Branch (2009).
Warner et al. Induction of the HIV-Specific and Antibody Responses in Mice Using Retroviral Vector-Transduced Cells, AIDS Res. and Human Retroviruses, vol. 7, No. 8, pp. 645-655 (1991).

* cited by examiner

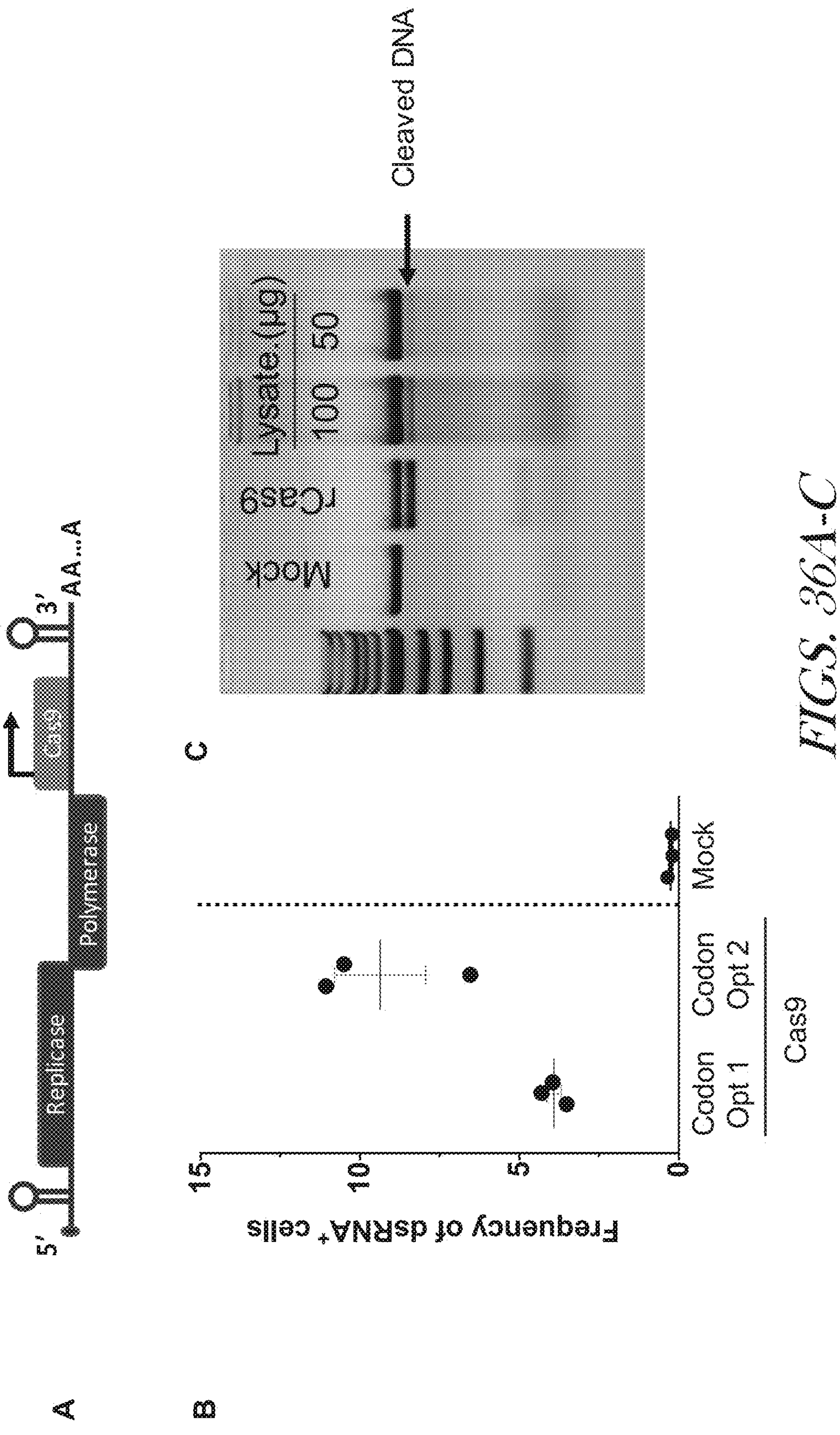
FIGS. 36A-C

RECOMBINANT ARTERIVIRUS REPLICON SYSTEMS AND USES THEREOF

RELATED APPLICATIONS

The present application claims priority to U.S. Provisional Patent Application Ser. No. 62/322,149; filed on Apr. 13, 2016, the content of which is hereby expressly incorporated by reference in its entirety.

INCORPORATION OF THE SEQUENCE LISTING

The material in the accompanying sequence listing is hereby incorporated by reference into this application. The accompanying sequence listing text file, name SGI010A_Sequence Listing, was created on Mar. 13, 2017 and is 240 KB, and updated by a Replacement Electronic Sequence Listing file entitled SGI010ASequenceListingReplacement.txt, created and last modified on Oct. 11, 2018, which is 246,131 bytes in size. The file can be assessed using Microsoft Word on a computer that uses Windows OS.

BACKGROUND

In recent years, several different groups of animal viruses have been subjected to genetic manipulation either by homologous recombination or by direct engineering of their genomes. The availability of reverse genetics systems for both DNA and RNA viruses has created new perspectives for the use of recombinant viruses as vaccines, expression vectors, anti-tumor agents, gene therapy vectors, and drug delivery vehicles.

For example, many viral-based expression vectors have been deployed for expression of heterologous proteins in cultured recombinant cells. For example, the application of modified viral vectors for gene expression in host cells continues to expand. Recent advances in this regard include further development of techniques and systems for production of multi-subunit protein complexes, and co-expression of protein-modifying enzymes to improve heterologous protein production. Other recent progresses regarding viral expression vector technologies include many advanced genome engineering applications for controlling gene expression, preparation of viral vectors, in vivo gene therapy applications, and creation of vaccine delivery vectors.

However, there is still a need for more efficient methods and systems for expressing a gene of interest in heterologous expression systems, including multigenic expression systems for simultaneously producing of multiple heterologous polypeptides in cells and/or host organisms.

SUMMARY OF CERTAIN INVENTIVE ASPECTS

This section provides a general summary of the present disclosure, and is not comprehensive of its full scope or all its features.

In one aspect, disclosed herein is a nucleic acid molecule including a nucleotide sequence that encodes a modified arterivirus genome or replicon RNA, in which the modified genome or replicon RNA includes a sequence fragment exhibiting at least 80% sequence identity to the sequence encoding open reading frame ORF7, and wherein the modified genome or replicon RNA is devoid of the sequence encoding open reading frame ORF2a. In some embodiments, the modified arterivirus genome or replicon RNA is further devoid of at least a portion of the sequence encoding one or more of the open reading frames ORF2b, ORF3, ORF4, ORF5a, and ORF5. In some embodiments, the nucleotide sequence is devoid of the ATG start codon of ORF7. In some embodiments, the modified arterivirus genome or replicon RNA is further devoid of a portion of the sequence encoding ORF6. In some embodiments, the modified arterivirus genome or replicon RNA is devoid of the ATG start codon of ORF6. In some embodiments, the modified arterivirus genome or replicon RNA is further devoid of TRS7 or comprises a mutated TRS7.

In various embodiments disclosed herein, the nucleic acid molecule can comprise a modified arterivirus genome or replicon RNA including one or more subgenomic (sg) promoters at a non-native site, wherein each of the one or more sg promoters includes a transcriptional regulatory sequence (TRS). In some embodiments, at least one of the one or more sg promoters includes a sequence exhibiting at least 80% sequence identity to a sequence selected from the group consisting of sg promoter 1, sg promoter 2, sg promoter 3, sg promoter 4, sg promoter 5, sg promoter 6, sg promoter 7, and a variant thereof. In some embodiments, at least one of the one or more sg promoters is a modified sg promoter. In some embodiments, the modified arterivirus genome or replicon RNA includes one or more modified sg promoters located at their respective native site, wherein each of the one or more modified sg promoters includes a TRS. In some embodiments, at least one of the one or more modified sg promoters is a modified sg promoter 7. In some embodiments, at least one of the one or more modified sg promoter includes one or more nucleotide modifications positioned within the primary sequence required for the formation of a secondary structure of RNA transcripts including the respective sg promoter sequence. In some embodiments, at least one of the one or more modified sg promoter includes a nucleotide modification positioned within the sequence of the TRS. In some exemplary embodiments, at least one of the one or more modified sg promoters includes a leader TRS or a variant thereof. In some exemplary embodiments, at least one of the one or more modified sg promoters includes a body TRS or a variant thereof.

In some embodiments, the modified arterivirus genome or replicon RNA disclosed herein includes one or more mutated T7 transcriptional termination signal sequences. In accordance with some exemplary embodiments, at least one of the one or more T7 mutated transcriptional termination signal sequences includes a nucleotide substitution selected from the group consisting of T9001G, T3185A, G3188A, and combinations of any two or more thereof. In some embodiments, the modified arterivirus genome or replicon RNA as disclosed herein includes one or more heterologous transcriptional termination signal sequences. In some embodiments, at least one of the one or more heterologous transcriptional termination signal sequences is a SP6 termination signal sequence, a T3 termination signal sequence, or a variant thereof. In some embodiments, at least one of the one or more heterologous transcriptional termination signal sequences is inactivated.

In some embodiments, the nucleic acid molecule disclosed herein further includes one or more spacer regions operably positioned adjacent to at least one of the one or more sg promoters. In some embodiments, at least one of the one or more spacer regions is positioned immediately 3' to the sg promoter. In some embodiments, at least one of the one or more spacer regions is positioned immediately 5' to the sg promoter. In some embodiments, the one or more spacer regions is about 20 to 400 nucleotides in length.

In various embodiments of this aspect and other aspects of the present disclosure, the nucleic acid molecule disclosed herein further includes one or more expression cassettes, wherein each of the expression cassettes includes a sg promoter operably linked to a heterologous nucleotide sequence. In some embodiments, the sg promoter includes a TRS, a first flanking region positioned immediately 5' to the TRS, and second flanking region positioned immediately 3' to the TRS, wherein the first flanking region is about 5 to 400 nucleotides in length and the second flanking region is about 15 to 115 nucleotides in length. In some embodiments, the nucleic acid molecule disclosed herein includes two, three, four, five, or six expression cassettes.

In some embodiments, the heterologous nucleotide sequence as disclosed herein includes a coding sequence of a gene of interest (GOI). In some embodiments, the coding sequence of the GOI is optimized for expression at a level higher than the expression level of a reference coding sequence. In some embodiment, the secondary structure of the RNA transcript including the coding sequence of the GOI is optimized for improved RNA replication.

In some embodiments, the nucleic acid molecule disclosed herein includes a nucleotide sequence encoding a modified arterivirus genome or replicon RNA, wherein the arterivirus is selected from the group consisting of Equine arteritis virus (EAV), Porcine respiratory and reproductive syndrome virus (PRRSV), Lactate dehydrogenase elevating virus (LDV), and Simian hemorrhagic fever virus (SHFV). In some embodiments, the arterivirus is an Equine arteritis virus (EAV), an EAV-virulent Bucyrus strain (VBS), or a Simian hemorrhagic fever virus (SHFV).

In some particular embodiments of the application, the nucleic acid molecule disclosed herein includes a nucleotide sequence encoding a modified arterivirus genome or replicon RNA, wherein the modified arterivirus genome or replicon RNA includes a nucleotide sequence exhibiting at least 80% sequence identity to SEQ ID NO: 1 and at least 80% sequence identity to SEQ ID NO: 2, and further wherein the modified genome or replicon RNA includes a nucleotide sequence exhibiting at least 80% sequence identity to the sequence encoding open reading frame ORF7, and is devoid of the sequence encoding ORF2a. In some embodiments, the modified arterivirus genome or replicon RNA includes a nucleotide sequence exhibiting at least about 80% sequence identity to SEQ ID NO: 3. In some embodiments, the modified arterivirus genome of replicon RNA includes a nucleotide sequence of SEQ ID NO: 3. In some particular embodiments of the application, the nucleic acid molecule disclosed herein includes a nucleotide sequence encoding a modified arterivirus genome or replicon RNA, wherein the modified arterivirus genome or replicon RNA includes a nucleotide sequence exhibiting at least 80% sequence identity to SEQ ID NO: 40 and at least 80% sequence identity to SEQ ID NO: 41, and further wherein the modified genome or replicon RNA includes a nucleotide sequence exhibiting at least 80% sequence identity to the sequence encoding open reading frame ORF7, and is devoid of the sequence encoding ORF2a. In some embodiments, the modified arterivirus genome or replicon RNA includes a nucleotide sequence exhibiting at least about 80% sequence identity to SEQ ID NO: 42. In some embodiments, the modified arterivirus genome of replicon RNA includes a nucleotide sequence of SEQ ID NO: 42.

In one aspect, some embodiments disclosed herein relate to a recombinant cell which includes a nucleic acid molecule described herein. In some embodiments, the recombinant cell is a prokaryotic cell or a eukaryotic cell. In some embodiments, the recombinant cell is an animal cell. In some embodiments, the animal cell is a vertebrate animal cell or an invertebrate animal cell. In some embodiments, the recombinant cell is selected from the group consisting of a pulmonary equine artery endothelial cell, equine dermis cell, baby hamster kidney cell, rabbit kidney cell, mouse muscle cell, mouse connective tissue cell, human cervix cell, human epidermoid larynx cell, Chinese hamster ovary cell (CHO), human HEK-293 cell, and mouse 3T3 cell. In a related aspect, some embodiments disclosed herein relate to a cell culture that includes at least one recombinant cell as disclosed herein.

In one aspect, some embodiments disclosed herein relate to a method for producing a polypeptide of interest that involves culturing a host cell including a nucleic acid molecule which includes (i) a nucleotide sequence encoding a modified arterivirus genome or replicon RNA, wherein the modified genome or replicon RNA includes a sequence fragment exhibiting at least 80% sequence identity to the sequence encoding open reading frame ORF7, and wherein the modified genome or replicon RNA is devoid of the sequence encoding ORF2a; and (ii) one or more expression cassettes, wherein each of the one or more expression cassettes includes a subgenomic (sg) promoter operably linked to a heterologous nucleotide sequence encoding a gene of interest.

In a further aspect, some embodiments disclosed herein relate to a method for producing a polypeptide of interest in a subject that involves administering to the subject a nucleic acid molecule which includes (i) a nucleotide sequence encoding a modified arterivirus genome or replicon RNA, wherein the modified genome or replicon RNA includes a sequence fragment exhibiting at least 80% sequence identity to the sequence encoding open reading frame ORF7, and wherein the modified genome or replicon RNA is devoid of the sequence encoding ORF2a; and (ii) one or more expression cassettes, wherein each of the one or more expression cassettes includes a subgenomic (sg) promoter operably linked to a heterologous nucleotide sequence encoding a gene of interest. In some embodiments, the subject is a vertebrate animal or an invertebrate animal.

Implementations of embodiments of the methods according to the present disclosure can include one or more of the following features. In some embodiments, the sg promoter includes a TRS, a first flanking region positioned immediately 5' to the TRS, and second flanking region positioned immediately 3' to the TRS, wherein the first flanking region is about 5 to 400 nucleotides in length and the second flanking region is about 15 to 115 nucleotides in length. In some embodiments, the modified arterivirus genome or replicon RNA is further devoid of a portion of the sequence encoding one or more of open reading frames ORF2b, ORF3, ORF4, ORF5a, and ORF5. In some embodiments, the modified arterivirus genome or replicon RNA includes a sequence fragment that is devoid of ATG start codon of ORF7. In some embodiments, the modified arterivirus genome or replicon RNA is further devoid of a portion of the sequence encoding ORF6. In some embodiments, the modified arterivirus genome or replicon RNA is devoid of the ATG start codon of ORF6. In some embodiments, the modified arterivirus genome or replicon RNA is further devoid of TRS7 or comprises a mutated TRS7.

In some embodiments, at least one of the one or more expression cassettes includes a modified sg promoter including at least one nucleotide modification introduced within the primary sequence required for the formation of a secondary structure of RNA transcripts including the sg promoter sequence. In some embodiments, at least one of the one or more expression cassettes includes a modified sg promoter including at least one nucleotide modification introduced within the sequence of the TRS. In some embodiments, at least one of the one or more expression cassettes includes a leader TRS or a variant thereof.

In some embodiments of the methods disclosed herein, the modified arterivirus genome or replicon RNA includes one or more mutated T7 transcriptional termination signal sequences. In some embodiments, at least one of the one or more mutated T7 transcriptional termination signal sequences includes a nucleotide substitution selected from the group consisting of T9001G, T3185A, G3188A, and combinations of any two or more thereof. In some embodiments, the modified arterivirus genome or replicon RNA includes one or more heterologous transcriptional termination signal sequences. In some particular embodiments, at least one of the one or more heterologous transcriptional termination signal sequences is a SP6 termination signal sequence, a T3 termination signal sequence, or a variant thereof.

In some embodiments of the methods disclosed herein, the modified arterivirus genome or replicon RNA includes one or more spacer regions operably positioned adjacent to at least one of the one or more sg promoters. In some embodiments, at least one of the one or more spacer regions is positioned immediately 3' to the sg promoter. In some embodiments, at least one of the one or more spacer regions is positioned immediately 5' to the sg promoter. In some embodiments, each of the one or more spacer regions is about 20 to 400 nucleotides in length. In some embodiments, the nucleic acid molecule of the methods disclosed herein includes two, three, four, five, or six expression cassettes.

In some embodiments of the methods disclosed herein, the coding sequence of the gene of interest in one of the expression cassettes is optimized for expression at a level higher than the expression level of a reference coding sequence. In some embodiments, the secondary structure of the RNA transcript comprising coding sequence of the gene of interest is optimized for improved RNA replication.

In some embodiments of the methods disclosed herein, the nucleic acid molecule includes a nucleotide sequence encoding a modified arterivirus genome or replicon RNA, wherein the modified arterivirus genome or replicon RNA includes a nucleotide sequence exhibiting at least 80%, 85%, 90%, 95%, 98%, 99%, or more sequence identity to SEQ ID NO: 1 and at least 80%, 85%, 90%, 95%, 98%, 99%, or more sequence identity to SEQ ID NO: 2, and further wherein the modified genome or replicon RNA includes a nucleotide sequence exhibiting at least 80%, 85%, 90%, 95%, 98%, 99%, or more sequence identity to the sequence encoding open reading frame ORF7, and is devoid of the sequence encoding ORF2a. In some embodiments, the modified arterivirus genome or replicon RNA includes a nucleotide sequence exhibiting at least about 80%, 85%, 90%, 95%, 98%, 99%, or more sequence identity to SEQ ID NO: 3. In some embodiments, the modified arterivirus genome of replicon RNA includes a nucleotide sequence of SEQ ID NO: 3. In some embodiments of the methods disclosed herein, the nucleic acid molecule includes a nucleotide sequence encoding a modified arterivirus genome or replicon RNA, wherein the modified arterivirus genome or replicon RNA includes a nucleotide sequence exhibiting at least 80%, 85%, 90%, 95%, 98%, 99%, or more sequence identity to SEQ ID NO: 40 and at least 80%, 85%, 90%, 95%, 98%, 99%, or more sequence identity to SEQ ID NO: 41, and further wherein the modified genome or replicon RNA includes a nucleotide sequence exhibiting at least 80%, 85%, 90%, 95%, 98%, 99%, or more sequence identity to the sequence encoding open reading frame ORF7, and is devoid of the sequence encoding ORF2a. In some embodiments, the modified arterivirus genome or replicon RNA includes a nucleotide sequence exhibiting at least about 80%, 85%, 90%, 95%, 98%, 99%, or more sequence identity to SEQ ID NO: 42. In some embodiments, the modified arterivirus genome of replicon RNA includes a nucleotide sequence of SEQ ID NO: 42. In some embodiments, the modified arterivirus genome of replicon RNA consists of a nucleotide sequence of SEQ ID NO: 3 or SEQ ID NO: 42. In some embodiments, the modified arterivirus genome of replicon RNA consists of a nucleotide sequence exhibit at least 80%, 85%, 90%, 95%, 98%, 99%, or more sequence identity to SEQ ID NO: 3 or SEQ ID NO: 42.

In a further aspect, some embodiments disclosed herein relate to recombinant polypeptides produced by a method in accordance with one or more embodiments described herein. In some embodiments, the polypeptide is selected from the group consisting of a therapeutic polypeptide, a prophylactic polypeptide, a diagnostic polypeptide, a nutraceutical polypeptide, an industrial enzyme, and a reporter polypeptide. In some embodiments, the polypeptide is selected from the group consisting of an antibody, an antigen, an immune modulator, and a cytokine.

In a related aspect, some embodiments disclosed herein relate to a composition including a recombinant polypeptide as described herein and a pharmaceutically acceptable carrier.

In yet a further aspect, some embodiments disclosed herein relate to a composition including a nucleic acid molecule as disclosed herein and a pharmaceutically acceptable carrier.

In yet a further aspect, some embodiments disclosed herein relate to a composition including a recombinant cell as disclosed herein and a pharmaceutically acceptable carrier.

The foregoing summary is illustrative only and is not intended to be in any way limiting. In addition to the illustrative embodiments and features described herein, further aspects, embodiments, objects and features of the application will become fully apparent from the drawings and the detailed description and the claims.

BRIEF DESCRIPTION OF THE DRAWINGS

FIG. 24 is a plasmid map of the pBR322+VBS-R-eGFP construct.

FIG. 33A schematically illustrates a molecular design of the rEx-herceptin replicon analyzed. FIG. 33B summarizes the results of an ELISA analysis of secreted antibody from electroporated cells at ~24 hours post electroporation, which was performed to compare DNA and EAV replicon expressed antibody (mg/L). FIG. 33C summarizes the results of experiments performed to demonstrate that rEx-herceptin expressed antibody can detect Her2 antigen FIG. 34 pictorially summarizes the results of experiments performed to further analyze the SHFv-R-TRS7-rFF replicon in vivo in Balb/c mice. In this experiment, 30 μg of RNA was injected into mice and whole body imaging was conducted. These data demonstrate the in vivo activity of the SHFv replicon vector and that it is equivalent to the EAV replicon.

FIG. 35A: percent cells transfected with bivalent IL-12-RSV F or IL-12 RNA. FIG. 35B: mean fluorescence intensity (MFI) of IL-12 specific protein expression. FIG. 35C: percent cells transfected with bivalent IL-12-RSV F or RSV F RNA. FIG. 35D: mean fluorescence intensity (MFI) of RSV F specific protein expression.

FIGS. 36A-36C are a pictorial summary of the results of experiments perform to analyze cas9 expression and cutting activity from an EAV replicon. FIG. 36A: Schematic of the EAV cas9 replicon vector. FIG. 36B: BHK cells were electroporated with 3 μg of each replicon RNA. The percent of cells transfected was determined using dsRNA-specific antibody. The cas9 gene was synthesized using two different codon usages. FIG. 36C: Cas9 functionality was determined in vitro using electroporated cell lysates combined with plasmid DNA and gRNA specific for the plasmid sequence. Specific DNA cleavage was detected in samples generated from cas9 EAV replicon RNA electroporated cell lysates.

Figure 1A:
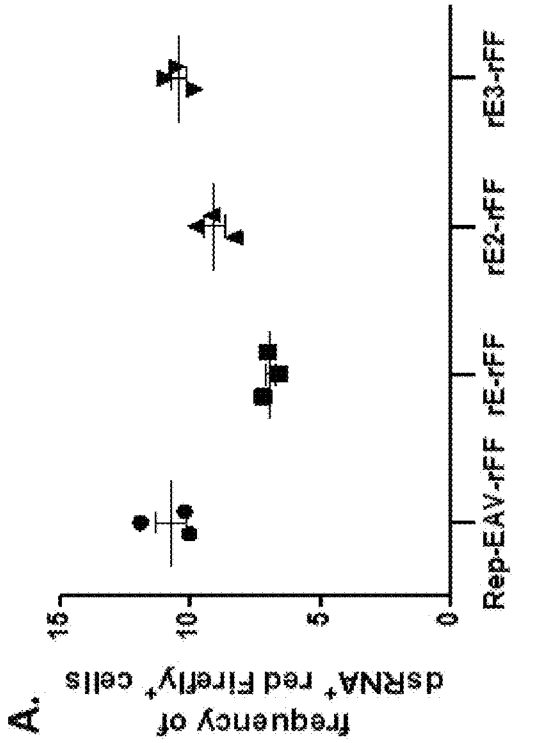
FIGS. 1A-1D graphically summarize the results of luciferase assays and flow cytometry experiments performed to demonstrate that mutations to cryptic T7 termination sites in the original EAV replicon system Rep-EAV allow for full-length RNA replicon transcription. Potential T7 polymerase termination sequences that are endogenous to the EAV genome were mutated to allow for full-length RNA transcription. Mutations T9001G (rE), T9001G and G3188A (rE2), and T9001G and T3185A (rE3) were compared to the initial replicon system Rep-EAV for replication and protein expression of red Firefly (1A, 1C) and green Renilla (1B, 1D).

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope; the disclosure will be described with additional specificity and detail through use of the accompanying drawings.

DETAILED DESCRIPTION OF CERTAIN EMBODIMENTS

The present disclosure generally relates to the development of arterivirus expression systems which are suitable for expressing multiple heterologous genes in recombinant cells in a tunable manner. In some embodiments, the disclosure relates to nucleic acid molecules containing a genetically engineered arterivirus genome or replicon RNA. For example, some embodiments relate to nucleic acid molecules including a recombinant arterivirus genome or replicon RNA in which at least some of its original nucleotide sequence encoding one or more structural proteins has been removed and/or replaced with a heterologous nucleotide sequence encoding, for example, a polypeptide of interest.

As disclosed herein, monogenic or multigenic arterivirus expression systems can be generated by removing a part or the entire coding region for one or more structural proteins of the subgenomic RNAs (sg RNAs) of EAV, and replacing each with coding sequence of a gene of interest (GOI). Because each sg RNA of EAV is naturally expressed at a distinct level, the arterivirus expression systems disclosed herein allows tunable expression of a GOI in either a monogenic or multigenic design. For example, as described in further detail below, the development of a single RNA expression platform capable of expressing multiple GOIs, each of which can be produced at the same or different levels relative to one another, represents significant utility and practicality. Among other advantages, this tunability of the expression platforms disclosed herein advantageously allows for tunable expression of multiple proteins in the same cell. As an example, in immunological applications, clonal expression of multiple proteins in the same host cell offers many practical utilities, including but not limited to: 1) it allows for complex protein interactions to occur to support conformationally accurate epitopes, in vivo and/or ex vivo, 2) it supports co-expression of immunomodulatory proteins along with, e.g. concurrently with, vaccines and/or tumor associated antigens, which in turn may illicit and/or drive robust immune responses, and 3) it supports advanced therapeutic approaches requiring multiple protein expression. Without being limited by any particular theory, it is believed that another non-limiting advantage of using arteriviruses as viral expression vectors is that they can direct the synthesis of large amounts of heterologous proteins in recombinant host cells.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be used, and other changes may be made, without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

Unless otherwise defined, all terms of art, notations and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Some Definitions

The singular form "a", "an", and "the" include plural references unless the context clearly dictates otherwise. For example, the term "a cell" includes one or more cells, comprising mixtures thereof. As used in this disclosure and the appended claims, the term "and/or" can be singular or inclusive. For example, "A and/or B" is used herein to include all of the following alternatives: "A", "B", "A or B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The terms, "cells", "cell cultures", "cell line", "recombinant host cells", "recipient cells" and "host cells" as used herein, include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell.

As used herein, the term "construct" is intended to mean any recombinant nucleic acid molecule such as an expression cassette, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, comprising a nucleic acid molecule where one or more nucleic acid sequences has been linked in a functionally operative manner, e.g. operably linked.

The term "gene" is used broadly to refer to any segment of nucleic acid molecule that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions, 3' untranslated regions, introns, etc. Further, genes may optionally further comprise regulatory sequences required for their expression, and such sequences may be, for example, sequences that are not transcribed or translated. Genes can be obtained from a variety of sources, including cloning from a source of interest or synthesizing from known or predicted sequence information, and may include sequences designed to have desired parameters.

The term "heterologous" when used in reference to a polynucleotide, a gene, or a nucleic acid molecule refers to a polynucleotide, gene, or a nucleic acid molecule that is not derived from the host species. For example, "heterologous gene" or "heterologous nucleic acid sequence" as used herein, refers to a gene or nucleic acid sequence from a different species than the species of the host organism it is introduced into. When referring to a gene regulatory sequence or to an auxiliary nucleic acid sequence used for manipulating expression of a gene sequence (e.g. a 5' untranslated region, 3' untranslated region, poly A addition sequence, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome. Thus, a promoter operably linked to a gene to which it is not operably linked to in its natural state (for example, in the genome of a non-genetically engineered organism) is referred to herein as a "heterologous promoter," even though the promoter may be derived from the same species (or, in some cases, the same organism) as the gene to which it is linked. For example, in some embodiments disclosed herein, a coding sequence of a heterologous gene of interest (GOI) is not linked to the EAV replicon sequence in its natural state. In some embodiments, the coding GOI sequence is derived from another organism, such as another virus, bacteria, fungi, human cell (tumor Ag), parasite (malaria), etc.)

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. Nucleic acid molecules can have any three-dimensional structure. A nucleic acid molecule can be double-stranded or single-stranded (e.g., a sense strand or an antisense strand). Non-limiting examples of nucleic acid molecules include genes, gene fragments, exons, introns, messenger RNA (mRNA), transfer RNA, ribosomal RNA, siRNA, micro-RNA, tracrRNAs, crRNAs, guide RNAs, ribozymes, cDNA, recombinant polynucleotides, branched polynucleotides, nucleic acid probes and nucleic acid primers. A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

Nucleic acid molecules of the present disclosure can be nucleic acid molecules of any length, including nucleic acid molecules that are preferably between about 5 Kb and about 50 Kb, for example between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

The polynucleotides of the present disclosure can be "biologically active" with respect to either a structural attribute, such as the capacity of a nucleic acid to hybridize to another nucleic acid, or the ability of a polynucleotide sequence to be recognized and bound by a transcription factor and/or a nucleic acid polymerase.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

As used herein, the term "replicon" refers to a viral nucleic acid that is capable of directing the generation of copies of itself. As used herein, the term "replicon" includes RNA as well as DNA. For example, double-stranded DNA versions of arterivirus genomes can be used to generate a single-stranded RNA transcript that constitutes an arterivirus replicon. Generally, a viral replicon contains the complete genome of the virus. "Sub-genomic replicon," as used herein, refers to a viral nucleic acid that contains something less than the full complement of genes and other features of the viral genome, yet is still capable of directing the generation of copies of itself. For example, the sub-genomic replicons of arterivirus described below contain most of the genes for the non-structural proteins of the virus, but are missing most of the genes coding for the structural proteins. Sub-genomic replicons are capable of directing the expression of all of the viral genes necessary for the replication of the viral sub-genome (replication of the sub-genomic replicon), without the production of viral particles.

A "vector" as used herein refers to any means for the transfer of a nucleic acid into a host cell. A vector may be a replicon to which another DNA segment may be attached so as to bring about the replication of the attached segment. The term "vector" includes both viral and non-viral means for introducing the nucleic acid into a cell in vitro, ex vivo or in vivo. Non-viral vectors include, but are not limited to plasmids, liposomes, electrically charged lipids (cytofectins), DNA-protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

In some embodiments of the methods or processes described herein, the steps can be carried out in any order, except when a temporal or operational sequence is explicitly recited. Furthermore, in some embodiments, the specified steps can be carried out concurrently unless explicit claim language recites that they be carried out separately. For example, in some embodiments a claimed step of doing X and a claimed step of doing Y can be conducted simultaneously within a single operation, and the resulting process will fall within the literal scope of the claimed method.

As used herein, "comprising" is synonymous with "including," "containing," or "characterized by," and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

The discussion of the general methods given herein is intended for illustrative purposes only. Other alternative methods and alternatives will be apparent to those of skill in the art upon review of this application, and are to be included within the spirit and purview of this application.

Arteriviruses

The arteriviruses belong to the genus Arterivirus in the family Arteriviridae, which is within the order Nidovirales, and encompass an important group of enveloped, single-stranded, positive-sense RNA viruses which infect domestic and wild animals.

The order Nidovirales can be divided into two clades depending on the size of the genome: those with large genomes (26.3-31.7 kilobases) which included the Coronaviridae and Roniviridae (the large nidoviruses) and those with small genomes (the small nidoviruses)—a clade that includes the distantly related Arteriviridae (12.7-15.7 kb). The large nidoviruses encode both an 2'-O-methyltransferase and a 3'-5' exoribonuclease (ExoN)—the latter being very unusual for an RNA virus. They also encode a superfamily 1 helicase, uridylate-specific endonuclease (an enzyme unique to nidoviruses) and several proteases.

It has been well documented that although arteriviruses share a similar genome organization and replication strategy to that of members of the family Coronaviridae (genera Coronavirus and Torovirus), they do differ considerably in their genetic complexity, genome length, biophysical properties, size, architecture, and structural protein composition of the viral particles (e.g., virion). Currently, the Arterivirus genus is considered to include equine arteritis virus (EAV), porcine reproductive and respiratory syndrome virus (PRRSV), lactate dehydrogenase-elevating virus (LDV) of mice, simian hemorrhagic fever virus (SHFV), and wobbly possum disease virus (WPDV). Recent studies have reported that the newly identified wobbly possum disease virus (WPDV) also belongs to the Arterivirus genus.

Figure 20:
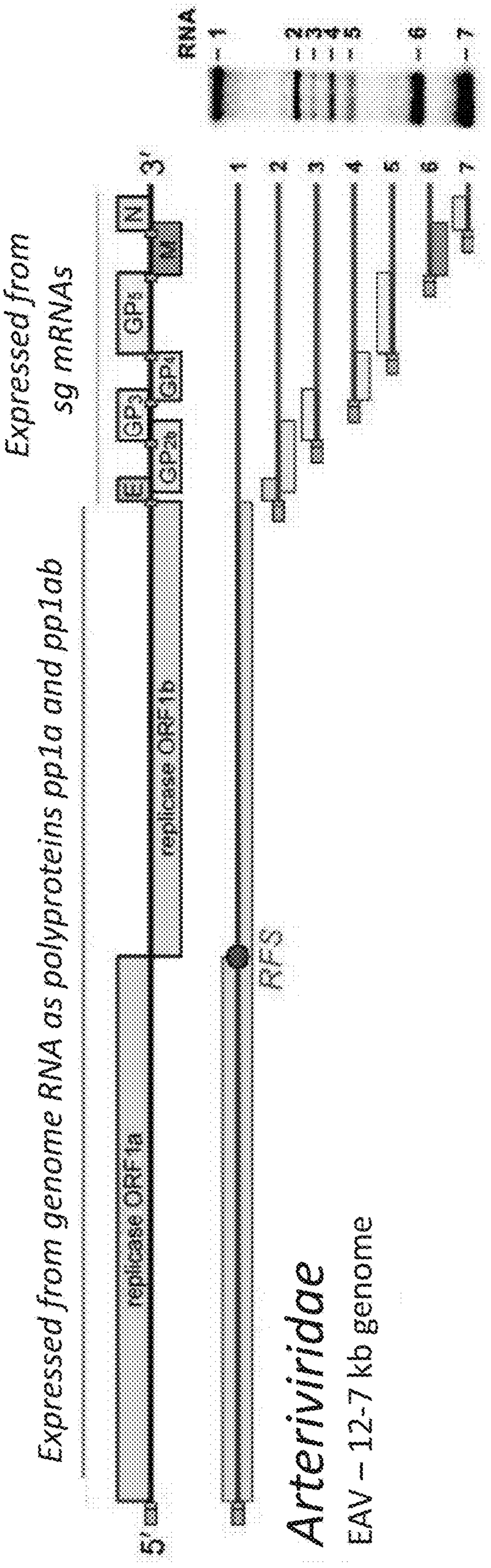
FIG. 20 schematically depicts EAV genomic structure and genome expression strategy. The names of the replicase gene and structural protein genes are given (references to the nomenclature of genes and proteins can be found in Snijder et al., 2005). Below the genome organization, the structural relationships of the genome and sg mRNAs are depicted. The leader sequence and TRSs found at the 5' end of the EAV mRNAs are indicated as blue and orange boxes, respectively. The ribosomal frameshifting element (RFS) found in the genome-length mRNA1 is indicated and the translated region of each mRNA is highlighted by a green line, whereas translationally silent regions are indicated by a red line. Only the translated open reading frames are indicated for each mRNA. The right-hand panels show a typical pattern of EAV mRNAs isolated from infected cells, visualized by hybridization to a probe complementary to the 3' end of the genome and therefore recognizing all viral mRNA species.

A typical arterivirus genome varies between 12.7 and 15.7 kb in length but their genome organization is relatively consistent with some minor variations. Exemplary genome organization and virion architecture of an arterivirus is shown in FIG. 20. The arterivirus genome is a polycistronic +RNA, with 5' and 3' non-translated regions (NTRs) that flank an array of 10-15 known ORFs. The large replicase ORFs 1a and 1b occupy the 5'-proximal three-quarters of the genome, with the size of ORF1a being much more variable than that of ORF1b. Translation of ORF1a produces replicase polyprotein (pp) 1a, whereas ORF1b is expressed by −1 programmed ribosomal frameshifting (PRF), which C-terminally extends pp1a into pp1ab. In addition, a short transframe ORF has been reported to overlap the nsp2-coding region of ORF1a in the +1 frame and to be expressed by −2 PRF. The 3'-proximal genome part has a compact organization and contains 8 to 12 relatively small genes, most of which overlap with neighboring genes. These ORFs encode structural proteins and are expressed from a 3'-co-terminal nested set of sg mRNAs. The organization of these ORFs is conserved, but downstream of ORF1b, SHFV and all recently identified SHFV-like viruses contain three or four additional ORFs (~1.6 kb) that may be derived from an ancient duplication of ORFs 2-4. Together with the size variation in ORF1a, this presumed duplication explains the genome size differences among arteriviruses.

With regard to equine arteritis virus (EAV), the wild-type EAV genome is approximately 12.7 Kb in size. The 5' three fourths of the genome codes for two large replicase proteins 1a and 1ab; the amino acid sequences of the two proteins are N-terminally identical but due to a ribosomal frameshift the amino acid sequence of the C-terminal region of 1ab is unique. The 3' one quarter of the EAV genome codes for the virus's structural protein genes, all of which are expressed from subgenomic RNAs. The subgenomic RNAs form a nested set of 3' co-terminal RNAs that are generated via a discontinuous transcriptional mechanism. The subgenomic RNAs are made up of sequences that are not contiguous with the genomic RNA. All of the EAV subgenomic RNAs share a common 5' leader sequence (156 to 221 nt in length) that is identical to the genomic 5' sequence. The leader and body parts of the subgenomic RNAs are connected by a conserved sequence termed a transcriptional-regulatory sequence (TRS). The TRS is found on the 3' end of the leader (leader TRS) as well as in the subgenomic promoter regions located upstream of each structural protein gene (body TRS). Subgenomic RNAs are generated as the negative strand replication intermediate RNA is transcribed. As transcription occurs the replication complex pauses as it comes to each body TRS and then the nascent negative strand RNA become associated with the complementary positive strand leader TRS where negative strand RNA transcription continues. This discontinuous transcription mechanism results in subgenomic RNA with both 5' and 3' EAV conserved sequences. The negative strand subgenomic RNAs then become the template for production of the subgenomic positive sense mRNA.

Infectious cDNA clones, representing the entire genome of EAV, have been reported (van Dinten 1997; de Vries et al., 2000, 2001; Glaser et al., 1999) and they been used to study EAV RNA replication and transcription for nearly two decades (van Marle 1999, van Marle 1999a, Molenkamp 2000, Molenkamp 2000a, Pasternak 2000, Tijms 2001, Pasternak 2001, Pasternak 2003, Pasternak 2004, van den Born 2005, Beerens & Snijder 2007, Tijms 2007, Kasteren 2013). In addition, infectious clones have been generated that contain the chloramphenicol acetyltransferase (CAT) gene inserted in place of ORF2 and ORF7 and CAT protein was shown to be expressed in cells electroporated with those RNAs (van Dinten 1997, van Marle 1999). Modifications of the infectious clone via site directed mutagenesis and deletion of the structural protein gene regions has been used to determine the requirement for each structural gene in support of RNA replication (Molenkamp 2000). The study reported by Molenkamp 2000 concluded that the structural genes are not required to support RNA replication. Analysis of sequence homology requirements for TRS activity in subgenomic RNA production was conducted and used to better define how discontinuous transcription mechanistically occurs (van Marle 1999, Pasternak 2000, Pasternak 2001, Pasternak 2003, van den Born 2005) and defective interfering RNAs have been used to understand the minimal genomic sequences required for replication and packaging of RNA into virus particles (Molenkamp 2000a). However, no attempt to construct a replicon vector from EAV capable of and designed specifically to efficiently express heterologous genes has been reported.

Development of an EAV replicon vector for expression of heterologous genes has not been conducted prior to the inventive work described herein because most other replicon systems have been focused on virus particle-based approaches. That is, packaging of a replicon RNA into a virus-like particle by supplying the deleted structural proteins back in-trans. Because EAV has two major and five minor structural proteins, the level of expression of each which is key to efficient virus particle production, it is considered too difficult to develop a virus particle-based system from EAV. For at least this reason, no attempt to develop an EAV replicon RNA as a vector has been conducted prior to the inventive work described herein.

The inventive work described herein is primarily based on the EAV RNA replicon and is not dependent on the formation of recombinant virus-like particle. Accordingly, the presently disclosed compositions and methods are not limited by the complexity of providing the EAV structural proteins back in order to produce a virus-like particle. In addition, because each subgenomic RNA is naturally expressed at a unique level the system also allows tunable expression of a GOI in either a monogenic or multigenic design. There is significant utility of a single RNA capable of expressing multiple GOI, each at the same or different levels relative to one another. This capacity allows for expression of multiple proteins in the same cell. In addition to the unique design of the EAV replicon, development of methods that can be employed to tune, e.g. to modulate protein expression from the vector is inventive. As used herein, the term "tunable expression" refers to the ability of the compositions and methods described herein to control the level of expression of a GOI operably linked to an arterivirus replicon according to the present disclosure. This can be achieved, for example, by a number of ways. For approaches that employ use of the system launched from a DNA plasmid from the nucleus of a cell the transcription of the replicon RNA could be controlled/tuned by an inducible DNA dependent RNA polymerase promoter. For example, transcription of RNA could be controlled using Tet technology to induce production of the replicon RNA from transformed cells. Once, replicon RNA is in the cytoplasm of a cell (either by transfecting the RNA into cells or having the cell produce the RNA from an integrated DNA version of the system) a number of additional techniques can be used to tune expression from the system. The first example 1) can utilize RNA structure-seq and next generation sequencing (NGS) to understand the secondary structure surrounding TRS elements. In some embodiments, this information can provide insights into formulating approaches to tune, e.g. to modulate, the activity of any TRS and inform tunable GOI expression from the EAV replicon. This information combined with the 2) relative position on the genomic RNA that the GOI is placed, 3) controlling secondary structure of each GOI by utilizing sequence optimization of the primary gene sequence, and 4) by optimizing 3' sequences key to optimal replication of replicons. For example, by optimizing the 3' EAV sequences included in the replicon and by inclusion of a longer polyA region. Employing all of these approaches enables tunable protein expression. The methods, compositions, and systems described herein can be used for tunable protein expression, for example, they can be used to express one or more proteins in various expression levels. In some embodiments, the methods, compositions, and systems described herein can be used for expressing one or more proteins at about 0.1%, 1%, 5%, 10%, 20%, 30%, 40%, 50%, 60%, 70%, 80%, 90%, 95%, 100%, 150%, 200%, 300%, 400%, 500%, 10-fold, or more of a reference expression level of the protein(s).

As described in further detail below, the present disclosure also relates to significant showing of unexpected results in connection with various arterivirus expression vectors designed and evaluated by the inventors. In a study published by Molenkamp et al. (2000), it has been indicated that the sequence encoding open reading frame ORF2a of EAV is needed in order to retain robust TRS2 subgenomic transcription activity (Molenkamp et al 2000). In fact, Molenkamp et al showed that an EAV infectious clone deleted from nucleotide residues 9,756 to 12,351, which retained only 5 bases of the ORF2a sequence, exhibited a significant reduction in subgenomic RNA synthesis. This property was in contrast to the subgenomic RNA synthesis demonstrated from a different EAV infectious clone (mutant 030-2319; also referred to as EAV030 mutant); mutant 030-2319 contained the same 3' sequences as mutant 2a-2594 but maintained an intact ORF 2a sequence and this construct demonstrated wild-type robust subgenomic RNA synthesis (Molenkamp et al 2000).

Surprisingly and in contrast to these teachings of Molenkamp et al., in the replicon design of disclosed herein (for example Rep-EAV (WT)) and all derivative versions of the replicon, the ORF2a sequence is completely absent, yet each of the replicons exhibits robust subgenomic transcription and high expression of one or more GOIs. Furthermore, Molenkamp et al 2000 define the optimal 3' terminal sequences that should be maintained for efficient replication using mutant 030-2319 as well. Molenkamp et al teach that the 3' terminal 354 nt of EAV are able to support wild type replication. Surprisingly, as described and demonstrated herein, replicon vectors that code for at least two GOIs did not replicate efficiently unless significantly more 3' terminal sequences are included. In addition, significant differences in both replication and protein expression were noted from replicons coding for the same protein but having different primary GOI sequences. More than a 50-fold difference in replication activity and a 2 to 4 fold difference in protein expression have been observed in replicons coding for the same GOI with different primary nucleotide sequences. Another non-limiting unexpected aspect of the methods, composition and systems described herein for protein expression is the magnitude of protein expression that they are capable of. It is well known in the RNA replicon field that alphavirus-based replicon systems are capable of expressing up to twenty percent of a cell's total protein content (Pushko et al 1997). Thus, it is surprising that the methods, arterivirus-based composition and systems described herein are capable of even higher expression levels on a per cell basis than an alphavirus replicon.

Nucleic Acid Molecules of the Disclosure

In one aspect, novel nucleic acid molecules which include a nucleotide sequence encoding a modified arterivirus genome or replicon RNA are disclosed. For example, a modified arterivirus genome or replicon RNA can comprise deletion(s), substitution(s), and/or insertion(s) in one or more of the genomic regions (e.g., open reading frames (ORFs)) of the parent arterivirus genome. In some embodiments, one or more of arterivirus ORF2a, ORF2b, ORF3, ORF4, ORF5, and ORF5a are absent and/or modified in the modified arterivirus genome or replicon RNA. In some embodiments, the modified genome or replicon RNA includes a sequence fragment exhibiting at least 80%, at least 85%, preferably at least 90%, or more preferably at least 95% identity to a nucleotide sequence encoding open reading frame ORF7. In some embodiments, the modified genome or replicon RNA includes a sequence fragment exhibiting at least 95%, 96%, 97%, 98%, 99%, or 100% sequence identity to a nucleotide sequence encoding open reading frame ORF7. In some embodiments, the modified genome or replicon RNA includes a sequence fragment exhibiting 100% sequence identity to a nucleotide sequence encoding open reading frame ORF7. In some embodiments, the modified arterivirus genome or replicon RNA is devoid of at least a portion of the sequence encoding one or more of the open reading frames ORF2b, ORF3, ORF4, ORF5, and ORF5a. For example, the modified arterivirus genome or replicon RNA can be devoid of about 10%, 20%, 30%, 40%, 50%, 60%, 70%, 80%, 90%, 95%, or more of the sequence encoding one or more of the open reading frames ORF2b, ORF3, ORF4, ORF5, and ORF5a. In some embodiments, the modified arterivirus genome or replicon RNA is devoid of the entire sequence encoding one or more of the open reading frames ORF2b, ORF3, ORF4, ORF5, and ORF5a. In some embodiments, the modified arterivirus genome or replicon RNA is devoid of a portion of or the entire sequence encoding one of the open reading frames ORF2b, ORF3, ORF4, ORF5, and ORF5a. In some embodiments, the modified arterivirus genome or replicon RNA is devoid of a portion of or the entire sequence encoding two of the open reading frames ORF2b, ORF3, ORF4, ORF5, and ORF5a. In some embodiments, the modified arterivirus genome or replicon RNA is devoid of a portion of or the entire sequence encoding three of the open reading frames ORF2b, ORF3, ORF4, ORF5, and ORF5a. In some embodiments, the modified arterivirus genome or replicon RNA is devoid of a portion of or the entire sequence encoding four of the open reading frames ORF2b, ORF3, ORF4, ORF5, and ORF5a. In some embodiments, the modified arterivirus genome or replicon RNA is devoid of a portion of or the entire sequence encoding all the open reading frames ORF2b, ORF3, ORF4, ORF5, and ORF5a. In some embodiments, the modified arterivirus genome or replicon RNA is devoid of ORF2b, ORF3, ORF4, and ORF5. In some embodiments, the modified arterivirus genome or replicon RNA is devoid of at least a portion of ORF6, for example the first one, two, three, four, five, six, seven, eight, nine, ten, or more nucleotides of ORF6. "Fragment", as used herein with respect to a polynucleotide, refers to a clone or any part of a polynucleotide molecule, particularly a part of a polynucleotide that retains a usable, functional characteristic. For example, a "polynucleotide fragment" refers to any subsequence of a polynucleotide, typically, of at least about 9 consecutive nucleotides, for example at least about 30 nucleotides, at least about 50 nucleotides, at least about 100 nucleotides, at least about 200 nucleotides, or at least about 300 nucleotides of any of the sequences provided herein. Exemplary polynucleotide fragments are the first sixty consecutive nucleotides (e.g., starting from the 5'-end or from the 3'-end) of the polynucleotides disclosed herein.

Nucleic acid fragments having a high degree of sequence identity (e.g., at least 85%, at least 90%, at least 95%, at least 96%, at least 97%, at least 98%, at least 99%, or 100%) to a sequence encoding open reading frame ORF7 of an arterivirus of interest can be identified and/or isolated by using the sequences identified herein (e.g., SEQ ID NO: 1, SEQ ID NO: 2, SEQ ID NO: 3, SEQ ID NO: 40, SEQ ID NO: 41, and SEQ ID NO: 42) or any others as they are known in the art, for example, the sequences having GenBank accession numbers NC_002532 (EAV), NC_001961.1 (PRRSV), NC_003092 (SHFV), and NC_001639.1 (LDV), by genome sequence analysis, hybridization, and/or PCR with degenerate primers or gene-specific primers from sequences identified in the respective arterivirus genome. As used herein "sequence identity" refers to the extent to which two optimally aligned polynucleotide are invariant throughout a window of alignment of components, e.g., nucleotides. An "identity fraction" for aligned segments of a test sequence and a reference sequence is the number of identical components which are shared by the two aligned sequences divided by the total number of components in reference sequence segment, e.g., the entire reference sequence or a smaller defined part of the reference sequence.

In some embodiments, a nucleic acid molecule disclosed herein comprises one or more nucleic acid fragments that specifically hybridize to a nucleic acid sequence encoding open reading frame ORF7 of an arterivirus; and complements of said nucleic acid sequences; and fragments of either, under low, moderate, or high stringency conditions. In a particular embodiment, nucleic acid molecules of the present application preferably include a nucleic acid sequence that hybridizes high stringency conditions, to a nucleic acid sequence encoding open reading frame ORF7 of an arterivirus; and complements of said nucleic acid sequences; and fragments of either.

In some embodiments, the nucleic acid molecules disclosed herein include a modified arterivirus genome or replicon RNA which is devoid of the sequence encoding a portion of or the entire open reading frame ORF2a. In some embodiments, the nucleic acid molecules disclosed herein includes a modified arterivirus genome or replicon RNA which is devoid of the ATG start codon of the sequence encoding open reading frame ORF7. In some embodiments, the nucleic acid molecules disclosed herein include a modified arterivirus genome or replicon RNA which is devoid of a portion of or the entire sequence encoding open reading frame ORF6. For example, the modified arterivirus genome or replicon RNA can be devoid of the ATG start codon of ORF6. In some embodiments, about 1%, 5%, 8%, 10%, 15%, 20%, 30%, 40%, 50%, 60%, 70%, 80%, 90%, or more of ORF6 is absent in the modified arterivirus genome or replicon RNA. In some embodiments, TRS7 within ORF6 is deleted or modified in the modified arterivirus genome or replicon RNA to reduce or abolish its activity. In some embodiments, about 1%, 5%, 8%, 10%, 15%, 20%, 30%, 40%, 50%, 60%, 70%, 80%, 90%, or more of ORF7 is absent in the modified arterivirus genome or replicon RNA.

The molecular techniques and methods by which these new nucleic acid molecules were constructed and characterized are described more fully in the examples herein.

In some embodiments, the nucleic acid molecules disclosed herein are recombinant nucleic acid molecules. As used herein, the term recombinant means any molecule (e.g. DNA, RNA, etc.), that is, or results, however indirect, from human manipulation of a polynucleotide. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination) of nucleic acid molecules; 2) includes conjoined nucleotide sequences that are not conjoined in nature; 3) has been engineered using molecular cloning techniques such that it lacks one or more nucleotides with respect to the naturally occurring nucleotide sequence; and/or 4) has been manipulated using molecular cloning techniques such that it has one or more sequence changes or rearrangements with respect to the naturally occurring nucleotide sequence.

Preferably, the nucleic acid molecules disclosed herein are produced using recombinant DNA technology (e.g., polymerase chain reaction (PCR) amplification, cloning, etc.) or chemical synthesis. Nucleic acid molecules as disclosed herein include natural nucleic acid molecules and homologs thereof, including, but not limited to, natural allelic variants and modified nucleic acid molecules in which one or more nucleotide residues have been inserted, deleted, and/or substituted, in such a manner that such modifications provide the desired property in effecting a biological activity as described herein.

A nucleic acid molecule, including a variant of a naturally-occurring nucleic acid sequence, can be produced using a number of methods known to those skilled in the art (see, for example, Sambrook et al., In: *Molecular Cloning, A Laboratory Manual,* 2nd Edition, Cold Spring Harbor Press, Cold Spring Harbor, N.Y. (1989)). The sequence of a nucleic acid molecule can be modified with respect to a naturally-occurring sequence from which it is derived using a variety of techniques including, but not limited to, classic mutagenesis techniques and recombinant DNA techniques, such as but not limited to site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, recombinational cloning, and chemical synthesis, including chemical synthesis of oligonucleotide mixtures and ligation of mixture groups to "build" a mixture of nucleic acid molecules, and combinations thereof. Nucleic acid molecule homologs can be selected from a mixture of modified nucleic acid molecules by screening for the function of the protein or the replicon encoded by the nucleic acid molecule and/or by hybridization with a wild-type gene or fragment thereof, or by PCR using primers having homology to a target or wild-type nucleic acid molecule or sequence.

In various embodiments disclosed herein, the nucleic acid molecule disclosed herein can include one or more of the following feature. In some embodiments, the nucleic acid molecule disclosed herein includes a modified arterivirus genome or replicon RNA including one or more subgenomic (sg) promoters at a non-native site, wherein each of the one or more sg promoters includes a transcriptional regulatory sequence (TRS).

The term "subgenomic promoter", as used herein, refers to a promoter of a subgenomic mRNA of a viral nucleic acid. As used herein, an "arterivirus subgenomic promoter" is a promoter as originally defined in a wild type arterivirus genome that directs transcription of a subgenomic messenger RNA as part of the arterivirus replication process. An arterivirus subgenomic (sg) promoter typically includes a conserved transcriptional regulatory sequence (TRS) with 5'- and 3' flanking sequences. Based on the particular arterivirus open reading frame (ORF) that it drives expression, the subgenomic promoter of the disclosure can be, for example, sg promoter 1 (which comprises arterivirus TRS1 or a variant thereof), sg promoter 2 (which comprises arterivirus TRS2 or a variant thereof), sg promoter 3 (which comprises arterivirus TRS3 or a variant thereof), sg promoter 4 (which comprises arterivirus TRS4 or a variant thereof), sg promoter 5 (which comprises arterivirus TRS5 or a variant thereof), sg promoter 6 (which comprises arterivirus TRS6 or a variant thereof), sg promoter 7 (which comprises arterivirus TRS7 or a variant thereof), or a variant thereof. In some embodiments described herein, the nucleic acid molecules of the application can include a sg promoter that is essentially devoid of a 5'-flanking sequence and/or a 3' flanking sequence. In some embodiments, the nucleic acid molecules of the disclosure can include a sg promoter that consists of a conserved transcriptional regulatory sequence (TRS), that is, such sg promoter does not include any flanking sequence. In some embodiments, a sg promoter can have a wild type sequence or a sequence that has been modified from wild type sequence but retains promoter activity.

Accordingly, in some embodiments, at least one of the one or more sg promoters includes a sequence exhibiting at least 80%, at least 85%, preferably at least 90%, or more preferably at least 95% identity sequence identity to a sequence selected from the group consisting of sg promoter 1, sg promoter 2, sg promoter 3, sg promoter 4, sg promoter 5, sg promoter 6, sg promoter 7, and a variant thereof. In some embodiments, at least one of the one or more sg promoters includes a sequence exhibiting 95%, 96%, 97%, 98%, 99%, or 100% sequence identity to sg promoter 1. In some embodiments, at least one of the one or more sg promoters includes a sequence exhibiting 95%, 96%, 97%, 98%, 99%, or 100% sequence identity to sg promoter 2. In some embodiments, at least one of the one or more sg promoters includes a sequence exhibiting 95%, 96%, 97%, 98%, 99%, or 100% sequence identity to sg promoter 3. In some embodiments, at least one of the one or more sg promoters includes a sequence exhibiting 95%, 96%, 97%, 98%, 99%, or 100% sequence identity to sg promoter 4. In some embodiments, at least one of the one or more sg promoters includes a sequence exhibiting 95%, 96%, 97%, 98%, 99%, or 100% sequence identity to sg promoter 5. In some embodiments, at least one of the one or more sg promoters includes a sequence exhibiting 95%, 96%, 97%, 98%, 99%, or 100% sequence identity to sg promoter 6. Such variants of the sg promoters may be naturally-occurring, including homologous polynucleotides from the same or a different species, or may be non-natural variants, for example polynucleotides synthesized using chemical synthesis methods, or generated using recombinant DNA techniques. Accordingly, in some embodiments, at least one of the one or more sg promoters is a modified sg promoter. The modified sg promoter can generally be any modified sg promote, and can be, for example, a modified sg promoter 1, a modified sg promoter 2, a modified sg promoter 3, a modified sg promoter 4, a modified sg promoter 5, a modified sg promoter 6, a modified sg promoter 7. In some particular embodiments, at least one of the one or more modified sg promoters is a modified sg promoter 7. In some embodiments, the nucleic acid molecules disclosed herein can include a modified arterivirus genome or replicon RNA which includes one or more modified sg promoters located at their respective native site, wherein each of the one or more modified sg promoters includes a TRS. In addition or alternatively, in some embodiments disclosed herein, at least one of the one or more modified sg promoter includes a nucleotide modification positioned within the sequence of the TRS. In some exemplary embodiments, at least one of the one or more modified sg promoters includes a leader TRS or a variant thereof. In some exemplary embodiments, at least one of the one or more modified sg promoters includes a body TRS or a variant thereof. In some embodiments, the leader TRS or a variant thereof and the body TRS or a variant thereof do not have the same sequence. In some embodiments, the nucleotide sequence of the leader TRS is not modified.

Alternatively or in addition, in some embodiments, the nucleic acid molecules disclosed herein can comprise at least one of the one or more modified sg promoter including one or more nucleotide modifications which are positioned within the primary sequence required for the formation of a secondary structure of RNA transcripts including the respective sg promoter sequence. In some embodiments, the secondary structure of RNA transcripts can include a hairpin structure. In some embodiments, the one or more nucleotide modifications are positioned within the leader TRS hairpin (LTH). In some embodiments, the nucleotide modifications positioned within the primary sequence of the hairpin structure involve in a conformational RNA switch in the 5' proximal region of the modified arterivirus genome or replicon RNA. In some embodiments, the nucleotide modifications positioned within the primary sequence of the hairpin structure modulate the production of one or more or all sg mRNA of the modified arterivirus genome or replicon RNA.

Further, in some embodiments disclosed herein, the modified arterivirus genome or replicon RNA can include one or more mutated T7 transcriptional termination signal sequences. The term "transcriptional termination signal", "terminator" or "terminator sequence" or "transcription terminator", as used interchangeably herein, refers to a regulatory section of genetic sequence that causes RNA polymerase to cease transcription. In accordance with some exemplary embodiments, at least one of the one or more T7 mutated transcriptional termination signal sequences includes a nucleotide substitution at a position selected from the group consisting of T9001, T3185, G3188, and combinations thereof. In some embodiments, the nucleotide substitution at position T9001 includes T9001G. In some embodiments, the nucleotide substitution at position T3185 includes T3185A. In some embodiments, the nucleotide substitution at position G3188 includes G3188A. In some embodiments, at least one of the one or more T7 mutated transcriptional termination signal sequences includes a nucleotide substitution at a position selected from the group consisting of T9001G, T3185A, G3188A, and combinations of any two or more thereof.

In some embodiments, the modified arterivirus genome or replicon RNA as disclosed herein includes one or more heterologous transcriptional termination signal sequences. The heterologous transcriptional termination signal sequences can generally be any heterologous transcriptional termination signal sequences, and can be, for example, SP6 termination signal sequence, a T3 termination signal sequence, or a variant thereof. Accordingly, the nucleic acid molecules according to some embodiments of the disclosure can include at least one of the one or more heterologous transcriptional termination signal sequences selected from the group consisting of a SP6 termination signal sequence, a T3 termination signal sequence, or a variant thereof. In some embodiments, at least one of the one or more heterologous transcriptional termination signal sequences is inactivated.

In various embodiments disclosed herein, the nucleic acid molecules can include one or more spacer regions. The spacer region can generally be any spacer region, and can be, for example, a spacer region that is operably positioned adjacent to at least one of the one or more sg promoters. In some embodiments disclosed herein, at least one of the one or more spacer regions is positioned immediately 3' to a sg promoter. In some embodiments, at least one of the one or more spacer regions is positioned immediately 5' to a sg promoter. In principle, the sequence of the spacer regions can be of any length, and can be, for example, about 20 to 400 nucleotides in length. In some embodiments, the sequence of the spacer regions is about 18 to 420, about 20 to 350, about 30 to 200, about 50 to 200 nucleotides in length. In some embodiments, the sequence of the spacer regions is about 100 to 300, about 200 to 350, about 300 to 350 nucleotides in length. In some embodiments, the sequence of the spacer regions is about 23 nucleotides in length. In some embodiments, the sequence of the spacer regions is about 98 nucleotides in length. In some embodiments, the sequence of the spacer regions is about 220 nucleotides in length. In some embodiments, the sequence of the spacer regions is about 343 nucleotides in length.

In some further embodiments, the nucleic acid molecules disclosed herein can include one or more expression cassettes. As used herein, the term "expression cassette" refers to a construct of genetic material that contains coding sequences and enough regulatory information to direct proper transcription and/or translation of the coding sequences in a recipient cell, in vivo and/or ex vivo. The expression cassette may be inserted into a vector for targeting to a desired host cell and/or into a subject. Further, the term expression cassette may be used interchangeably with the term "expression construct". The term "expression cassette" as used herein, refers to a nucleic acid construct that encodes a protein or functional RNA operably linked to expression control elements, such as a promoter, and optionally, any or a combination of other nucleic acid sequences that affect the transcription or translation of the gene.

In some embodiments, the nucleic acid molecules disclosed herein can include one or more expression cassettes, each of which includes a sg promoter operably linked to a heterologous nucleotide sequence. The term "operably linked", as used herein, denotes a functional linkage between two or more sequences. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous.

The basic techniques for operably linking two or more sequences of DNA together are familiar to the skilled worker, and such methods have been described in a number of texts for standard molecular biological manipulation (see, for example, Maniatis et al., "*Molecular Cloning: A Labo-*

*ratory Manual"* 2nd ed. Cold Spring Harbor Laboratory Press, Cold Spring Harbor, N.Y.; and Gibson et al., *Nature Methods* 6:343-45, 2009).

In some embodiments disclosed herein, the sg promoter can include a transcription regulatory sequence (TRS) and, optionally, one or more flanking regions. A flanking region can be generally of any length, and can be, for example, about 5 to 400 nucleotides in length. In some embodiments, the flanking region can be about 5 to 350, about 10 to 300, about 20 to 200, about 50 to 150, about 50 to 100 nucleotides in length. In some embodiments, the flanking region can be about 5 to 100, about 10 to 150, about 15 to 115, about 20 to 300, about 50 to 350, about 100 to 350 nucleotides in length. In some embodiments, the flanking region can be, or be about, 17 nucleotides in length. In some embodiments, the flanking region can be, or be about 17, 23, 25, 56, 73, or 112 nucleotides in length. In some embodiments, the flanking region can be, or be about, 25 nucleotides in length. In some embodiments, the flanking region can be, or be about 56 nucleotides in length. In some embodiments, the flanking region can be, or be about, 73 nucleotides in length. In some embodiments, the flanking region can be, or be about, 112 nucleotides in length. In some embodiments, the sg promoter can include a flanking region positioned 5' to the TRS. In some embodiments, the sg promoter can include a flanking region positioned immediately 5' to the TRS. In some embodiments, the sg promoter can include a flanking region positioned 3' to the TRS. In some embodiments, the sg promoter can include a flanking region positioned immediately 3' to the TRS. In some embodiments, the sg promoter can include 5' flanking region and a 3' flanking region. In some embodiments, the 5' flanking region and a 3' flanking region can be of the same length. In some embodiments, the 5' flanking region and a 3' flanking region can differ in their respective length. In some particular embodiments, the 5' flanking region can be, or be about, 23 nucleotides in length. In some embodiments, the 3' flanking region can be, or be about, 17, 25, 56, 73, or 112 nucleotides in length. In some particular embodiments, the 3' flanking region of the sg promoter 3 can be, or be about, 73 nucleotides in length. In some embodiments, the 3' flanking region of the sg promoter 4 can be, or be about, 17 nucleotides in length. In some embodiments, the 3' flanking region of the sg promoter 5 can be, or be about, 112 nucleotides in length. In some embodiments, the 3' flanking region of the sg promoter 6 can be, or be about, 25 nucleotides in length.

In some embodiments, the nucleic acid molecules disclosed herein can include more than one expression cassette. In principle, the nucleic acid molecules disclosed herein can generally include any number of expression cassettes. In some particular embodiments, the nucleic acid molecules disclosed herein can include at least two, at least three, at least four, at least five, or at least six expression cassettes.

Accordingly, the nucleic acid molecules as provided herein can find use, for example, as an expression vector that, when operably linked to a heterologous nucleic acid sequence, can affect expression of the heterologous nucleic acid sequence. In some embodiments, the heterologous nucleotide sequence includes a coding sequence of a gene of interest (GOI). In some embodiments, the coding sequence of the GOI is optimized for expression at a level higher than the expression level of a reference coding sequence. In some embodiments, the reference coding sequence is a sequence that has not been optimized. In some embodiments, the optimization of the GOI coding sequence can include codon optimization. With respect to codon-optimization of nucleotide sequences, degeneracy of the genetic code provides the possibility to substitute at least one base of the protein encoding sequence of a gene with a different base without causing the amino acid sequence of the polypeptide produced from the gene to be changed. Hence, the nucleic acid molecules of the present application may also have any base sequence that has been changed from any polynucleotide sequence disclosed herein by substitution in accordance with degeneracy of the genetic code. References describing codon usage are readily publicly available. In some further embodiments of the disclosure, polynucleotide sequence variants can be produced for a variety of reasons, e.g., to optimize codon expression for a particular host (e.g., changing codons in the arterivirus mRNA to those preferred by other organisms such as human, hamster, mice, or monkey).

In some embodiments disclosed herein, the GOI can encode amino acid sequence of a polypeptide. The polypeptide can generally any polypeptide, and can be, for example a therapeutic polypeptide, a prophylactic polypeptide, a diagnostic polypeptide, a nutraceutical polypeptide, an industrial enzyme, or a reporter polypeptide. In some embodiments, the GOI encodes a polypeptide selected from the group consisting of an antibody, an antigen, an immune modulator, and a cytokine.

Non-limiting examples of polypeptides that the GOI can encode include blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-α), transforming growth factor beta (TGF-β), and the like; soluble receptors, such as soluble TNF-.alpha. receptors, soluble VEGF receptors, soluble interleukin receptors (e.g., soluble IL-1 receptors and soluble type II IL-1 receptors), soluble γ or δ T cell receptors, ligand-binding fragments of a soluble receptor, and the like; enzymes, such as .alpha.-glucosidase, imiglucarase, β-glucocerebrosidase, and alglucerase; enzyme activators, such as tissue plasminogen activator; chemokines, such as IP-10, monokine induced by interferon-gamma (Mig), Groα/IL-8, RANTES, MIP-1α, MIP-1β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopres sin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LW); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other non-limiting examples of protein of interest include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or nini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, .beta.-enolase, and glycogen synthase; lysosomal enzymes (e.g., beta-N-acetylhexosaminidase A); and any variants thereof.

The peptide encoded by the GOI can be a multi-subunit protein or single-subunit protein. The peptide can be, for example, luciferases; fluorescent proteins (e.g., GFP); growth hormones (GHs) and variants thereof; insulin-like growth factors (IGFs) and variants thereof; granulocyte colony-stimulating factors (G-CSFs) and variants thereof; erythropoietin (EPO) and variants thereof; insulin, such as proinsulin, preproinsulin, insulin, insulin analogs, and the like; antibodies and variants thereof, such as hybrid antibodies, chimeric antibodies, humanized antibodies, monoclonal antibodies; antigen binding fragments of an antibody (Fab fragments), single-chain variable fragments of an antibody (scFV fragments); dystrophin and variants thereof; clotting factors and variants thereof; cystic fibrosis transmembrane conductance regulator (CFTR) and variants thereof; and interferons and variants thereof.

In some embodiments, the secondary structure of the RNA transcript including the coding sequence of the GOI is optimized for a desired property. In some particular embodiments, the secondary structure of the RNA transcript including the coding sequence of the GOI is optimized for improved RNA replication.

The modified genome or replicon RNA disclosed herein is preferably a genome or replicon RNA of an arterivirus, such as a genome or replicon RNA of a viral species of the family Arteriviridae, genus Arterivirus.

Suitable arterivirus species includes Equine arteritis virus (EAV), Porcine respiratory and reproductive syndrome virus (PRRSV), Lactate dehydrogenase elevating virus (LDV), Simian hemorrhagic fever virus (SHFV), and wobbly possum disease virus (WPDV). In some embodiments, the modified genome or replicon RNA disclosed herein is of an Equine arteritis virus (EAV). In some embodiments, the modified genome or replicon RNA disclosed herein is of an EAV-virulent Bucyrus strain (VBS). In some embodiments, the modified genome or replicon RNA disclosed herein is of a Simian hemorrhagic fever virus (SHFV). Virulent and avirulent arterivirus strains are both suitable. Non-limiting examples of preferred arterivirus strains include, but not limited to, EAV-virulent Bucyrus strain (VBS), LDV-Plagemann, LDV-C, PRRSV-type 1, and PRRSV-type 2. Exemplary preferred EAV strains include, but not limited to, EAV VB53, EAV ATCC VR-796, EAV HK25, EAV HK116, EAV ARVAC MLV, EAV Bucyrus strain (Ohio), modified EAV Bucyrus, avirulant strain CA95, Red Mile (Kentucky), 84KY-A 1 (Kentucky), Wroclaw-2 (Poland), Bibuna (Switzerland), and Vienna (Australia). Non-limiting preferred examples of PRRSV strains include PRRSV LV4.2.1, PRRSV 16244B, PRRSV HB-1(sh)/2002, PRRSV HB-2 (sh)/2002, PRRSV HN1, PRRSV SD 01-08, PRRSV SD0802, PRRSV SD0803, PRRSV VR2332. Non-limiting preferred examples of SHFV strains and variants include SHFV variants SHFV-krtg1a and -krtg1b (SHFV-krtg1a/b), SHFVkrtg2a/b (GenBank accession # JX473847 to JX473850), SHFV-LVR, the SHFV prototype variant LVR 42-0/M6941 (NC_003092); SHFV-krc1 and SHFVkrc2 from Kibale red colobus (HQ845737 and HQ845738, respectively). Other non-limiting examples of preferred arteriviruses include PRRSV-Lelystad, the European (type 1) type strain (M96262); PRRSVVR2332, the North American (type 2) type strain (U87392); EAV-Bucyrus (NC_002532); EAV-s3685 (GQ903794); LDV-P, the Plagemann strain (U15146); and LDV-C, the neurovirulent type C strain (L13298).

Recombinant Cells

In one aspect, some embodiments disclosed herein relate to a method of transforming a cell that includes introducing into a host cell, such as an animal cell, a nucleic acid molecule as provided herein, and selecting or screening for a transformed cell. In some embodiments, the nucleic acid molecule is introduced into the eukaryotic cell by an electroporation procedure or a biolistic procedure.

In a related aspect, some embodiments disclosed herein relate to recombinant host cells, for example, recombinant animal cells that include a nucleic acid molecule described herein. The nucleic acid molecule can be stably integrated in the host genome, or can be episomally replicating, or present in the recombinant host cell as a mini-circle expression vector for a stable or transient expression. Accordingly, in some embodiments disclosed herein, the nucleic acid molecule is maintained and replicated in the recombinant host cell as an episomal unit. In some embodiments, the nucleic acid molecule is stably integrated into the genome of the recombinant cell. Stable integration can be completed using classical random genomic recombination techniques or with more precise genome editing techniques such as using guide RNA directed CRISPR/Cas9 or TALEN genome editing. In some embodiments, the nucleic acid molecule present in the recombinant host cell as a mini-circle expression vector for a stable or transient expression.

In some embodiments, host cells can be genetically engineered (e.g. transduced or transformed or transfected) with, for example, a vector construct of the present application that can be, for example, a vector for homologous recombination that includes nucleic acid sequences homologous to a portion of the genome of the host cell, or can be an expression vector for the expression of any or a combination of the genes of interest. The vector can be, for example, in the form of a plasmid, a viral particle, a phage, etc. In some embodiments, a vector for expression of a polypeptide of interest can also be designed for integration into the host, e.g., by homologous recombination. The vector containing a polynucleotide sequence as described herein, e.g., nucleic acid molecule comprising a modified arterivirus genome or replicon RNA, as well as, optionally, a selectable marker or reporter gene, can be employed to transform an appropriate host cell.

In principle, the methods and compositions disclosed herein may be deployed for genetic engineering of any species, including, but not limited to, prokaryotic and eukaryotic species. Suitable host cells to be modified using the compositions and methods according to the present disclosure can include, but not limited to, algal cells, bacterial cells, heterokonts, fungal cells, chytrid cells, microfungi, microalgae, and animal cells. In some embodiments, the animal cells are invertebrate animal cells. In some embodiments, the vertebrate animal cells are mammalians cells. Host cells can be either untransformed cells or cells that have already been transfected with at least one nucleic acid molecule.

The methods and compositions disclosed herein are preferably used with host cells that are important or interesting for aquaculture, agriculture, animal husbandry, and/or for therapeutic and medicinal applications, including production of polypeptides used in the manufacturing of vaccine, pharmaceutical products, industrial products, chemicals, and the like. In some embodiments, the host cells can be cells in ex vivo tissues, organs, or cell cultures (e.g., ex vivo). In some embodiments, the host cells can be cells within a living subject or organism (e.g., in vivo). In some embodiments, the compositions and methods of the present application can be suitably used with host cells from species that are natural hosts of arteriviruses, such as horse, pig, mice, monkey, and apes. Particularly preferred species, in some embodiments of the application, are vertebrate animal species and invertebrate animal species. In principle, any animal species can be generally used and can be, for example, human, dog, bird, fish, horse, pig, primate, mouse, cattle, swine, sheep, rabbit, cat, goat, donkey, hamster, or buffalo. Non-limiting examples of suitable bird species include chicken, duck, goose, turkey, ostrich, emu, swan, peafowl, pheasant, partridge, and guinea fowl. In some particular embodiments, the fish species is a salmon species. Non-limiting examples of suitable animal host cells include, but not limited to, pulmonary equine artery endothelial cell, equine dermis cell, baby hamster kidney cell, rabbit kidney cell, mouse muscle cell, mouse connective tissue cell, human cervix cell, human epidermoid larynx cell, Chinese hamster ovary cell (CHO), human HEK-293 cell, and mouse 3T3 cell. In some embodiments, the host cell is baby hamster kidney cell. In some embodiments, the baby hamster kidney cell is a BHK-21 cell.

Techniques for transforming a wide variety of the above-mentioned host cells and species are known in the art and described in the technical and scientific literature. Accordingly, cell cultures including at least one recombinant cell as disclosed herein are also within the scope of this application. Methods and systems suitable for generating and maintaining cell cultures are known in the art In some embodiments, the compositions and methods of the present disclosure can be used to achieve tissue specific expression which enables a therapeutic arterivirus vector to be delivered systemically into a patient. If the vector should infect a cell which does not express the appropriate RNA species, the vector will only be capable of expressing nonstructural proteins and not the gene of interest. Eventually, the arterivirus vector will be harmlessly degraded.

In one non-limiting example, use of the compositions and methods described herein enables virtual tissue-specific expression possible for a variety of therapeutic applications, including for example, targeting vectors for the treatment for various types of cancers. This rationale relies on specific expression of tumor-specific markers such as the carcinoembryonic tumor specific antigen (CEA) and the alpha-fetoprotein tumor marker. Briefly, utilizing such tumor-specific RNA to target specific tumors allows for the tumor-specific expression of toxic molecules, cytokines or pro-drugs discussed below. Such methods may be utilized for a wide variety of tumors, including for example, colorectal, lung, breast, ovary, bladder and prostate cancers because all these tumors express the CEA.

Briefly, CEA was one of the first tumor-specific markers to be described, along with the alpha-fetoprotein tumor marker. CEA is a normal glycoprotein in the embryonic tissue of the gut, pancreas and liver during the first two trimesters of fetal development (Pathologic Basis of Disease, 3rd edition 1984, Robbins et al. (eds.)). Previously, CEA was believed to be specific for adenocarcinomas of the colon, however, with the subsequent development of more sensitive radioimmunoassays it became apparent that CEA was presented in the plasma with many endodermally derived cancers, particularly pancreatic, gastric and bronchogenic.

In some embodiments, the arterivirus genome or replicon RNAs disclosed herein may be constructed to express viral antigens, ribozyme, antisense sequences or immunostimulatory factors such as gamma-interferon (γ-IFN), IL-2 or IL-5 for the targeted treatment of virus infected cell types. In particular, in order to target arterivirus vectors to specific foreign organism or pathogen-infected cells, inverted repeats of the arterivirus vector may be selected to hybridize to any pathogen-specific RNA, for instance target cells infected by pathogens such as HIV, CMV, HBV, HPV and HSV.

In some embodiments, specific organ tissues may be targeted for the treatment of tissue-specific metabolic diseases utilizing gene replacement therapies. For example, the liver is an important target tissue because it is responsible for many of the body's metabolic functions and is associated with many metabolic genetic disorders. Such diseases include many of the glycogen storage diseases, phenylketonuria, Gaucher's disease and familial hypercholesterolemia. Presently there are many liver-specific enzymes and markers which have been sequenced which may be used to engineer appropriate inverted repeats for arterivirus vectors. Such liver-specific cDNAs include sequences encoding for S-adenosylmethione synthetase (Horikawa et al., *Biochem. Int.* 25:81, 1991); lecithin: cholesterolacyl transferase (Rogne et al., *Biochem. Biophys. Res. Commun.* 148:161, 1987); as well as other liver-specific cDNAs (Chin et al., *Ann. N.Y. Acad. Sci.* 478:120, 1986). Such a liver-specific arterivirus vector could be used to deliver the low density lipoprotein receptor (Yamamoto et al., *Cell* 39:27, 1984) to liver cells for the treatment of familial hypercholesterolemia (Wilson et al., *Mol. Biol. Med.* 7:223, 1990).

The arterivirus genome or replicon RNAs disclosed herein can be used to express one or more heterologous coding sequence(s) or functional RNA(s) of interest, also referred to herein as a heterologous RNA or heterologous sequence, which can be chosen from a wide variety of sequences derived from viruses, prokaryotes and eukaryotes. Examples of categories of heterologous sequences include, but are not limited to, sequences coding for immunogens (including native, modified or synthetic antigenic proteins, peptides, epitopes or immunogenic fragments), cytokines, toxins, therapeutic proteins, enzymes, antisense sequences, and immune response modulators.

Heterologous Nucleotide Sequences

In accordance of some embodiments of the present disclosure, a wide variety of nucleotide sequences can be carried by the modified arterivirus genome or replicon RNA of the present disclosure. In some embodiments, the modified arterivirus genome or replicon RNA as described herein does not contain any additional heterologous nucleotide sequence. In some embodiments, the modified arterivirus genome or replicon RNA of the present disclosure contains one or more additional heterologous or foreign nucleotide sequences. In some embodiments, the heterologous nucleotide sequence comprises a heterologous nucleotide sequence of at least about 100 bases, 2 kb, 3.5 kb, 5 kb, 7 kb, or even a heterologous sequence of at least about 8 kb.

A wide variety of heterologous nucleotide sequences may be included in the modified arterivirus genome or replicon RNA of the present disclosure, including for example sequences which encode palliatives such as cytokines, toxins, prodrugs, antigens which stimulate an immune response, ribozymes, and proteins which assist or inhibit an immune response, as well as antisense sequences (or sense sequences for "antisense applications"). As noted above, within various embodiments of the disclosure the modified arterivirus genome or replicon RNAs provided herein may contain (and express, within certain embodiments) two or more heterologous nucleotide sequence.

1). Cytokines

In some embodiments disclosed herein, the heterologous nucleotide sequence encodes a cytokine. Briefly, cytokines act to proliferate, activate, or differentiate immune effectors cells. Representative examples of cytokines include, macrophages, B lymphocytes, T lymphocytes, endothelial cells, fibroblasts, lymphokines likes gamma interferon, tumor necrosis factor, interleukin, IL-1, IL-2, IL-3, IL-4, IL-5, IL-6, IL-7, IL-8, IL-9, IL-10, IL-1, IL-12, IL-13, IL-14, IL-15, GM-CSF, CSF-1 and G-CSF.

In some related embodiments, the heterologous nucleotide sequence encodes an immunomodulatory cofactor. Briefly, as utilized within the context of the present disclosure, "immunomodulatory cofactor" refers to factors which, when manufactured by one or more of the cells involved in an immune response, or when added exogenously to the cells, cause the immune response to be different in quality or potency from that which would have occurred in the absence of the cofactor. The quality or potency of a response may be measured by a variety of assays known to one of skill in the art including, for example, in vitro assays which measure cellular proliferation (e.g., 3 H thymidine uptake), and in vitro cytotoxic assays (e.g., which measure 51 Cr release) (see Warner et al., AIDS Res. and Human Retroviruses 7:645-655, 1991).

Representative examples of immunomodulatory co-factors include alpha interferon (Finter et al., *Drugs* 42(5):749-765, 1991; U.S. Pat. Nos. 4,892,743; 4,966,843; WO 85/02862; Nagata et al., *Nature* 284:316-320, 1980; Familletti et al., *Methods in Enz.* 78:387-394, 1981; Twu et al., *Proc. Natl. Acad. Sci. USA* 86:2046-2050, 1989; Faktor et al., *Oncogene* 5:867-872, 1990), beta interferon (Seif et al., *J. Virol.* 65:664-671, 1991), gamma interferons (Radford et al., *American Society of Hepatology:* 2008-2015, 1991; Watanabe et al., *Proc. Natl. Acad. Sci. USA* 86:9456-9460, 1989; Gansbacher et al., *Cancer Research* 50:7820-7825, 1990; Maio et al., *Can. Immunol. Immunother.* 30:34-42, 1989; U.S. Pat. Nos. 4,762,791 and 4,727,138), G-CSF (U.S. Pat. Nos. 4,999,291 and 4,810,643), GM-CSF (WO 85/04188), TNFs (Jayaraman et al., *J. Immunology* 144:942-951, 1990), Interleukin-2 (IL-2) (Karupiah et al., *J. Immunology* 144:290-298, 1990; Weber et al., *J. Exp. Med.* 166:1716-1733, 1987; Gansbacher et al., *J. Exp. Med.* 172:1217-1224, 1990; U.S. Pat. No. 4,738,927), IL-4 (Tepper et al., *Cell* 57:503-512, 1989; Golumbek et al., *Science* 254:713-716, 1991; U.S. Pat. No. 5,017,691), IL-6 (Brakenhof et al., *J. Immunol.* 139:4116-4121, 1987; WO 90/06370), IL-12, IL-15 (Grabstein et al., *Science* 264:965-968, 1994; Genbank-EMBL Accession No. V03099), ICAM-1 (Altman et al., *Nature* 338:512-514, 1989), ICAM-2, LFA-1, LFA-3, MHC class I molecules, MHC class II molecules, 2-microglobulin, chaperones, CD3, B7/BB 1, MHC linked transporter proteins or analogues thereof.

The choice of which immunomodulatory cofactor to include within the modified arterivirus genome or replicon RNA of the present disclosure may be based upon known therapeutic effects of the cofactor, or experimentally determined. For example, in chronic hepatitis B infections alpha interferon has been found to be efficacious in compensating a patient's immunological deficit and thereby assisting recovery from the disease. Alternatively, a suitable immunomodulatory cofactor may be experimentally determined. Briefly, blood samples are first taken from patients with a hepatic disease. Peripheral blood lymphocytes (PBLs) are restimulated in vitro with autologous or HLA-matched cells (e.g., EBV transformed cells), and transduced with modified arterivirus genome or replicon RNA of the present disclosure which directs the expression of an immunogenic portion of a hepatitis antigen and the immunomodulatory cofactor. Stimulated PBLs are used as effectors in a CTL assay with the BLA-matched transduced cells as targets. An increase in CTL response over that seen in the same assay performed using HLA-matched stimulator and target cells transduced with a vector encoding the antigen alone, indicates a useful immunomodulatory cofactor. In some embodiments, the immunomodulatory cofactor gamma interferon is particularly preferred.

Another non-limiting example of an immunomodulatory cofactor is the B7/BB1 costimulatory factor. Briefly, activation of the full functional activity of T cells requires two signals. One signal is provided by interaction of the antigen-specific T cell receptor with peptides which are bound to major histocompatibility complex (MHC) molecules, and the second signal, referred to as costimulation, is delivered to the T cell by antigen-presenting cells. Briefly, the second signal is required for interleukin-2 (IL-2) production by T cells and appears to involve interaction of the B7/BB 1 molecule on antigen-presenting cells with CD28 and CTLA-4 receptors on T lymphocytes (Linsley et al., *J. Exp. Med.,* 173:721-730, 1991a, and *J. Exp. Med.,* 174:561-570, 1991). In some embodiments, B7/BB 1 may be introduced into tumor cells in order to cause costimulation of CD8+T cells, such that the CD8+T cells produce enough IL-2 to expand and become fully activated. These CD8+T cells can kill tumor cells that are not expressing B7 because costimulation is no longer required for further CTL function. Vectors that express both the costimulatory B7/BB1 factor and, for example, an immunogenic HBV core protein, may be made utilizing methods which are described herein. Cells transduced with these vectors will become more effective antigen-presenting cells. The HBV core-specific CTL response will be augmented from the fully activated CD8+T cell via the costimulatory ligand B7/BB 1.

2). Toxins

In some embodiments disclosed herein, the heterologous nucleotide sequence encodes a toxin. Briefly, toxins act to directly inhibit the growth of a cell. Representative examples of toxins include ricin (Lamb et al., *Eur. J. Biochem.* 148:265-270, 1985), abrin (Wood et al., *Eur. J. Biochem.* 198:723-732, 1991; Evensen et al., *J. of Biol. Chem.* 266:6848-6852, 1991; Collins et al., *J. of Biol. Chem.* 265:8665-8669, 1990; Chen et al., *Fed. of Eur. Biochem Soc.* 309:115-118, 1992), diphtheria toxin (Tweten et al., *J. Biol. Chem.* 260:10392-10394, 1985), cholera toxin (Mekalanos et al., *Nature* 306:551-557, 1983; Sanchez and Holmgren, PNAS 86:481-485, 1989), gelonin (Stirpe et al., *J. Biol. Chem.* 255:6947-6953, 1980), pokeweed (Irvin, *Pharmac. Ther.* 21:371-387, 1983), antiviral protein (Barbieri et al.,

*Biochem. J.* 203:55-59, 1982; Irvin et al., *Arch. Biochem. & Biophys.* 200:418-425, 1980; Irvin, Arch. Biochem. & Biophys. 169:522-528, 1975), tritin, Shigella toxin (Calderwood et al., *PNAS* 84:4364-4368, 1987; Jackson et al., *Microb. Path.* 2:147-153, 1987), Pseudomonas exotoxin A (Carroll and Collier, *J. Biol. Chem.* 262:8707-8711, 1987), herpes simplex virus thymidine kinase (HSVTK) (Field et al., *J. Gen. Virol.* 49:115-124, 1980), and *E. coli.* guanine phosphoribosyl transferase.

3). Pro-Drugs

In some embodiments disclosed herein, the heterologous nucleotide sequence encodes a “pro-drug”. Briefly, as utilized within the context of the present disclosure, “pro-drug” refers to a gene product that activates a compound with little or no cytotoxicity into a toxic product. Representative examples of such gene products include HSVTK and VZVTK (as well as analogues and derivatives thereof), which selectively monophosphorylate certain purine arabinosides and substituted pyrimidine compounds, converting them to cytotoxic or cytostatic metabolites. More specifically, exposure of the drugs ganciclovir, acyclovir, or any of their analogues (e.g., FIAU, FIAC, DHPG) to HSVTK phosphorylates the drug into its corresponding active nucleotide triphosphate form.

Representative examples of other pro-drugs which may be utilized within the context of the present disclosure include: *E. coli* guanine phosphoribosyl transferase which converts thioxanthine into toxic thioxanthine monophosphate (Besnard et al., *Mol. Cell. Biol.* 7:4139-4141, 1987); alkaline phosphatase, which will convert inactive phosphorylated compounds such as mitomycin phosphate and doxorubicin-phosphate to toxic dephosphorylated compounds; fungal (e.g., *Fusarium oxysporum*) or bacterial cytosine deaminase, which will convert 5-fluorocytosine to the toxic compound 5-fluorouracil (Mullen, *PNAS* 89:33, 1992); carboxypeptidase G2, which will cleave the glutamic acid from para-N-bis (2-chloroethyl) aminobenzoyl glutamic acid, thereby creating a toxic benzoic acid mustard; and Penicillin-V amidase, which will convert phenoxyacetabide derivatives of doxorubicin and melphalan to toxic compounds (see generally, Vrudhula et al., *J. of Med. Chem.* 36(7):919-923, 1993; Kern et al., *Canc. Immun. Immunother.* 31(4):202-206, 1990).

4). Antisense Sequence

In some embodiments disclosed herein, the heterologous nucleotide sequence is an antisense sequence. Briefly, antisense sequences are designed to bind to RNA transcripts, and thereby prevent cellular synthesis of a particular protein or prevent use of that RNA sequence by the cell. Representative examples of such sequences include antisense thymidine kinase, antisense dihydrofolate reductase (Maher and Dolnick, *Arch. Biochem. & Biophys.* 253:214-220, 1987; Bzik et al., *PNAS* 84:8360-8364, 1987), antisense HER2 (Coussens et al., *Science* 230:1132-1139, 1985), antisense ABL (Fainstein et al., *Oncogene* 4:1477-1481, 1989), antisense Myc (Stanton et al., *Nature* 310:423-425, 1984) and antisense ras, as well as antisense sequences which block any of the enzymes in the nucleotide biosynthetic pathway. In addition, in accordance with some embodiments disclosed herein, antisense sequences to interferon and 2 microglobulin may be utilized in order to decrease immune response.

Alternatively or in addition, in some embodiments, antisense RNA may be utilized as an anti-tumor agent in order to induce a potent Class I restricted response. Briefly, in addition to binding RNA and thereby preventing translation of a specific mRNA, high levels of specific antisense sequences are believed to induce the increased expression of interferons (including gamma-interferon) due to the formation of large quantities of double-stranded RNA. The increased expression of gamma interferon, in turn, boosts the expression of MHC Class I antigens. Preferred antisense sequences for use in this regard include actin RNA, myosin RNA, and histone RNA. Antisense RNA which forms a mismatch with actin RNA is particularly preferred.

5). Ribozymes

In some embodiments disclosed herein, modified arterivirus genome or replicon RNAs are provided which produce ribozymes upon infection of a host cell. Briefly, ribozymes are used to cleave specific RNAs and are designed such that it can only affect one specific RNA sequence. Generally, the substrate binding sequence of a ribozyme is between 10 and 20 nucleotides long. The length of this sequence is sufficient to allow a hybridization with target RNA and disassociation of the ribozyme from the cleaved RNA. Representative examples for creating ribozymes include those described in U.S. Pat. Nos. 5,116,742; 5,225,337 and 5,246,921.

6). Proteins and Other Cellular Constituents

In some embodiments disclosed herein, a wide variety of proteins or other cellular constituents can be carried by the modified arterivirus genome or replicon RNAs of the disclosure. Representative examples of such proteins include native or altered cellular components, as well as foreign proteins or cellular constituents, found in for example, viruses, bacteria, parasites, fungus or animal such as mammalian.

Methods for Producing Polypeptides

In another aspect, the present application provides methods for producing one or more polypeptide of interests. The polypeptides of interest according the present disclosure can be generally any polypeptide and can be, for example recombinant proteins and peptides suitable for pharmaceutical, nutraceutical, and/or industrial compositions. Non-limiting examples of suitable recombinant polypeptides include therapeutic polypeptides, prophylactic polypeptides, diagnostic polypeptides, nutraceutical polypeptides, industrial enzymes, and reporter polypeptides. In some embodiments, polypeptides of interest made in accordance with the present disclosure have a variety of uses including, but not limited to, use as vaccines and other therapeutic compounds, use as diagnostic agents and use as antigens in the production of polyclonal or monoclonal antibodies.

In some embodiments, the host cells can be recombinant cells in culture (e.g., ex vivo). In some embodiments, the host cells can be recombinant cells in a living subject (e.g., (in vivo). Accordingly, in some embodiments, the method for producing a polypeptide of interest according to this aspect of the disclosure can include the cultivation of a recombinant host cell, such as a recombinant mammalian cell, including a nucleic acid molecule according to any one of the preceding aspects and embodiments. To produce one or more polypeptides of interest according the present disclosure, a recombinant cell, produced as described above, is cultured in an effective medium, using any one of cell culturing techniques known in the art. As used herein, an effective medium refers to any medium in which the transfected cells can produce one or more polypeptides of interest according the present disclosure. An effective medium is typically an aqueous medium comprising assimilable carbohydrate, nitrogen and phosphate sources, as well as appropriate salts, minerals, metals and other nutrients, such as vitamins, growth factors and other hormones. The medium may comprise complex nutrients or may be a defined medium. Recombinant cells of the present disclosure can be cultured in conventional fermentation bioreactors, which include, but are not limited to, batch, fed-batch, cell recycle and continuous fermenters. Culturing can also be conducted in shake flasks, test tubes, microtiter dishes and petri plates. Culturing is carried out at a temperature, pH and oxygen content appropriate for the recombinant cell. Such culturing conditions are well within the expertise of one of ordinary skill in the art. Non-limiting examples of preferred effective media and culturing conditions are included in the Examples section.

Depending on whether expression results in a polypeptide of interest having or lacking a signal segment, the resultant polypeptide may be secreted into the medium or remain within the recombinant cell. The phrase “recovering the protein” refers simply to collecting the whole fermentation medium (including cells) containing the polypeptide and can, but need not, entail additional steps of separation or purification. Polypeptides of interest of the present disclosure can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

Isolated polypeptides of interest of the present disclosure are preferably retrieved in “substantially pure” form. As used herein, “substantially pure” refers to a purity that allows for the effective use of the compound as a therapeutic composition or diagnostic. A vaccine for animals, for example, should exhibit no preferably substantial toxicity and should be capable of stimulating the production of antibodies in a vaccinated animal.

In some embodiments, the method for producing a polypeptide of interest of the present disclosure includes culturing a host cell comprising a nucleic acid as described herein. In some embodiments, the nucleic acid includes (i) nucleotide sequence encoding a modified arterivirus genome or replicon RNA, wherein the modified genome or replicon RNA comprises a sequence fragment exhibiting at least 80% sequence identity to the sequence encoding open reading frame ORF7, and wherein the modified genome or replicon RNA is devoid of the sequence encoding ORF2a; and (ii) one or more expression cassettes, wherein each of the one or more expression cassettes comprises a subgenomic (sg) promoter operably linked to a heterologous nucleotide sequence encoding a gene of interest (GOI).

In some embodiments, the method for producing a polypeptide of interest of the present disclosure includes administering to a subject a nucleic acid as described herein. In some embodiments, the nucleic acid nucleic acid includes (i) nucleotide sequence encoding a modified arterivirus genome or replicon RNA, wherein the modified genome or replicon RNA comprises a sequence fragment exhibiting at least 80% sequence identity to the sequence encoding open reading frame ORF7, and wherein the modified genome or replicon RNA is devoid of the sequence encoding ORF2a; and (ii) one or more expression cassettes, wherein each of the one or more expression cassettes comprises a subgenomic (sg) promoter operably linked to a heterologous nucleotide sequence encoding a gene of interest (GOI).

Accordingly, biological samples, biomass, and progeny of a recombinant cell according to any one of the preceding aspects and embodiments are also within the scope of the present application. Thus, polypeptides produced by a method according to this aspect of the application are also within the scope of this application.

In some embodiments, the methods according to this aspect are preferably deployed in host cells that are important or interesting for aquaculture, agriculture, animal husbandry, and/or for therapeutic and medicinal applications, including production of polypeptides used in the manufacturing of vaccine, pharmaceutical products, industrial products, chemicals, and the like. In some embodiments, the methods of this aspect can be suitably deployed in animal cells. Therapeutic protein production in small and large scale is important field of development in pharmaceutical industry, because proteins produced in animal cells are believe to generally have proper processing, post-translational modification and therefore have adequate activity for treatment of the physiological condition. In some embodiments, the host cells can be of animal species that are natural hosts of arteriviruses, such as horse, pig, mice, monkey, and apes. Particularly preferred species, in some embodiments of the application, are vertebrate animal species and invertebrate animal species. In principle, any animal species can be generally used and can be, for example, human, dog, bird, fish, horse, pig, primate, mouse, cattle, swine, sheep, rabbit, cat, goat, donkey, hamster, or buffalo. Non-limiting examples of suitable bird species include chicken, duck, goose, turkey, ostrich, emu, swan, peafowl, pheasant, partridge, and guinea fowl. In some particular embodiments, the fish species is a salmon species. Non-limiting examples of suitable animal host cells include, but not limited to, pulmonary equine artery endothelial cell, equine dermis cell, baby hamster kidney cell, rabbit kidney cell, mouse muscle cell, mouse connective tissue cell, human cervix cell, human epidermoid larynx cell, Chinese hamster ovary cell (CHO), human HEK-293 cell, and mouse 3T3 cell. In some embodiments, the host cell is baby hamster kidney (BHK) cell, as described in more details in Examples 10-13 and 17-18. In some embodiments, the baby hamster kidney cell is a BHK-21 cell.

Recombinant Polypeptides

In a further aspect, some embodiments disclosed herein relate to recombinant polypeptides produced by a method in accordance with one or more embodiments described in the present application.

The recombinant polypeptide according the present disclosure can be generally any polypeptide and can be, for example recombinant proteins and peptides suitable for pharmaceutical, nutraceutical, and/or industrial compositions. Non-limiting examples of suitable recombinant polypeptides include therapeutic polypeptides, prophylactic polypeptides, diagnostic polypeptides, nutraceutical polypeptides, industrial enzymes, and reporter polypeptides.

The term “therapeutic polypeptide,” as used herein denotes a bioactive polypeptide that has therapeutic utility. The term encompasses any polypeptide that can be administered to a patient to produce a beneficial therapeutic or diagnostic effect though binding to and/or altering the function of a biological target molecule in the patient. The target molecule can be an endogenous target molecule encoded by the patient’s genome (e.g., an enzyme, receptor, growth factor, cytokine encoded by the patient’s genome) or an exogenous target molecule encoded by the genome of a pathogen (e.g., an enzyme encoded by the genome of a virus, bacterium, fungus, nematode or other pathogen). Illustrative categories of therapeutic peptides suitable for practicing the compositions and methods of the present disclosure are hormones, monoclonal antibodies, vaccines, enzymes, cytokines, toxins, and the like. The term therapeutic polypeptide includes functional fragments of therapeutic polypeptides.

The term "nutraceutical polypeptide" as used herein refers to any polypeptide which may prevent, ameliorate or otherwise confer benefits against an undesirable condition, and used for its associated health benefits, to maintain the healthy condition of the consumer. The term "nutraceutical" as used herein denotes a usefulness in both the nutritional and pharmaceutical field of application. Thus, the nutraceutical polypeptides and compositions of the present disclosure can find use as supplement to food and beverages, and as pharmaceutical formulations not associated with food, suitable for consumption by an individual and usually sold in medicinal forms which may be solid formulations such as caplets, tablet, capsules, soft gel capsules, gel caps and the like, or liquid formulations, such as solutions or suspensions. As such, the term nutraceutical composition comprises food and beverages containing the nutraceutical polypeptides disclosed herein, for example protein hydrolysates which are rich in tripeptides.

A "reporter polypeptide", as used herein, is a polypeptide that is detectable or has an activity that produces a detectable product. A reporter polypeptide can include a visual marker or enzyme that produces a detectable signal. Non-limiting examples of reporter polypeptides includes cat, lacZ, uidA, xylE, an alkaline phosphatase gene, an $\alpha$-amylase gene, an $\alpha$-galactosidase gene, a $\beta$-glucuronidase gene, a $\beta$-lactamase gene, a horseradish peroxidase gene, a luciferin/luciferase gene, an R-locus gene, a tyrosinase gene, or a gene encoding a fluorescent protein, including but not limited to a blue, cyan, green, red, or yellow fluorescent protein, a photoconvertible, photoswitchable, or optical highlighter fluorescent protein, or any of variant thereof, including, without limitation, codon-optimized, rapidly folding, monomeric, increased stability, and enhanced fluorescence variants.

Pharmaceutical Compositions

In a further aspect, some embodiments disclosed herein relate to a composition including a recombinant polypeptide as described herein and a pharmaceutically acceptable carrier.

In yet further aspect, some embodiments disclosed herein relate to a composition including a nucleic acid molecule as disclosed herein and a pharmaceutically acceptable carrier.

In yet a further aspect, some embodiments disclosed herein relate to a composition including a recombinant cell as disclosed herein and a pharmaceutically acceptable carrier.

In some embodiments disclosed herein, the compositions of the present application can be further formulated for use as a protective composition (e.g., vaccine) or therapeutic composition. In particular, protective compositions made in accordance with the present disclosure have a variety of uses including, but not limited to, use as vaccines and other therapeutic agents, use as diagnostic agents and use as antigens in the production of polyclonal or monoclonal antibodies. Thus, in the case of vaccines, the compositions of the present application can provide a method for inducing an immune response in a nucleic acid of the composition in an immunogenic amount to a subject, particles, which method comprises administering a population and/or composition, the target.

When used as vaccines, the compositions in general must be stored at low temperature, or they have to be in a freeze-dried form. Freeze-dried vaccines can be kept under moderate cooling conditions or even at room temperature. Often, the vaccine is mixed with stabilizers, e.g. to protect degradation-prone proteins from being degraded, to enhance the shelf-life of the vaccine, or to improve freeze-drying efficiency. Useful stabilizers include, but are not limited to, SPGA, carbohydrates such as, for example, sorbitol, mannitol, trehalose, starch, sucrose, dextran or glucose, proteins such as albumin or casein or degradation products thereof, and buffers, such as alkali metal phosphate. Accordingly, in some embodiments, vaccine according to the present disclosure is in a freeze-dried form. Alternatively or in addition, the vaccine may be suspended in a physiologically acceptable diluent and/or buffer.

In some embodiments disclosed herein, the compositions of the present application can be further formulated into a therapeutic composition capable of protecting an animal from disease caused by a parasite when the composition is administered to the animal in an effective amount. In some embodiments, the therapeutic composition is a multivalent therapeutic composition which contains multiple protective polypeptides targeting multiple targets and/or multiple parasites. Such multivalent therapeutic compositions can be produced by combining one or more protective polypeptides after production, by culturing more than one recombinant cell in a culturing reaction or by producing more than one protective polypeptides in a recombinant cell by, for example, transfecting an animal cell with one or more recombinant molecules and/or by transfecting an animal cell with a recombinant molecule containing more than one nucleic acid sequence encoding one or more protective polypeptides as disclosed herein.

In some embodiments, the therapeutic composition as described herein can also include an immunopotentiator, such as an adjuvant or a carrier. Suitable adjuvants or carriers include the adjuvants and carriers suitable for administration of recombinant polypeptides of the present disclosure. Therapeutic compositions of the present disclosure can be formulated in an excipient that the animal to be administered can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m or o-cresol, formalin and benzyl alcohol. Standard formulations will either be liquid injectables or solids which can be taken up in a suitable liquid as a suspension or solution for injection. Thus, in a non-liquid formulation, the excipient may comprise dextrose, human serum albumin, preservatives, etc., to which sterile water or saline could be added prior to administration.

As used herein, the term "pharmaceutically-acceptable carrier" means a carrier that is useful in preparing a pharmaceutical composition or formulation that is generally safe, non-toxic, and neither biologically nor otherwise undesirable, and includes a carrier that is acceptable for veterinary use as well as human pharmaceutical use. In some embodiments, a pharmaceutically acceptable carrier as simple as water, but it can also include, for example, a solution of physiological salt concentration. In some embodiments, a pharmaceutically acceptable carrier can be, or may include, stabilizers, diluents and buffers. Suitable stabilizers are for example SPGA, carbohydrates (such as dried milk, serum albumin or casein) or degradation products thereof. Suitable buffers are for example alkali metal phosphates. Diluents include water, aqueous buffers (such as buffered saline), alcohols and polyols (such as glycerol). For administration to animals or humans, the composition according to the present application can be given inter alia intranasally, by spraying, intradermally, subcutaneously, orally, by aerosol or intramuscularly.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

Additional alternatives are disclosed in further detail in the following examples, which are not in any way intended to limit the scope of the claims.

Example 1

Construction of Base Vectors

This Example describes the generation of the base arterivirus expression vector that was then further modified and subsequently used in the construction of monovalent, bivalent, and trivalent vectors.

Construction of the Base Vector REP-EAV(WT)

The Rep-EAV-Ren(1G)v2-N-seq vector was assembled as follows. The Renilla luciferase gene and three EAV fragments (EAV F1-F3) were synthesized.

Figure 2:
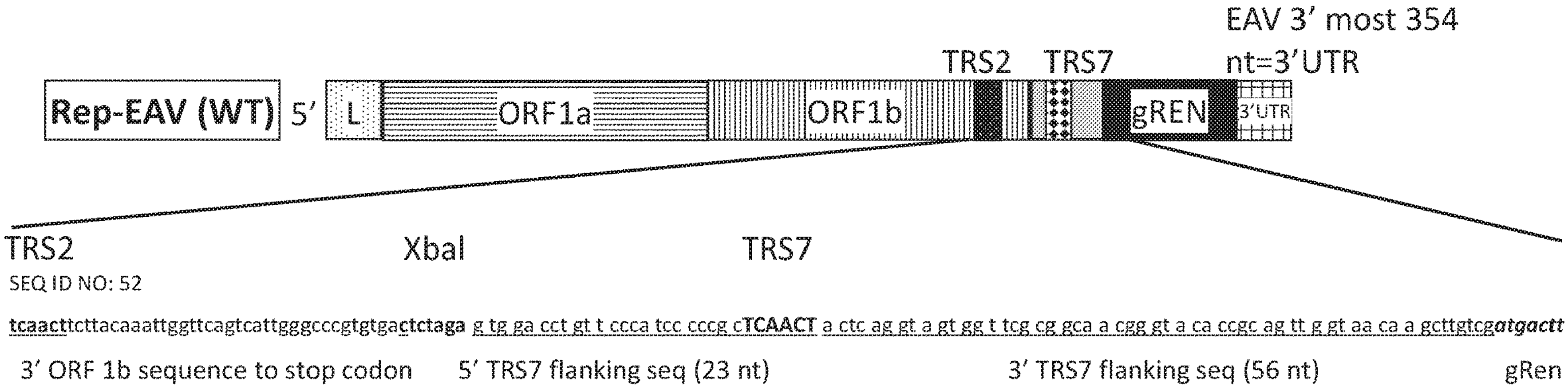
FIG. 2 graphically depicts the structure of a base monovalent EAV replicon design, Rep-EAV (WT), which is a replicon vector with the region between TRS2 and the start of the green Renilla luciferase reporter gene magnified for details of the sequence included. The EAV sequences that flank the TRS7 element are in gray and underlined. XbaI is the unique restriction site engineered downstream of ORF1b stop codon; a single nucleotide "C" separates the XbaI sequence from the ORF1b stop codon. L: Leader sequence; ORF1a and ORF1b: EAV nonstructural genes.

The sequence contig of the three synthesized fragments EAV F1 (SEQ ID NO: 4), EAV F2 (SEQ ID NO: 5, and EAV F3 (SEQ ID NO: 6) included (1) an upstream portion of the reporter Renilla luciferase gene, (2) the EAV leader sequence, and (3) the coding sequence of the non-structural polypeptide pp1ab, which corresponded to nucleotide residues 1-9751 of the EAV genome (NCBI Accession Number gil14571796). The Renilla luciferase gene (SEQ ID NO: 7) contained a 5' XbaI site and a 3' PsiI site. To include the 40 nucleotide polyA-tail, a synthetic nucleic acid design, named EAV_ultramer, was designed (SEQ ID NO: 8), containing the polyA sequence in the middle and flanking regions to the Renilla luciferase gene and a portion of the linear vector sequence respectively. In the final replicon, the sequence of each of the synthesized fragments had a 50 bp overlap to its neighboring fragment in the following order: 5'—linear vector—EAV F1 fragment—EAV F2 fragment—EAV F3 fragment—Renilla luciferase gene—EAV_ultramer—linear vector—3'. A schematic representation of this final replicon is shown in FIG. 2 of the disclosure. The nucleotide sequence of the final replicon assembled as described above, minus the sequence encoding the Renilla luciferase reporter is provided as SEQ ID NO: 3 in the Sequence Listing. In addition, the sequence contig that contains the 5' leader, ORF1a, ORF1b is provided as SEQ ID NO: 1 in the Sequence Listing.

Construction of Backbone Plasmids Containing Mutated T7 Termination Sequence

In some experiments, mutations in the T7 terminator sequences were introduced into various vectors using the QuikChange Lightning Site-Directed Mutagenesis kit (Agilent Technologies) in accordance with the manufacturer's instructions. Mutagenesis primers were designed using the QuikChange Primer Design Tool in accordance with the manufacturer's instructions (www.genomics.agilent.com/primerDesignProgram.jsp).

The following mutations were introduced into the Rep-EAV(WT) vector, T9001G, T9001G and G3188A, and T9001G and T3185A, resulting in new constructs rE(WT)-Ren (T9001G), rE2(WT)-Ren (containing T9001G and G3188A mutations), and rE3(WT)-Ren (containing T9001G and T3185C mutations), respectively. In addition, an XhoI restriction enzyme site was added immediately 3' to the sequence of the Renilla gene by QuikChange mutagenesis for future cloning needs.

TRS Mutations

Towards the design of tunable regulation system of gene expression, six mutations were introduced to both the leader TRS and body TRS7 present in the Rep-EAV(WT) backbone. The wild type TRS sequence was TCAACT and the sequences of the mutated TRS1-6 were as follows: TRS1-CTAACC, TRS2-CCAACC, TRS3-CCAAGC, TRS4-CCAGGC, TRS5-CCAGGT, TRS6-GGTTAG. The resulting vectors were named Rep-EAV(TRS1), Rep-EAV(TRS2), Rep-EAV(TRS3), Rep-EAV(TRS4), Rep-EAV(TRS5), and Rep-EAV(TRS6), respectively.

Vector Constructs with Spacers

In some experiments described below, four different spacer sequences, named Spacer 1-4, were introduced into various vectors to insulate the TRS7 region (FIG. 11). The spacer sequences are provided as SEQ ID NOs: 9-12 in the Sequence Listing. Spacer 1 (SEQ ID NO: 9) was designed to include the entire ORF6 and mutations were also introduced to eliminate two start codons and a native XbaI site. Spacer 2 (SEQ ID NO: 10) included a conserved AT-rich region upstream of the TRS7 sequence. Spacer 3 (SEQ ID NO: 11) included an additional sequence downstream of the TRS7 and ends near the second start codon 3' of TRS7. Spacer 4 (SEQ ID NO: 12) represents a sequence that has been extended in the 5' direction from TRS7 to include Spacer 1 and in the 3' direction to include Spacer 3. These spacers were assembled into the rE2(WT) backbone replicon with four different reporter genes, Cypridina (Cypr; SEQ ID NO: 13), Green Renilla (gRen; SEQ ID NO: 14), Red Firefly (rFF; SEQ ID NO: 15), and Renilla (Ren; SEQ ID NO: 7).

Bivalent Expression Constructs

In some experiments described below, two different base designs of bivalent expression constructs were constructed. The construction of version 'A' bivalent constructs utilized the XbaI restriction site between TRS2 and TRS7 to introduce another reporter gene into the rE2(WT)-reporter constructs. The construction of version 'B' bivalent constructs used the PsiI restriction site located immediately downstream of the reporter genes to introduce a PCR amplified DNA fragment that carries another reporter gene, as well as an upstream fragment with both TRS2 and TRS7 (also referred to as 2/7 block henceforth). Bivalent constructs made according to this Example and subsequently evaluated in some Examples below include rE2(WT)-gRen-rFF-A, rE2(WT)-gRen-rFF-B, rE2(WT)-rFF-gRen-A, rE2(WT)-rFF-gRen-B.

3' UTR Modifications

In some experiments described herein, 3'UTR sequences were modified to enhance expression of the genes of interest encoded in the replicon. Whereas the initial base vector contained 366 bp from the stop codon of the gene of interest to the polyA string, two different modified 3'UTR sequences were designed to contain 801 bp 3' terminal region of the EAV genome (SEQ ID NO: 41). To clone this additional 3' UTR region, the rE2(WT) vectors were digested with XhoI and column purified, the insert was amplified from an infectious clone sequence and gel purified, then both DNA fragments were assembled together by using the Gibson Assembly® procedure. Monovalent versions of this replicon are referred to as rEna constructs. Another monovalent version of this backbone was made to inactivate both the TRS7 used to drive a GOI and the TRS7 in the 801-nt 3' region; these vectors are subsequently referred to as rExa constructs. A bivalent vector form of the rExa replicon was generated and this vector is referred to as rExb. Because the bivalent rExb construct did not have any functional TRS7 sequences, another version of it was made so that only the TRS7 in the 801-nt region was inactivated, these vectors are referred to as rExc constructs.

Non-Reporter Replicon Constructs

Genes other than luciferase reporter genes that were cloned into the rE2 replicon are as follows: hemagglutinin (HA), RSV F0 precursor protein, EGFP (SEQ ID NO: 24), Cas9 (SEQ ID NO: 25 and SEQ ID NO: 26), Csy4 (SEQ ID NO: 27), neomycin resistance gene (SEQ ID NO: 28), puromycin resistance gene (SEQ ID NO: 29), anti-NP antibody (light chain-IRES-heavy chain; SEQ ID NO: 30 and SEQ ID NO: 31), Humira (anti-TNF antibody; SEQ ID NO: 33), Herceptin (anti-Her2 antibody; SEQ ID NO: 32), and GFP-ApoAI fusion gene (SEQ ID NO: 34). Some of the above genes and the following genes were cloned into the rEn replicon: Interleukin12 (IL12; SEQ ID NO: 35), EpCam (SEQ ID NO: 36), and His6 or myc-tagged peptide string (CT26; SEQ ID NO: 37). For HA and F0 proteins, 4 different sequence-optimized genes each were tested (SEQ ID Nos: 16-19 and 20-23, respectively). For Cas9, 2 sequence-optimized genes were tested (SEQ ID NO: 25 and SEQ ID NO: 26). To construct all the above genes into the rE2 base plasmid, an rE2 reporter construct was digested with XbaI and XhoI to remove the existing reporter gene, followed by gel extraction of the backbone vector. The non-reporter genes were amplified with primers that contain flanking sequences and 40-60 bp of overlapping sequence with the backbone vector, gel purified, then assembled with the backbone vector using Gibson Assembly® as described below. To clone into the rEna plasmid, the rEna-rFF plasmid was digested with XbaI, the backbone vector as gel extracted to remove the original insert. A neomycin resistance gene and EGFP bivalent (A) design was also cloned into rEna base vector. For this bivalent construct, the coding sequence of EGFP was sequence-optimized (SEQ ID NO: 24).

Gibson Assembly® Protocol

SGI's Archetype® Software was used to design 60-bp long, overlapping oligonucleotides covering the DNA sequence of interest. The 60-bp oligonucleotides overlapped neighboring oligonucleotides by 30 bp. Oligonucleotides were ordered from Integrated Digital Technologies (IDT) at a concentration of 100 μM and then pooled to reach a target concentration of 25 nM for subsequent gene assembly.

Gene assembly was performed according to the method described in Gibson et al. (Enzymatic assembly of DNA molecules up to several hundred kilobases. *Nat. Methods* 6, 343-345, 2009). Error correction was performed by forming heteroduplexes of any error containing PCR products by incubation at 98° C. for 2 min, to 85° C. at a rate of 2° C./sec, incubation for 2 min, to 25° C. at a rate of 0.1° C./sec, and incubation for 2 min. Resulting heteroduplexes were then cleaved by adding 2.7 μL of each PCR reaction to 5.3 microliters water, 2 μL Surveyor Nuclease and 1 μL of 1:4000 diluted NEB ExoIII, followed by incubation at 42° C. for 1 hour. A recovery PCR reaction (PCR2) was identical to the first amplification except 2.5 μL of error corrected DNA was added to 47.4 μL of mastermix. In addition, 0.12 μL of the EAV_ultramer (10 nM) was added to the PCR2 for the generation of the Renilla luciferase insert.

DNA Template Preparation

Plasmid DNA templates were purified (Qiagen Cat. no. 12163) from 300 mL of saturated *E. coli* TransforMax Epi300 (Epicentre Cat. no. EC300105) cultures grown in LB broth media (Teknova Cat. no. L8000 06) supplemented with 50 ng/ml carbamicilin (Teknova Cat. no. NC9730116). Plasmid DNA was linearized by Not-I digestion (New England Biolabs NEB cat. no. R3189S) for one hour at 37° C. Linearized template DNA was then re-purified (Zymo Cat. no. D4003), and analyzed by 0.8% agarose gel (Life Technologies Cat. no. G5018-08) against a commercial 2-log DNA ladder (New England Biolabs, NEB Cat. no. N3200S). The presence of a single band was confirmed in each sample, corresponding to the expected fragment size of the linear DNA template, prior to proceeding with in vitro transcription.

In Vitro Transcription

In vitro transcription (IVT) reactions were performed using 1 μg of DNA template prepared as described above, in a 20 μl reaction over a one hour incubation at 37° C. (NEB cat. no. E2065S). 1U of DNaseI, provided by the supplier was then added directly to the IVT reaction, and incubated at 37° C. for an additional 15 mins. Reactions were then placed on ice, and purified using the manufactures suggested method (Qiagen Cat. no. 74104). Purified RNA was then quantified using a NanoDrop 2000c UV-Vis Spectrophotometer. RNA was visualized by electrophoresis through 0.8% Agarose gels (Life Technologies Cat. no. G5018-08) and compared with Millennium RNA Marker (Ambion Cat. No. AM7150), prior to proceeding with electroporation.

Transfection and Analysis

In a typical cell transfection experiment, replicon RNA was introduced into BHK-21 cells by electroporation using the SF Cell Line Nucleofector™ kit for the 4D-Nucleofector™ System (Lonza). BHK-21 cells were harvested using 0.25% trypsin and washed once with cold PBS. Cells were resuspended in SF Buffer at a cell density of $1\times10^6$ cells per 20 μL electroporation reaction. Three micrograms of RNA were electroporated into cells in triplicate in a 16-well cuvette strip and incubated at room temperature for 10 minutes. Electroporated cells were recovered into plates containing Dulbecco's Modified Eagle Medium containing 10% fetal bovine serum, followed by incubation for 16-18 h at standard cell culture conditions.

Intracellular analyses of replicon transfection efficiency and protein production were performed by flow cytometry. Transfected BHK-21 cells were fixed and permeabilized using fix/perm concentrate and permeabilization buffer (eBioscience). Cells were incubated with antibodies for double-stranded RNA production (J2 anti-dsRNA IgG2A monoclonal antibody, English & Scientific Company) conjugated with R-Phycoerythrin (Innova Biosciences). Antigen production was assessed by additional incubation with antigen-specific antibodies conjugated with PE-Cy5 (Innova Biosciences) (e.g. antibodies for green Renilla, red Firefly, HA, or RSV-F0 (Abcam)). Cells were then washed once and analyzed using a FACSAria™ Fusion Cell Sorter (BD Biosciences) or FACSAria™ II Cell Sorter (BD Biosciences). Transfected BHK-21 cells stained with single colors for compensation controls were run prior to sample collection. Data was collected using FACSDiva (BD Biosciences) and further analyzed using FlowJo software. Initial gating was performed to exclude dead cells and debris using forward and side scatter plots. Further gating was conducted to identify cell populations that were positive for both dsRNA (R-PE-positive) and protein expression (PE-Cy5-positive or FITC-positive for GFP expression). Frequencies and mean fluorescence intensities were collected and utilized for construct comparison and optimization.

In Vivo Studies

In vivo bioluminescence imaging was performed using an IVIS® Spectrum optical imaging system (PerkinElmer, Inc.). In a typical experiment, animals were imaged up to three at a time under 2% isoflurane gas anesthesia. Each mouse was injected intraperitoneally (IP) with 200 mg/kg D-luciferin and RO with 5 mg/kg coelenterazine and imaged in the supine position immediately following substrate injection. Coelenterazine was injected immediately prior to D-luciferin for all time points. Scans were acquired at the following wavelengths for the first 2 time points: 520, 540, 560, 620, 640, and 660 nm. At all other time points, only 540 nm and 640 nm wavelengths were used during scanning. On Day 8, animals were scanned for 10 minutes, in vivo post-substrate injections then euthanized via CO2 overexposure, animals were then debrided and the thoracic cavity was opened to expose the lungs for in situ BLI imaging. Large binning of the CCD chip was used and the exposure time was adjusted (10 minutes to 10 seconds) to obtain at least several hundred counts from the hind limbs in each mouse in the image and to avoid saturation of the CCD chip.

Example 2

T7 Termination Sequence Modifications

This Example describes the results of experiments assessing impact of various point mutations introduced into the sequence of T7 RNA polymerase transcription termination signals identified in the coding sequence of EAV non-structural polypeptides.

Initial replicon designs were modified to remove cryptic T7 RNA polymerase transcription termination signals identified in the non-structural gene coding region of the EAV genome. In these experiments, the T7 terminator containing replicon vector versions were designated Rep-EAV (WT), rE, rE2 and rE3; each of these replicons contain various T7 terminator modifications by using the procedure described above. Subsequently, agarose gel electrophoresis analysis of in vitro transcribed RNAs derived from two exemplary replicon vectors containing modified T7 terminator sequences, rE-rFF and rE2-rFF, has been performed to demonstrate that modification of the T7 terminator sites resulted in the loss of RNA bands that are not full length.

Figure 1B:
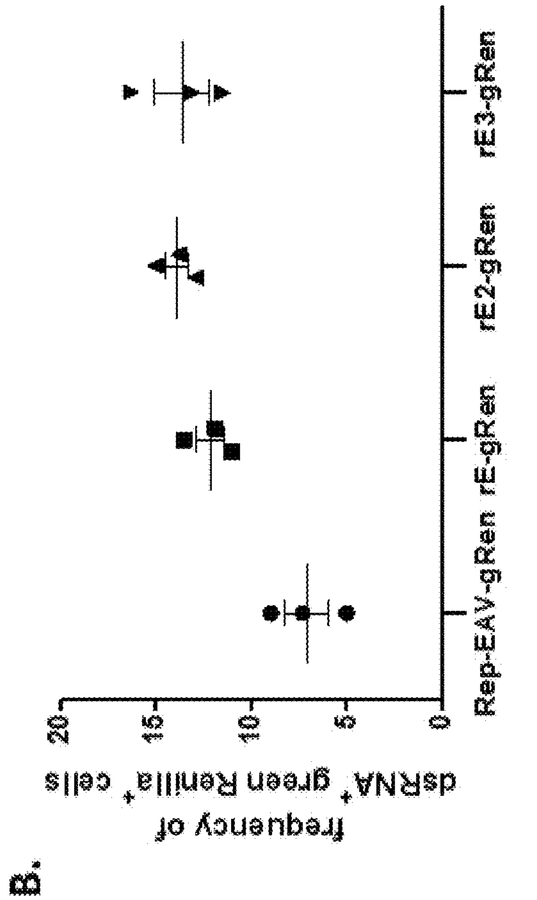
Figure 1C:
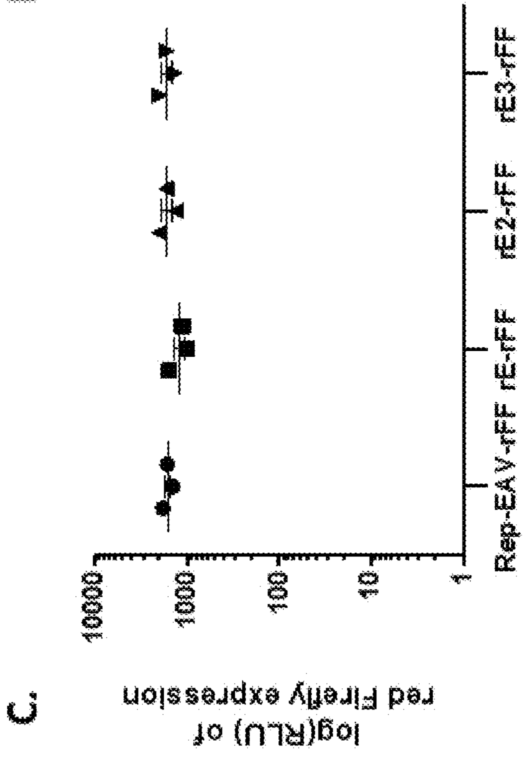
Figure 1D:
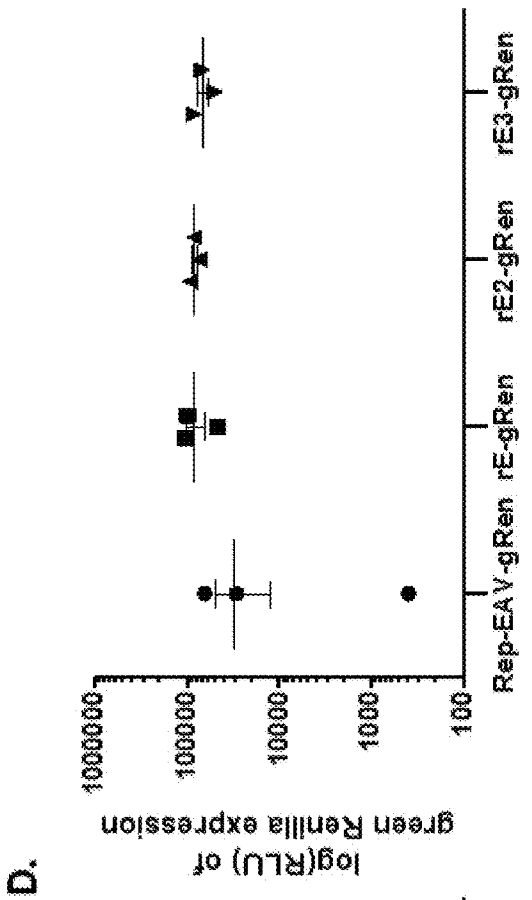

Luciferase reporter gene was then cloned into each of these replicon vectors. Cells were electroporated with individual replicon RNAs and analyzed by both bulk-cell luciferase assay and flow cytometry technique. Flow cytometry analysis allowed both percent cell transfection determination and mean fluorescence intensity (MFI) evaluations as a measure of protein expression. An example of flow cytometry analysis with replicons expressing either rFF or gREN luciferase genes is shown in FIGS. 1A-1D. All versions of both reporter gene replicons expressed similar levels of luciferase on a per cell basis (FIGS. 1C and 1D). Some variation in the percent of cells transfected based on the replicon vector version was observed (FIGS. 1A and 1B). The EAV replicon vector rE2 was selected as the base vector in subsequent experiments of replicon construction and optimization.

Example 3

Monovalent EAV Replicon Design

This Example describes experiments performed to construct and evaluate a monovalent EAV replicon, which was subsequently deployed for expression of single polypeptides in recombinant cells.

As discussed above, the present disclosure is partly based on significant showing of unexpected results in connection with various arterivirus expression vectors designed and evaluated by the inventors. The first unexpected result relates to the amount of the structural protein gene ORF 2a that should be retained in a replicon to maintain TRS2 activity based on the published literature. In particular, in a study published in 2000, Molenkamp et al. concluded that the ORF 2a sequence is needed in order to retain robust TRS2 subgenomic transcription activity (Molenkamp et al 2000). This conclusion was drawn based on an observation that an EAV infectious clone deleted from nucleotide residues 9,756 to 12,351 (termed mutant 2a-2594), that retained only 5 bases of the ORF 2a sequence, exhibited a significant reduction in subgenomic RNA synthesis. This observation was in contrast to the subgenomic RNA synthesis exhibited by a different EAV infectious clone (mutant 030-2319). Mutant 030-2319 contained the same 3' sequences as mutant 2a-2594 but maintained an intact ORF 2a sequence and this construct demonstrated wild-type robust subgenomic RNA synthesis (Molenkamp et al 2000).

Surprisingly and in contrast to the above teachings of Molenkamp et al 2000, the base replicon design of the inventive work described in the present disclosure (Rep-EAV (WT)) and all subsequent versions were completely devoid of any ORF 2a sequences yet each demonstrated robust subgenomic transcription and expression of a gene of interest (GOI). A schematic of a base replicon design in accordance with some embodiments of the present disclosure is shown in FIG. 2. The TRS7 cassette driving expression of a gene of interest (GOI, which was gRen in this example) has been cloned immediately downstream of the ORF1b stop codon.

Example 4

Bivalent EAV Replicon Design

Figure 3:
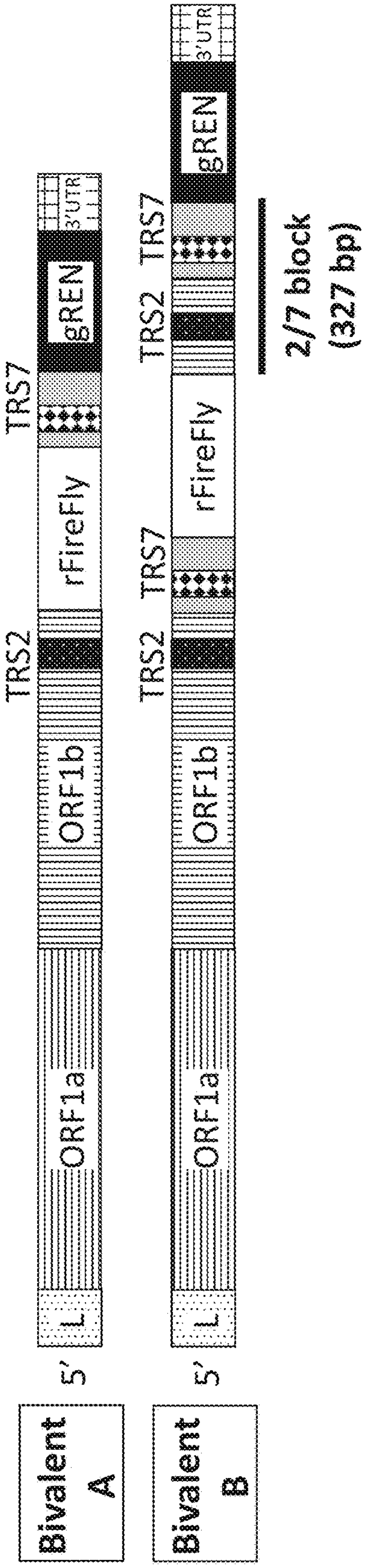
FIG. 3 graphically depicts the structure of two initial bivalent EAV replicon designs. Schematic representation of the bivalent replicon vectors shows differences between A design and B design. The 2/7 block is highlighted in the B design.

This Example describes experiments performed to construct and evaluate some bivalent EAV replicon, which were subsequently deployed for expression of two different polypeptides in recombinant cells. In these experiments, two initial bivalent designs were generated and they were based on iterations using the rE2 backbone described above. The construction of version 'A' bivalent replicon utilized the unique XbaI restriction site present between TRS2 and TRS7 to introduce a coding sequence of the gene of interest (GOI). Version 'B' bivalent constructs maintain both TRS2 and TRS7 as a tandem cassette for cloning of the GOI coding sequence (also referred to as a 2/7 block). A schematic representation of the A and B bivalent designs is shown in FIG. 3.

Figure 4A:
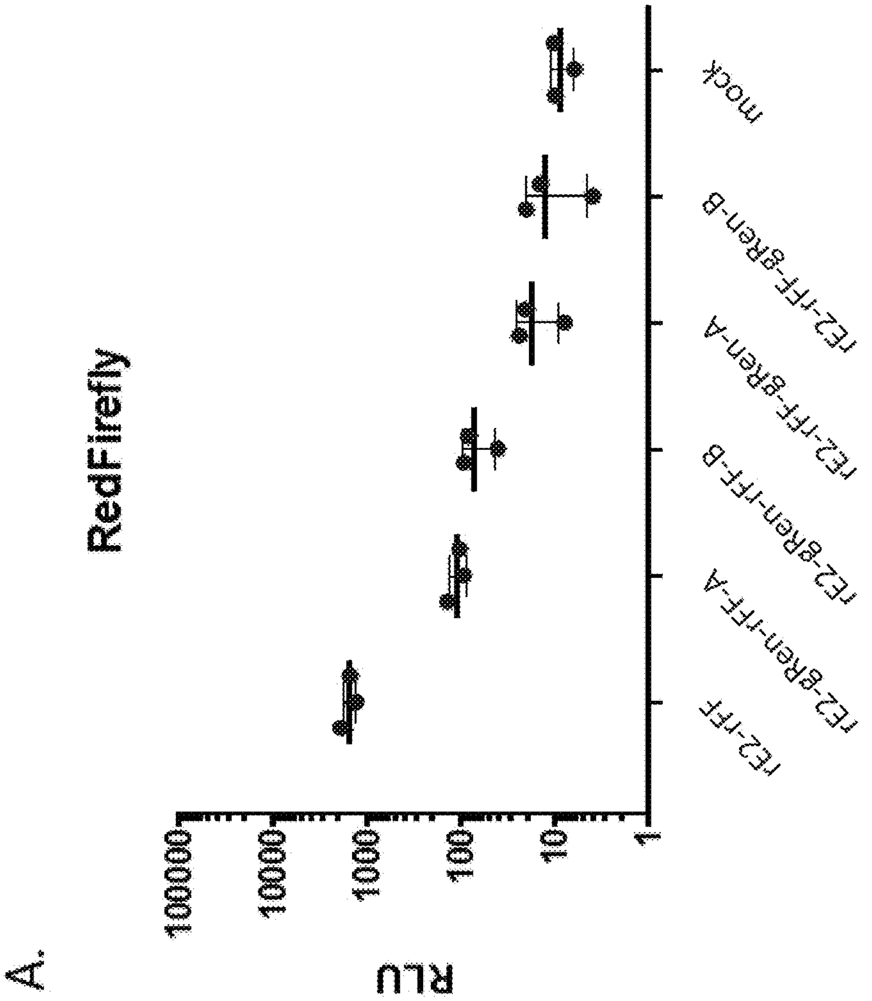
FIGS. 4A-4B graphically summarize the results of luciferase assays performed to assess expression of a heterologous polypeptide contained in the initial bivalent replicon designs. Bulk-cell luciferase assays carried out on electroporated cells. 4A). Analysis of red firefly luciferase expression from A and B bivalent replicon designs. 4B). Analysis of green Renilla luciferase expression from A and B bivalent replicon designs.
Figure 4B:
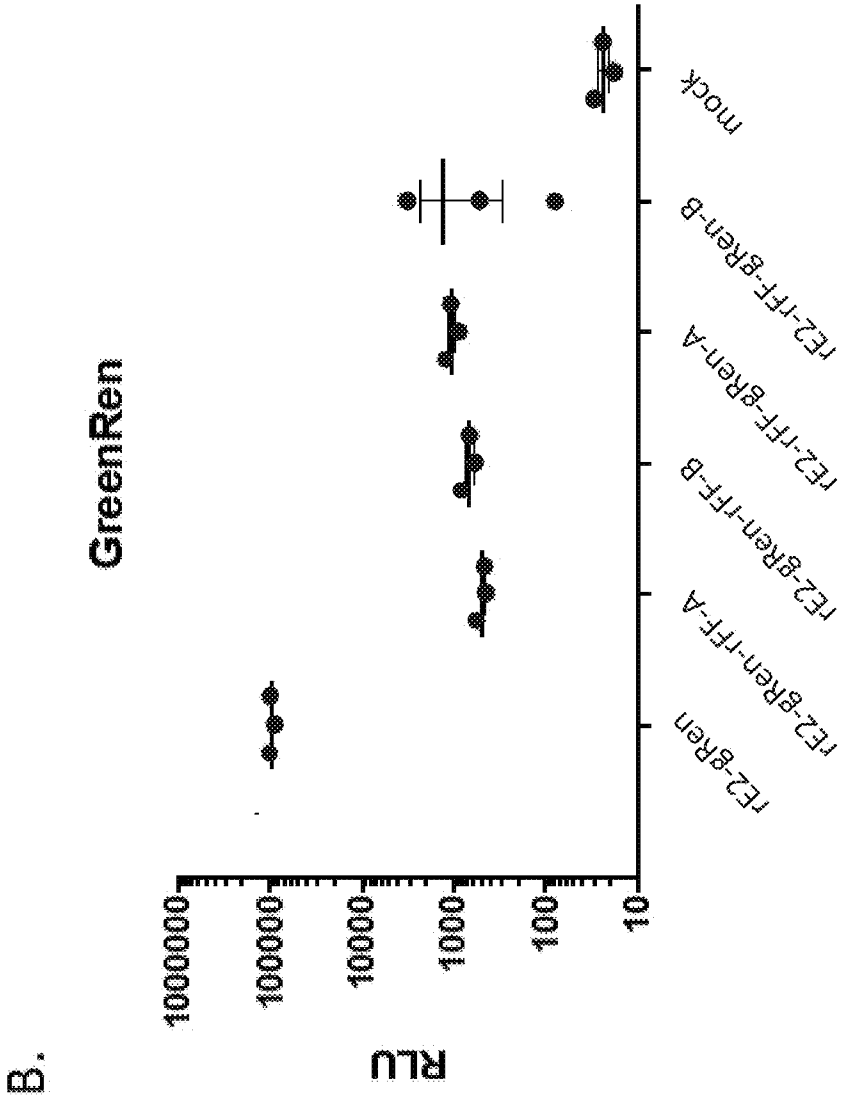

Two versions of each design were constructed so that each of the reporter genes could be tested in either the first or second position in the bivalent replicons. Cells were electroporated with both designs and luciferase expression level were compared with a monogenic replicon vector. The results of a representative bulk-cell luciferase assay carried out for all the bivalent versions generated as described above are shown in FIGS. 4A-4B. It was observed that the level of reporter gene expression from the bivalent vectors was lower than that detected from the monovalent version no matter which position the respective reporter gene was cloned into. Nevertheless, expression of both reporter genes from a single RNA was detected demonstrating that the bivalent EAV replicons constructed as described in this example were functional. Furthermore, the expression of the 5' most gene driven from TRS2 alone was no different than when it was driven as a TRS 2/7 block in direct contradiction to the requirement for ORF2a sequence teachings of Molenkamp et al 2000 described above The second unexpected result relates to the requirement of the 3' EAV sequences important for EAV replication and transcription. Specifically, Molenkamp et al. 2000 define the optimal 3' terminal sequences that should be maintained for efficient replication using mutant 030-2319. Molenkamp et al. 2000 teach that the 3' terminal 354 nucleotides of the EAV genome are able to support wild type level of replication. However, surprisingly and unexpectedly, we found that replicon vectors described herein (especially those expressing more than one genes of interest) did not replicate efficiently unless significantly more 3' terminal sequences were included in the replicon vectors.

Figure 5:
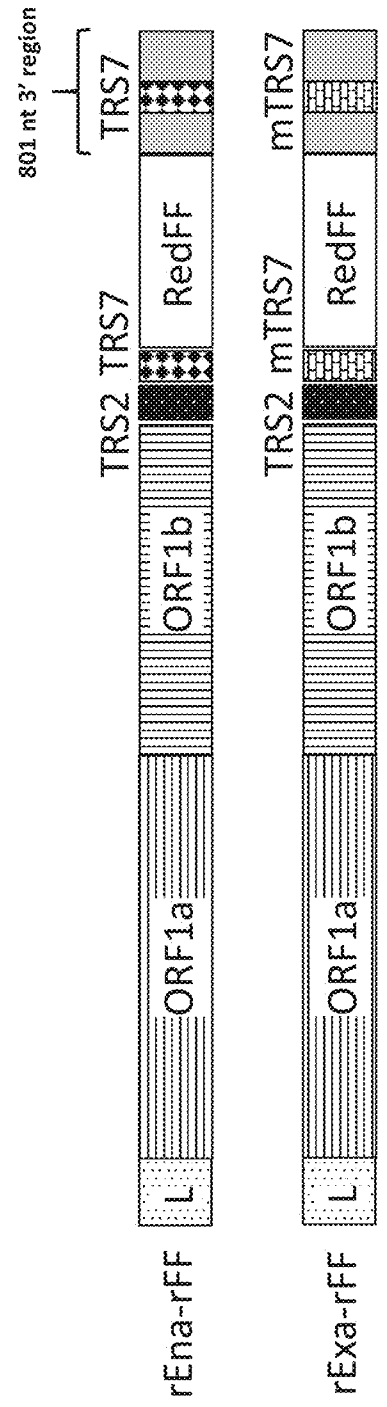
FIG. 5 graphically depicts the structure of exemplary EAV replicon designs containing the extended 3' nucleotide region. L: leader sequence; ORF1a and ORF1b: EAV nonstructural gene region; mTRS7: mutated TRS7 sequence.
Figure 6B:
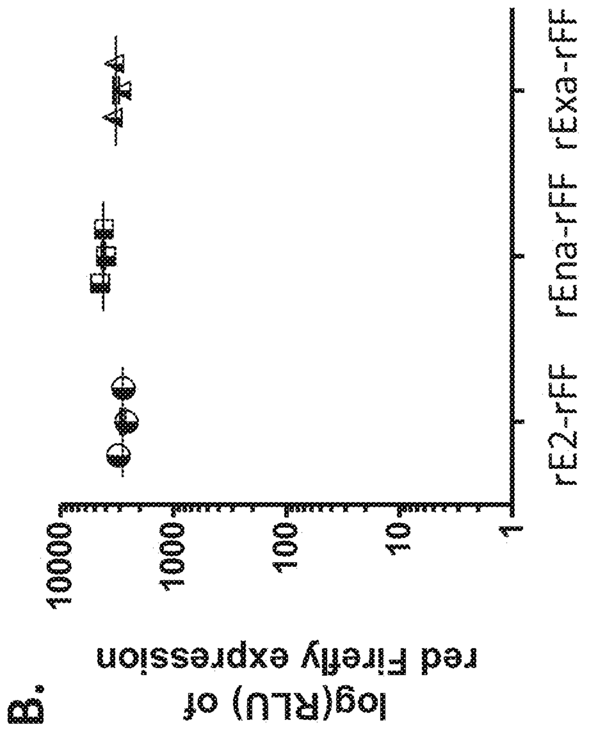
FIGS. 6A-6B graphically summarize the results of experiments assessing effects of the incorporation of additional of 3' sequence into the monovalent base vector rE2-rFF. 6A). Introduction of 801 nucleotides of EAV sequence into the 3' region of the base vector rE2-rFF increases transfection efficiency. 6B). Introduction of 801 nucleotides of EAV sequence into the 3' region of the base vector rE2-rFF results in no change in expression level.
Figure 6A:
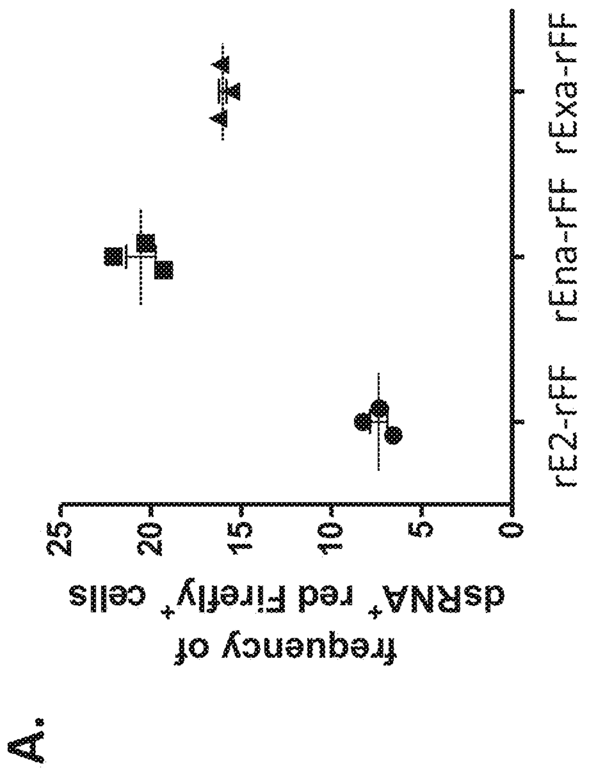

In particular, in some experiments, an additional 801-nt of 3' terminal sequence was included in a number of EAV replicon vectors described herein. This additional 3' terminal sequence contained all but the first two nucleotides of ORF6, a TRS7 sequence, all of the ORF7 gene and the 3' UTR sequence of an EAV genome. Accordingly, the ATG start codon of ORF6 is absent in this particular design. Two versions of a monovalent EAV replicon expressing the rFF luciferase gene were constructed. The first replicon maintained a functional TRS2, a TRS7 to drive the reporter gene, and a functional TRS7 sequence in the 801-nt region (vector termed rEna). The second replicon was the same as the rEna vector except that both of the TRS7 elements were modified to be inactivated (vector termed rExa). A schematic representation of each of the vectors is shown in FIG. 5.

An example of flow cytometry analysis with replicons rExa-rFF and rEna, both of which expressing the rFF luciferase gene, is shown in FIGS. 6A-7B. It was observed that incorporation of the additional 3' sequence had a significant positive impact on replication of both replicons containing additional 3' sequences while expression levels were not impacted. Furthermore, the rExa vector that only has a functional TRS2 element expresses an equivalent amount of protein to the rEna vector, indicating that no aspect of the ORF 2a structural gene was required for robust replication or transcription of these replicons.

Figure 7:
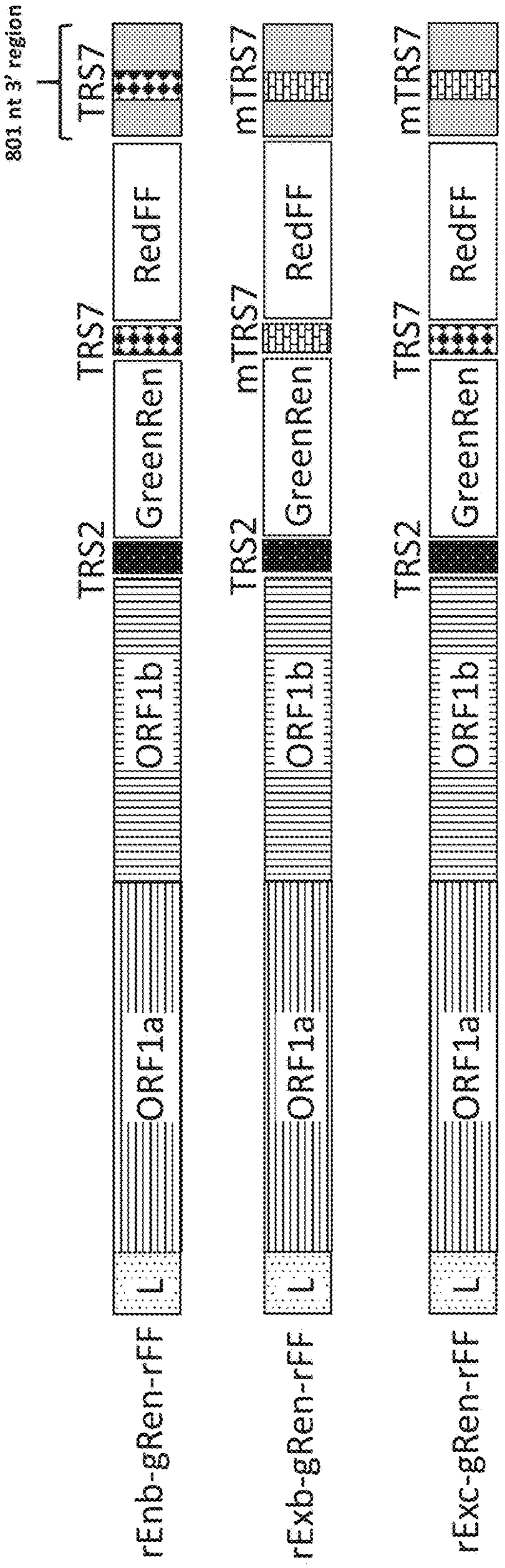
FIG. 7 graphically describes the structure of three bivalent EAV replicon designs containing the extended 3' nucleotide region. L: leader sequence; ORF1a and ORF1b: EAV nonstructural gene region; mTRS7: mutated TRS7 sequence.

In the context of a bivalent replicon expressing gREN and rFF luciferase genes, three versions of this replicon vector were also constructed. The first replicon maintained a functional TRS2 to drive the first reporter gene, a TRS7 to drive the second reporter gene and a functional TRS7 sequence in the 801-nt region (vector termed rEnb). The second replicon was the same as the rEnb vector accept that both of the TRS7 elements were modified to be inactivated (vector termed rExb). The third replicon maintained a functional TRS2 to drive the first reporter gene, a TRS7 to drive the second reporter gene and an inactivated TRS7 sequence in the 801-nt region (vector termed rExc). A schematic representation of each of these vectors is shown in FIG. 7.

Figure 8B:
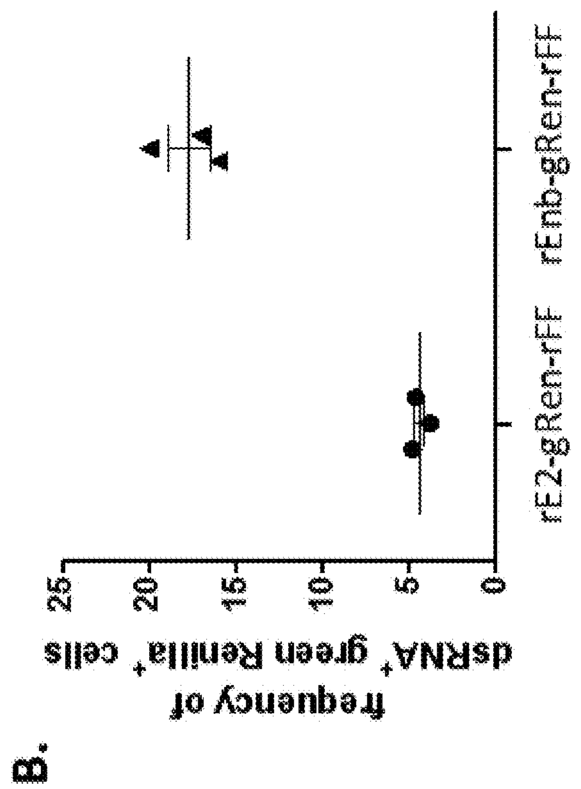
FIGS. 8A-8D graphically summarize the results of experiments demonstrating that the incorporation of additional of 3' UTR sequence into the bi-genic base vector rE2-gRen-rFF results in enhanced expression of genes of interest. The introduction of 801 nucleotides of EAV sequence into the 3' UTR region of the base vector rE2-gRen-rFF increases transfection efficiency (8A, 8B) and enhances luciferase production for both red Firefly (8C) and green Renilla (8D).
Figure 8A:
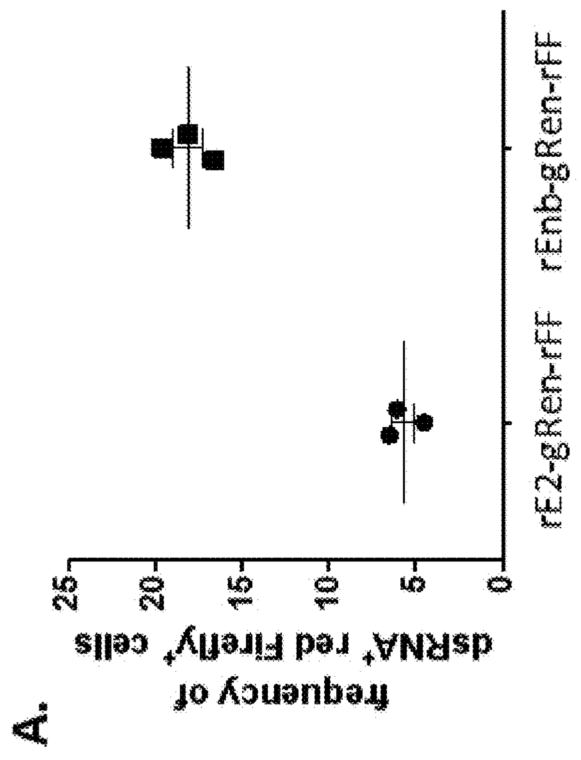
Figure 8D:
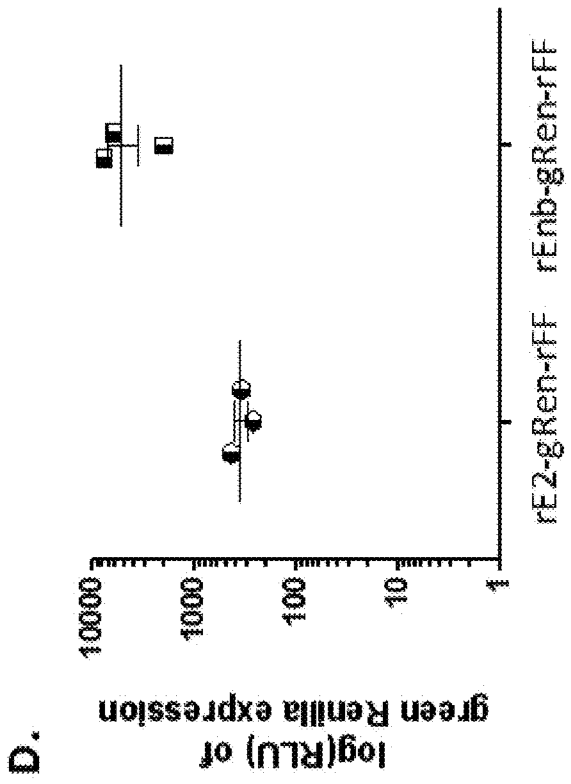
Figure 8C:
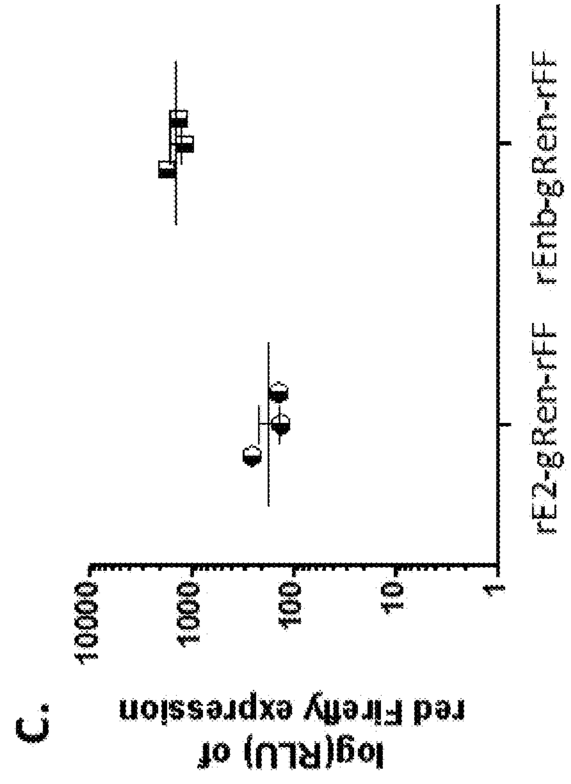

The inventors have additionally demonstrated that addition of the 801-nt 3' region was required for robust replication of replicons carrying more than one GOI. An example of flow cytometry analysis with replicons expressing both rFF and gREN luciferase genes from vectors that do or do not contain the additional 801-nt 3' region (rEnb-gRen-rFF and rE2-gRen-rFF, respectively) is shown in FIGS. 8A-8D. Addition of the 801-nt 3' sequence resulted in ~4 fold increase in replication (FIGS. 8A and 9B) and a ~10 fold increase in GOI expression (FIGS. 8C and 8D).

Figure 9B:
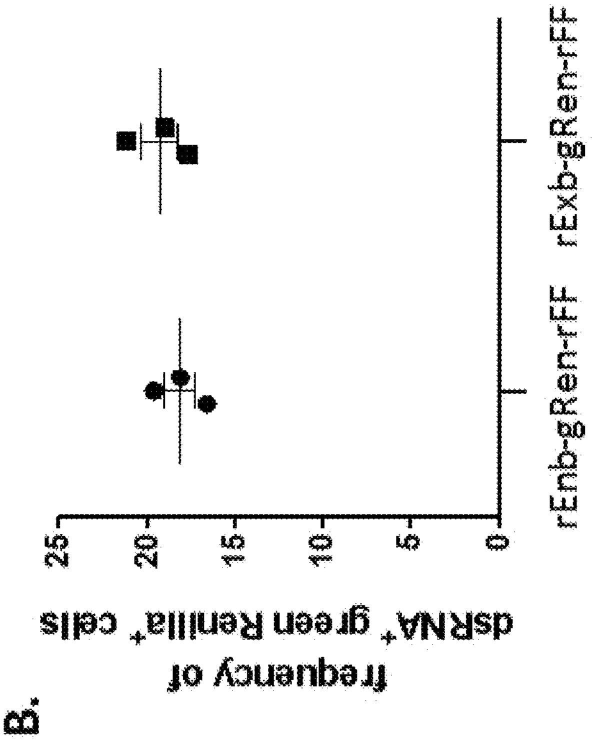
FIGS. 9A-9D graphically summarize the results of experiments assessing effect of various TRS7 mutations on replication and expression in replicons with additional 3' sequences. 9A and 9B: Impact of exemplary TRS7 mutations on replication of rEnb and rExb bivalent replicons. 9C and 9D: Impact of exemplary TRS7 mutations on reporter gene expression from rEnb and rExb bivalent replicons.
Figure 9A:
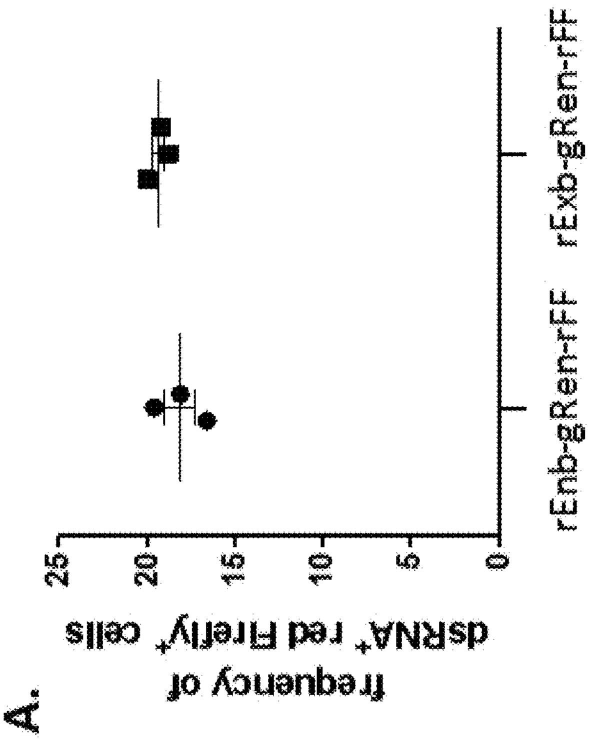
Figure 9D:
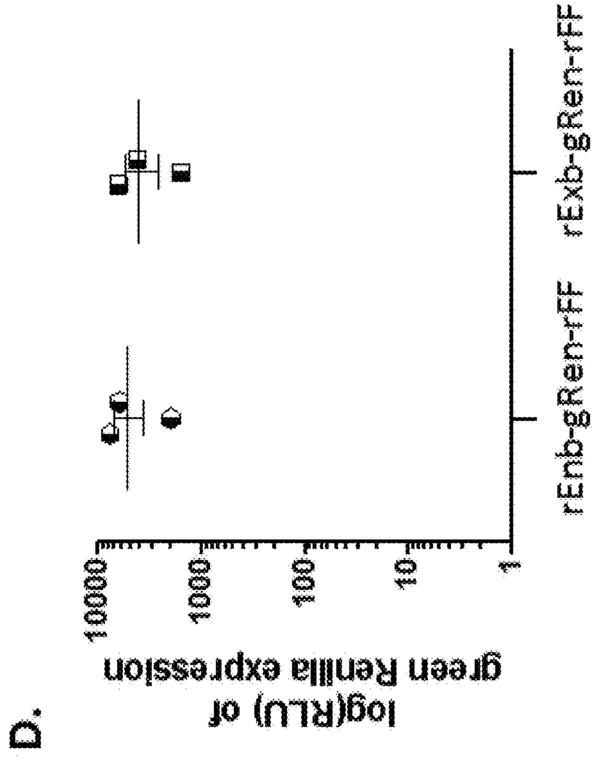
Figure 9C:
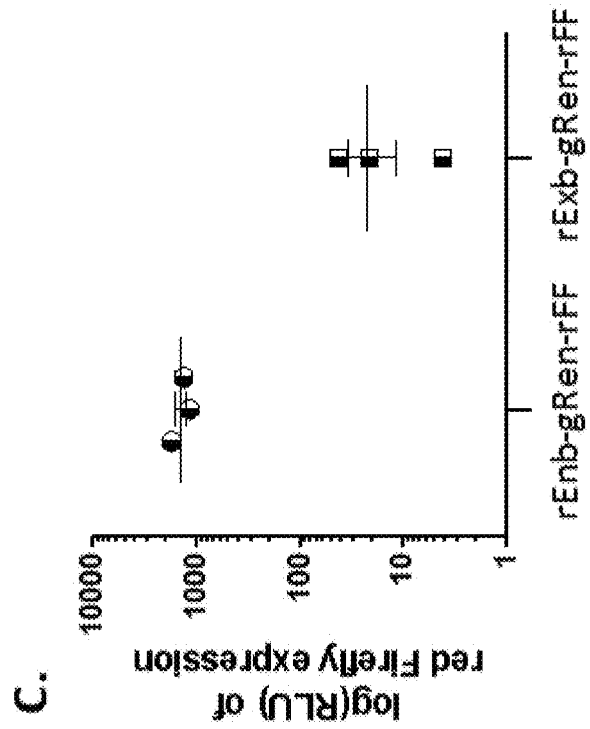

Next a comparison of the rEnb and rExb bivalent replicons was conducted. An example of flow cytometry analysis for this comparison is shown in FIGS. 9A-9D. The data indicate that having a functional TR7 in the801-nt sequence is not required for the increase in replication as the transfection efficiency noted was not impacted in the rExb design when compared to the rEnb design (FIGS. 9A and 9B). Mutating the TRS7 controlling the rFF luciferase gene (rExb-gRen-rFF) significantly reduced the expression of the rFF reporter while the gREN expression (controlled by the TRS2 element) was not impacted in either of the replicon designs (FIGS. 9C and 9D).

Figure 10B:
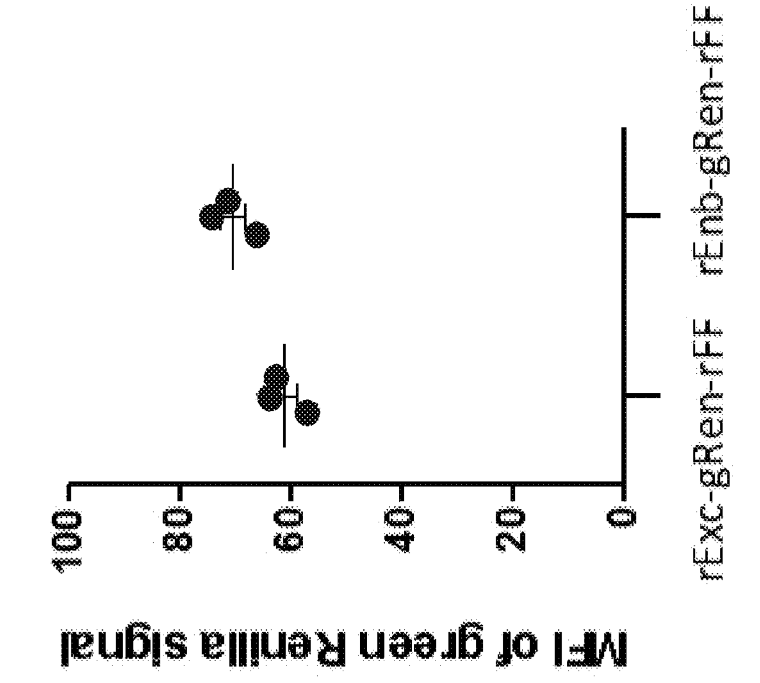
FIGS. 10A-10D graphically illustrate the results of experiments assessing effect of restoring TRS7 element in rExb bivalent replicon with additional 3' sequences. 10A and 10B: Impact of restoring the TRS7 element on replication of rExb compared to rEnb bivalent replicons. 10C and 10D: Impact of restoring the TRS7 element on gene expression from rExb compared to rEnb bivalent replicons.
Figure 10A:
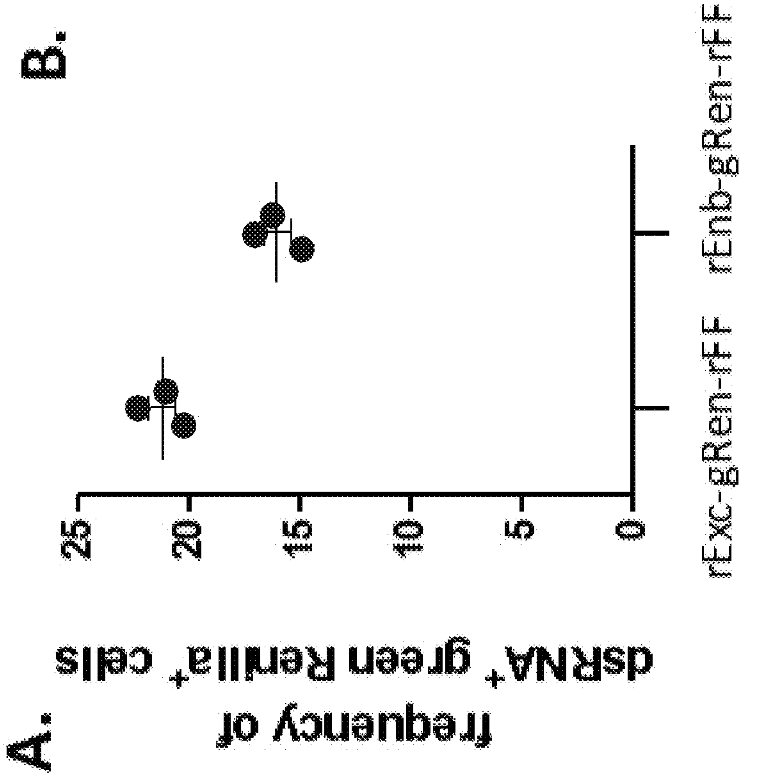
Figure 10D:
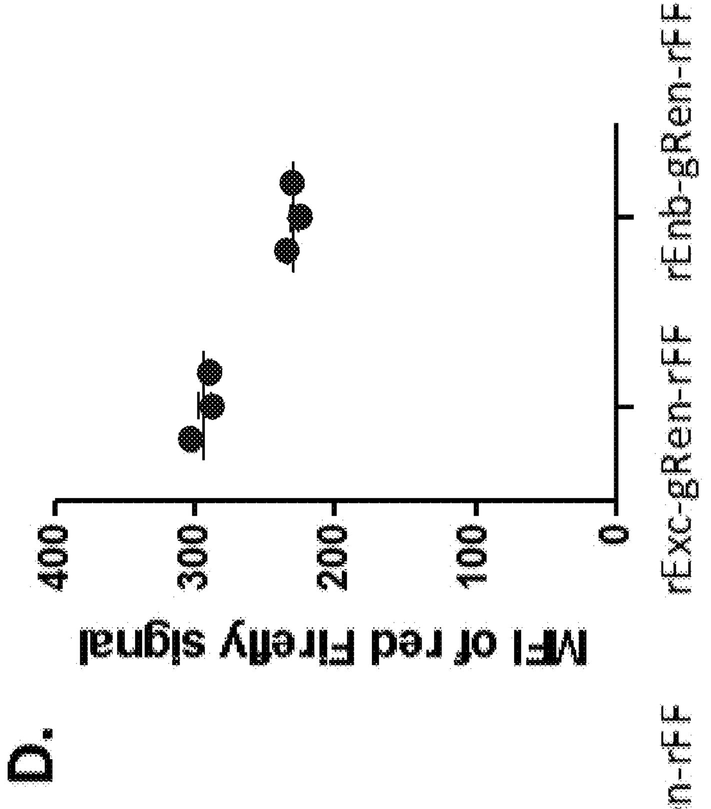
Figure 10C:
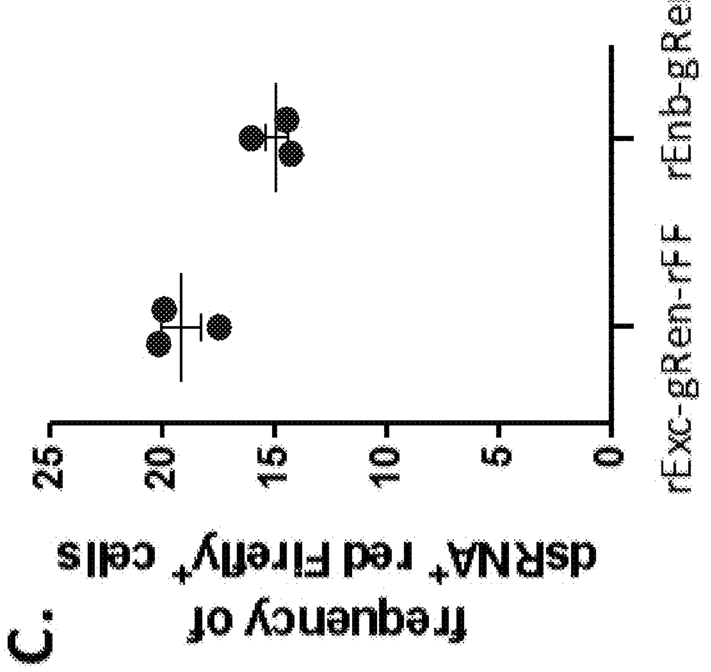

In order to restore expression from the second reporter gene (rFF) a vector with a functional TRS2 element to drive the first gene, a functional TRS7 element to drive the second gene and an 801-nt region with a mutated TRS7 element was constructed (rExc-gRen-rFF) and it was compared to the rEnb-gRen-rFF replicon design. An example of flow cytometry analysis for this comparison is shown in FIGS. 10A-10D. Restoration of the TRS7 element in the rExc-gRen-rFF resulted in robust rFF expression comparable to that seen with rEnb-gRen-rFF (FIG. 10D).

Example 5

Trivalent EAV Replicon Design

A replicon vector containing three different luciferase genes was constructed as follows. The bivalent vector rEnb-gRen-rFF was modified to include a third luciferase gene (Cypridina (Cypr)) by designing oligonucleotides to amplify the Cypridina gene from a monovalent rE2-Cypr backbone. The PCR product was designed to include TRS7 and its flanking sequences to produce a TRS7 Cyp expression cassette. The PCR product was introduced into the rEnb-gRen-rFF vector by using the Gibson Assembly® procedure downstream of the rFF reporter gene, thereby generating the tri-genic rEnb-gRen-rFF-Cyp vector.

Figure 11A:
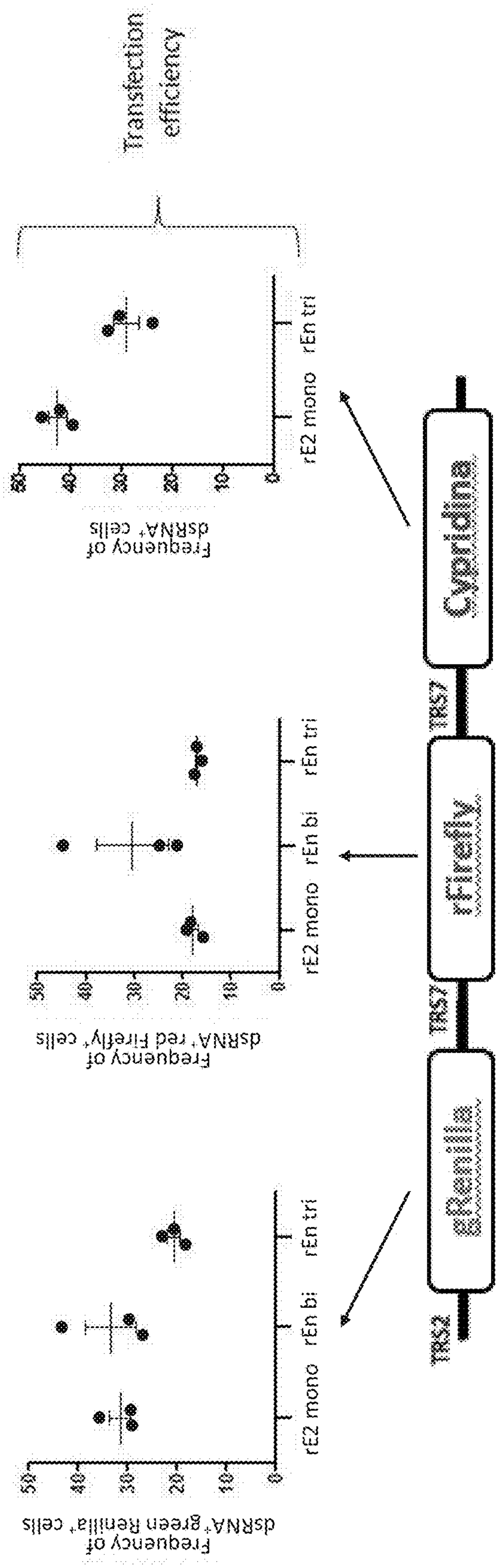
FIGS. 11A-11B graphically summarize the results of experiments assessing functionality of an EAV tri-genic expression design containing gRen, rFF and Cypr vs monogenic and bi-genic replicon controls. Two types of data are shown. 11A). The top row of the figures shows the percent of cells transfected with each of the replicons; this is a measure of replication for each RNA. 11B). The lower row of the figures shows protein expression for each of the luciferase constructs from electroporated cell lysates and normalized for the amount of lysate used in the assay. The TRS used to drive each of the genes is shown for the trivalent construct. RLU: relative light units.
Figure 11B:
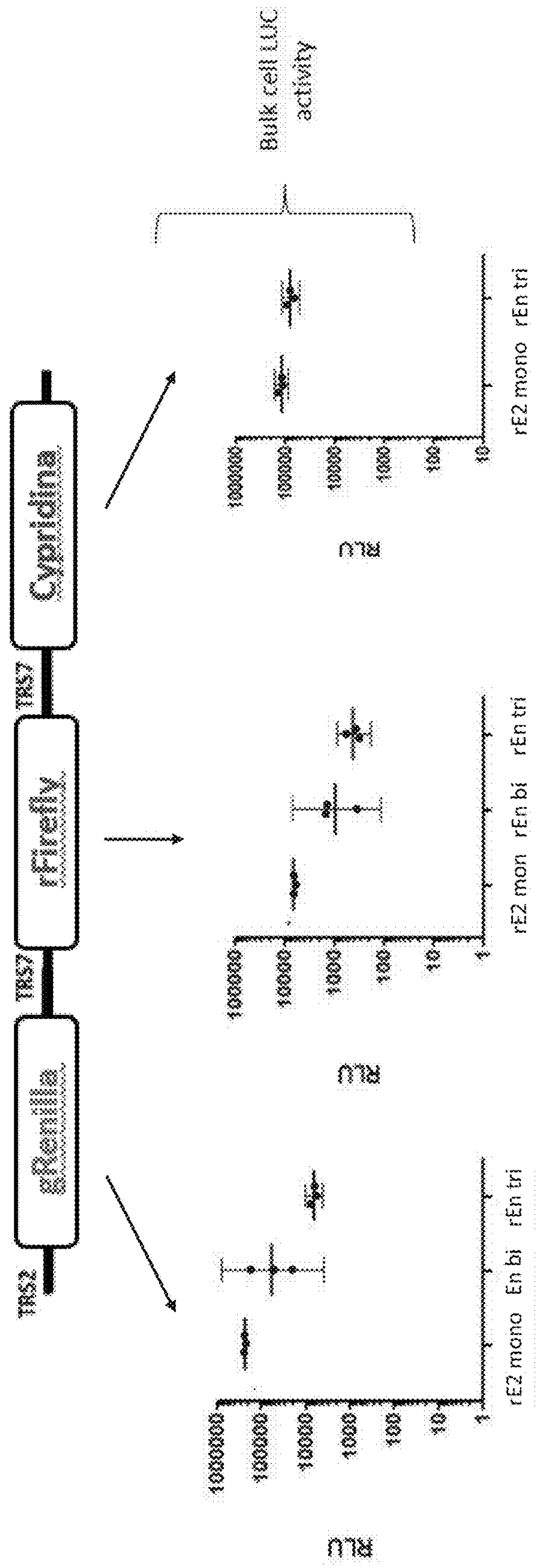

Cells were electroporated with individual tri-genic replicon RNAs and analyzed by both bulk-cell luciferase assay and flow cytometry technique. The results of these experiments are shown in FIGS. 11A-11B where two types of data are shown. FIG. 11A). The top row of the figures is showing the percent of cells transfected with each of the replicons; this is a measure of replication activity for each RNA replicon construct. FIG. 11B). The lower row is showing protein expression for each of the luciferase constructs from electroporated cell lysates and normalized for the amount of lysate used in the assay. The TRS used to drive each of the genes is also shown for the trivalent construct. RLU: relative light units.

Example 6

EAV TRS Spacer Design

Figure 12A:
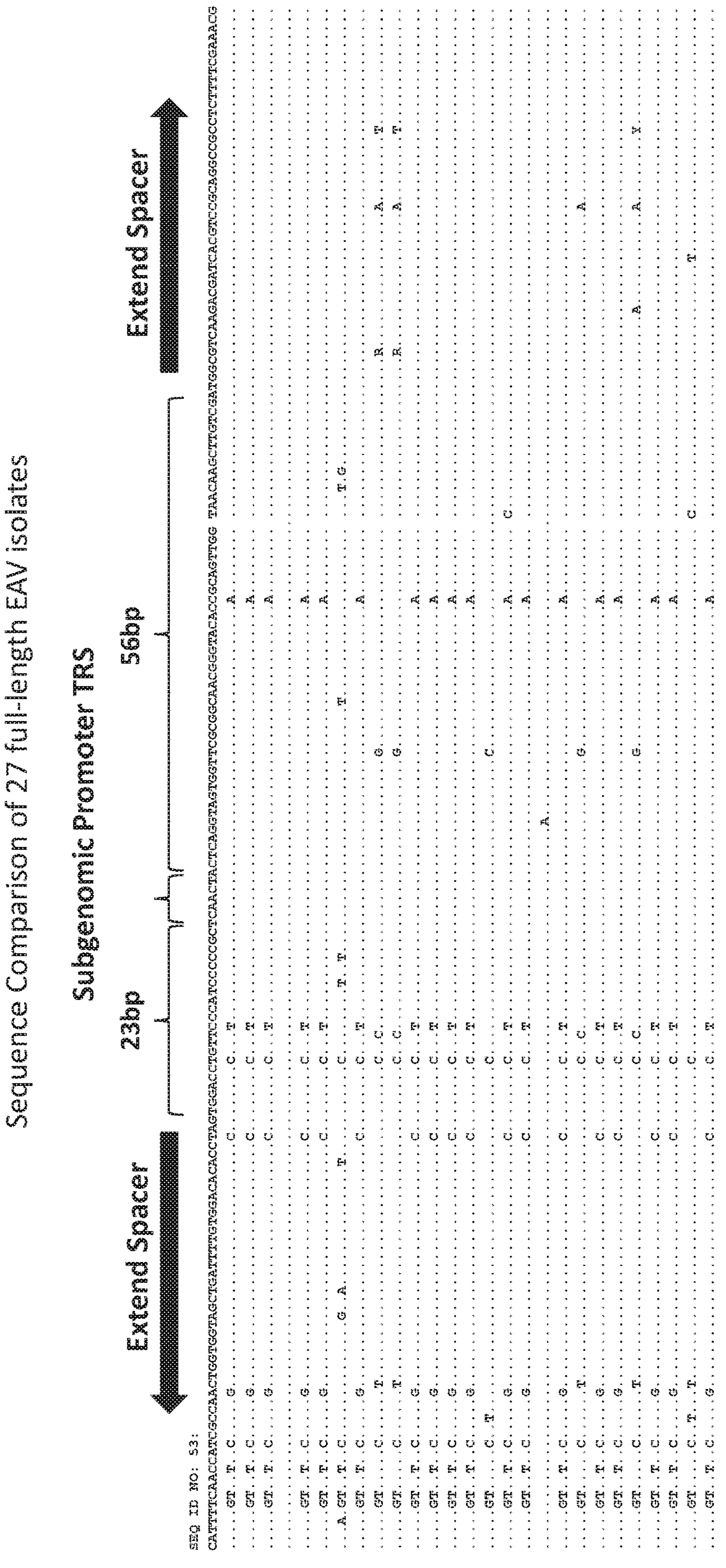
FIGS. 12A-12B graphically summarize the design of various spacer replicon constructs according to some exemplary embodiments described herein. 12A). Alignment of EAV sequences upstream and downstream of TRS7 subgenomic promoter. 12B). Nucleotides included in new Spacer replicon constructs.
Figure 12B:
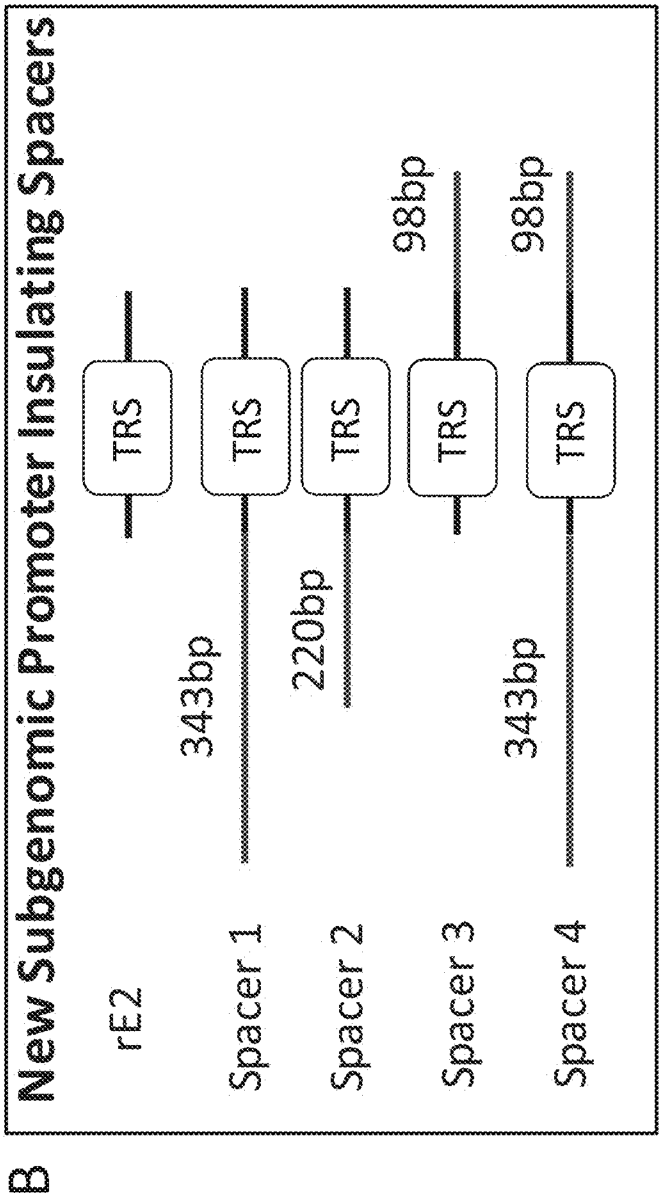

Incorporation of additional 3' UTR sequences represents one approach to modulate expression of a gene of interest in the RNA replicon designs. EAV vectors with shorter 3' UTR (e.g., rE2 vector) express lower amounts of protein than EAV vectors with additional 3' UTR sequences (e.g., rEn or rEx vectors). Development of multiple methods to attenuate or modify GOI expression levels from the EAV replicon is another key aspect of the inventive work described herein. Another approach to tune protein expression involves increasing or decreasing the amount of native sequence surrounding the body TRS elements. An example of employing this strategy is described below. Four different monogenic spacer replicons were designed that include varying amounts of EAV sequence (FIGS. 12A-12B). The base rE2 vector represents the starting point for the modifications. The incorporated spacers were delimited by regions of high homology separated by AT rich runs. There were two such regions 5' of TRS7 resulting in ORF6 spacers of 343 bp and 220 bp (Spacer 1 and Spacer 2, respectively). An additional 98 bp of ORF7 sequence was included; the ORF7 wild type ATG was inactivated and no additional ATG were present in the 3' spacer construct (Spacer 3). A fourth construct (Spacer 4) included both the Spacer 1 and Spacer 3 sequences.

Figure 13B:
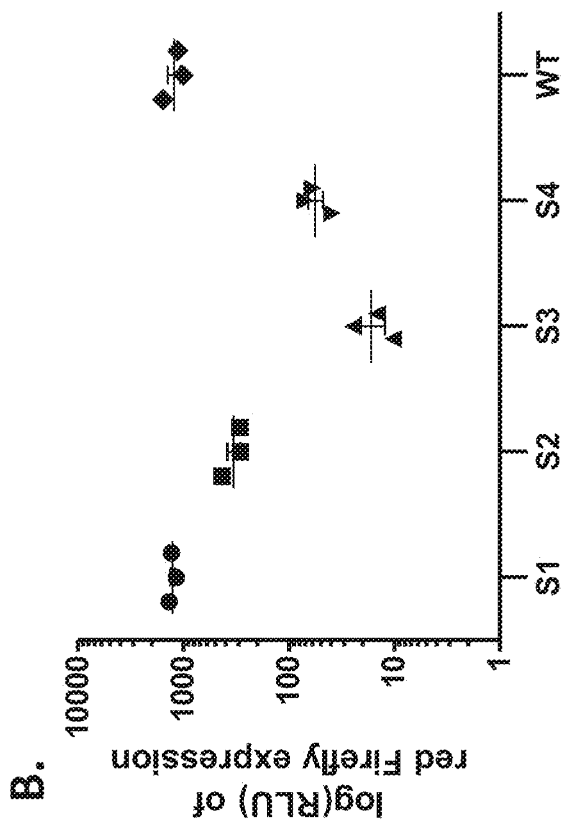
FIGS. 13A-13B graphically summarize the results of experiments performed to demonstrate that addition of spacer sequences for TRS7 region insulation impacted replication and protein production relative to the rE2-rFF base vector. S1: Spacer 1 rE2-rFF. S2: Spacer 2 rE2-rFF, S3: Spacer 3 rE2-rFF, S4: Spacer 4 rE2-rFF, WT: rE2-rFF. The introduction of sequences upstream of the TRS7 (S1, S2) and downstream of the region (S3, S4) modified replication capacity (13A) and protein expression (13A, 13B).
Figure 13A:
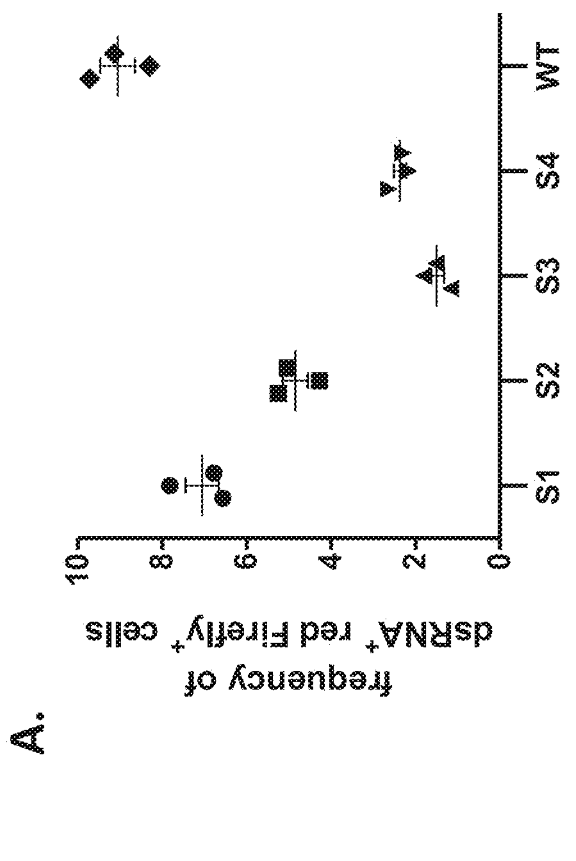

The rFF luciferase gene was cloned into each of the spacer-containing replicons described above and each resulting RNA replicons was electroporated into cells. The results of flow cytometry analysis of the electroporated cells are shown in FIGS. 13A-13B. It was observed that introduction of the spacer regions impacted expression levels and showed a range of activity relative to the rE2-rFF base vector. These results demonstrate that an effective approach to modulate GOI expression by modifying the amount of sequence included either 5' or 3' of the TRS used for subgenomic transcription.

Figure 14A:
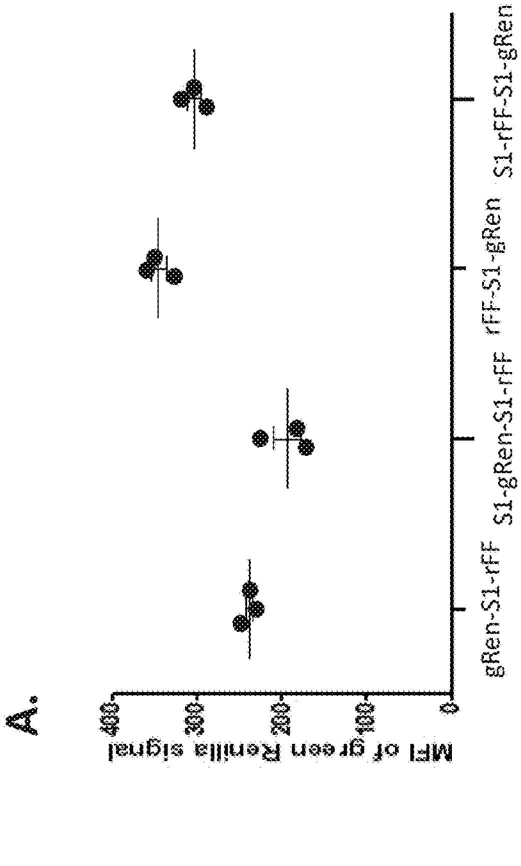
FIGS. 14A-14B graphically describe the results of experiments assessing the impact on expression of bivalent EAV replicons containing added Spacer 1 sequences. S1: Spacer 1 region. 14A). Expression analysis of green Renilla luciferase in different Spacer 1 bivalent replicons. 14B). Expression analysis of red firefly luciferase in different Spacer 1 bivalent replicons.
Figure 14B:
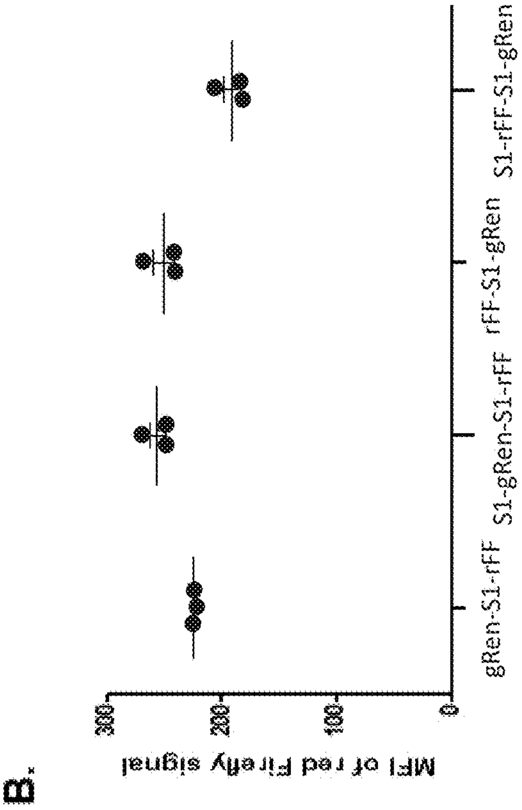

In a subsequent experiment, the spacer regions described above were used to generate bigenic EAV replicons. For this purpose, the spacer regions were introduced either upstream of the 5' most gene, upstream of the 3' most gene or upstream of both genes. An example of the impact of the inclusion of Spacer 1 in an EAV replicon expressing both the gREN and rFF reporter genes is shown in FIGS. 14A-14B. In conclusion, the location of a spacer sequence, for instance Spacer 1, in the bivalent replicons impacted luciferase expression levels representing another example of protein expression modulation in EAV replicon vectors.

Example 7

RNA Structure Sequence

RNA structure sequence analysis (Tijerina 2007; Ding 2014) was conducted on wild type EAV as well as on the RNA replicons of the inventive compositions and methods described herein. That analysis has revealed key non-TRS sequence elements that significantly impact subgenomic transcription levels. The result of this novel approach is that we have developed a method that can be used to rationally tune GOI expression levels.

Example 8

Impact of the Primary Sequence of the Gene of Interest (GOI)

This example illustrates a fourth approach to modulate GOI expression from EAV replicons. The development of this approach was based on the understanding that modifying codon usage of GOI can impact RNA secondary structure.

Four different codon usage versions of the H5N1 influenza A/VietNam/1203/04 hemagglutinin (HA) gene and the respiratory syncytial virus (RSV) fusion (F) gene were generated. The nucleotide sequences of the codon-optimized fusion glycoprotein F0 and HA genes are provided in the Sequence Listing (SEQ ID Nos: 16-19 and 20-24).

Figure 15A:
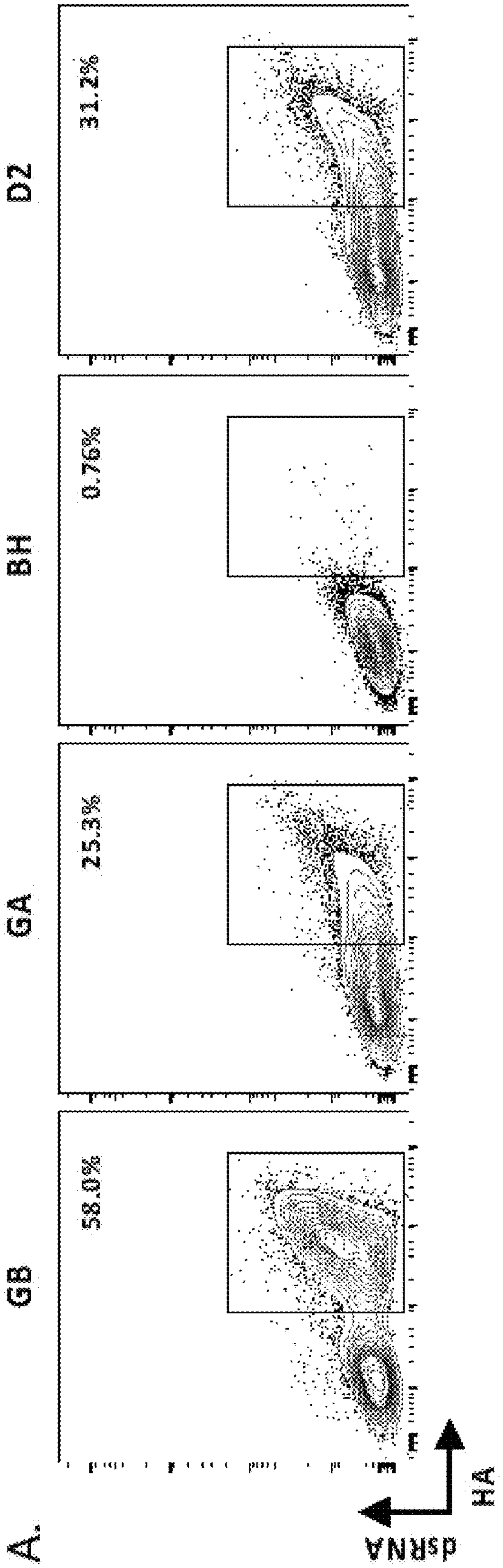
FIGS. 15A-15B graphically describe the results of experiments illustrating the impact of HA primary sequence on replication and expression. Flow cytometry analysis of cells electroporated with rE2 replicons coding for HA genes with different primary sequences. 15A). dsRNA and HA protein double positive cell populations detected from replicons with HA genes with differing primary sequence. 15B). HA protein expression MFI analysis (mean fluorescence intensity) of EAV replicons with HA genes having differing primary sequence.
Figure 15B:
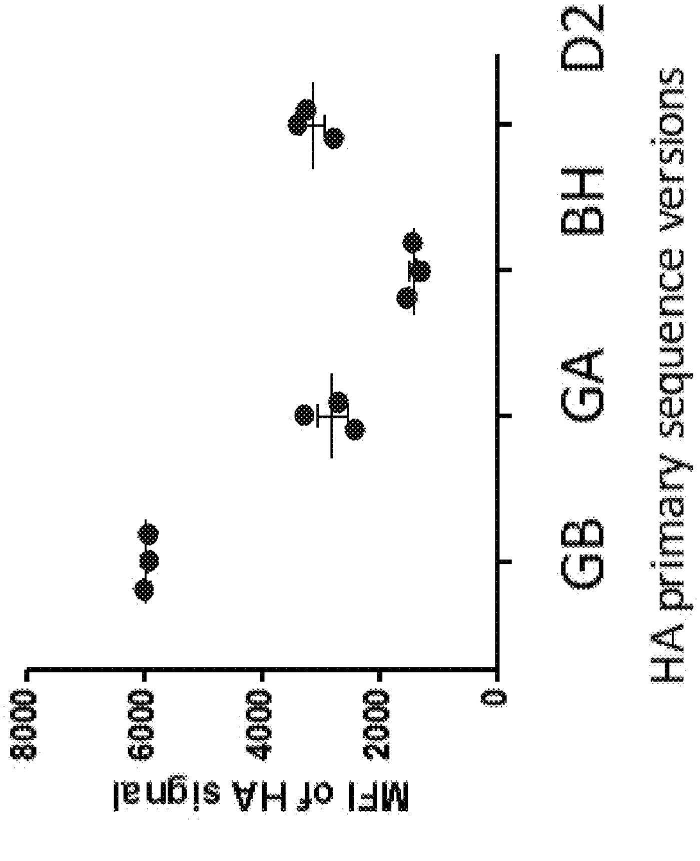

The different HA and F codon-optimized genes were each cloned into the rE2 vector. Cells were electroporated with RNA generated from each of the constructs and the cells were then analyzed by flow cytometry with protein-specific antibodies. The results of flow cytometry analysis of the different HA replicons are shown in FIGS. 15A-15B. Significant differences in both replication and protein expression were noted from replicons coding for the same protein but having different primary sequences. More than a 50-fold difference in replication was noted between the different HA versions (FIG. 15A). Modulation in protein expression (2-4 fold) was also demonstrated with the different HA gene versions (FIG. 15B).

Figure 16A:
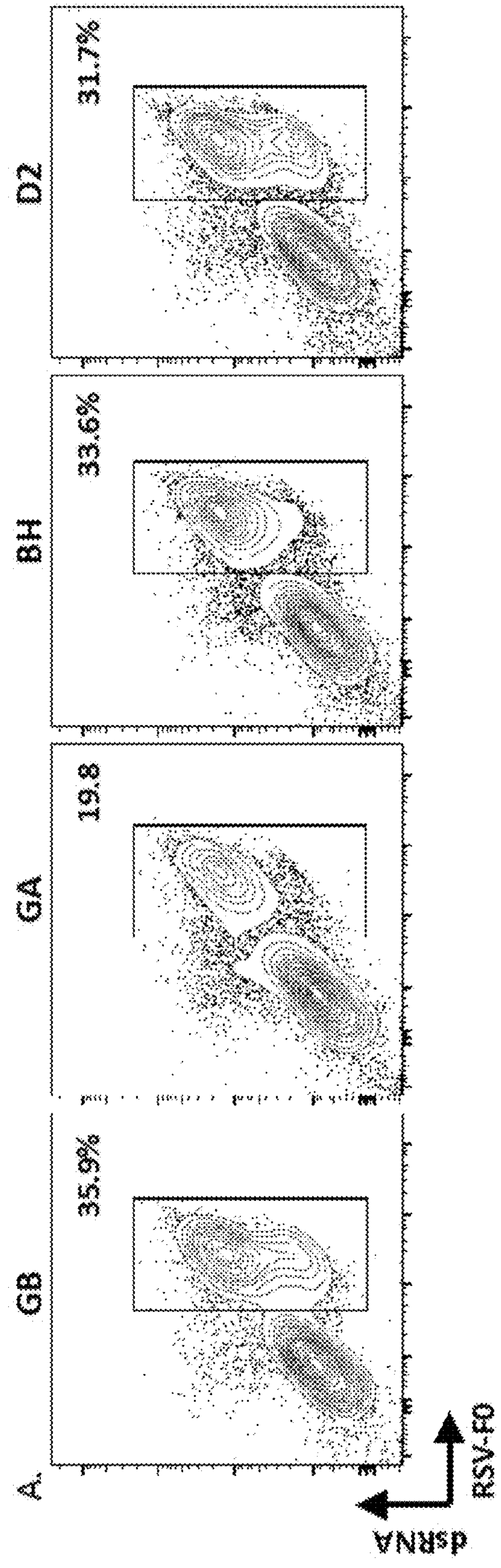
FIGS. 16A-16B graphically describe the results of experiments illustrating the impact of F primary sequence on replication and expression. Flow cytometry analysis of cells electroporated with rE2 replicons coding for F genes with different primary sequences. 16A). dsRNA and F protein double positive cell populations detected from replicons with F genes with differing primary sequence. 16B). F protein expression MFI analysis of replicons with F genes with differing primary sequence.
Figure 16B:
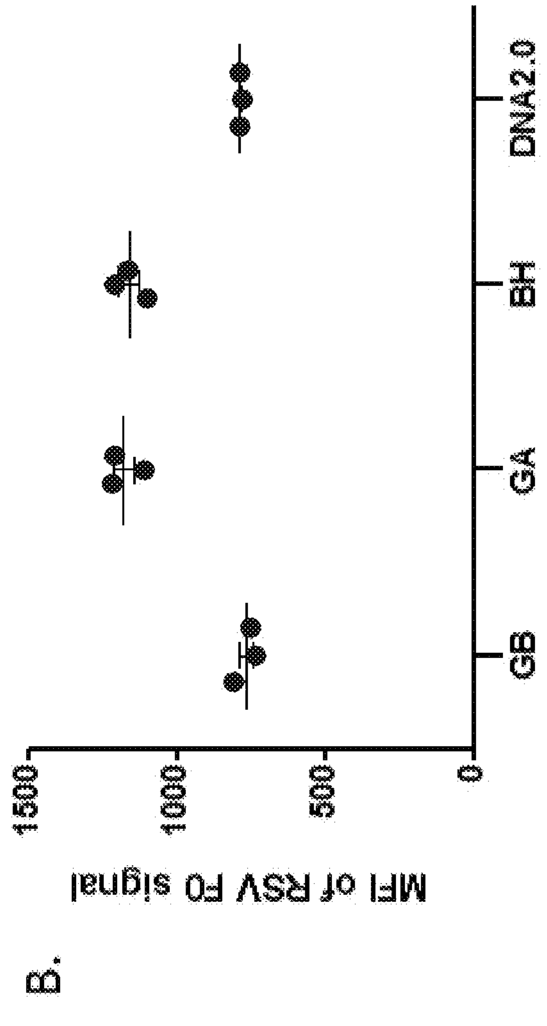

Further, the results of flow cytometry analysis of the different F replicons are shown in FIGS. 16A-16B. Similar to what was noted with HA differences in both replication and protein expression were noted from replicons coding for the same F protein but having different primary sequences. Interestingly, replication did not always predict protein expression as the rE2-F (GA) replicon expressed as much or more F protein than the replicons yet had the lowest transfection percentage.

Example 9

Analysis of GOI Expression from EAV Replicon Vectors

Another non-limiting unexpected aspect of the inventive work described in the present disclosure is the magnitude of protein expression that the RNA replicons described herein are capable of. It has been previously reported in the RNA replicon field that alphavirus-based replicon systems are capable of expressing up to twenty percent of a cell's total protein content (Pushko 1997). Thus, it is surprising and unexpected that the inventive work described here is capable of even higher expression levels on a per cell basis than an alphavirus replicon based on the fact that alphaviruses grow to titers 2-3 orders of magnitude higher than EAV does (Castillo-Olivares 2003). Two examples of the EAV replicon GOI expression potential are described below. The gREN luciferase gene or green fluorescent protein (GFP) genes were cloned into the rE2 vector. The two genes were also cloned into an alphavirus replicon vector based on the TC-83 strain of Venezuelan equine encephalitis virus (Hooper 2009). An equivalent amount of RNA in vitro transcribed from each replicon was electroporated into cells. Cells were analyzed by flow cytometry to determine both the percent of cells transfected as well as the GOI mean fluorescent intensity (MFI) as an assessment of protein expression. The results of a representative experiment are shown in FIGS.

Figures 17A, 17B, 17C:
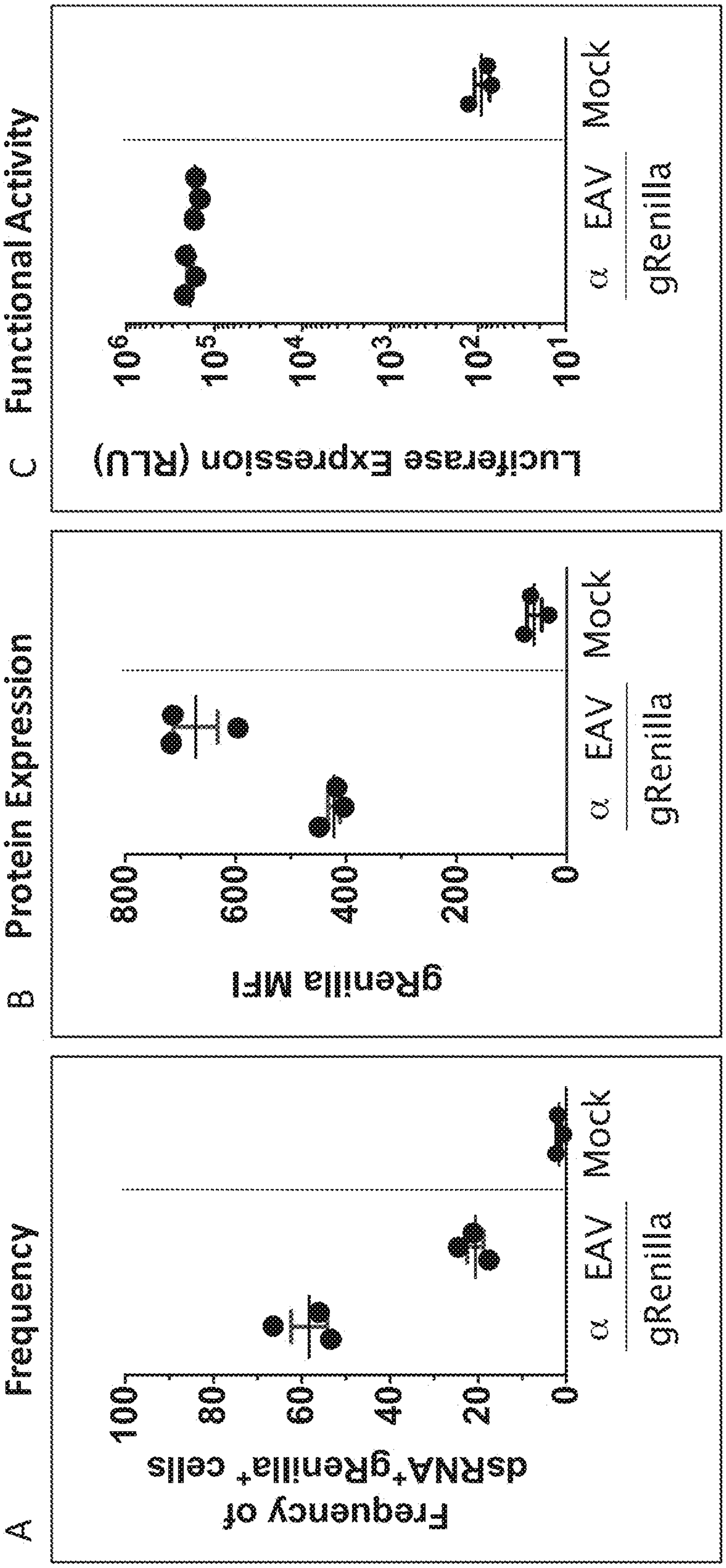
FIGS. 17A-17C graphically summarize the results of experiments illustrating the robust green Renilla protein expression driven from EAV replicon. Flow cytometry analysis of cells electroporated with rE2 (EAV) and alphavirus (a) replicons coding for gREN luciferase. 17A). dsRNA and gREN protein double positive cell populations detected. 17B). gREN protein expression MFI analysis of electroporated cells. 17C). Bulk-cell luciferase assay analysis of electroporated cells.
Figure 18:
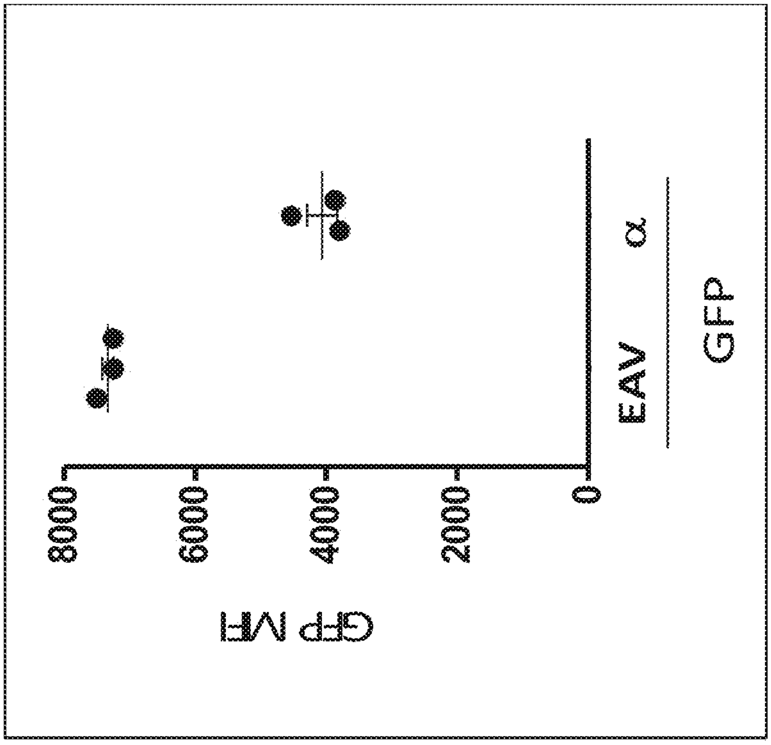
FIG. 18 graphically summarizes the results of experiments demonstrating the robust GFP protein expression driven from EAV replicon. Flow cytometry MFI analysis of cells electroporated with rE2 (EAV) and alphavirus ($\alpha$) replicons expressing GFP reporter gene.

17A-17C. and FIG. 18. For cells transfected with gREN expressing replicons (FIGS. 17A-17C), approximately three times as many cells were transfected with the alphavirus gREN RNA than the rE2-gREN RNA (FIG. 17A) but the MFI for rE2-gREN electroporated cells was more than 1.5 times higher than the alphavirus gREN cells (FIG. 17B). Bulk luciferase assays performed on the cells in parallel indicate that even though three times fewer cells received replicon RNA the rE2-gREN produced an equivalent amount of luciferase.

A similar higher expression level was detected in cells transfected with GFP expressing replicons (FIG. 18). In these experiments, cells electroporated with rE2-GFP expressed more than 1.5 times more GFP reporter protein than the alphavirus GFP replicon electroporated cells (FIG. 18).

Example 10

Molecular Evolution of EAV Replicons for Specific Phenotypes

This Example demonstrates the ability to tune protein expression levels when the replicon vector has been modified to have additional characteristics specific for the intended use of the system. If extended GOI expression time is required for a particular indication, a vector with long term protein expression would be ideal. Ultimately, the impact of EAV replicon RNA replication in a cell would result in cell death. To determine when that occurs with EAV replicons, an analysis of when cell toxicity occurs in vitro was carried out. Different cell types were transfected with rE2-GFP RNA, and the cells were subsequently monitored for the presence of cytopathic effects (CPE). Time course studies were conducted to determine how long the different cell types (BHK-21, CHO and HEK-293) could maintain EAV replicons before CPE eliminated the presence of green cells. GFP was detected in cells for up to four days before CPE was complete in all of the cells tested.

To generate an EAV replicon that is capable of expressing a GOI in a cell for more than four days, molecular evolution experiments were conducted by cloning a selective marker (neomycin or puromycin) into the rE2 replicon vector (rE2-neo or rE2-pur, respectively). Cells were transfected with rE2-neo replicon RNA and 24 hours after transfection the cells were put under 400-600 μg/ml geneticin antibiotic selection. By 72 hours post antibiotic treatment all cells in control wells were dead while patches of growing cells from samples that had been transfected with the rE2-neo RNA remained for up to 12 days. In an exemplary experiment performed to assess molecular evolution of EAV replicon vectors for extended expression of a gene of interest (GOI) in vitro, BHK-21 cells electroporated with rE2-neo RNA were placed under geneticin antibiotic selection and the growth under selection of a patch of cells at 5 and 6 days were examined. In this experiment, a patch of BHK-21 cells were found significantly expanding from Day 5 to Day 6 while under selective pressure. In comparison, all control cells had died by Day 3. The rE2-neo vectors were molecularly evolved, by antibiotic selection, to express protein in cells for up to 3 times longer than was possible with rE2-GFP. In conclusion, the results of this experiment illustrates that the molecularly evolved EAV replicons represent new vectors with longer term protein expression capability.

Example 11

In Vivo EAV Replicon Expression Analysis

Figure 19A:
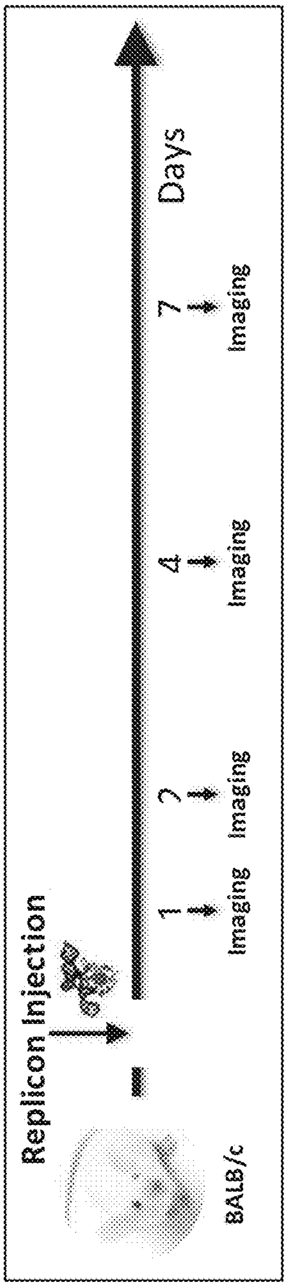
FIGS. 19A-19B illustrate an example of IVIS analysis in mice injected with rE2-rFF RNA. Analysis of expression from EAV replicons was carried out in vivo using whole body imaging analysis to detect rFF luciferase expression.
Figure 19B:
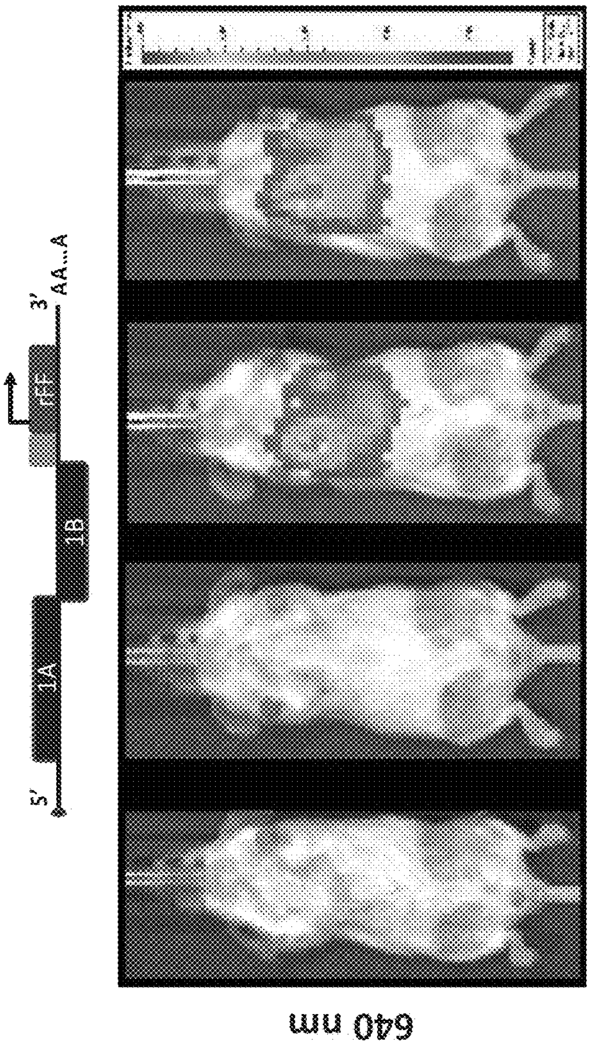

This Example summarizes the results of experiments assessing expression from EAV replicons, which were carried out in vivo using whole body imaging analysis to detect rFF luciferase expression. An example of IVIS® analysis in mice injected with 30 μg of rE2-rFF RNA is shown in FIGS. 19A-19B. The schedule of injection and image analysis as well as representative IVIS whole body analysis study is shown in FIGS. 19A and 19B, respectively. Luciferase activity was detected in the lungs of all rE2-rFF injected mice (15 out of 15 animals) between days 4 and 7 post injection. This data shows in vivo protein expression from the EAV replicon vector.

Example 12

Expression of Antibody in EAV Replicon Expression System

SGI's Archetype® Software was used to generate Herceptin codon optimized DNA sequences for expression in CHOK1 cells. These sequences were then synthesized de novo from oligonucleotides, cloned into a plasmid, and their sequences were then verified. Assembly of the Herceptin expressing EAV replicon was performed as follows. The EAV replicon backbone was PCR amplified using primers specific to the 3' end of pp1ab, which includes the TRS2, and 5' end of ORF6 excluding the start codon. The Herceptin light chain (LC) forward primer and heavy chain (HC) reverse primer were designed with the gene specific amplification region and an additional 30 bp of sequence complementary to the EAV backbone. The TRS7 sequence (84-bp), which controlled the expression of HC, was introduced on the LC reverse primer and HC forward primer. These two primers were designed with the gene specific amplification region and 65 bp of the TRS7 Promoter region. The 46-bp portion of homology was shared between the LC and HC PCR products allowing for overlap extension PCR amplification to join the two products together to generate a single fragment containing the sequences of Herceptin LC and TRS7, which was followed by the sequence of Herceptin HC. Two-step Gibson Assembly® procedure as described in Example 1 was performed with the EAV replicon backbone and the Herceptin LC-TRS7-HC gene fragment. The assembly reaction was transformed into *E. coli* TransforMax EPI300 cells (Epicentre Cat. no. EC300105) and plated on selective LB agar plates. *E. coli* clones were screened using colony PCR with primers annealing within the EAV backbone just outside the assembly junctions. *E. coli* clones containing the Herceptin gene cassette could be easily identified based upon expected PCR fragment size. Positive *E. coli* clones were then verified by sequencing using Sanger and Illumina MiSeq platforms.

Analysis of Antibody Expressed from EAV Replicon Expression System

Antibody expressed from EAV replicon expression systems described in the disclosure was analyzed by using solid-phase binding assays. Media from BHK-21 cells was collected 24 h after transfection with the replicon and treated with protease inhibitor (Pierce). To measure Herceptin expression, a quantitative total IgG capture ELISA was performed. An anti-human IgG heavy chain (mouse anti-Human IgG unlabeled, #9040-01, Southern Biotech) was coated on microtiter wells overnight. The wells were incubated with 100 μl of media, probed with an HRP-labeled anti-human IgG light chain (mouse Anti-Human Kappa-HRP, #9230-05, Southern Biotech) and developed with TMB substrate solution (Pierce). Standard curves of a human IgG1 antibody (IgG1 Kappa-UNLB, 0151K-01, Southern Biotech) and Herceptin were used to estimate the amount of antibody expressed by BHK-21 cells in pg/cell/day. A similar assay was used for specific antigen binding, in which recombinant Erb2 receptor (Thermo Fisher Scientific) was used to capture the Herceptin antibody present in the cell culture media. In this experiment, standard curves were based on Herceptin and were correlated with the total IgG amount.

Example 13

Figure 21:
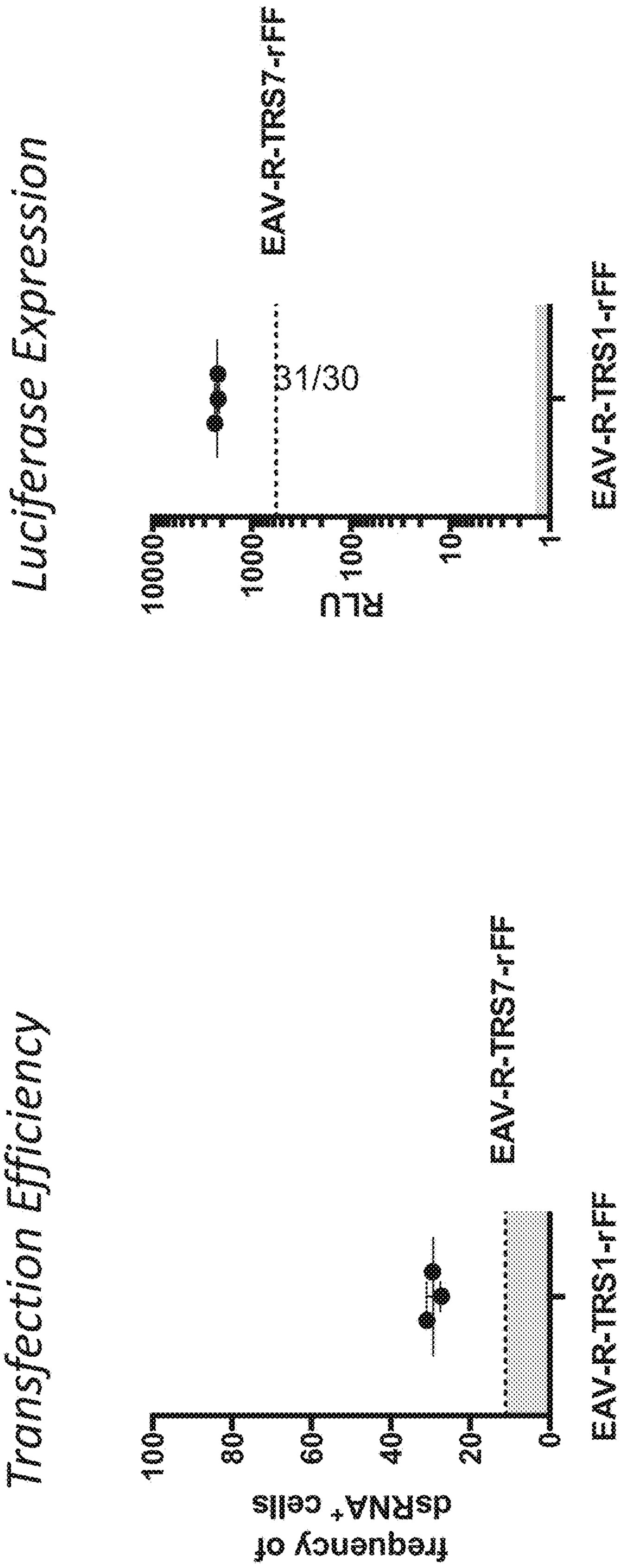
FIG. 21 summarizes the results of experiments analyzing luciferase expression from an EAV TRS1 replicon vector in BHK cells. BHK cells were electroporated with 3 μg of replicon RNA. The TRS1 replicon vector demonstrated robust expression that was higher than expression detected from an EAV replicon using the TRS7 subgenomic promoter.

Construction of EAV Replicon Vectors with GOI Expression Under Control of TRS1 Subgenomic Promoter In this experiment, an EAV replicon was engineered to use the TRS1 subgenomic promoter to express the red firefly (rFF) luciferase reporter. A comparison of the level of rFF expression from another EAV replicon is shown in FIGS. 21A and 21B. In this experiment, BHK cells were electroporated with 3 μg of replicon RNA. The TRS1 replicon vector demonstrated robust expression that was higher than expression detected from an EAV replicon using the TRS7 subgenomic promoter. In FIGS. 21A-21B, the dotted line represents the amount of expression detected from a replicon engineered to use the TRS7 subgenomic promoter to drive the expression of rFF reporter. As illustrated in FIGS. 21A-21B, robust expression was detected from the TRS1 replicon, as indicated by transfection efficiency (FIG. 21A) and Luciferase expression level (FIG. 21B).

Example 14

Construction of VBS-R-eGFP and VBS-IC

To extend vector development to additional EAV strains, the virulent Bucyrus strain (VBS) was selected. The VBS strain is more virulent than the highly attenuated EAV030 strain, as such, a replicon based on it may have different expression characteristics than the replicon based on the EAV030 strain. To this end, the complete genomic sequence for the VBS strain was downloaded from Genbank (Accession No. DQ846751). The sequences of a VBS replicon containing an eGFP reporter gene driven by TRS2 subgenomic promoter within the polyprotein pp1b gene (VBS-R-eGFP) and a VBS infectious clone (VBS-IC) containing overlap regions to pW70, the T7 promoter, and a polyA tail with 125 A's, are provided in the Sequence Listing as SEQ ID NO: 46 and SEQ ID NO: 47, respectively.

Figure 22:
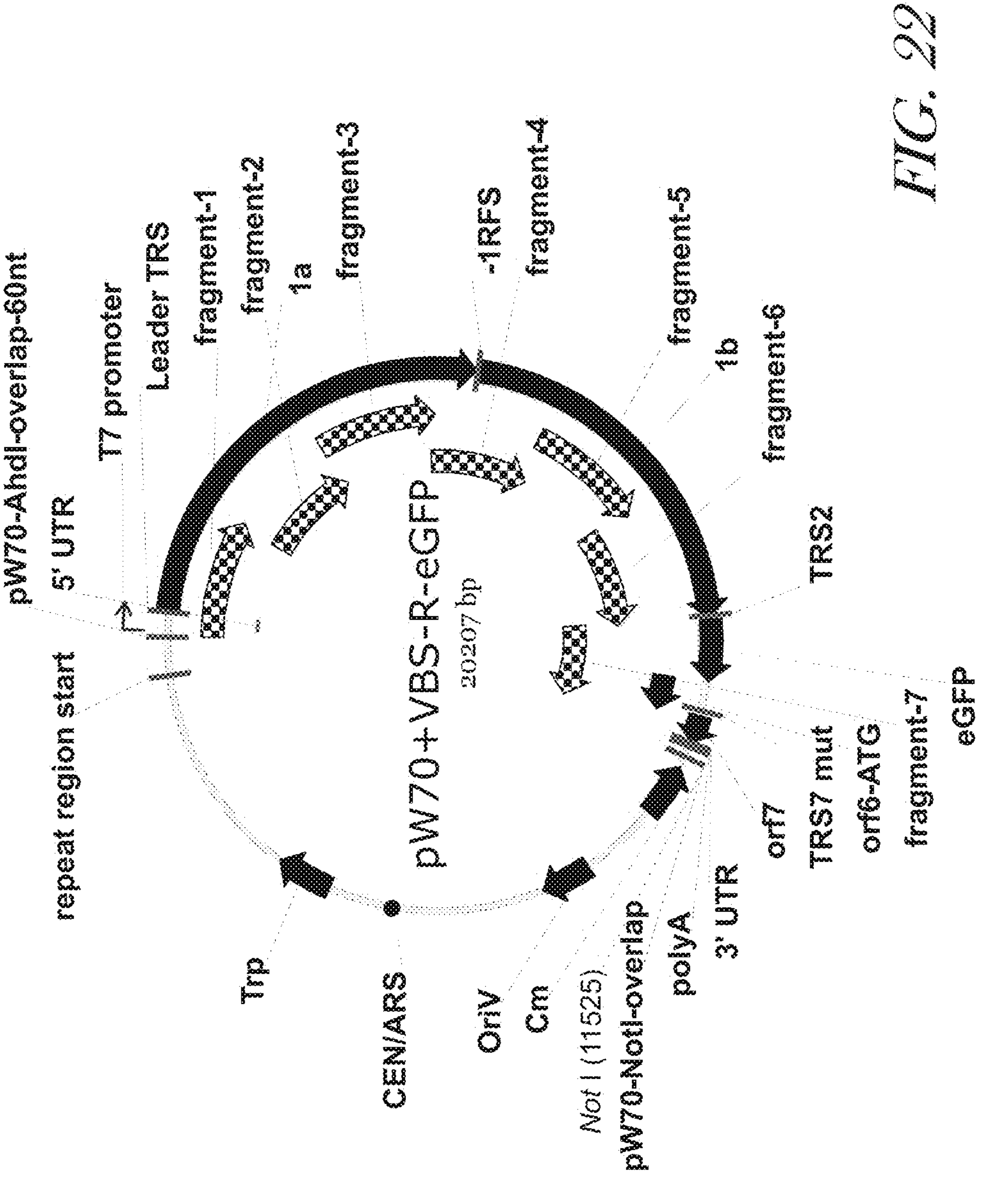
FIG. 22 is a plasmid map of the VBS-R-eGFP construct.
Figure 23:
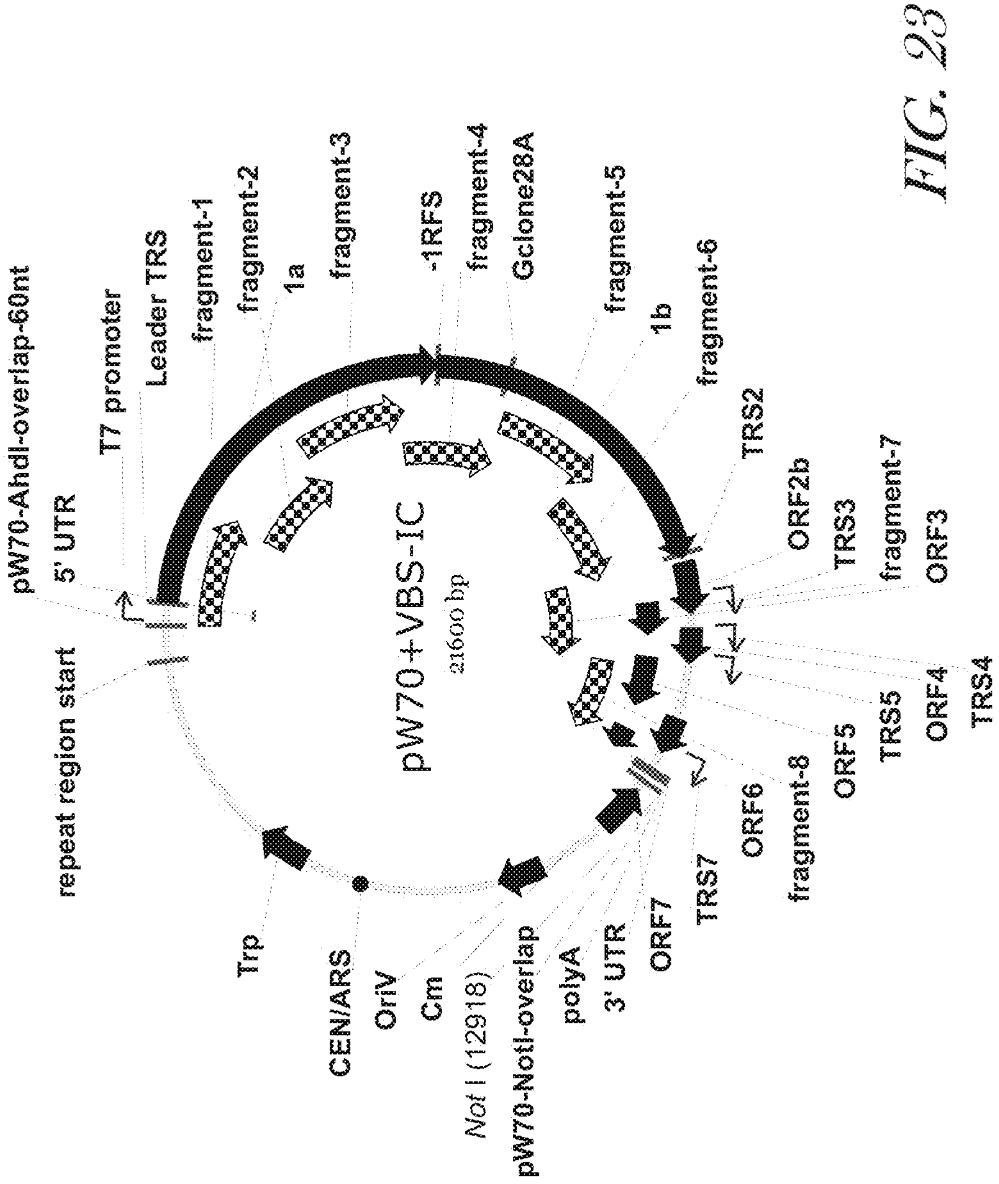
FIG. 23 is a plasmid map of the VBS-IC construct.
Figure 2A:
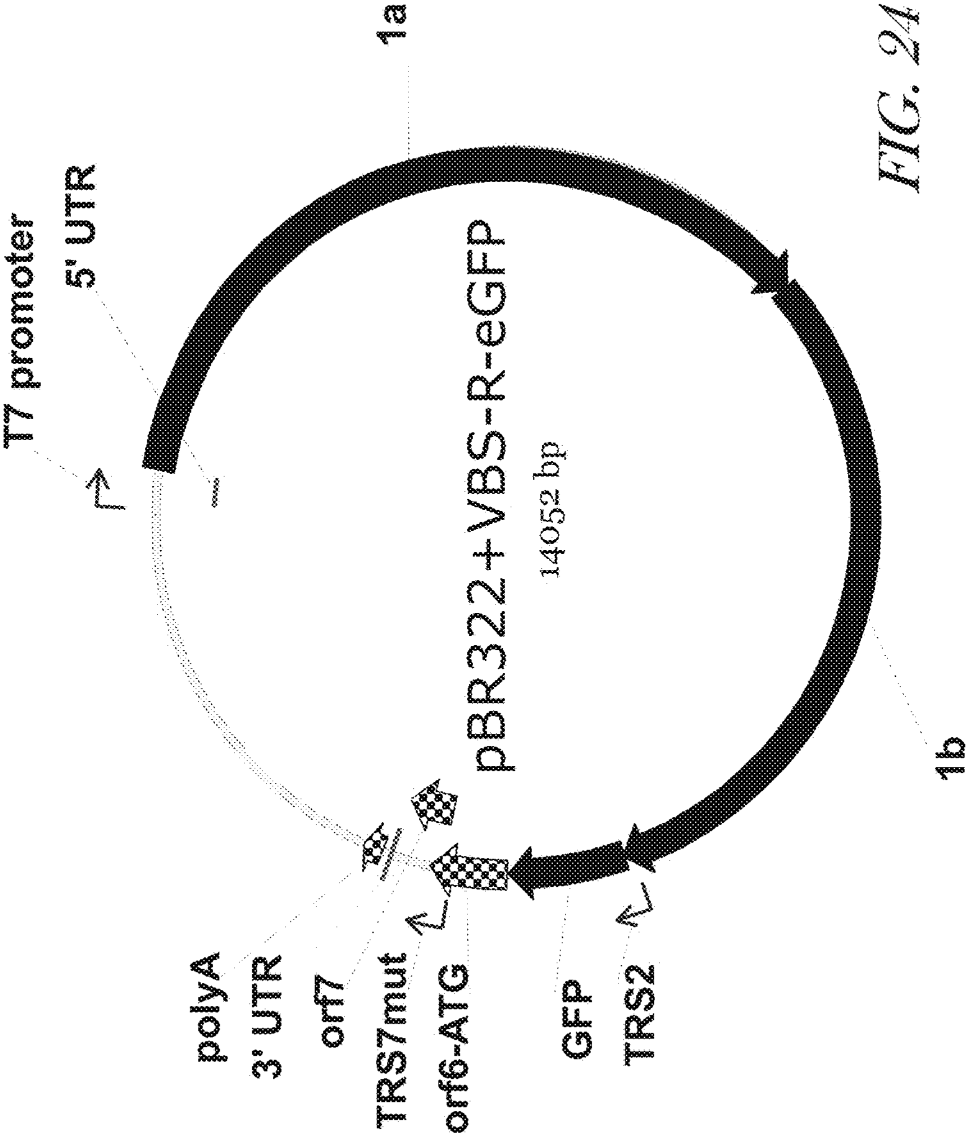

The VBS-R-eGFP and VBS-IC constructs were intended to be built via homologous recombination in *S. cerevisiae* using an *E. coli*-yeast shuttle vector pW70. The VBS-R-eGFP construct was split into 7 fragments (excluding the vector), the first 6 of which are shared by the VBS-IC with two additional fragments, as shown in FIG. 22 and FIG. 23, respectively.

The g-blocks for the fragments were ordered from IDT for assembly. To be used as a vector, pW70 was digested with restriction enzymes AhdI/NotI. The last fragment of each construct was PCR-amplified for the addition of the polyA tail using an appropriate primer set.

Yeast colonies were obtained from plating of 100 μL for both constructs (VBS-R-eGFP and VBS-IC). Colonies were pooled for each construct, and plasmids were isolated from each pool.

The isolated plasmid pool of each construct was then transformed into *E. coli* (EPI300 from Epicenter) for screening in bacteria. The transformed culture (10-100 μL) was plated.

*E. coli* colonies from transformations of plasmids pools isolated from yeast colonies were screened for 5' and 3' ends.

Multiple "positive" clones were found. Sanger sequencing results revealed two completely sequence-correct clones for the VBS-IC (clones 33 and 36) and 4 positive clones for VBS-R-eGFP (clones 6, 30, 33, and 47). A schematic map of the pBR322+VBS-R-eGFP is shown in FIG. 24.

Demonstration of the Functionality of VBS IC and VBS-R-eGFP Replicons

Figure 25:
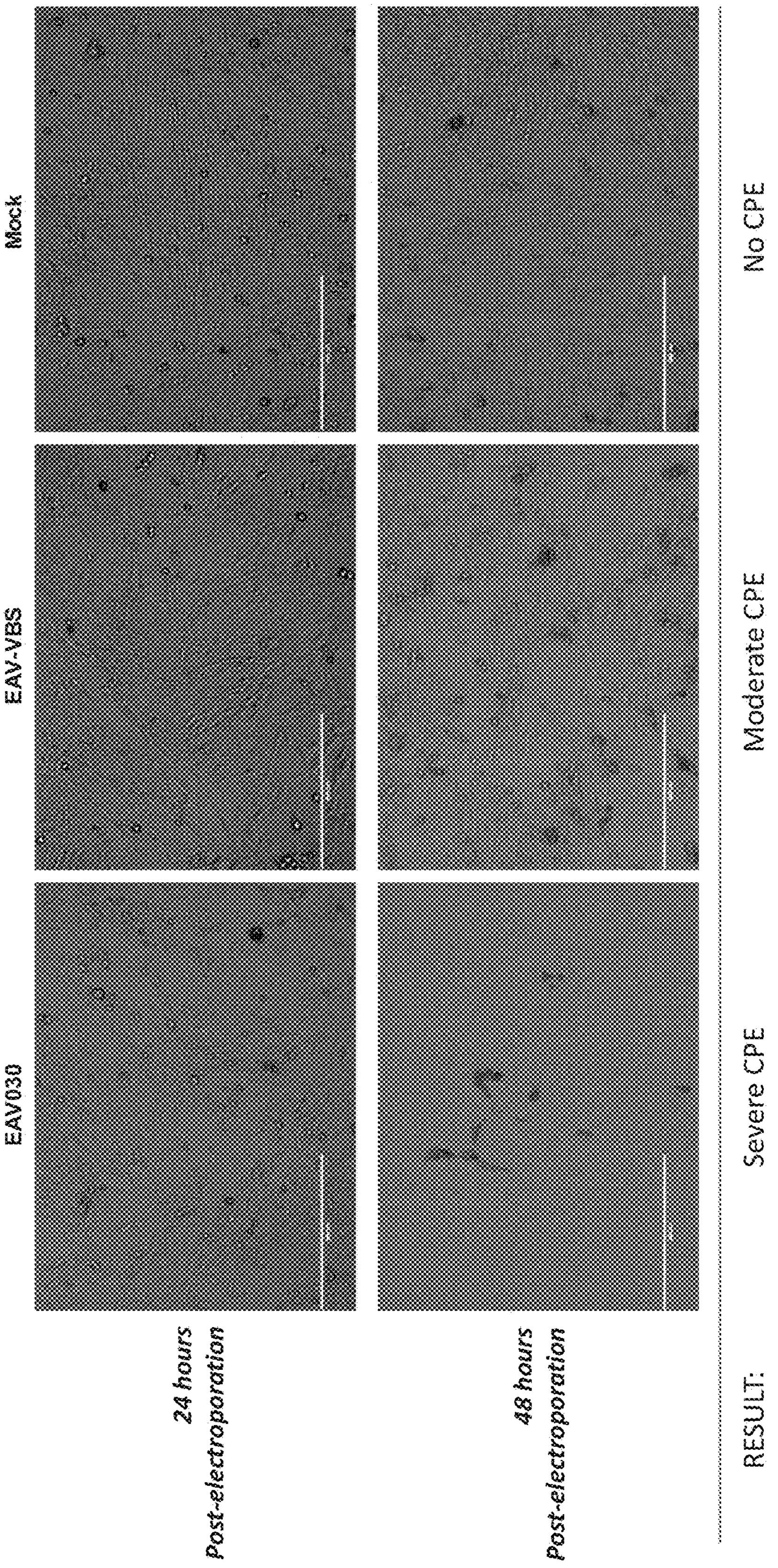
FIG. 25 is a pictorial summary of the results of experiments performed to demonstrate functionality of VBS IC construct in BHK cells. BHK cells were electroporated with 3 μg of either EAV strain 030 IC RNA (EAV030), EAV strain VS IC RNA (EAV-VBS) or no RNA (Mock). Cells were examined for the presence of CPE at 24 and 48 hours post electroporation. CPE was noted in both the EAV030 and EAV-VBS electroporated cells by 48 hours, demonstrating that both IC were functional.

The VBS IC was tested to demonstrate functionality by producing in vitro transcribed RNAs from the VBS IC c33 plasmid DNA, followed by electroporating the transcribed RNAs into BHK cells. As a positive control, RNA generated from an infectious clone for EAV strain EAV030 was included in a separate electroporation. The generation of cytopathic effects (CPE) in cells electroporated with IC RNA indicated that the IC RNA was functional. As shown in FIG. 25, CPE was noted in both the VBS and EAV030 strain by 48 hours post electroporation (see, e.g., FIG. 25). This data demonstrated that the VBS IC RNA was functional.

Figure 26:
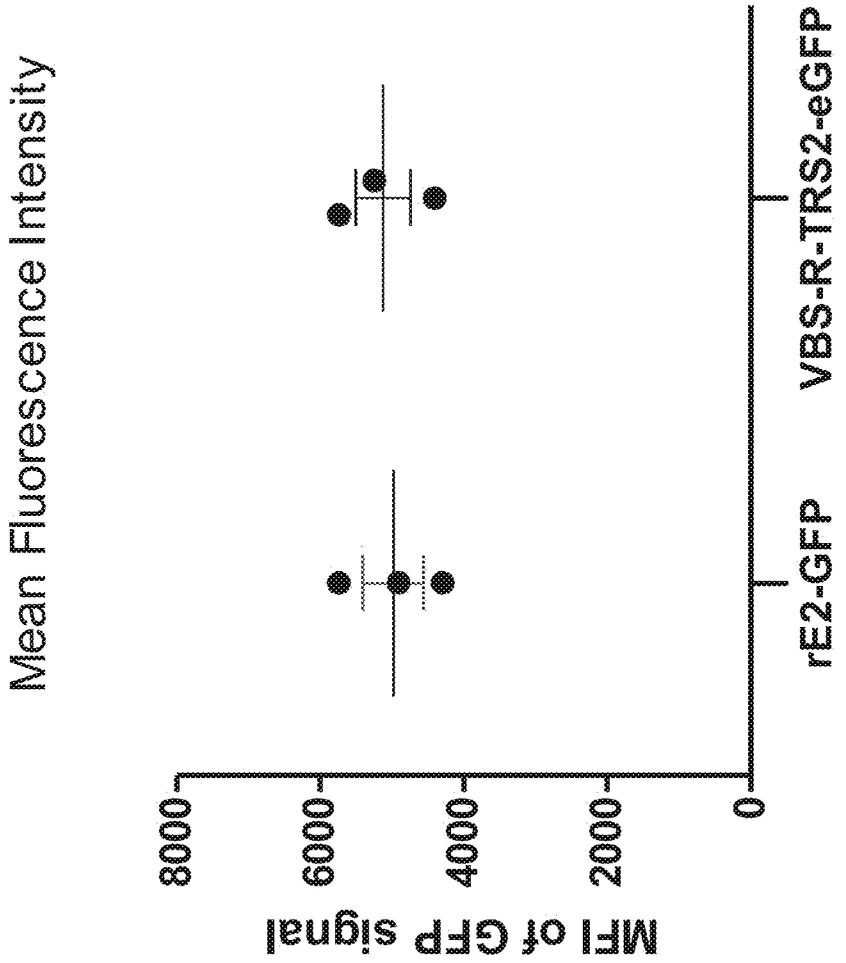
FIG. 26 schematically summarizes of the results of experiments performed to analyze eGFP expression from a VBS-based replicon vector in BHK cells. BHK cells were electroporated with 3 μg of either EAV strain EAV030 eGFP replicon RNA (rE2-GFP) or EAV strain VBS eGFP replicon RNA (VBS-R-TRS2-eGFP). Cells were examined for the relative expression of GFP by FACS analysis. The EAV VBS-based replicon was found to express GFP protein at the same level as the EAV030-based replicon.

The VBS-R-eGFP vector was tested to demonstrate functionality by producing in vitro transcribed RNA from the VBS-R-eGFP c30 plasmid DNA, followed by electroporation the transcribed RNA into BHK cells. As a positive control, RNA generated from an EAV strain EAV030 replicon expressing eGFP was included in a separate electroporation. BHK cells were electroporated with 3 μg of either VBS-R-eGFP RNA (VBS-R-TRS2-eGFP) or EAV030 eGFP replicon RNA (rE2-GFP). An example of flow cytometry analysis for this comparison is shown in FIG. 26. Analysis of the mean fluorescence intensity of GFP expressed from both vector backbones demonstrated that the EAV strain VBS and EAV strain EAV030 replicon systems were expressing protein at very similar levels and that the VBS replicon system was completely functional.

Example 15

Construction of VBS-R-rFF Replicon

Figure 27:
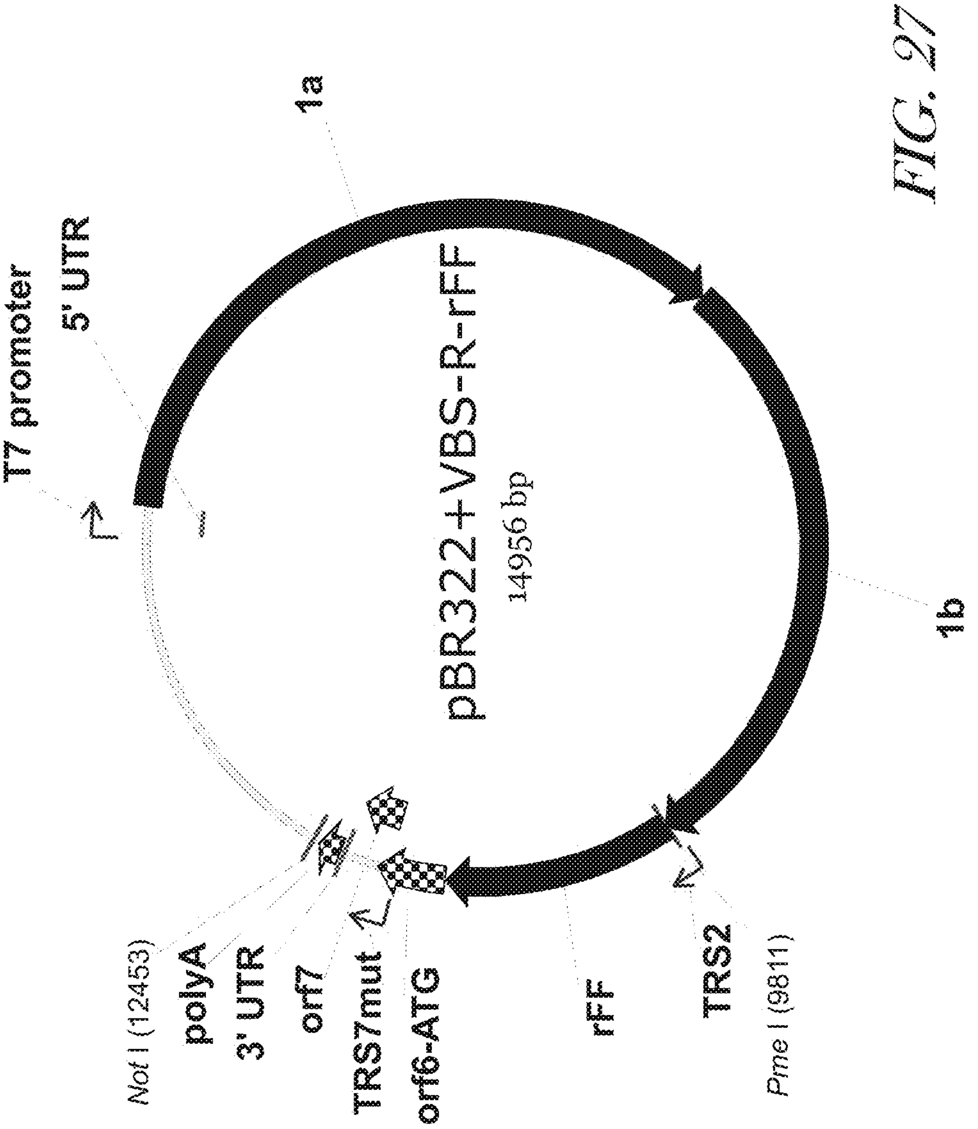
FIG. 27 is a plasmid map of the pBR322+VBS-R-rFF construct.

To evaluate VBS-R in mice for IVIS® analysis as an alternative backbone, VBS-R-rFF was needed to be made. Therefore, the primers were designed and ordered to replace eGFP in pBR322+VBS-R-eGFP. A schematic map of pBR322+VBS-R-rFF is shown FIG. 27.

Two fragments, PCR-amplified using the primers RP52 and PR53 and the primers RP54 and RP20, respectively, from their appropriate templates, were gel-extracted and assembled via a fusion PCR using RP55 and RP6 as primers. The resulting assembled fragment was then gel-extracted again and cloned into the vector pBR322+VBS-R-eGFP pre-digested with restriction enzymes PmeI and NotI. One clone—Clone 7—was sequence-confirmed to be completely correct via MiSeq procedure. The sequence of resulting construct VBS-R-rFF includes the T7 promoter and a polyA tail with 125 A's, and is set forth in the Sequence Listing as SEQ ID NO: 48.

Example 16

Construction of VBS-R-TRS7-rFF Replicon

In pBR322+VBS-R-rFF (c7), the expression of rFF reporter is driven by TRS2 embedded in the pp1b gene. To make pBR322+VBS-R-TRS7-rFF, where rFF expression would be driven by TRS7 located downstream of the pp1b gene, a g-block consisting of the following sequence was used as an insert and cloned into the vector pBR322+VBS-R-rFF (c7) pre-digested with restriction enzymes PmeI/EcoRI via Gibson Assembly® procedure. Clone 11 was sequence-confirmed to be completely correct via MiSeq. The sequence of g-block for construction of pBR322+VBS-R-TRS7-rFF is provided in the Sequence Listing as SEQ ID NO: 49.

Figure 28:
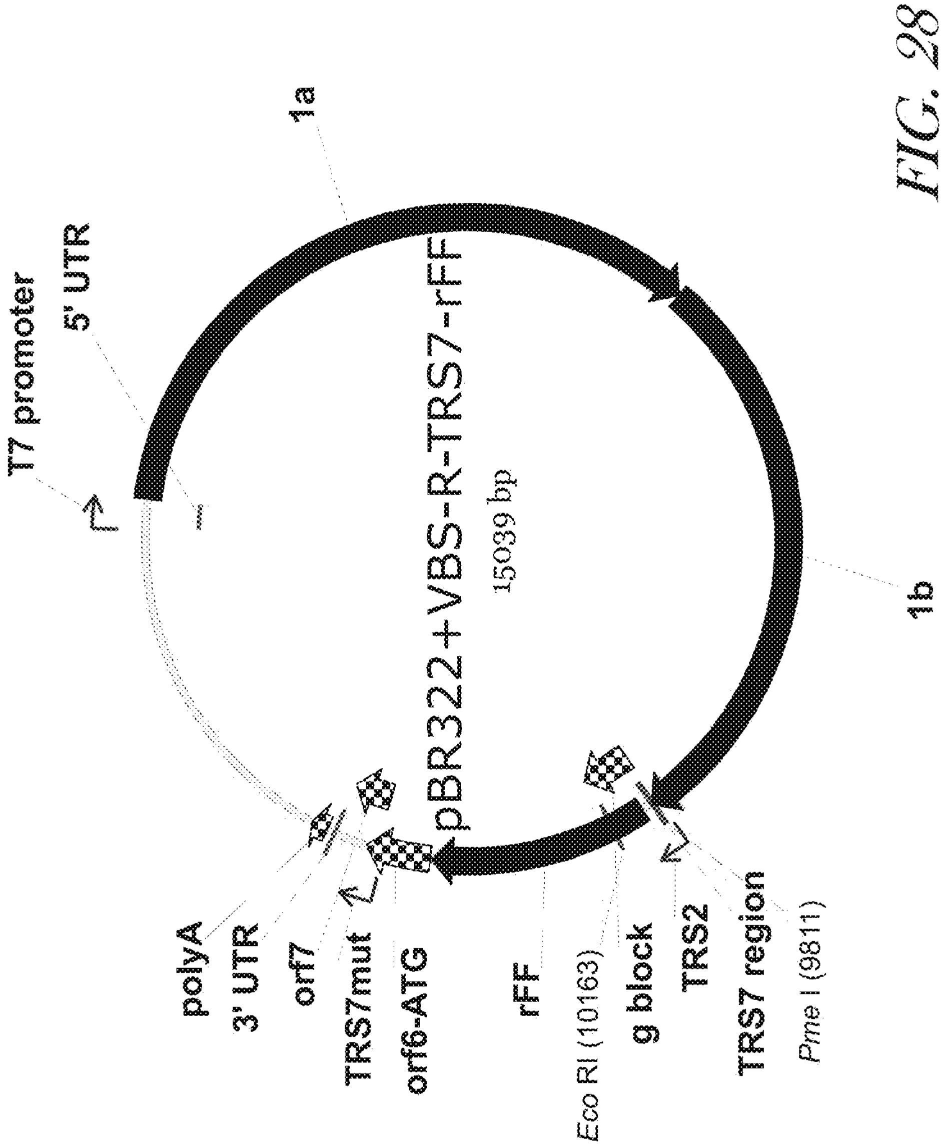
FIG. 28 is a plasmid map of the pBR322+VBS-R-TRS7-rFF construct.

A schematic map of the pBR322+VBS-R-TRS7-rFF is shown in FIG. 28.

The sequence of VBS-R-TRS7-rFF is provided in the Sequence Listing as SEQ ID NO: 50 with the T7 promoter and a polyA tail with 125 A's.

Figure 29:
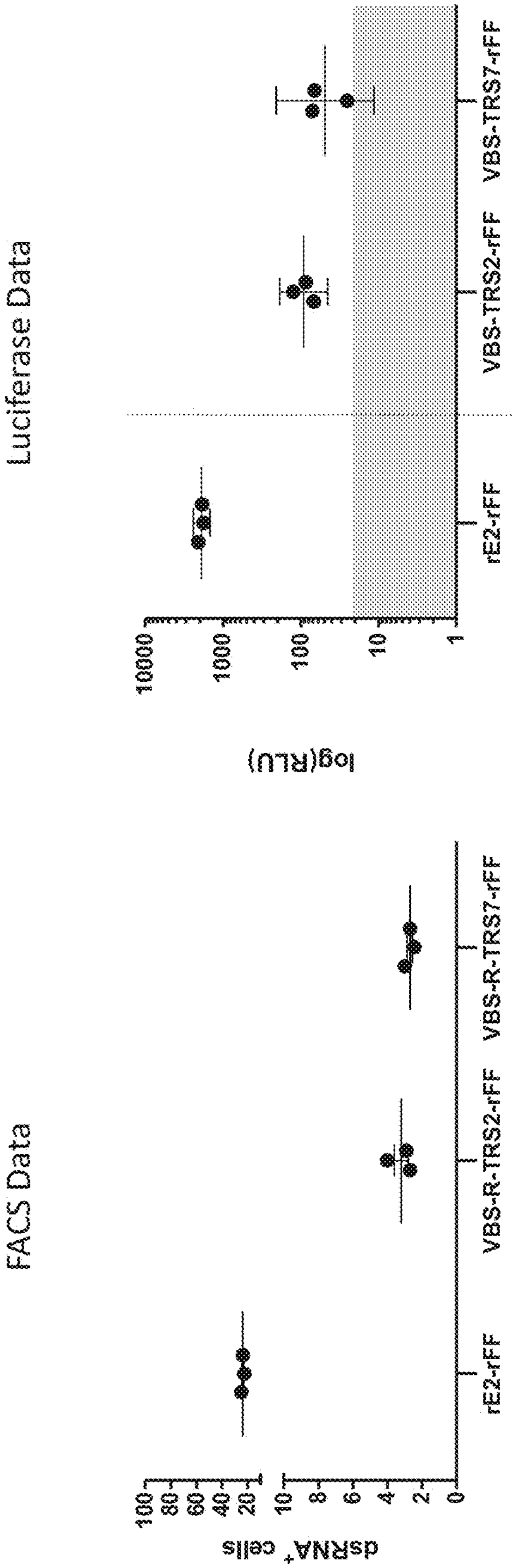
FIG. 29 schematically summarizes of the results of experiments performed to analyze rFF expression from a VBS-based replicon vector in BHK cells. BHK cells were electroporated with 3 μg of either EAV strain 030 rFF replicon RNA (rE2-GFP) or EAV strain VBS-rFF replicon RNAs (VBS-R-TRS2-rFF or VBS-R-TRS7-rFF). Cells were examined for the expression of rFF by FACS analysis and bulk luciferase assay. Each of the EAV VBS-based replicon was observed to express rFF protein at similar levels when compared to each other.

The VBS-R-TRS2-rFF (previously identified as pBR322+VBS-R-eGFP above) and VBS-R-TRS7-rFF vectors were tested to demonstrate functionality by producing in vitro transcribed RNA from each plasmid DNA (clone 7 and clone 11, respectively), followed by electroporating the transcribed RNA into BHK cells. As a positive control, RNA generated from an EAV strain EAV030 replicon expressing rFF (rE2-rFF) was included in a separate electroporation. BHK cells were electroporated with 3 μg of each RNA and cells were analyzed by FACS. An example of flow cytometry analysis for this comparison is shown in FIG. 29, in which both VBS-rFF vectors were observed to express luciferase protein. These data demonstrate that the VBS replicons described herein can express the rFF reporter gene and these vectors can be used for in vivo expression analysis.

Figure 30:
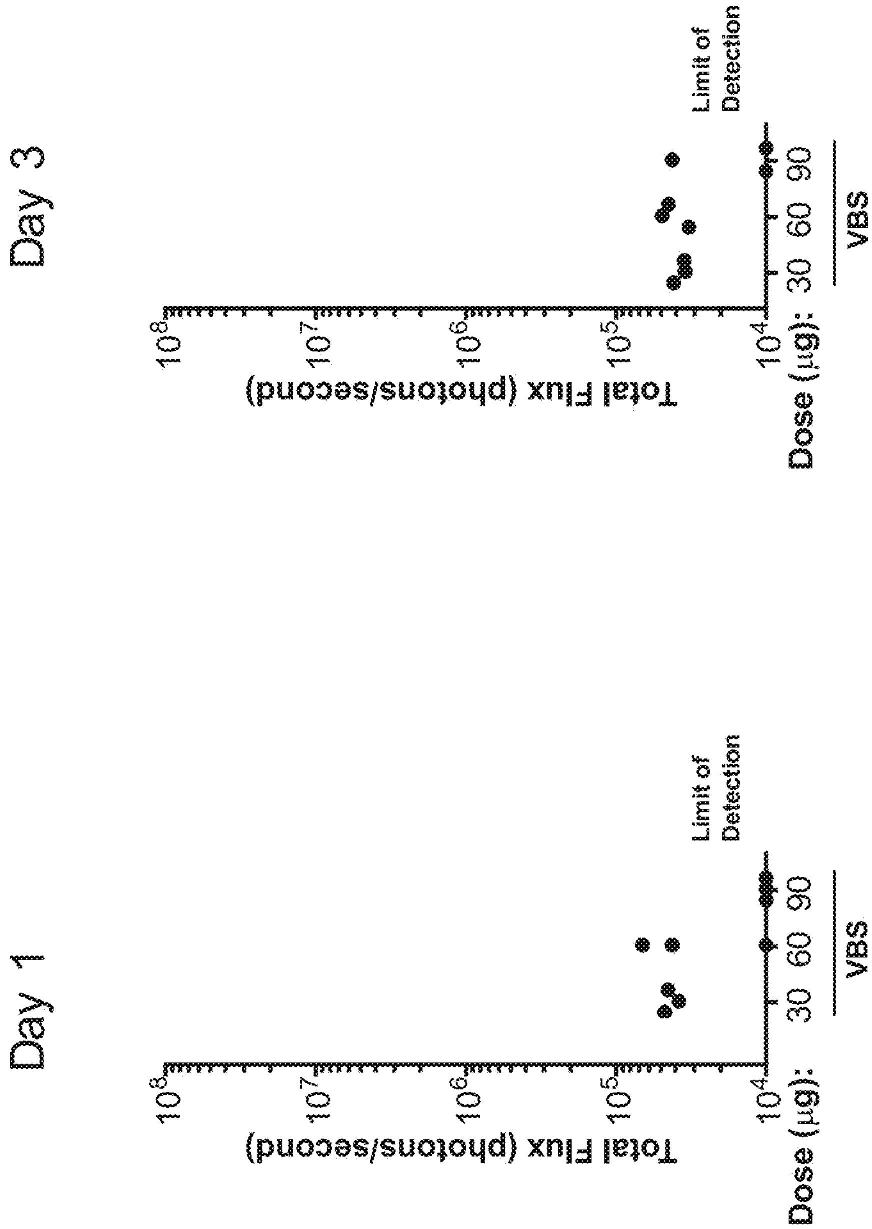
FIG. 30 is a schematic summary of the results of experiments performed to analyze rFF expression from a VBS-based replicon vector in Balb/c mice. In this experiment, mice were intramuscularly injected with 30, 60 or 90 μg of VBS-R-TRS2-rFF in ringers lactate. Animals were examined by whole body imaging one and three days post RNA injection.

The VBS-R-TRS2-rFF replicon was further analyzed in vivo in Balb/c mice. In this experiment, a range of RNA doses were tested and whole body imaging was conducted one and three days post intramuscular injection. Interestingly, animals that received the highest dose were observed to express luciferase less well than animals that received the lowest dose. A summary of the results of these experiments is presented in FIG. 30. These data demonstrate the in vivo activity of the VBS replicon vector.

Example 17

Construction of SHFv-R-TRS7-rFF

In addition to the EAV strain EAV030 and EAV strain VBS replicon systems, an alternative backbone was constructed based on another virus within the Arterivirus genus. This was to extend the development of arterivirus replicon systems based on other species within the Arteriviridae Family of viruses. A replicon vector system derived from the Simian Hemorrhagic Fever virus (SHFv) was developed. The complete genomic sequence of SHFv was downloaded from Genebank (Accession No. AF180391 L39091 U20522 U63121). The complete SHFv nonstructural gene sequence and a portion of the 3' most structural region was divided into 9 fragments including rFF, and the corresponding g-blocks except rFF and respective primers for amplifying each fragment were ordered. In this design, rFF expression is driven by an independent TRS7 subgenomic promoter.

The reporter rFF gene was PCR-amplified. The PCR-amplified fragments were then assembled in *S. cerevisiae* following the previously described transformation protocols.

Figure 31:
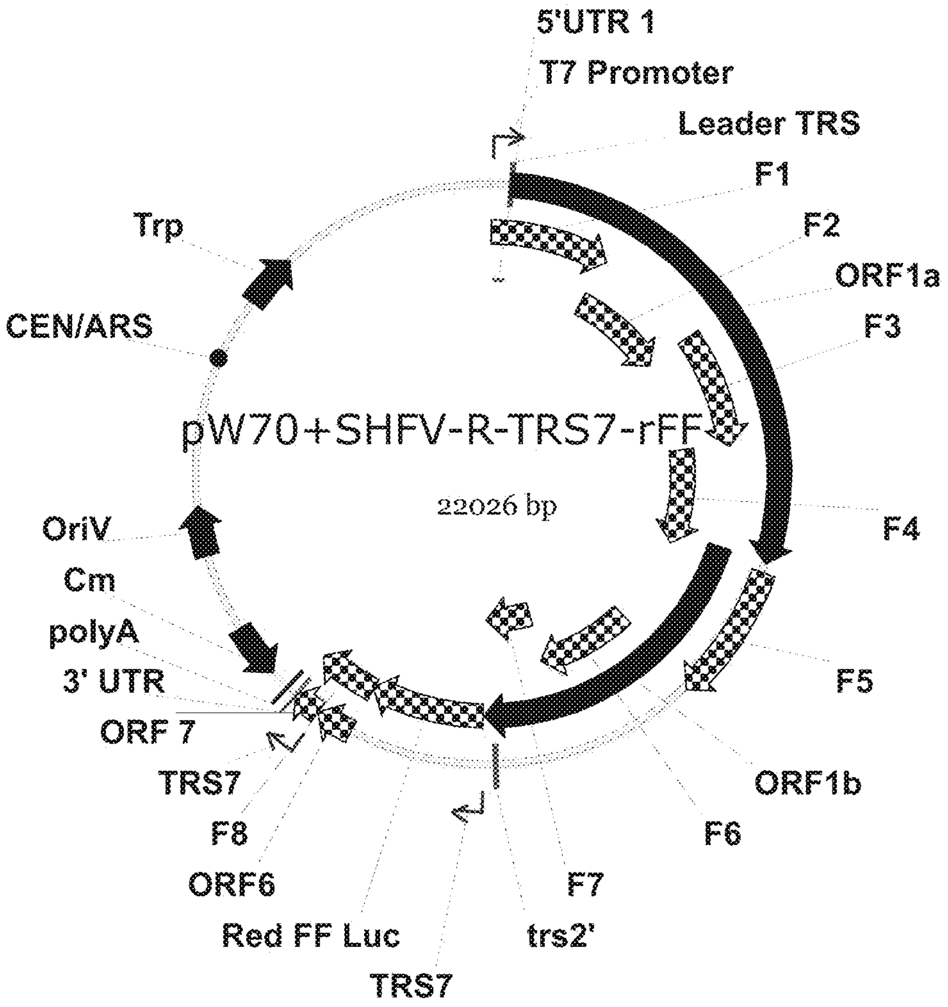
FIG. 31 is a plasmid map of the pW70+SHFV-R-TRS7-rFF construct.

A schematic map of the pW70+SHFV-R-TRS7-rFF construct is shown in FIG. 31. In addition, the sequence of the SHFV replicon with rFF expression driven by TRS7 (SHFV-R-TRS7-rFF) is provided in the Sequence Listing as SEQ ID NO:51, which includes overlap regions to the vector pW70, the T7 promoter, and a polyA tail with 125 A's.

Plasmids from the yeast colonies resulting from the assembly transformation of pW70+SHFV-R-TRS7-rFF construct were isolated as a pool and transformed back into *E. coli*. A total of 12 of the resulting *E. coli* colonies were sequenced via MiSeq. Error correction and assembly of the clones were performed to correct any mutations via Gibson Assembly® procedure.

The resulting *E. coli* clones from the correcting transformation were screened by Sanger sequencing using RP77 specific for that region. Clone 2 was identified to contain the correct nucleotide, and its subsequent MiSeq sequencing result revealed that the entire replicon sequence was also found to be completely correct.

Figure 32:
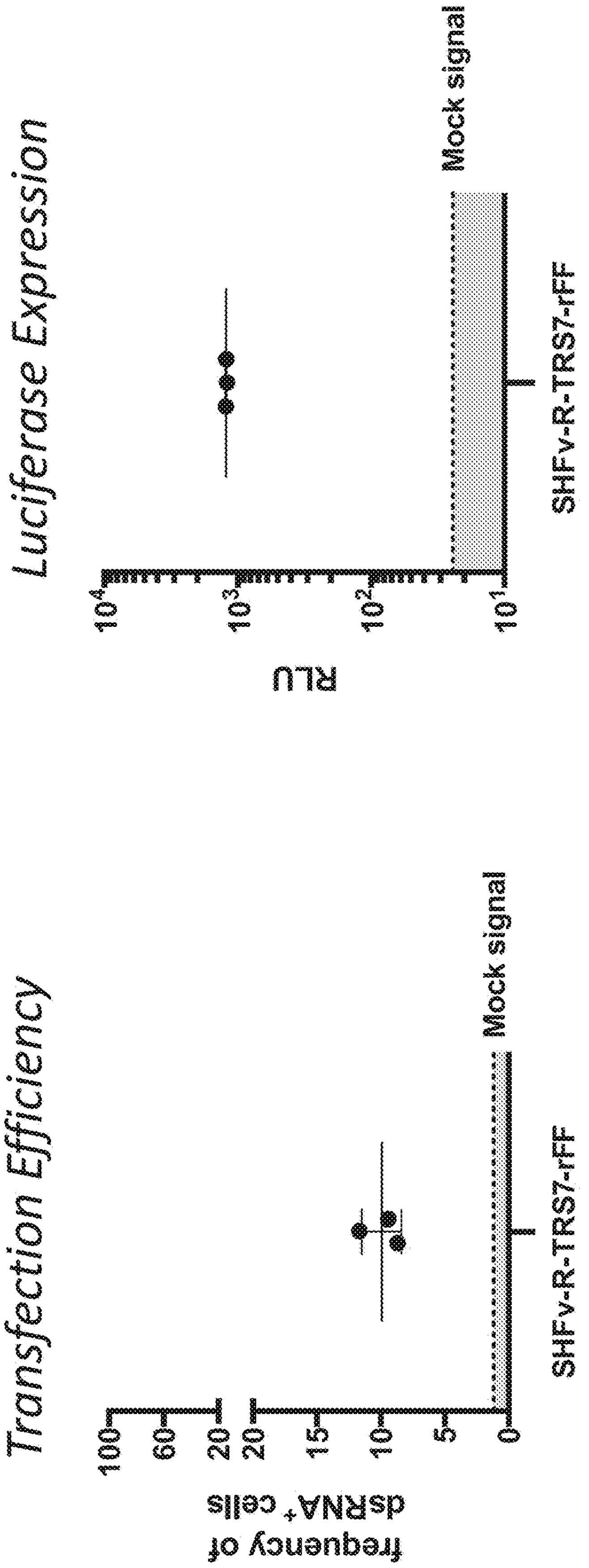
FIG. 32 is a schematic summary of experiments performed to analyze rFF expression from a SHFv-based replicon vector in BHK cells. BHK cells were electroporated with 3 μg of SHFv-R-TRS7-rFF replicon RNA. Cells were examined for the expression of rFF by FACS analysis and bulk luciferase assay. The SHFv-based replicon was observed to express rFF protein in BHK cells.

The SHFv-R-TRS7-rFF vector was tested to demonstrate functionality by producing in vitro transcribed RNA from the SHFv-R-TRS7-rFF plasmid DNA and electroporating it into BHK cells. BHK cells were electroporated with 3 μg of each RNA and electroporated cells were analyzed by FACS. An example of flow cytometry analysis for this comparison is shown in FIGS. 32A-32B. These data demonstrate that SHFv replicon can express the rFF reporter gene and the vector can be used for in vivo expression analysis.

Figure 34:
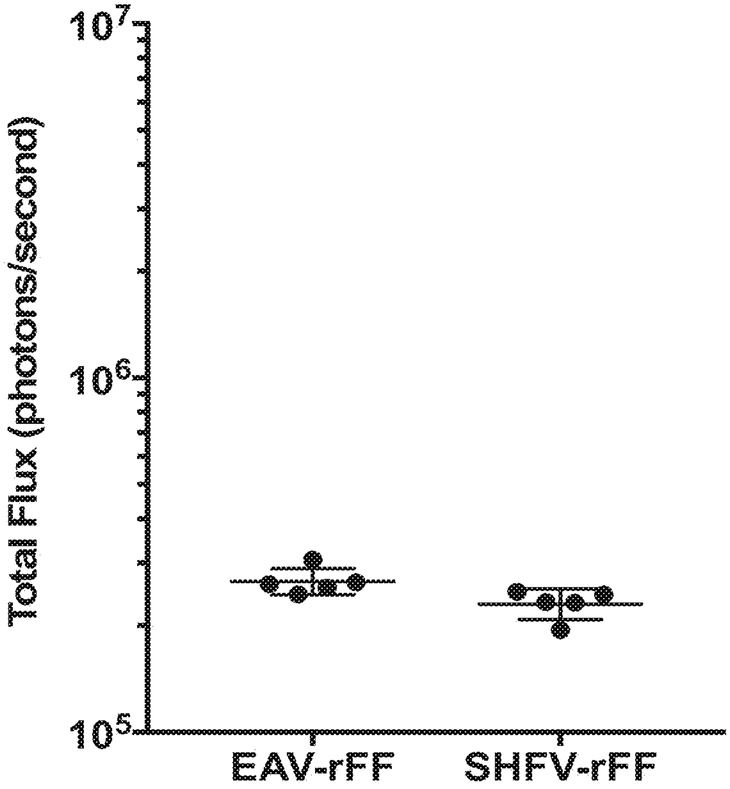
Figure 35A:
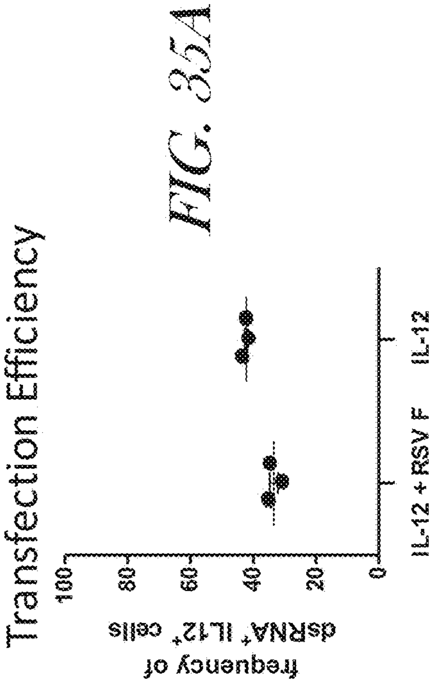
FIGS. 35A-35D are a schematic summary of the results of experiments perform to analyze mouse IL-12 and RSV F expression from monovalent and bivalent replicon vectors in BHK cells. BHK cells were electroporated with 3 μg of each replicon RNA. Cells were examined for the expression of IL-12 or RSV F by FACS analysis using protein-specific antibodies. Percent cells transfected was determined using dsRNA-specific antibody.
Figure 35B:
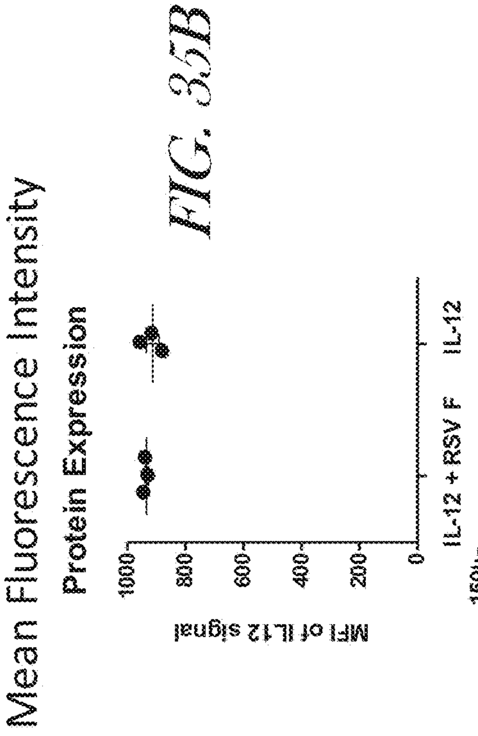
Figure 35C:
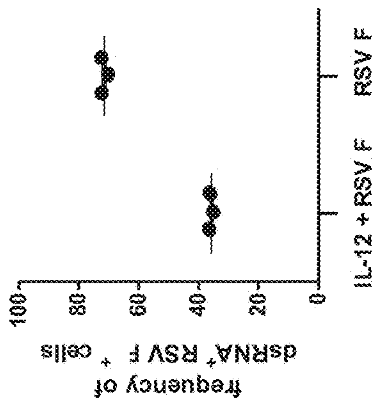
Figure 35D:
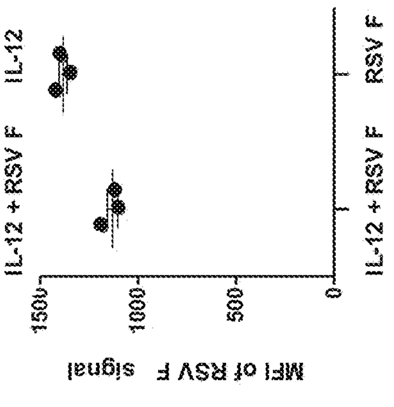
Figure 37:
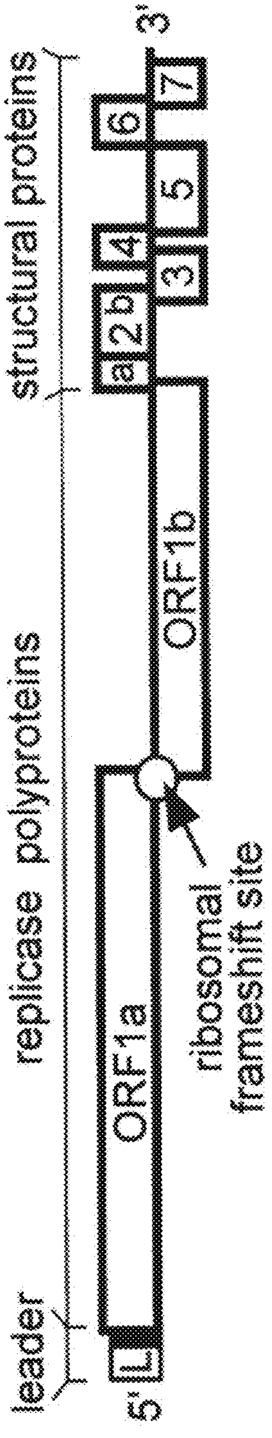
FIG. 37 is a schematic EAV genome.

Subsequently, the SHFv-R-TRS7-rFF replicon was further analyzed in vivo in Balb/c mice. In this experiment, 30 μg of RNA was injected into mice and whole body imaging was conducted. A summary of the results of these experiments is presented in FIG. 34. These data demonstrate the in vivo activity of the SHFv replicon vector and that it is equivalent to the EAV replicon.

Example 18

Antibody Expression Using EAV Replicon Expression Systems

Figure 33:
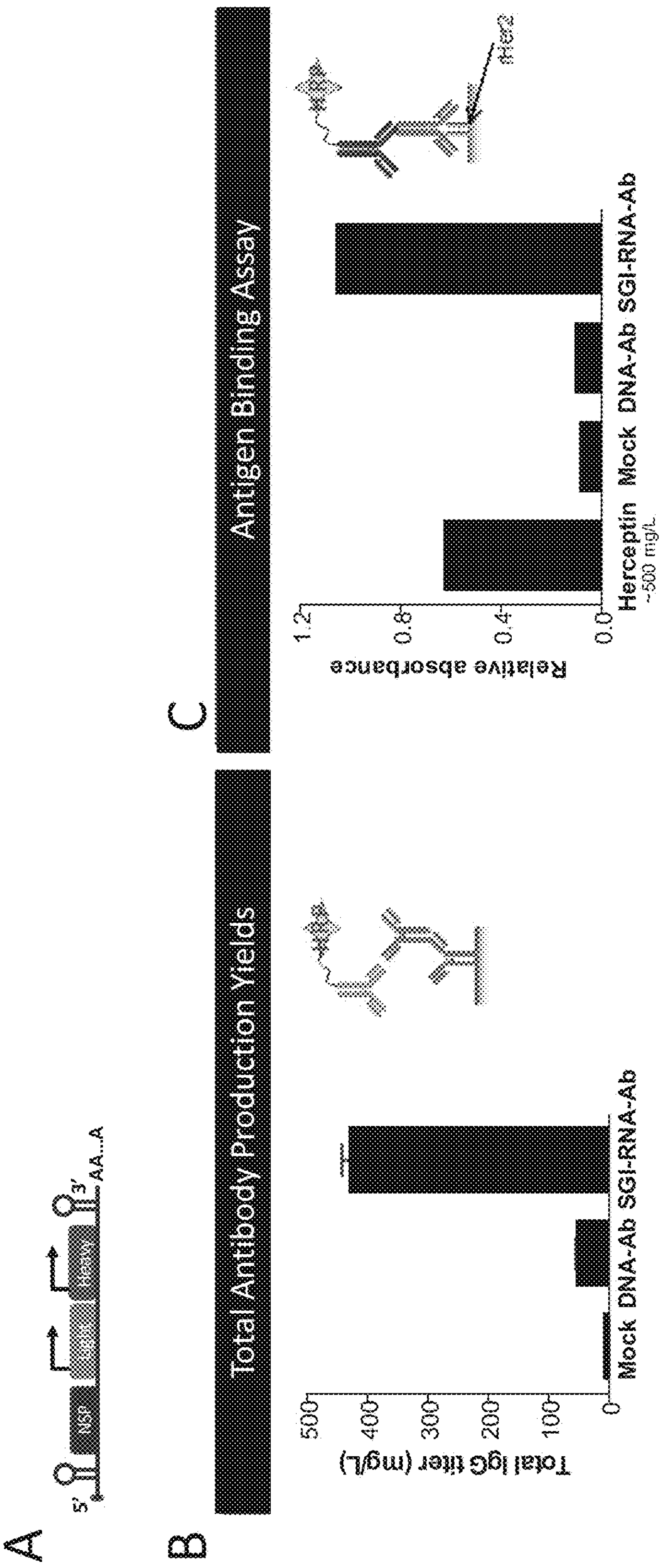
FIGS. 33A-33C pictorially summarize of the results of experiments perform to analyze antibody expression from EAV bivalent replicon vector in BHK cells. BHK cells were electroporated with 3 μg of rEx-herceptin (SGI-RNA-Ab) replicon RNA.

The EAV replicon has also been shown to express antibody constructs as well. The vector used for these experiments was rEx-herceptin. The light and heavy chain genes for the Herceptin monoclonal antibody were cloned into the either the first or second position within the replicon. Data collected from BHK cells electroporated with 3 μg of purified RNA from a representative rEx-herceptin construct are shown in FIG. 33A. The amount of antibody produced was determined by an ELISA procedure in which heavy chain capture and light chain detection to only measure complete antibody structures (FIG. 33B). The yields of antibody from the EAV replicon are ~10 times the amount expressed from an equivalent DNA construct. The expressed antibody was also used to detect Her2 antigen by ELISA to demonstrate activity of the antibody (FIG. 33C).

Example 19

EAV RSV and Cas9 Expression

Several additional genes have been cloned into EAV replicons. These additional genes include mouse IL-12, respiratory syncytial virus (RSV) F and cas9. A bivalent EAV replicon expressing IL-12 and RSV F was constructed along with monovalent versions of each. These replicon RNAs were electroporated into BHK-21 cells and examined for protein expression by flow cytometry using IL-12 and RSV F specific antibodies. The results of that analysis are shown in FIGS. 35A-35D. Both IL-12 and RSV F protein were readily detected in electroporated cells.

A cas9 gene optimized to use two different codon usages was cloned into the EAB replicon vector. RNA was generated from both cas9 replicon vectors and electroporated into BHK-21 cells. Eighteen hours post electroporation cell lysates were generated and different amounts of cell lysate were used to treat plasmid DNA. Guide RNA (gRNA) specific for a target sequence in the plasmid was added to the cell lysate and after incubation the DNA was analyzed on an agarose gel. The results of a representative experiment are shown in FIGS. 36A-36C. The cas9 protein expressed from the EAV replicon was able to cleave the plasmid DNA combined with the gRNA indicating that the enzyme was active.

Throughout this disclosure, various information sources are referred to and incorporated by reference. The information sources include, for example, scientific journal articles, patent documents, textbooks, and World Wide Web browser-inactive page addresses. The reference to such information sources is solely for the purpose of providing an indication of the general state of the art at the time of filing. While the contents and teachings of each and every one of the information sources can be relied on and used by one of skill in the art to make and use the embodiments disclosed herein, any discussion and comment in a specific information source should no way be considered as an admission that such comment was widely accepted as the general opinion in the field.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A nucleic acid molecule comprising a nucleotide sequence encoding a modified equine arterivirus genome or replicon RNA, wherein the modified equine arterivirus genome or replicon RNA comprises:

a sequence encoding an arterivirus replicase;

a sequence encoding a gene of interest;

a transcriptional regulatory sequence (TRS) for expressing the gene of interest;

a sequence fragment encoding an equine arterivirus open reading frame ORF7, wherein said sequence fragment is devoid of an ATG start codon or comprises an inactivated ATG start codon; and wherein the modified equine arterivirus genome or replicon RNA does not comprise an equine arterivirus open reading frame ORF2a.

2. The nucleic acid molecule of claim 1, wherein the modified arterivirus genome or replicon RNA is further devoid of equine arterivirus TRS7 or comprises an inactivated equine arterivirus TRS7.

3. The nucleic acid molecule of claim 1, further comprising at least one transcriptional termination signal sequence.

4. The nucleic acid molecule of claim 3, wherein the at least one transcriptional termination signal sequence is a mutated T7 transcriptional termination signal sequence comprising a nucleotide substitution selected from the group consisting of T9001G, T3185A, G3188A and combinations of any two or more thereof.

5. The nucleic acid molecule of claim 1, further comprising one or more spacer regions operably positioned adjacent to the TRS.

6. The nucleic acid molecule of claim 5 comprising a spacer region operably positioned 5' to the TRS and comprising 18-420 nucleotides.

7. The nucleic acid molecule of claim 5 comprising a spacer region operably positioned 5' to the TRS and comprising 20-350 nucleotides.

8. The nucleic acid molecule of claim 5 comprising a spacer region operably positioned 3' to the TRS and comprising 50-200 nucleotides.

9. The nucleic acid molecule of claim 8, comprising a spacer region operably positioned 3' to the TRS and consisting of about 98 nucleotides.

10. The nucleic acid molecule of claim 6, further comprising a spacer region operably positioned 3' to the TRS and consisting of about 98 nucleotides.

11. The nucleic acid molecule of claim 10, wherein the spacer region operably positioned 5' to TRS consists of about 343 nucleotides.

12. The nucleic acid molecule of claim 5, comprising a spacer region operably positioned 5' to the TRS and consisting of about 220 nucleotides or about 343 nucleotides.

13. The nucleic acid molecule of claim 1, comprising one or more expression cassettes, wherein each of the expression cassettes comprises a subgenomic promoter operably linked to a heterologous nucleotide sequence, the subgenomic promoter comprises the TRS and the heterologous nucleotide sequence comprises the gene of interest.

14. The nucleic acid molecule of claim 13, wherein the subgenomic promoter comprises an equine arterivirus TRS1.

15. The nucleic acid molecule of claim 1, wherein the arterivirus is a Bucyrus strain arterivirus.

16. The nucleic acid molecule of claim 1, wherein the gene of interest comprises an influenza hemagglutinin gene or a respiratory syncytial virus gene.

17. The nucleic acid of claim 16, wherein the influenza hemagglutinin gene comprises a sequence selected from the group consisting of: SEQ ID NOs: 20-23, and the respiratory syncytial virus gene comprises a respiratory syncytial virus fusion (F) gene selected from the group consisting of: SEQ ID NOs: 16-19.

18. The nucleic acid molecule of claim 1, wherein the modified arterivirus genome or replicon RNA is further devoid of at least a portion of a sequence encoding one or more of equine arterivirus ORF2b, ORF3, ORF4, ORF5a, and ORF5.

19. The nucleic acid molecule of claim 1, wherein the modified arterivirus genome or replicon RNA is devoid of the ATG start codon of an equine arterivirus ORF6.

20. The nucleic acid molecule of claim 1, wherein the transcription termination sequence comprises SEQ ID NO: 41.

21. The nucleic acid molecule of claim 20 wherein the modified arterivirus genome or replicon RNA comprises a first gene of interest and a second gene of interest.

22. The nucleic acid molecule of claim 21 comprising a TRS2 sequence for expressing the first gene of interest, and a TRS7 sequence for expressing the second gene of interest.

23. The nucleic acid molecule of claim 22 that expresses a gene of interest in a cell for more than four days.

24. The nucleic acid molecule of claim 1 wherein the gene of interest encodes an antibody molecule.

25. A recombinant cell comprising the nucleic acid molecule of claim 1.

26. A nucleic acid molecule comprising a nucleotide sequence encoding a modified equine arterivirus genome or replicon RNA, wherein the modified equine arterivirus genome or replicon RNA comprises:

a sequence encoding an arterivirus replicase;

an expression cassette comprising a transcriptional regulatory sequence (TRS) operably linked to a sequence encoding a gene of interest;

a sequence fragment encoding an equine arterivirus open reading frame ORF7, wherein said sequence fragment is devoid of an ATG start codon or comprises an inactivated ATG start codon;

a mutated T7 transcriptional termination signal sequence comprising a nucleotide substitution selected from the group consisting of T9001G, T3185A, G3188A and combinations of any two or more thereof; and one or more spacer regions operably positioned adjacent to the TRS;

wherein the modified equine arterivirus genome or replicon RNA does not comprise an equine arterivirus open reading frame ORF2a.

27. The nucleic acid molecule of claim 26, wherein the modified arterivirus genome or replicon RNA is further devoid of an equine arterivirus TRS7 or comprises an inactivated equine arterivirus TRS7.

28. The nucleic acid molecule of claim 26, wherein the modified arterivirus genome or replicon RNA is further devoid of at least a portion of a sequence encoding one or more of equine arterivirus ORF2b, ORF3, ORF4, ORF5a, and ORF5, or the ATG start codon of an equine arterivirus ORF6.

* * * * *

SEQUENCE LISTING

```
<160> NUMBER OF SEQ ID NOS: 53

<210> SEQ ID NO 1
<211> LENGTH: 9752
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Rep-EAV-WT replicon
<220> FEATURE:
<221> NAME/KEY: misc_feature
<223> OTHER INFORMATION: EAV genomic region encoding 5'-leader, ORF1a,
      and ORF1b

<400> SEQUENCE: 1

gctcgaagtg tgtatggtgc catatacggc tcaccaccat atacactgca agaattacta     60

ttcttgtggg cccctctcgg taaatcctag agggctttcc tctcgttatt gcgagattcg    120

tcgttagata acggcaagtt ccctttctta ctatcctatt ttcatcttgt ggcttgacgg    180

gtcactgcca tcgtcgtcga tctctatcaa ctacccttgc gactatggca accttctccg    240

ctactggatt tggagggagt tttgttaggg actggtccct ggacttaccc gacgcttgtg    300

agcatggcgc gggattgtgc tgcgaagtgg acggctccac cttatgcgcc gagtgttttc    360

gcggttgcga aggaatggag caatgtcctg gcttgttcat gggactgtta aaactggctt    420

cgccagttcc agtgggacat aagttcctga ttggttggta tcgagctgcc aaagtcaccg    480

ggcgttacaa tttccttgag ctgttgcaac accctgcttt cgcccagctg cgtgtggttg    540

atgctaggtt agccattgaa gaggcaagtg tgtttatttc cactgaccac gcgtctgcta    600

agcgtttccc tggcgctaga tttgcgctga caccggtgta tgctaacgct tgggttgtga    660

gcccggctgc taacagtttg atagtgacca ctgaccagga acaagatggg ttctgctggt    720

taaaactttt gccacctgac cgccgtgagg ctggtttgcg gttgtattac aaccattacc    780

gcgaacaaag gaccgggtgg ctgtctaaaa caggacttcg cttatggctt ggagacctgg    840

gtttgggcat caatgcgagc tctggagggc tgaaattcca cattatgagg ggttcgcctc    900

agcgagcttg gcatatcaca acacgcagct gcaagctgaa gagctactac gtttgtgaca    960

tctctgaagc agactggtcc tgtttgcctg ctggcaacta cggcggctac aatccaccag   1020
```

gggacggagc ttgcggttac aggtgcttgg ccttcatgaa tggcgccact gttgtgtcgg 1080
ctggttgcag ttctgacttg tggtgtgatg atgagttggc ttatcgagtc tttcaattgt 1140
cacccacgtt cacggttacc atcccaggtg ggcgagtttg tccgaatgcc aagtacgcaa 1200
tgatttgtga caagcagcac tggcgcgtca aacgtgcaaa gggcgtcggc ctgtgtctcg 1260
atgaaagctg tttcaggggc atctgcaatt gccaacgcat gagtggacca ccacctgcac 1320
ccgtgtcagc cgccgtgtta gatcacatac tggaggcggc gacgtttggc aacgttcgcg 1380
tggttacacc tgaagggcag ccacgccccg taccagcgcc gcgagttcgt cccagcgcca 1440
actcttctgg agatgtcaaa gatccggcgc ccgttccgcc agtaccaaaa ccaaggacca 1500
agcttgccac accgaaccca actcaggcgc ccatcccagc accgcgcacg cgacttcaag 1560
gggcctcaac acaggagcca ctggcgagtg caggagttgc ttctgactcg gcacctaaat 1620
ggcgtgtggc caaaactgtg tacagctccg cggagcgctt tcggaccgaa ctggtacaac 1680
gtgctcggtc cgttggggac gttcttgttc aagcgctacc gctcaaaacc ccagcagtgc 1740
agcggtatac catgactctg aagatgatgc gttcacgctt cagttggcac tgcgacgtgt 1800
ggtacccttt ggctgtaatc gcttgtttgc tccctatatg gccatctctt gctttgctcc 1860
ttagctttgc cattgggttg atacccagtg tgggcaataa tgttgttctg acagcgcttc 1920
tggtttcatc agctaattat gttgcgtcaa tggaccatca atgtgaaggt gcggcttgct 1980
tagccttgct ggaagaagaa cactattata gagcggtccg ttggcgcccg attacaggcg 2040
cgctgtcgct tgtgctcaat ttactggggc aggtaggcta tgtagctcgt tccacctttg 2100
atgcagctta tgttccttgc actgtgttcg atctttgcag ctttgctatt ctgtacctct 2160
gccgcaatcg ttgctggaga tgcttcggac gctgtgtgcg agttgggcct gccacgcatg 2220
ttttgggctc caccgggcaa cgagtttcca aactggcgct cattgatttg tgtgaccact 2280
tttcaaagcc caccatcgat gttgtgggca tggcaactgg ttggagcgga tgttacacag 2340
gaaccgccgc aatggagcgt cagtgtgcct ctacggtgga ccctcactcg ttcgaccaga 2400
agaaggcagg agcgactgtt tacctcaccc cccctgtcaa cagcgggtca gcgctgcagt 2460
gcctcaatgt catgtggaag cgaccaattg ggtccactgt ccttggggaa caaacaggag 2520
ctgttgtgac ggcggtcaag agtatctctt tctcacctcc ctgctgcgtc tctaccactt 2580
tgcccacccg acccggtgtg accgttgtcg accatgctct ttacaaccgg ttgactgctt 2640
caggggtcga tcccgcttta ttgcgtgttg ggcaaggtga ttttctaaaa cttaatccgg 2700
ggttccggct gataggtgga tggatttatg ggatatgcta ttttgtgttg gtggttgtgt 2760
caacttttac ctgcttacct atcaaatgtg gcattggcac ccgcgaccct ttctgccgca 2820
gagtgttttc tgtacccgtc accaagaccc aagagcactg ccatgctgga atgtgtgcta 2880
gcgctgaagg catctctctg gactctctgg ggttaactca gttacaaagt tactggatcg 2940
cagccgtcac tagcggatta gtgatcttgt tggtctgcca ccgcctggcc atcagcgcct 3000
tggacttgtt gactctagct tccccttag tgttgcttgt gttcccttgg gcatctgtgg 3060
ggcttttact tgcttgcagt ctcgctggtg ctgctgtgaa aatacagttg ttggcgacgc 3120
tttttgtgaa tctgttcttt ccccaagcta cccttgtcac tatgggatac tgggcgtgcg 3180
tggcggcttt ggccgtttac agtttgatgg gcttgcgagt gaaagtgaat gtgcccatgt 3240
gtgtgacacc tgcccatttt ctgctgctgg cgaggtcagc tggacagtca agagagcaga 3300
tgctccgggt cagcgctgct gcccccacca attcactgct tggagtggct cgtgattgtt 3360

-continued

```
atgtcacagg cacaactcgg ctgtacatac ccaaggaagg cgggatggtg tttgaagggc   3420

tattcaggtc accgaaggcg cgcggcaacg tcggcttcgt ggctggtagc agctacggca   3480

cagggtcagt gtggaccagg aacaacgagg tcgtcgtact gacagcgtca cacgtggttg   3540

gccgcgctaa catggccact ctgaagatcg gtgacgcaat gctgactctg actttcaaaa   3600

agaatggcga cttcgccgag gcagtgacga cacagtccga gctcccaggc aattggccac   3660

agttgcattt cgcccaacca acaaccgggc ccgcttcatg gtgcactgcc acaggagatg   3720

aagaaggctt gctcagtggc gaggtttgtc tggcgtggac tactagtggc gactctggat   3780

ctgcagtggt tcagggtgac gctgtggtag ggtccacac cggttcgaac acaagtggtg   3840

ttgcctacgt gaccaccca agcggaaaac tccttggcgc cgacaccgtg actttgtcat   3900

cactgtcaaa gcatttcaca ggccctttga catcaatccc gaaggacatc cctgacaaca   3960

ttattgccga tgttgatgct gttcctcgtt ctctggccat gctgattgat ggcttatcca   4020

atagagagag cagcctttct ggacctcagt tgttgttaat tgcttgtttt atgtggtctt   4080

atcttaacca acctgcttac ttgccttatg tgctgggctt ctttgccgct aacttcttcc   4140

tgccaaaaag tgttggccgc cctgtggtca ctgggcttct atggttgtgc tgcctcttca   4200

caccgctttc catgcgcttg tgcttgttcc atctggtctg tgctaccgtc acgggaaacg   4260

tgatatcttt gtggttctac atcactgccg ctggcacgtc ttacctttct gagatgtggt   4320

tcggaggcta tcccaccatg ttgtttgtgc cacggttcct agtgtaccag ttccccggct   4380

gggctattgg cacagtacta gcggtatgca gcatcaccat gctggctgct gccctcggtc   4440

acaccctgtt actggatgtg ttctccgcct caggtcgctt tgacaggact ttcatgatga   4500

aatacttcct ggagggagga gtgaaagaga gtgtcaccgc ctcagtcacc cgcgcttatg   4560

gcaaaccaat tacccaggag agtctcactg caacattagc tgccctcact gatgatgact   4620

tccaattcct ctctgatgtg cttgactgtc gggccgtccg atcggcaatg aatctgcgtg   4680

ccgctctcac aagttttcaa gtggcgcagt atcgtaacat ccttaatgca tccttgcaag   4740

tcgatcgtga cgctgctcgt agtcgcagac taatggcaaa actggctgat tttgcggttg   4800

aacaagaagt aacagctgga gaccgtgttg tggttatcga cggtctggac cgcatggctc   4860

acttcaaaga cgatttggtg ctggttcctt tgaccaccaa agtagtaggc ggttctaggt   4920

gcaccatttg tgacgtcgtt aaggaagaag ccaatgacac cccagttaag ccaatgccca   4980

gcaggagacg ccgcaagggc ctgcctaaag gtgctcagtt ggagtgggac cgtcaccagg   5040

aagagaagag gaacgccggt gatgatgatt ttgcggtctc gaatgattat gtcaagagag   5100

tgccaaagta ctgggatccc agcgacaccc gaggcacgac agtgaaaatc gccggcacta   5160

cctatcagaa agtggttgac tattcaggca atgtgcatta cgtggagcat caggaagatc   5220

tgctagacta cgtgctgggc aaggggagct atgaaggcct agatcaggac aaagtgttgg   5280

acctcacaaa catgcttaaa gtggacccca cggagctctc ctccaaagac aaagccaagg   5340

cgcgtcagct tgctcatctg ctgttggatc tggctaaccc agttgaggca gtgaatcagt   5400

taaactgaga gcgccccaca tctttcccgg cgatgtgggg cgtcggacct ttgctgactc   5460

taaagacaag ggtttcgtgg ctctacacag tcgcacaatg tttttagctg cccgggactt   5520

tttatttaac atcaaatttg tgtgcgacga agagttcaca aagaccccaa aagacacact   5580

gcttgggtac gtacgcgcct gccctggtta ctggtttatt ttccgtcgta cgcaccggtc   5640

gctgattgat gcatactggg acagtatgga gtgcgtttac gcgcttccca ccatatctga   5700

ttttgatgtg agcccaggtg acgtcgcagt gacgggcgag cgatgggatt ttgaatctcc   5760
```

```
cggaggaggc cgtgcaaaac gtctcacagc tgatctggtg cacgcttttc aagggttcca   5820
cggagcctct tattcctatg atgacaaggt ggcagctgct gtcagtggtg acccgtatcg   5880
gtcggacggc gtcttgtata acacccgttg ggcaacatt ccatattctg tcccaaccaa   5940
tgctttggaa gccacagctt gctaccgtgc tggatgtgag gccgttaccg acgggaccaa   6000
cgtcatcgca acaattgggc ccttcccgga gcaacaaccc ataccggaca tcccaaagag   6060
cgtgcttgac aactgcgctg acatcagctg tgacgctttc atagcgcccg ctgcagagac   6120
agccctgtgt ggagatttag agaaatacaa cctatccacg cagggttttg tgttgcctag   6180
tgttttctcc atggtgcggg cgtacttaaa agaggagatt ggagacgctc caccactcta   6240
cttgccatct actgtaccat ctaaaaattc acaagccgga attaacggcg ctgagtttcc   6300
tacaaagtct ttacagagct actgtttgat tgatgacatg gtgtcacagt ccatgaaaag   6360
caatctacaa accgccacca tggcgacttg taaacggcaa tactgttcca aatacaagat   6420
taggagcatt ctgggcacca acaattacat tggcctaggt ttgcgtgcct gcctttcggg   6480
ggttacggcc gcattccaaa aagctggaaa ggatgggtca ccgatttatt tgggcaagtc   6540
aaaattcgac ccgataccag ctcctgacaa gtactgcctt gaaacagacc tggagagttg   6600
tgatcgctcc accccggctt tggtgcgttg gttcgctact aatcttattt ttgagctagc   6660
tggccagccc gagttggtgc acagctacgt gttgaattgc tgtcacgatc tagttgtggc   6720
gggtagtgta gcattcacca aacgcggggg tttgtcatct ggagacccta tcacttccat   6780
ttccaatacc atctattcat tggtgctgta cacccagcac atgttgctat gtggacttga   6840
aggctatttc ccagagattg cagaaaaata tcttgatggc agcctggagc tgcgggacat   6900
gttcaagtac gttcgagtgt acatctactc ggacgatgtg gttctaacca cacccaacca   6960
gcattacgcg gccagctttg accgctgggt cccccacctg caggcgctgc taggtttcaa   7020
ggttgaccca aagaaaactg tgaacaccag ctccccttcc tttttgggct gccggttcaa   7080
gcaagtggac ggcaagtgtt atctagccag tcttcaggac cgcgttacac gctctctgtt   7140
ataccacatt ggtgcaaaga atccctcaga gtactatgaa gctgctgttt ccatctttaa   7200
ggactccatt atctgctgtg atgaagactg gtggacggac ctccatcgac gtatcagtgg   7260
cgctgcgcgt accgacggag ttgagttccc caccattgaa atgttaacat ccttccgcac   7320
caagcagtat gagagtgccg tgtgcacagt ttgtggggcc gcccccgtgg ccaagtctgc   7380
ttgtggaggg tggttctgtg gcaattgtgt cccgtaccac gcgggtcatt gtcacacaac   7440
ctcgctcttc gccaactgcg ggcacgacat catgtaccgc tccacttact gcacaatgtg   7500
tgagggttcc ccaaaacaga tggtaccaaa agtgcctcac ccgatcctgg atcatttgct   7560
gtgccacatt gattacggca gtaaagagga actaactctg gtagtggcgg atggtcgaac   7620
aacatcaccg cccgggcgct acaaagtggg tcacaaggta gtcgccgtgg ttgcagatgt   7680
gggaggcaac attgtgtttg ggtgcggtcc tggatcacac atcgcagtac cacttcagga   7740
tacgctcaag ggcgtggtgg tgaataaagc tctgaagaac gccgccgcct ctgagtacgt   7800
ggaaggaccc cctgggagtg ggaagacttt tcacctggtc aaagatgtgc tagccgtggt   7860
cggtagcgcg accttggttg tgcccaccca cgcgtccatg ctggactgca tcaacaagct   7920
caaacaagcg ggcgccgatc catactttgt ggtgcccaag tatacagttc ttgactttcc   7980
ccggcctggc agtggaaaca tcacagtgcg actgccacag gtcggaacca gtgagggaga   8000
aacctttgtg gatgaggtgg cctacttctc accagtggat ctggcgcgca ttttaaccca   8100
```

-continued

```
gggtcgagtc aagggttacg gtgatttaaa tcagctcggg tgcgtcggac ccgcgagcgt   8160

gccacgtaac ctttggctcc gacattttgt cagcctggag cccttgcgag tgtgccatcg   8220

attcggcgct gctgtgtgtg atttgatcaa gggcatttat ccttattatg agccagctcc   8280

acataccact aaagtggtgt ttgtgccaaa tccagacttt gagaaaggtg tagtcatcac   8340

cgcctaccac aaagatcgcg gtcttggtca ccgcacaatt gattcaattc aaggctgtac   8400

attccctgtt gtgactcttc gactgcccac accccaatca ctgacgcgcc cgcgcgcagt   8460

tgtggcggtt actagggcgt ctcaggaatt atacatctac gaccccttg atcagcttag   8520

cgggttgttg aagttcacca aggaagcaga ggcgcaggac ttgatccatg gcccacctac   8580

agcatgccac ctgggccaag aaattgacct ttggtccaat gagggcctcg aatattacaa   8640

ggaagtcaac ctgctgtaca cacacgtccc catcaaggat ggtgtaatac acagttaccc   8700

taattgtggc cctgcctgtg gctgggaaaa gcaatccaac aaaatttcgt gcctcccgag   8760

agtggcacaa aatttgggct accactattc cccagactta ccaggatttt gccccatacc   8820

aaaagaactc gctgagcatt ggcccgtagt gtccaatgat agatacccga attgcttgca   8880

aattacctta cagcaagtat gtgaactcag taaaccgtgc tcagcgggct atatggttgg   8940

acaatcggtt ttcgtgcaga cgcctggtgt gacatcttac tggcttactg aatgggtcga   9000

cggcaaagcg cgtgctctac cagattcctt attctcgtcc ggtaggttcg agactaacag   9060

ccgcgctttc ctcgatgaag ccgaggaaaa gtttgccgcc gctcaccctc atgcctgttt   9120

gggagaaatt aataagtcca ccgtgggagg atcccacttc atcttttccc aatatttacc   9180

accattgcta cccgcagacg ctgttgccct ggtaggtgct tcattggctg ggaaagctgc   9240

taaagctgct tgcagcgttg ttgatgtcta tgctccatca tttgaacctt atctacaccc   9300

tgagacactg agtcgcgtgt acaagattat gatcgatttc aagccgtgta ggcttatggt   9360

gtggagaaac gcgacctttt atgtccaaga gggtgttgat gcagttacat cagcactagc   9420

agctgtgtcc aaactcatca aagtgccggc caatgagcct gtttcattcc atgtggcatc   9480

agggtacaga accaacgcgc tggtagcgcc ccaggctaaa atttcaattg gagcctacgc   9540

cgccgagtgg gcactgtcaa ctgaaccgcc acctgctggt tatgcgatcg tgcggcgata   9600

tattgtaaag aggctcctca gctcaacaga agtgttcttg tgccgcaggg gtgttgtgtc   9660

ttccacctca gtgcagacca tttgtgcact agagggatgt aaacctctgt tcaacttctt   9720

acaaattggt tcagtcattg ggcccgtgtg ac                                9752
```

```
<210> SEQ ID NO 2
<211> LENGTH: 354
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Rep-EAV-WT replicon
<220> FEATURE:
<221> NAME/KEY: misc_feature
<223> OTHER INFORMATION: 354-nucleotide 3' terminal region of EAV genome

<400> SEQUENCE: 2

tcgaaacgga cggcggcgac agcctacaag ctacaatgac ctactgcgca tgtttggtca     60

gatgcgggtc cgcaaaccgc ccgcgcaacc cactcaggct attattgcag agcctggaga    120

ccttaggcat gatttaaatc aacaggagcg cgccaccctt tcgtcgaacg tacaacggtt    180

cttcatgatt gggcatggtt cactcactgc agatgccgga ggactcacgt acaccgtcag    240
```

-continued ttgggttcct accaaacaaa tccagcgcaa agttgcgcct ccagcagggc cgtaagacgt 300
ggatattctc ctgtgtggcg tcatgttgaa gtagttatta gccacccagg aacc 354

<210> SEQ ID NO 3
<211> LENGTH: 10124
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Rep-EAV-WT replicon
<220> FEATURE:
<221> NAME/KEY: misc_feature
<223> OTHER INFORMATION: Sequence contig for Rep-EAV-WT replicon; Include sequence of SEQ ID NO 1 and sequence of SEQ ID NO 2

<400> SEQUENCE: 3
gctcgaagtg tgtatggtgc catatacggc tcaccaccat atacactgca agaattacta 60
ttcttgtggg cccctctcgg taaatcctag agggctttcc tctcgttatt gcgagattcg 120
tcgttagata acggcaagtt ccctttctta ctatcctatt ttcatcttgt ggcttgacgg 180
gtcactgcca tcgtcgtcga tctctatcaa ctacccttgc gactatggca accttctccg 240
ctactggatt tggagggagt tttgttaggg actggtccct ggacttaccc gacgcttgtg 300
agcatggcgc gggattgtgc tgcgaagtgg acggctccac cttatgcgcc gagtgttttc 360
gcggttgcga aggaatggag caatgtcctg gcttgttcat gggactgtta aaactggctt 420
cgccagttcc agtgggacat aagttcctga ttggttggta tcgagctgcc aaagtcaccg 480
ggcgttacaa tttccttgag ctgttgcaac accctgcttt cgcccagctg cgtgtggttg 540
atgctaggtt agccattgaa gaggcaagtg tgtttatttc cactgaccac gcgtctgcta 600
agcgtttccc tggcgctaga tttgcgctga caccggtgta tgctaacgct tgggttgtga 660
gcccggctgc taacagtttg atagtgacca ctgaccagga acaagatggg ttctgctggt 720
taaaactttt gccacctgac cgccgtgagg ctggtttgcg gttgtattac aaccattacc 780
gcgaacaaag gaccgggtgg ctgtctaaaa caggacttcg cttatggctt ggagacctgg 840
gtttgggcat caatgcgagc tctggagggc tgaaattcca cattatgagg ggttcgcctc 900
agcgagcttg gcatatcaca acacgcagct gcaagctgaa gagctactac gtttgtgaca 960
tctctgaagc agactggtcc tgtttgcctg ctggcaacta cggcggctac aatccaccag 1020
gggacggagc ttgcggttac aggtgcttgg ccttcatgaa tggcgccact gttgtgtcgg 1080
ctggttgcag ttctgacttg tggtgtgatg atgagttggc ttatcgagtc tttcaattgt 1140
cacccacgtt cacggttacc atcccaggtg ggcgagtttg tccgaatgcc aagtacgcaa 1200
tgatttgtga caagcagcac tggcgcgtca aacgtgcaaa gggcgtcggc ctgtgtctcg 1260
atgaaagctg tttcaggggc atctgcaatt gccaacgcat gagtggacca ccacctgcac 1320
ccgtgtcagc cgccgtgtta gatcacatac tggaggcggc gacgtttggc aacgttcgcg 1380
tggttacacc tgaagggcag ccacgccccg taccagcgcc gcgagttcgt cccagcgcca 1440
actcttctgg agatgtcaaa gatccggcgc ccgttccgcc agtaccaaaa ccaaggacca 1500
agcttgccac accgaaccca actcaggcgc ccatcccagc accgcgcacg cgacttcaag 1560
gggcctcaac acaggagcca ctggcgagtg caggagttgc ttctgactcg gcacctaaat 1620
ggcgtgtggc caaaactgtg tacagctccg cggagcgctt tcggaccgaa ctggtacaac 1680
gtgctcggtc cgttggggac gttcttgttc aagcgctacc gctcaaaacc ccagcagtgc 1740

-continued agcggtatac catgactctg aagatgatgc gttcacgctt cagttggcac tgcgacgtgt 1800
ggtacccttt ggctgtaatc gcttgtttgc tccctatatg gccatctctt gctttgctcc 1860
ttagctttgc cattgggttg atacccagtg tgggcaataa tgttgttctg acagcgcttc 1920
tggtttcatc agctaattat gttgcgtcaa tggaccatca atgtgaaggt gcggcttgct 1980
tagccttgct ggaagaagaa cactattata gagcggtccg ttggcgcccg attacaggcg 2040
cgctgtcgct tgtgctcaat ttactggggc aggtaggcta tgtagctcgt tccacctttg 2100
atgcagctta tgttccttgc actgtgttcg atctttgcag ctttgctatt ctgtacctct 2160
gccgcaatcg ttgctggaga tgcttcggac gctgtgtgcg agttgggcct gccacgcatg 2220
ttttgggctc caccgggcaa cgagtttcca aactggcgct cattgatttg tgtgaccact 2280
tttcaaagcc caccatcgat gttgtgggca tggcaactgg ttggagcgga tgttacacag 2340
gaaccgccgc aatggagcgt cagtgtgcct ctacggtgga ccctcactcg ttcgaccaga 2400
agaaggcagg agcgactgtt tacctcaccc cccctgtcaa cagcgggtca gcgctgcagt 2460
gcctcaatgt catgtggaag cgaccaattg ggtccactgt ccttggggaa caaacaggag 2520
ctgttgtgac ggcggtcaag agtatctctt tctcacctcc ctgctgcgtc tctaccactt 2580
tgcccacccg acccggtgtg accgttgtcg accatgctct ttacaaccgg ttgactgctt 2640
caggggtcga tcccgcttta ttgcgtgttg ggcaaggtga ttttctaaaa cttaatccgg 2700
ggttccggct gataggtgga tggatttatg ggatatgcta ttttgtgttg gtggttgtgt 2760
caacttttac ctgcttacct atcaaatgtg gcattggcac ccgcgaccct ttctgccgca 2820
gagtgttttc tgtacccgtc accaagaccc aagagcactg ccatgctgga atgtgtgcta 2880
gcgctgaagg catctctctg gactctctgg ggttaactca gttacaaagt tactggatcg 2940
cagccgtcac tagcggatta gtgatcttgt tggtctgcca ccgcctggcc atcagcgcct 3000
tggacttgtt gactctagct tccccttag tgttgcttgt gttcccttgg gcatctgtgg 3060
ggcttttact tgcttgcagt ctcgctggtg ctgctgtgaa aatacagttg ttggcgacgc 3120
tttttgtgaa tctgttcttt ccccaagcta cccttgtcac tatgggatac tgggcgtgcg 3180
tggcggcttt ggccgtttac agtttgatgg gcttgcgagt gaaagtgaat gtgcccatgt 3240
gtgtgacacc tgcccatttt ctgctgctgg cgaggtcagc tggacagtca agagagcaga 3300
tgctccgggt cagcgctgct gcccccacca attcactgct tggagtggct cgtgattgtt 3360
atgtcacagg cacaactcgg ctgtacatac ccaaggaagg cgggatggtg tttgaagggc 3420
tattcaggtc accgaaggcg cgcggcaacg tcggcttcgt ggctggtagc agctacggca 3480
cagggtcagt gtggaccagg aacaacgagg tcgtcgtact gacagcgtca cacgtggttg 3540
gccgcgctaa catggccact ctgaagatcg gtgacgcaat gctgactctg actttcaaaa 3600
agaatggcga cttcgccgag gcagtgacga cacagtccga gctcccaggc aattggccac 3660
agttgcattt cgcccaacca acaaccgggc ccgcttcatg gtgcactgcc acaggagatg 3720
aagaaggctt gctcagtggc gaggtttgtc tggcgtggac tactagtggc gactctggat 3780
ctgcagtggt tcagggtgac gctgtggtag gggtccacac cggttcgaac acaagtggtg 3840
ttgcctacgt gaccacccca agcggaaaac tccttggcgc cgacaccgtg actttgtcat 3900
cactgtcaaa gcatttcaca ggccctttga catcaatccc gaaggacatc cctgacaaca 3960
ttattgccga tgttgatgct gttcctcgtt ctctggccat gctgattgat ggcttatcca 4020
atagagagag cagcctttct ggacctcagt tgttgttaat tgcttgtttt atgtggtctt 4080

-continued atcttaacca acctgcttac ttgccttatg tgctgggctt ctttgccgct aacttcttcc 4140
tgccaaaaag tgttggccgc cctgtggtca ctgggcttct atggttgtgc tgcctcttca 4200
caccgctttc catgcgcttg tgcttgttcc atctggtctg tgctaccgtc acgggaaacg 4260
tgatatcttt gtggttctac atcactgccg ctggcacgtc ttacctttct gagatgtggt 4320
tcggaggcta tcccaccatg ttgtttgtgc cacggttcct agtgtaccag ttccccggct 4380
gggctattgg cacagtacta gcggtatgca gcatcaccat gctggctgct gccctcggtc 4440
acaccctgtt actggatgtg ttctccgcct caggtcgctt tgacaggact ttcatgatga 4500
aatacttcct ggagggagga gtgaaagaga gtgtcaccgc ctcagtcacc cgcgcttatg 4560
gcaaaccaat tacccaggag agtctcactg caacattagc tgccctcact gatgatgact 4620
tccaattcct ctctgatgtg cttgactgtc gggccgtccg atcggcaatg aatctgcgtg 4680
ccgctctcac aagttttcaa gtggcgcagt atcgtaacat ccttaatgca tccttgcaag 4740
tcgatcgtga cgctgctcgt agtcgcagac taatggcaaa actggctgat tttgcggttg 4800
aacaagaagt aacagctgga gaccgtgttg tggttatcga cggtctggac cgcatggctc 4860
acttcaaaga cgatttggtg ctggttcctt tgaccaccaa agtagtaggc ggttctaggt 4920
gcaccatttg tgacgtcgtt aaggaagaag ccaatgacac cccagttaag ccaatgccca 4980
gcaggagacg ccgcaagggc ctgcctaaag gtgctcagtt ggagtgggac cgtcaccagg 5040
aagagaagag gaacgccggt gatgatgatt ttgcggtctc gaatgattat gtcaagagag 5100
tgccaaagta ctgggatccc agcgacaccc gaggcacgac agtgaaaatc gccggcacta 5160
cctatcagaa agtggttgac tattcaggca atgtgcatta cgtggagcat caggaagatc 5220
tgctagacta cgtgctgggc aaggggagct atgaaggcct agatcaggac aaagtgttgg 5280
acctcacaaa catgcttaaa gtggacccca cggagctctc ctccaaagac aaagccaagg 5340
cgcgtcagct tgctcatctg ctgttggatc tggctaaccc agttgaggca gtgaatcagt 5400
taaactgaga gcgccccaca tctttcccgg cgatgtgggg cgtcggacct ttgctgactc 5460
taaagacaag ggtttcgtgg ctctacacag tcgcacaatg tttttagctg cccgggactt 5520
tttatttaac atcaaatttg tgtgcgacga agagttcaca aagaccccaa aagacacact 5580
gcttgggtac gtacgcgcct gccctggtta ctggtttatt ttccgtcgta cgcaccggtc 5640
gctgattgat gcatactggg acagtatgga gtgcgtttac gcgcttccca ccatatctga 5700
ttttgatgtg agcccaggtg acgtcgcagt gacgggcgag cgatgggatt ttgaatctcc 5760
cggaggaggc cgtgcaaaac gtctcacagc tgatctggtg cacgcttttc aagggttcca 5820
cggagcctct tattcctatg atgacaaggt ggcagctgct gtcagtggtg acccgtatcg 5880
gtcggacggc gtcttgtata acacccgttg gggcaacatt ccatattctg tcccaaccaa 5940
tgctttggaa gccacagctt gctaccgtgc tggatgtgag gccgttaccg acggaccaa 6000
cgtcatcgca acaattgggc ccttcccgga gcaacaaccc ataccggaca tcccaaagag 6060
cgtgcttgac aactgcgctg acatcagctg tgacgctttc atagcgcccg ctgcagagac 6120
agccctgtgt ggagatttag agaaatacaa cctatccacg cagggttttg tgttgcctag 6180
tgttttctcc atggtgcggg cgtacttaaa agaggagatt ggagacgctc caccactcta 6240
cttgccatct actgtaccat ctaaaaattc acaagccgga attaacggcg ctgagtttcc 6300
tacaaagtct ttacagagct actgtttgat tgatgacatg gtgtcacagt ccatgaaaag 6360
caatctacaa accgccacca tggcgacttg taaacggcaa tactgttcca aatacaagat 6420
taggagcatt ctgggcacca acaattacat tggcctaggt ttgcgtgcct gcctttcggg 6480

-continued ggttacggcc gcattccaaa aagctggaaa ggatgggtca ccgatttatt tgggcaagtc 6540
aaaattcgac ccgataccag ctcctgacaa gtactgcctt gaaacagacc tggagagttg 6600
tgatcgctcc accccggctt tggtgcgttg gttcgctact aatcttattt ttgagctagc 6660
tggccagccc gagttggtgc acagctacgt gttgaattgc tgtcacgatc tagttgtggc 6720
gggtagtgta gcattcacca aacgcggggg tttgtcatct ggagacccta tcacttccat 6780
ttccaatacc atctattcat tggtgctgta cacccagcac atgttgctat gtggacttga 6840
aggctatttc ccagagattg cagaaaaata tcttgatggc agcctggagc tgcgggacat 6900
gttcaagtac gttcgagtgt acatctactc ggacgatgtg gttctaacca cacccaacca 6960
gcattacgcg gccagctttg accgctgggt cccccacctg caggcgctgc taggtttcaa 7020
ggttgaccca aagaaaactg tgaacaccag ctccccttcc tttttgggct gccggttcaa 7080
gcaagtggac ggcaagtgtt atctagccag tcttcaggac cgcgttacac gctctctgtt 7140
ataccacatt ggtgcaaaga atccctcaga gtactatgaa gctgctgttt ccatctttaa 7200
ggactccatt atctgctgtg atgaagactg gtggacggac ctccatcgac gtatcagtgg 7260
cgctgcgcgt accgacggag ttgagttccc caccattgaa atgttaacat ccttccgcac 7320
caagcagtat gagagtgccg tgtgcacagt ttgtggggcc gcccccgtgg ccaagtctgc 7380
ttgtggaggg tggttctgtg gcaattgtgt cccgtaccac gcgggtcatt gtcacacaac 7440
ctcgctcttc gccaactgcg ggcacgacat catgtaccgc tccacttact gcacaatgtg 7500
tgagggttcc ccaaaacaga tggtaccaaa agtgcctcac ccgatcctgg atcatttgct 7560
gtgccacatt gattacggca gtaaagagga actaactctg gtagtggcgg atggtcgaac 7620
aacatcaccg cccgggcgct acaaagtggg tcacaaggta gtcgccgtgg ttgcagatgt 7680
gggaggcaac attgtgtttg ggtgcggtcc tggatcacac atcgcagtac cacttcagga 7740
tacgctcaag ggcgtggtgg tgaataaagc tctgaagaac gccgccgcct ctgagtacgt 7800
ggaaggaccc cctgggagtg ggaagacttt tcacctggtc aaagatgtgc tagccgtggt 7860
cggtagcgcg accttggttg tgcccaccca cgcgtccatg ctggactgca tcaacaagct 7920
caaacaagcg ggcgccgatc catactttgt ggtgcccaag tatacagttc ttgactttcc 7980
ccggcctggc agtggaaaca tcacagtgcg actgccacag gtcggaacca gtgagggaga 8040
aacctttgtg gatgaggtgg cctacttctc accagtggat ctggcgcgca ttttaaccca 8100
gggtcgagtc aagggttacg gtgatttaaa tcagctcggg tgcgtcggac ccgcgagcgt 8160
gccacgtaac ctttggctcc gacattttgt cagcctggag cccttgcgag tgtgccatcg 8220
attcggcgct gctgtgtgtg atttgatcaa gggcatttat ccttattatg agccagctcc 8280
acataccact aaagtggtgt ttgtgccaaa tccagacttt gagaaaggtg tagtcatcac 8340
cgcctaccac aaagatcgcg gtcttggtca ccgcacaatt gattcaattc aaggctgtac 8400
attccctgtt gtgactcttc gactgcccac accccaatca ctgacgcgcc cgcgcgcagt 8460
tgtggcggtt actagggcgt ctcaggaatt atacatctac gaccccttg atcagcttag 8520
cgggttgttg aagttcacca aggaagcaga ggcgcaggac ttgatccatg gcccacctac 8580
agcatgccac ctgggccaag aaattgacct ttggtccaat gagggcctcg aatattacaa 8640
ggaagtcaac ctgctgtaca cacacgtccc catcaaggat ggtgtaatac acagttaccc 8700
taattgtggc cctgcctgtg gctgggaaaa gcaatccaac aaaatttcgt gcctcccgag 8760
agtggcacaa aatttgggct accactattc cccagactta ccaggatttt gccccatacc 8820

-continued aaaagaactc gctgagcatt ggcccgtagt gtccaatgat agatacccga attgcttgca 8880
aattacctta cagcaagtat gtgaactcag taaaccgtgc tcagcgggct atatggttgg 8940
acaatcggtt ttcgtgcaga cgcctggtgt gacatcttac tggcttactg aatgggtcga 9000
cggcaaagcg cgtgctctac cagattcctt attctcgtcc ggtaggttcg agactaacag 9060
ccgcgctttc ctcgatgaag ccgaggaaaa gtttgccgcc gctcaccctc atgcctgttt 9120
gggagaaatt aataagtcca ccgtgggagg atcccacttc atcttttccc aatatttacc 9180
accattgcta cccgcagacg ctgttgccct ggtaggtgct tcattggctg ggaaagctgc 9240
taaagctgct tgcagcgttg ttgatgtcta tgctccatca tttgaacctt atctacaccc 9300
tgagacactg agtcgcgtgt acaagattat gatcgatttc aagccgtgta ggcttatggt 9360
gtggagaaac gcgacctttt atgtccaaga gggtgttgat gcagttacat cagcactagc 9420
agctgtgtcc aaactcatca aagtgccggc caatgagcct gtttcattcc atgtggcatc 9480
agggtacaga accaacgcgc tggtagcgcc ccaggctaaa atttcaattg gagcctacgc 9540
cgccgagtgg gcactgtcaa ctgaaccgcc acctgctggt tatgcgatcg tgcggcgata 9600
tattgtaaag aggctcctca gctcaacaga agtgttcttg tgccgcaggg gtgttgtgtc 9660
ttccacctca gtgcagacca tttgtgcact agagggatgt aaacctctgt tcaacttctt 9720
acaaattggt tcagtcattg ggcccgtgtg actctagatt ataactcgag tcgaaacgga 9780
cggcggcgac agcctacaag ctacaatgac ctactgcgca tgtttggtca gatgcgggtc 9840
cgcaaaccgc ccgcgcaacc cactcaggct attattgcag agcctggaga ccttaggcat 9900
gatttaaatc aacaggagcg cgccaccctt tcgtcgaacg tacaacggtt cttcatgatt 9960
gggcatggtt cactcactgc agatgccgga ggactcacgt acaccgtcag ttgggttcct 10020
accaaacaaa tccagcgcaa agttgcgcct ccagcagggc cgtaagacgt ggatattctc 10080
ctgtgtggcg tcatgttgaa gtagttatta gccacccagg aacc 10124

<210> SEQ ID NO 4
<211> LENGTH: 3266
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: EAV F1

<400> SEQUENCE: 4
gctcgaagtg tgtatggtgc catatacggc tcaccaccat atacactgca agaattacta 60
ttcttgtggg cccctctcgg taaatcctag agggctttcc tctcgttatt gcgagattcg 120
tcgttagata acggcaagtt ccctttctta ctatcctatt ttcatcttgt ggcttgacgg 180
gtcactgcca tcgtcgtcga tctctatcaa ctacccttgc gactatggca accttctccg 240
ctactggatt tggagggagt tttgttaggg actggtccct ggacttaccc gacgcttgtg 300
agcatggcgc gggattgtgc tgcgaagtgg acggctccac cttatgcgcc gagtgttttc 360
gcggttgcga aggaatggag caatgtcctg gcttgttcat gggactgtta aaactggctt 420
cgccagttcc agtgggacat aagttcctga ttggttggta tcgagctgcc aaagtcaccg 480
ggcgttacaa tttccttgag ctgttgcaac accctgcttt cgcccagctg cgtgtggttg 540
atgctaggtt agccattgaa gaggcaagtg tgtttatttc cactgaccac gcgtctgcta 600
agcgtttccc tggcgctaga tttgcgctga caccggtgta tgctaacgct tgggttgtga 660

-continued

```
gcccggctgc taacagtttg atagtgacca ctgaccagga acaagatggg ttctgctggt    720
taaaactttt gccacctgac cgccgtgagg ctggtttgcg gttgtattac aaccattacc    780
gcgaacaaag gaccgggtgg ctgtctaaaa caggacttcg cttatggctt ggagacctgg    840
gtttgggcat caatgcgagc tctggagggc tgaaattcca cattatgagg ggttcgcctc    900
agcgagcttg gcatatcaca acacgcagct gcaagctgaa gagctactac gtttgtgaca    960
tctctgaagc agactggtcc tgtttgcctg ctggcaacta cggcggctac aatccaccag   1020
gggacggagc ttgcggttac aggtgcttgg ccttcatgaa tggcgccact gttgtgtcgg   1080
ctggttgcag ttctgacttg tggtgtgatg atgagttggc ttatcgagtc tttcaattgt   1140
cacccacgtt cacggttacc atcccaggtg ggcgagtttg tccgaatgcc aagtacgcaa   1200
tgatttgtga caagcagcac tggcgcgtca aacgtgcaaa gggcgtcggc ctgtgtctcg   1260
atgaaagctg tttcaggggc atctgcaatt gccaacgcat gagtggacca ccacctgcac   1320
ccgtgtcagc cgccgtgtta gatcacatac tggaggcggc gacgtttggc aacgttcgcg   1380
tggttacacc tgaagggcag ccacgccccg taccagcgcc gcgagttcgt cccagcgcca   1440
actcttctgg agatgtcaaa gatccggcgc ccgttccgcc agtaccaaaa ccaaggacca   1500
agcttgccac accgaaccca actcaggcgc ccatcccagc accgcgcacg cgacttcaag   1560
gggcctcaac acaggagcca ctggcgagtg caggagttgc ttctgactcg gcacctaaat   1620
ggcgtgtggc caaaactgtg tacagctccg cggagcgctt tcggaccgaa ctggtacaac   1680
gtgctcggtc cgttggggac gttcttgttc aagcgctacc gctcaaaacc ccagcagtgc   1740
agcggtatac catgactctg aagatgatgc gttcacgctt cagttggcac tgcgacgtgt   1800
ggtacccttt ggctgtaatc gcttgtttgc tccctatatg gccatctctt gctttgctcc   1860
ttagctttgc cattgggttg atacccagtg tgggcaataa tgttgttctg acagcgcttc   1920
tggtttcatc agctaattat gttgcgtcaa tggaccatca atgtgaaggt gcggcttgct   1980
tagccttgct ggaagaagaa cactattata gagcggtccg ttggcgcccg attacaggcg   2040
cgctgtcgct tgtgctcaat ttactggggc aggtaggcta tgtagctcgt tccacctttg   2100
atgcagctta tgttccttgc actgtgttcg atctttgcag ctttgctatt ctgtacctct   2160
gccgcaatcg ttgctggaga tgcttcggac gctgtgtgcg agttgggcct gccacgcatg   2220
ttttgggctc caccgggcaa cgagtttcca aactggcgct cattgatttg tgtgaccact   2280
tttcaaagcc caccatcgat gttgtgggca tggcaactgg ttggagcgga tgttacacag   2340
gaaccgccgc aatggagcgt cagtgtgcct ctacggtgga ccctcactcg ttcgaccaga   2400
agaaggcagg agcgactgtt tacctcaccc cccctgtcaa cagcgggtca gcgctgcagt   2460
gcctcaatgt catgtggaag cgaccaattg ggtccactgt ccttggggaa caaacaggag   2520
ctgttgtgac ggcggtcaag agtatctctt tctcacctcc ctgctgcgtc tctaccactt   2580
tgcccacccg acccggtgtg accgttgtcg accatgctct ttacaaccgg ttgactgctt   2640
caggggtcga tcccgcttta ttgcgtgttg ggcaaggtga ttttctaaaa cttaatccgg   2700
ggttccggct gataggtgga tggatttatg ggatatgcta ttttgtgttg gtggttgtgt   2760
caacttttac ctgcttacct atcaaatgtg gcattggcac ccgcgaccct ttctgccgca   2820
gagtgttttc tgtacccgtc accaagaccc aagagcactg ccatgctgga atgtgtgcta   2880
gcgctgaagg catctctctg gactctctgg ggttaactca gttacaaagt tactggatcg   2940
cagccgtcac tagcggatta gtgatcttgt tggtctgcca ccgcctggcc atcagcgcct   3000
tggacttgtt gactctagct tccccttag tgttgcttgt gttcccttgg gcatctgtgg    3060
```

ggcttttact tgcttgcagt ctcgctggtg ctgctgtgaa aatacagttg ttggcgacgc 3120
tttttgtgaa tctgttcttt ccccaagcta cccttgtcac tatgggatac tgggcgtgcg 3180
tggcggcttt ggccgtttac agtttgatgg gcttgcgagt gaaagtgaat gtgcccatgt 3240
gtgtgacacc tgcccatttt ctgctg 3266

<210> SEQ ID NO 5
<211> LENGTH: 3376
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: EAV F2

<400> SEQUENCE: 5
gagtgaaagt gaatgtgccc atgtgtgtga cacctgccca ttttctgctg ctggcgaggt 60
cagctggaca gtcaagagag cagatgctcc gggtcagcgc tgctgccccc accaattcac 120
tgcttggagt ggctcgtgat tgttatgtca caggcacaac tcggctgtac atacccaagg 180
aaggcgggat ggtgtttgaa gggctattca ggtcaccgaa ggcgcgcggc aacgtcggct 240
tcgtggctgg tagcagctac ggcacagggt cagtgtggac caggaacaac gaggtcgtcg 300
tactgacagc gtcacacgtg gttggccgcg ctaacatggc cactctgaag atcggtgacg 360
caatgctgac tctgactttc aaaaagaatg gcgacttcgc cgaggcagtg acgacacagt 420
ccgagctccc aggcaattgg ccacagttgc atttcgccca accaacaacc gggcccgctt 480
catggtgcac tgccacagga gatgaagaag gcttgctcag tggcgaggtt tgtctggcgt 540
ggactactag tggcgactct ggatctgcag tggttcaggg tgacgctgtg gtaggggtcc 600
acaccggttc gaacacaagt ggtgttgcct acgtgaccac cccaagcgga aaactccttg 660
gcgccgacac cgtgactttg tcatcactgt caaagcattt cacaggccct ttgacatcaa 720
tcccgaagga catccctgac aacattattg ccgatgttga tgctgttcct cgttctctgg 780
ccatgctgat tgatggctta tccaatagag agagcagcct ttctggacct cagttgttgt 840
taattgcttg ttttatgtgg tcttatctta accaacctgc ttacttgcct tatgtgctgg 900
gcttctttgc cgctaacttc ttcctgccaa aaagtgttgg ccgccctgtg gtcactgggc 960
ttctatggtt gtgctgcctc ttcacaccgc tttccatgcg cttgtgcttg ttccatctgg 1020
tctgtgctac cgtcacggga aacgtgatat ctttgtggtt ctacatcact gccgctggca 1080
cgtcttacct ttctgagatg tggttcggag gctatcccac catgttgttt gtgccacggt 1140
tcctagtgta ccagttcccc ggctgggcta ttggcacagt actagcggta tgcagcatca 1200
ccatgctggc tgctgccctc ggtcacaccc tgttactgga tgtgttctcc gcctcaggtc 1260
gctttgacag gactttcatg atgaaatact tcctggaggg aggagtgaaa gagagtgtca 1320
ccgcctcagt cacccgcgct tatggcaaac caattaccca ggagagtctc actgcaacat 1380
tagctgccct cactgatgat gacttccaat tcctctctga tgtgcttgac tgtcgggccg 1440
tccgatcggc aatgaatctg cgtgccgctc tcacaagttt tcaagtggcg cagtatcgta 1500
acatccttaa tgcatccttg caagtcgatc gtgacgctgc tcgtagtcgc agactaatgg 1560
caaaactggc tgattttgcg gttgaacaag aagtaacagc tggagaccgt gttgtggtta 1620
tcgacggtct ggaccgcatg gctcacttca aagacgattt ggtgctggtt cctttgacca 1680
ccaaagtagt aggcggttct aggtgcacca tttgtgacgt cgttaaggaa gaagccaatg 1740
acaccccagt taagccaatg cccagcagga gacgccgcaa gggcctgcct aaaggtgctc 1800
agttggagtg ggaccgtcac caggaagaga agaggaacgc cggtgatgat gattttgcgg 1860
tctcgaatga ttatgtcaag agagtgccaa agtactggga tcccagcgac acccgaggca 1920
cgacagtgaa aatcgccggc actacctatc agaaagtggt tgactattca ggcaatgtgc 1980
attacgtgga gcatcaggaa gatctgctag actacgtgct gggcaagggg agctatgaag 2040
gcctagatca ggacaaagtg ttggacctca caaacatgct taaagtggac cccacggagc 2100
tctcctccaa agacaaagcc aaggcgcgtc agcttgctca tctgctgttg gatctggcta 2160
acccagttga ggcagtgaat cagttaaact gagagcgccc cacatctttc ccggcgatgt 2220
ggggcgtcgg acctttgctg actctaaaga caagggtttc gtggctctac acagtcgcac 2280
aatgttttta gctgcccggg actttttatt taacatcaaa tttgtgtgcg acgaagagtt 2340
cacaaagacc ccaaaagaca cactgcttgg gtacgtacgc gcctgccctg gttactggtt 2400
tattttccgt cgtacgcacc ggtcgctgat tgatgcatac tgggacagta tggagtgcgt 2460
ttacgcgctt cccaccatat ctgattttga tgtgagccca ggtgacgtcg cagtgacggg 2520
cgagcgatgg gattttgaat ctcccggagg aggccgtgca aaacgtctca cagctgatct 2580
ggtgcacgct tttcaagggt tccacggagc ctcttattcc tatgatgaca aggtggcagc 2640
tgctgtcagt ggtgacccgt atcggtcgga cggcgtcttg tataacaccc gttggggcaa 2700
cattccatat tctgtcccaa ccaatgcttt ggaagccaca gcttgctacc gtgctggatg 2760
tgaggccgtt accgacggga ccaacgtcat cgcaacaatt gggcccttcc cggagcaaca 2820
acccataccg gacatcccaa agagcgtgct tgacaactgc gctgacatca gctgtgacgc 2880
tttcatagcg cccgctgcag agacagccct gtgtggagat ttagagaaat acaacctatc 2940
cacgcagggt tttgtgttgc ctagtgtttt ctccatggtg cgggcgtact taaaagagga 3000
gattggagac gctccaccac tctacttgcc atctactgta ccatctaaaa attcacaagc 3060
cggaattaac ggcgctgagt ttcctacaaa gtctttacag agctactgtt tgattgatga 3120
catggtgtca cagtccatga aaagcaatct acaaaccgcc accatggcga cttgtaaacg 3180
gcaatactgt tccaaataca agattaggag cattctgggc accaacaatt acattggcct 3240
aggtttgcgt gcctgccttt cgggggttac ggccgcattc caaaaagctg gaaaggatgg 3300
gtcaccgatt tatttgggca agtcaaaatt cgacccgata ccagctcctg acaagtactg 3360
ccttgaaaca gacctg 3376

<210> SEQ ID NO 6
<211> LENGTH: 3220
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: EAV F3

<400> SEQUENCE: 6
ggcaagtcaa aattcgaccc gataccagct cctgacaagt actgccttga aacagacctg 60
gagagttgtg atcgctccac cccggctttg gtgcgttggt tcgctactaa tcttattttt 120
gagctagctg gccagcccga gttggtgcac agctacgtgt tgaattgctg tcacgatcta 180
gttgtggcgg gtagtgtagc attcaccaaa cgcgggggtt tgtcatctgg agaccctatc 240
acttccattt ccaataccat ctattcattg gtgctgtaca cccagcacat gttgctatgt 300

```
ggacttgaag gctatttccc agagattgca gaaaaatatc ttgatggcag cctggagctg    360
cgggacatgt tcaagtacgt tcgagtgtac atctactcgg acgatgtggt tctaaccaca    420
cccaaccagc attacgcggc cagctttgac cgctgggtcc cccacctgca ggcgctgcta    480
ggtttcaagg ttgacccaaa gaaaactgtg aacaccagct ccccttcctt tttgggctgc    540
cggttcaagc aagtggacgg caagtgttat ctagccagtc ttcaggaccg cgttacacgc    600
tctctgttat accacattgg tgcaaagaat ccctcagagt actatgaagc tgctgtttcc    660
atctttaagg actccattat ctgctgtgat gaagactggt ggacggacct ccatcgacgt    720
atcagtggcg ctgcgcgtac cgacggagtt gagttcccca ccattgaaat gttaacatcc    780
ttccgcacca agcagtatga gagtgccgtg tgcacagttt gtggggccgc ccccgtggcc    840
aagtctgctt gtggagggtg gttctgtggc aattgtgtcc cgtaccacgc gggtcattgt    900
cacacaacct cgctcttcgc caactgcggg cacgacatca tgtaccgctc cacttactgc    960
acaatgtgtg agggttcccc aaaacagatg gtaccaaaag tgcctcaccc gatcctggat   1020
catttgctgt gccacattga ttacggcagt aaagaggaac taactctggt agtggcggat   1080
ggtcgaacaa catcaccgcc cgggcgctac aaagtgggtc acaaggtagt cgccgtggtt   1140
gcagatgtgg gaggcaacat tgtgtttggg tgcggtcctg gatcacacat cgcagtacca   1200
cttcaggata cgctcaaggg cgtggtggtg aataaagctc tgaagaacgc cgccgcctct   1260
gagtacgtgg aaggaccccc tgggagtggg aagacttttc acctggtcaa agatgtgcta   1320
gccgtggtcg gtagcgcgac cttggttgtg cccacccacg cgtccatgct ggactgcatc   1380
aacaagctca aacaagcggg cgccgatcca tactttgtgg tgcccaagta tacagttctt   1440
gactttcccc ggcctggcag tggaaacatc acagtgcgac tgccacaggt cggaaccagt   1500
gagggagaaa cctttgtgga tgaggtggcc tacttctcac cagtggatct ggcgcgcatt   1560
ttaacccagg gtcgagtcaa gggttacggt gatttaaatc agctcgggtg cgtcggaccc   1620
gcgagcgtgc cacgtaacct ttggctccga cattttgtca gcctggagcc cttgcgagtg   1680
tgccatcgat tcggcgctgc tgtgtgtgat ttgatcaagg gcatttatcc ttattatgag   1740
ccagctccac ataccactaa agtggtgttt gtgccaaatc cagactttga gaaaggtgta   1800
gtcatcaccg cctaccacaa agatcgcggt cttggtcacc gcacaattga ttcaattcaa   1860
ggctgtacat tccctgttgt gactcttcga ctgcccacac cccaatcact gacgcgcccg   1920
cgcgcagttg tggcggttac tagggcgtct caggaattat acatctacga ccccttgat    1980
cagcttagcg ggttgttgaa gttcaccaag gaagcagagg cgcaggactt gatccatggc   2040
ccacctacag catgccacct gggccaagaa attgaccttt ggtccaatga gggcctcgaa   2100
tattacaagg aagtcaacct gctgtacaca cacgtcccca tcaaggatgg tgtaatacac   2160
agttacccta attgtggccc tgcctgtggc tgggaaaagc aatccaacaa aatttcgtgc   2220
ctcccgagag tggcacaaaa tttgggctac cactattccc cagacttacc aggattttgc   2280
cccataccaa aagaactcgc tgagcattgg cccgtagtgt ccaatgatag atacccgaat   2340
tgcttgcaaa ttaccttaca gcaagtatgt gaactcagta aaccgtgctc agcgggctat   2400
atggttggac aatctgtttt cgtgcagacg cctggtgtga catcttactg gcttactgaa   2460
tgggtcgacg gcaaagcgcg tgctctacca gattccttat tctcgtccgg taggttcgag   2520
actaacagcc gcgctttcct cgatgaagcc gaggaaaagt ttgccgccgc tcaccctcat   2580
gcctgtttgg gagaaattaa taagtccacc gtgggaggat cccacttcat cttttcccaa   2640
```

-continued

```
tatttaccac cattgctacc cgcagacgct gttgccctgg taggtgcttc attggctggg   2700

aaagctgcta aagctgcttg cagcgttgtt gatgtctatg ctccatcatt tgaaccttat   2760

ctacaccctg agacactgag tcgcgtgtac aagattatga tcgatttcaa gccgtgtagg   2820

cttatggtgt ggagaaacgc gaccttttat gtccaagagg gtgttgatgc agttacatca   2880

gcactagcag ctgtgtccaa actcatcaaa gtgccggcca atgagcctgt ttcattccat   2940

gtggcatcag ggtacagaac caacgcgctg gtagcgcccc aggctaaaat ttcaattgga   3000

gcctacgccg ccgagtgggc actgtcaact gaaccgccac ctgctggtta tgcgatcgtg   3060

cggcgatata ttgtaaagag gctcctcagc tcaacagaag tgttcttgtg ccgcaggggt   3120

gttgtgtctt ccacctcagt gcagaccatt tgtgcactag agggatgtaa acctctgttt   3180

aatttcctgc agattggttc agtcattggg cccgtgtgac                         3220
```

```
<210> SEQ ID NO 7
<211> LENGTH: 1102
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Renilla luciferase

<400> SEQUENCE: 7

aatttcctgc agattggttc agtcattggg cccgtgtgac tctagagtgg acctgttccc     60

atcccccgct caactactca ggtagtggtt cgcggcaacg ggtacaccgc agttggtaac    120

aagcttgtcg atgacttcga aagtttatga tccagaacaa aggaaacgga tgataactgg    180

tccgcagtgg tgggccagat gtaaacaaat gaatgttctt gattcattta ttaattatta    240

tgattcagaa aaacatgcag aaaatgctgt tatttttta catggtaacg cggcctcttc    300

ttatttatgg cgacatgttg tgccacatat tgagccagta gcgcggtgta ttataccaga    360

tcttattggt atgggcaaat caggcaaatc tggtaatggt tcttataggt tacttgatca    420

ttacaaatat cttactgcat ggtttgaact tcttaattta ccaaagaaga tcatttttgt    480

cggccatgat tggggtgctt gtttggcatt tcattatagc tatgagcatc aagataagat    540

caaagcaata gttcacgctg aaagtgtagt agatgtgatt gaatcatggg atgaatggcc    600

tgatattgaa gaagatattg cgttgatcaa atctgaagaa ggagaaaaaa tggttttgga    660

gaataacttc ttcgtggaaa ccatgttgcc atcaaaaatc atgagaaagt tagaaccaga    720

agaatttgca gcatatcttg aaccattcaa agagaaaggt gaagttcgtc gtccaacatt    780

atcatggcct cgtgaaatcc cgttagtaaa aggtggtaaa cctgacgttg tacaaattgt    840

taggaattac aatgcttatc tacgtgcaag tgatgattta ccaaaaatgt ttattgaatc    900

ggatccagga ttcttttcca atgctattgt tgaaggcgcc aagaagtttc ctaatactga    960

atttgtcaaa gtaaaaggtc ttcatttttc gcaagaagat gcacctgatg aaatgggaaa   1020

atatatcaaa tcgttcgttg agcgagttct caaaaatgaa caataattat aagacgtgga   1080

tattctcctg tgtggcgtca tg                                            1102
```

```
<210> SEQ ID NO 8
<211> LENGTH: 200
<212> TYPE: DNA
<213> ORGANISM: Artificial Sequence
<220> FEATURE:
<223> OTHER INFORMATION: Synthetic polynucleotide
<220> FEATURE:
```

<221> NAME/KEY: misc_feature
<223> OTHER INFORMATION: EAV_ultramer

<400> SEQUENCE: 8
gacgtggata ttctcctgtg tggcgtcatg ttgaagtagt tattagccac ccaggaacca 60
aaaaaaaaaa aaaaaaaaaa aaaaaaaaaa aaaaaaaaac ccctctctaa acggaggggt 120 tttttcagc gtaactggac tggccacagt taggcggccg cgcatgttca tcatcagtaa 180
cccgtatcgt gagcatcctc 200

<210> SEQ ID NO 9
<211> LENGTH: 443
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Spacer 1

<400> SEQUENCE: 9
tctagattgt gaggttgggg gcagctgagg tataggagcc atagattcat tttgtggtga 60
cgggatttta ggtgagtatt tagattactt tattctgtcc gtcccactct tgctgttgct 120
tactaggtat gtagcatctg ggttagtgta tgttttgact gccttgttct attcctttgt 180
attagcagct tatatttggt ttgttatagt tggaagagcc ttttctactg cttatgcttt 240
tgtgcttttg gctgcttttc tgttattagt aatgaggatg attgtgggta tgatgcctcg 300
tcttcggtcc attttcaacc atcgccaact ggtggtagct gattttgtgg acacaccttc 360
cggacctgtt cccatccccc gctcaactac tcaggtagtg gttcgcggca acgggtacac 420
cgcagttggt aacaagcttg tcg 443

<210> SEQ ID NO 10
<211> LENGTH: 310
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Spacer 2

<400> SEQUENCE: 10
tctagagggt tagtgtatgt tttgactgcc ttgttctatt cctttgtatt agcagcttat 60
atttggtttg ttatagttgg aagagccttt tctactgctt atgcttttgt gcttttggct 120
gcttttctgt tattagtaat gaggatgatt gtgggtatga tgcctcgtct tcggtccatt 180
ttcaaccatc gccaactggt ggtagctgat tttgtggaca caccttccgg acctgttccc 240
atcccccgct caactactca ggtagtggtt cgcggcaacg ggtacaccgc agttggtaac 300
aagcttgtcg 310

<210> SEQ ID NO 11
<211> LENGTH: 190
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Spacer 3

<400> SEQUENCE: 11

```
tctagatccg gacctgttcc catcccccgc tcaactactc aggtagtggt tcgcggcaac     60

gggtacaccg cagttggtaa caagcttgtc gatagcgtca agacgatcac gtccgcaggc    120

cgcctctttt cgaaacggac ggcggcgaca gcctacaagc tacaatgacc tactgcgcat    180

gtttggtcag                                                           190


<210> SEQ ID NO 12
<211> LENGTH: 542
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Spacer 4

<400> SEQUENCE: 12

tctagattgt gaggttgggg gcagctgagg tataggagcc atagattcat tttgtggtga     60

cgggatttta ggtgagtatt tagattactt tattctgtcc gtcccactct tgctgttgct    120

tactaggtat gtagcatctg ggttagtgta tgttttgact gccttgttct attcctttgt    180

attagcagct tatatttggt ttgttatagt tggaagagcc ttttctactg cttatgcttt    240

tgtgcttttg gctgcttttc tgttattagt aatgaggatg attgtgggta tgatgcctcg    300

tcttcggtcc attttcaacc atcgccaact ggtggtagct gattttgtgg acacaccttc    360

cggacctgtt cccatccccc gctcaactac tcaggtagtg gttcgcggca acgggtacac    420

cgcagttggt aacaagcttg tcgatagcgt caagacgatc acgtccgcag gccgcctctt    480

ttcgaaacgg acggcggcga cagcctacaa gctacaatga cctactgcgc atgtttggtc    540

ag                                                                   542


<210> SEQ ID NO 13
<211> LENGTH: 1662
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Cypridina reporter gene - Cypr

<400> SEQUENCE: 13

atgaagaccc tgatcctggc cgtggccctg gtgtactgcg ccaccgtgca ctgccaggac     60

tgcccctacg agcccgaccc ccccaatacc gtgcctacca gctgcgaggc caaagagggc    120

gaatgcatcg acagcagctg cggcacctgt acccgggaca tcctgagcga cggcctgtgc    180

gagaacaagc ccggcaagac ctgctgccgg atgtgccagt acgtgatcga gtgccgggtg    240

gaagccgccg gatggttccg gaccttctac ggcaagcggt tccagtttca ggaacccggc    300

acctacgtcc tgggccaggg cacaaagggc ggcgactgga aggtgtccat caccctggaa    360

aacctggacg gcaccaaggg cgccgtgctg accaagacca gactggaagt ggccggcgac    420

atcatcgata tcgcccaggc caccgagaac cccatcaccg tgaacggcgg agccgacccc    480

atcattgcca accccctacac catcggcgaa gtgacaatcg ctgtggtgga aatgcccggc    540

ttcaatatca ccgtcatcga gttcttcaag ctgatcgtga tcgacatcct gggcggcaga    600

agcgtgcgga tcgcccccga taccgccaac aagggcatga tcagcggcct gtgtggcgac    660

ctgaagatga tggaagatac cgacttcacc agcgaccccg agcagctggc catccagccc    720
```

-continued aagatcaacc aggaatttga cggctgcccc ctgtacggca accccgacga cgtggcctac 780
tgcaagggcc tgctggaacc ctacaaggac agctgcagaa accccatcaa cttctactac 840
tacaccatca gctgcgcctt cgcccggtgc atgggcggag atgagcgcgc tagccacgtg 900
ctgctggact acagagagac atgcgccgct cccgagacac ggggcacatg tgtgctgagc 960
ggccacacct tctacgacac cttcgacaag gccagatacc agttccaggg cccctgcaaa 1020
gaaatcctga tggccgccga ctgcttctgg aacacctggg acgtgaaggt gtcccaccgg 1080
aacgtggaca gctataccga ggtggaaaaa gtgcggatca gaaagcagag caccgtggtc 1140
gagctgattg tggacggcaa gcagatcctc gtgggcggcg aggccgtgtc cgtgccctac 1200
agcagccaga acaccagcat ctactggcag gacggcgaca tcctgaccac cgccatcctg 1260
cctgaggccc tggtggtcaa gttcaacttc aagcagctgc tggtggtgca catccgggac 1320
cccttcgacg gcaagacatg cggcatctgc ggcaactaca accaggactt cagcgacgac 1380
agcttcgacg ccgagggcgc ctgcgacctg accccctaatc ctcccggctg caccgaggaa 1440
cagaagcccg aggccgagcg gctgtgcaat agcctgttcg ccggccagag cgacctggac 1500
cagaaatgca acgtgtgcca caagcccgac cgggtggaac ggtgtatgta cgagtactgc 1560
ctgcggggcc agcagggctt ctgcgatcac gcctgggagt tcaagaaaga gtgctacatc 1620
aagcacggcg acaccctgga agtgcccgac gagtgcaagt ga 1662

<210> SEQ ID NO 14
<211> LENGTH: 936
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Green Renilla reporter gene - gRen

<400> SEQUENCE: 14
atggccagca aggtgtacga ccccgagcag cggaagcgga tgatcaccgg ccctcagtgg 60
tgggctcggt gcaagcagat gaacgtgctg gacagcttca tcaactacta cgacagcgag 120
aagcacgccg agaacgccgt gatcttcctg cacggcaacg ccaccagcag ctacctgtgg 180
cggcacgtgg tgccccacat cgagcctgtg gccagatgca tcatccccga cctgatcggc 240
atgggcaaga gcggcaagtc cggcaacggc agctaccggc tgctggacca ctacaagtac 300
ctgaccgctt ggtttgagct gctgaacctg cccaagaaga tcatcttcgt cggccacgac 360
tggggcagcg ccctggcctt tcactacgcc tacgagcacc aggaccggat caaggccatc 420
gtgcacatgg aaagcgtggt ggacgtgatc gagagctgga tgggctggcc cgacatcgag 480
gaagaactgg ccctgatcaa gagcgaagag ggcgagaaga tggtgctgga aaacaacttc 540
ttcgtggaaa ccctgctgcc cagcaagatc atgcggaagc tggaacccga agagttcgcc 600
gcctacctgg aacccttcaa agaaaagggc gaagtgcgga ggcccaccct gagctggccc 660
agagagatcc ccctggtcaa gggcggcaag cccgacgtgg tgcagatcgt gcggaactac 720
aacgcctacc tgcgggccag cgacgacctg cctaagctgt tcatcgagag cgacccccggc 780 ttcttcagca acgccatcgt ggaaggcgcc aagaagttcc ccaacaccga gttcgtgaaa 840
gtgaagggcc tgcacttcct ccaggaagat gccccccgacg agatgggcaa gtacatcaag 900
agcttcgtgg aacgggtgct gaagaacgag cagtga 936

<210> SEQ ID NO 15

<211> LENGTH: 1647
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Red Firefly reporter gene - rFF

<400> SEQUENCE: 15

```
atggaaaata tggaaaacga cgagaacatc gtggtgggcc ccaagccctt ctaccccatc      60

gaggaaggca gcgccggcac ccagctgcgg aagtacatgg aaagatacgc caagctgggc     120

gccattgcct tcaccaacgc cgtgaccggc gtggactaca gctacgccga gtacctggaa     180

aagagctgct gcctgggcaa ggctctgcag aactacggcc tggtggtgga cggccggatc     240

gccctgtgca gcgagaactg cgaggaattc ttcatccccg tgatcgccgg cctgttcatc     300

ggcgtgggcg tggctcccac caacgagatc tacaccctgc gggagctggt gcacagcctg     360

ggcatcagca agcccaccat cgtgttcagc agcaagaagg gcctggacaa agtcatcacc     420

gtgcagaaaa ccgtgaccac catcaagacc atcgtgatcc tggacagcaa ggtggactac     480

cggggctacc agtgcctgga caccttcatc aagcggaaca ccccccctgg cttccaggcc     540

agcagcttca agaccgtgga ggtggaccgg aaagaacagg tggccctgat catgaacagc     600

agcggcagca ccggcctgcc caagggcgtg cagctgaccc acgagaacac cgtgacccgg     660

ttcagccacg ccagggaccc catctacggc aaccaggtgt cccccggcac cgccgtgctg     720

accgtggtgc ccttccacca cggcttcggc atgttcacca ccctgggcta cctgatctgc     780

ggcttccggg tggtgatgct gaccaagttc gacgaggaaa ccttcctgaa aaccctgcag     840

gactacaagt gcacctacgt gattctggtg cccaccctgt tcgccatcct gaacaagagc     900

gagctgctga acaagtacga cctgagcaac ctggtggaga tcgccagcgg cggagccccc     960

ctgagcaaag aagtgggaga ggccgtcgcc aggcggttca atctgcccgg cgtgcggcag    1020

ggctacggcc tgaccgagac aaccagcgcc atcatcatca cccccgaggg cgacgacaag    1080

cctggagcca gcggcaaggt ggtgcccctg ttcaaggcca aagtgatcga cctggacacc    1140

aagaagagcc tgggccccaa cagacggggc gaagtgtgcg tgaagggccc catgctgatg    1200

aagggctacg tgaacaaccc cgaggccacc aaagagctga tcgacgaaga gggctggctg    1260

cacaccggcg acatcggcta ctacgacgaa gagaagcact tcttcatcgt ggaccggctg    1320

aagagcctga tcaagtacaa gggctatcag gtgccccctg ccgagctgga aagcgtcctg    1380

ctgcagcacc ccagcatctt cgacgccggc gtggccgggg tgccagatcc tgtggccggc    1440

gagctgcctg gcgccgtggt ggtgctggaa tccggcaaga acatgaccga gaaagaagtg    1500

atggactacg tcgccagcca ggtgtccaac gccaagcggc tgagaggcgg cgtgagattc    1560

gtggacgaag tgccaaaggg cctgaccggc aagatcgacg gcagggccat ccgggagatc    1620

ctgaagaaac ccgtggccaa gatgtga                                        1647
```

<210> SEQ ID NO 16
<211> LENGTH: 1725
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Fusion glycoprotein F0
      Human respiratory syncytial virus A (strain A2) - GenBank

<400> SEQUENCE: 16

```
atggagttgc taatcctcaa agcaaatgca attaccacaa tcctcactgc agtcacattt     60
tgttttgctt ctggtcaaaa catcactgaa gaattttatc aatcaacatg cagtgcagtt    120
agcaaaggct atcttagtgc tctgagaact ggttggtata ccagtgttat aactatagaa    180
ttaagtaata tcaaggaaaa taagtgtaat ggaacagatg ctaaggtaaa attgataaaa    240
caagaattag ataaatataa aaatgctgta acagaattgc agttgctcat gcaaagcaca    300
ccaccaacaa acaatcgagc cagaagagaa ctaccaaggt ttatgaatta tacactcaac    360
aatgccaaaa aaaccaatgt aacattaagc aagaaaagga aaagaagatt tcttggtttt    420
ttgttaggtg ttggatctgc aatcgccagt ggcgttgctg tatctaaggt cctgcaccta    480
gaaggggaag tgaacaagat caaaagtgct ctactatcca caaacaaggc tgtagtcagc    540
ttatcaaatg gagttagtgt cttaaccagc aaagtgttag acctcaaaaa ctatatagat    600
aaacaattgt tacctattgt gaacaagcaa agctgcagca tatcaaatat agaaactgtg    660
atagagttcc aacaaaagaa caacagacta ctagagatta ccagggaatt tagtgttaat    720
gcaggtgtaa ctacacctgt aagcacttac atgttaacta atagtgaatt attgtcatta    780
atcaatgata tgcctataac aaatgatcag aaaaagttaa tgtccaacaa tgttcaaata    840
gttagacagc aaagttactc tatcatgtcc ataataaaag aggaagtctt agcatatgta    900
gtacaattac cactatatgg tgttatagat acaccctgtt ggaaactaca cacatcccct    960
ctatgtacaa ccaacacaaa agaagggtcc aacatctgtt taacaagaac tgacagagga   1020
tggtactgtg acaatgcagg atcagtatct ttcttcccac aagctgaaac atgtaaagtt   1080
caatcaaatc gagtattttg tgacacaatg aacagtttaa cattaccaag tgaaataaat   1140
ctctgcaatg ttgacatatt caaccccaaa tatgattgta aaattatgac ttcaaaaaca   1200
gatgtaagca gctccgttat cacatctcta ggagccattg tgtcatgcta tggcaaaact   1260
aaatgtacag catccaataa aaatcgtgga atcataaaga cattttctaa cgggtgcgat   1320
tatgtatcaa ataaagggat ggacactgtg tctgtaggta acacattata ttatgtaaat   1380
aagcaagaag gtaaaagtct ctatgtaaaa ggtgaaccaa taataaattt ctatgaccca   1440
ttagtattcc cctctgatga atttgatgca tcaatatctc aagtcaacga gaagattaac   1500
cagagcctag catttattcg taaatccgat gaattattac ataatgtaaa tgctggtaaa   1560
tccaccacaa atatcatgat aactactata attatagtga ttatagtaat attgttatca   1620
ttaattgctg ttggactgct cttatactgt aaggccagaa gcacaccagt cacactaagc   1680
aaagatcaac tgagtggtat aaataatatt gcatttagta actaa                   1725
```

<210> SEQ ID NO 17
<211> LENGTH: 1725
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Fusion glycoprotein F0
Human respiratory syncytial virus A (strain A2) - GeneArt

<400> SEQUENCE: 17

```
atggaactgc tgatcctgaa ggccaacgcc atcaccacca tcctgaccgc cgtgaccttc     60
tgctttgcca gcggccagaa catcaccgag gaattctacc agagcacctg tagcgccgtg    120
tccaagggct acctgagcgc cctgagaacc ggctggtaca ccagcgtgat caccatcgag    180
```

ctgagcaaca tcaaagaaaa caagtgcaac ggcaccgacg ccaaagtgaa gctgatcaag 240
caggaactgg acaagtacaa gaatgccgtg accgaactgc agctgctgat gcagagcacc 300
ccccccacca acaaccgggc cagaagagaa ctgcccagat tcatgaacta caccctgaac 360
aacgccaaaa agaccaacgt gaccctgagc aagaagcgga agcggcggtt cctgggcttt 420
ctgctgggag tgggaagcgc cattgctagc ggagtggccg tgtctaaggt gctgcacctg 480
gaaggcgaag tgaacaagat caagtccgcc ctgctgagca ccaacaaggc cgtggtgtct 540
ctgagcaacg gcgtgtccgt gctgaccagc aaggtgctgg atctgaagaa ctacatcgac 600
aaacagctgc tgcccatcgt gaacaagcag agctgcagca tcagcaacat cgagacagtg 660
atcgagttcc agcagaagaa caaccggctg ctggaaatca cccgcgagtt cagcgtgaac 720
gctggcgtga ccaccccccgt gtccacctac atgctgacca acagcgagct gctgtccctg 780
atcaacgaca tgcccatcac caacgaccag aaaaagctga tgagcaacaa cgtgcagatc 840
gtgcggcagc agagctactc catcatgagc attatcaaag aagaggtgct ggcctacgtg 900
gtgcagctgc ctctgtacgg cgtgatcgac accccctgct ggaagctgca caccagccct 960
ctgtgcacca ccaacaccaa agagggctcc aacatctgcc tgacccggac cgacagaggc 1020
tggtactgcg ataatgccgg ctccgtctca ttctttccac aagccgagac atgcaaggtg 1080
cagagcaacc gggtgttctg cgacaccatg aacagcctga ccctgcccag cgagatcaac 1140
ctgtgcaacg tggacatctt caaccctaag tacgactgca agatcatgac ctccaagacc 1200
gacgtgtcca gctccgtgat cacaagcctg ggcgccatcg tgtcctgcta cggcaagacc 1260
aagtgcaccg ccagcaacaa gaaccggggc atcatcaaga ccttcagcaa cggctgcgac 1320
tacgtgtcca acaagggcat ggacaccgtg tctgtgggca acaccctgta ctacgtgaac 1380
aaacaggaag gcaagagcct gtacgtgaag ggcgagccca tcatcaactt ctacgacccc 1440
ctggtgttcc ccagcgacga gttcgatgcc agcatctccc aagtgaacga gaagatcaac 1500
cagagcctgg ccttcatcag aaagtccgat gagctgctgc acaatgtgaa cgccggcaag 1560
tccaccacca atatcatgat caccacaatc atcatcgtga ttatcgtgat cctgctgagc 1620
ctgatcgccg tgggcctgct gctgtactgc aaggccagat ccacccctgt gaccctgtcc 1680
aaggatcagc tgagcggcat caacaatatc gccttctcca actga 1725

<210> SEQ ID NO 18
<211> LENGTH: 1725
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Fusion glycoprotein F0
Human respiratory syncytial virus A (strain A2) - Blue Heron

<400> SEQUENCE: 18
atggaactgc ttattcttaa ggccaacgct ataactacca tcctgaccgc cgtcacgttt 60
tgcttcgcat ccggccagaa cataaccgag gagttctacc agagtacctg cagcgccgta 120
tccaagggat acctctccgc cctccgcaca ggatggtata catccgtgat cactattgag 180
ctgtcaaaca tcaaggaaaa caagtgtaac ggaaccgatg ccaaagtgaa actgatcaaa 240
caagagctgg ataagtataa gaacgctgtg accgaactgc agctcctgat gcagtcaaca 300
cctccaacca ataaccgcgc taggagagaa ctcccccggt ttatgaatta taccctgaac 360

-continued

```
aatgcaaaaa aaactaatgt caccctgagt aaaaaacgga agcggaggtt ccttggcttt    420
ctcttgggcg ttggatcagc catagccagc ggtgtggccg tttctaaagt gctgcacctt    480
gaaggcgaag tcaataaaat taaatcagcc ctcctctcca ctaacaaggc agtcgtttct    540
ctgtcaaatg gagtgtccgt actcactagc aaagtgctcg acctcaagaa ctacattgac    600
aaacaactcc ttcctatcgt gaacaaacaa tcctgctcca tctccaatat tgaaacagta    660
atcgagttcc aacaaaaaaa caatagactt ctcgaaatca ctcgcgagtt ttccgtaaat    720
gcgggcgtta caacccctgt gagtacttac atgctgacaa attctgaact gctctcactg    780
attaacgaca tgcctatcac gaacgaccag aagaagctca tgagtaataa cgttcaaatc    840
gtcaggcagc aaagttactc catcatgtct attatcaaag aggaagtttt ggcctatgtg    900
gttcagctcc cactttatgg cgtgatcgat acaccttgct ggaaactgca cacttctcca    960
ttgtgtacca caaataccaa ggaaggaagc aatatatgtt tgacaagaac tgaccggggg   1020
tggtattgtg ataatgccgg atcagttagt tttttccccc aagccgagac ctgcaaggtt   1080
cagtccaatc gagtattttg tgacactatg aactccctga ccctgccctc tgaaattaat   1140
ttgtgcaacg tggatatctt caacccgaaa tacgattgta aaataatgac aagcaaaacc   1200
gatgtgtctt ctagcgtgat cacctctctg ggcgcaatcg tgtcctgcta cggaaaaaca   1260
aagtgtaccg cctcaaacaa aaataggggc atcatcaaaa cttttagtaa tggctgtgat   1320
tatgtgagta ataagggaat ggacaccgtt tctgttggta acactctcta ctatgttaat   1380
aagcaggaag gaaaatcact gtacgtcaaa ggcgaaccta tcatcaactt ctatgatcca   1440
ctggtgttcc caagcgacga atttgatgct agtataagcc aagtgaacga gaaaataaat   1500
cagagtttgg cctttatccg aaagagcgac gaactccttc acaacgtgaa tgcaggcaag   1560
tctactacca atattatgat caccaccatc atcatcgtta tcatcgtgat cctcctcagc   1620
ctcatcgccg tcggattgct cttgtattgt aaagccagat ctacccctgt taccctgtcc   1680
aaagaccagc tgagcggaat aaacaatata gccttcagca actga                   1725
```

<210> SEQ ID NO 19
<211> LENGTH: 1725
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Fusion glycoprotein F0
Human respiratory syncytial virus A (strain A2) - DNA 2.0

<400> SEQUENCE: 19

```
atggaactgc tgatccttaa agcgaacgcc attacaacca tcctgactgc cgtgactttc     60
tgctttgcgt ccggacagaa tatcaccgaa gagttctacc agagcacctg ttccgccgtg    120
tccaagggtt acttgtccgc cctgagaacc gggtggtaca cttcggtgat cactattgaa    180
ctcagcaaca ttaaggagaa caagtgcaac ggtactgacg ccaaggtcaa gctgatcaag    240
caggagctcg acaagtacaa gaacgccgtg accgaactgc agctgctgat gcagtccacc    300
cctcccacta acaaccgcgc ccggagggag cttcctcggt tcatgaatta caccctgaac    360
aacgccaaaa agacgaacgt gaccctgagc aagaagagaa agcggcgctt cctgggtttc    420
cttctgggcg tgggaagcgc cattgcctcc ggcgtggccg tgtcaaaggt cctgcacctg    480
gagggggaag tcaacaagat caagtccgcc ttgctgtcta ccaacaaggc ggtcgtgtcc    540
ctctccaacg gagtgtcagt gctgacctcc aaagtgctgg atctgaagaa ctacatcgac    600
```

aagcagctgc tcccgattgt gaacaagcaa tcctgtagca tctccaacat cgagactgtg 660
attgagttcc aacagaagaa caaccgcctg ctggagatta cccgggaatt ctccgtgaat 720
gctggcgtca ccaccccgt cagcacctat atgctcacca actcggagct gctgtccctg 780
atcaacgaca tgcctatcac caacgaccag aagaagctga tgtctaacaa cgtccagatc 840
gtgcgccagc agtcgtactc gattatgagc atcatcaagg aagaggtgct ggcatacgtg 900
gtgcagctcc ctctgtacgg cgtgatcgac accccgtgtt ggaagttgca tacctccccg 960
ctttgcacta ccaacaccaa ggaaggctcg aatatctgcc tcacccgcac tgatcgggga 1020
tggtactgcg acaacgccgg atccgtgtcc ttctttccgc aagcggagac ttgcaaagtg 1080
cagagcaata gagtgttctg tgacacgatg aacagcctta ccctcccatc ggaaatcaat 1140
ctgtgcaacg tggacatctt caacccgaaa tacgactgca agatcatgac ctcaaagact 1200
gatgtgtcct cctccgtgat cacttccctg ggagccattg tgtcgtgcta cggaaagacc 1260
aagtgcaccg cgtcgaacaa gaaccggggc atcattaaga ccttcagcaa cggctgcgac 1320
tacgtgtcca acaagggaat ggacaccgtg tccgtcggaa acaccctcta ctacgtcaac 1380
aagcaggagg ggaagtcact ctatgtgaag ggcgaaccga ttatcaactt ttacgatcca 1440
ctggtgttcc cctccgatga attcgatgcc agcatcagcc aggtcaacga aaagatcaat 1500
caatccttgg cattcatacg gaagtccgac gaactcctcc acaacgtgaa cgcaggaaag 1560
agcactacta acattatgat caccaccatt atcattgtga tcatcgtgat cctgctctca 1620
ctgattgccg tcggactgtt gctgtactgc aaagccaggt cgacgcccgt gaccctcagc 1680
aaggaccaac tgtcaggcat caacaacatt gctttctcaa actga 1725

<210> SEQ ID NO 20
<211> LENGTH: 1707
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HA Influenza A virus
A-VietNam-1203-2004 (H5N1) - GenBank

<400> SEQUENCE: 20
atggagaaaa tagtgcttct tttgcaata gtcagtcttg ttaaaagtga tcagatttgc 60
attggttacc atgcaaacaa ctcgacagag caggttgaca caataatgga aaagaacgtt 120
actgttacac atgcccaaga catactggaa aagaaacaca acgggaagct ctgcgatcta 180
gatggagtga agcctctaat tttgagagat tgtagcgtag ctggatggct cctcggaaac 240
ccaatgtgtg acgaattcat caatgtgccg gaatggtctt acatagtgga gaaggccaat 300
ccagtcaatg acctctgtta cccaggggat ttcaatgact atgaagaatt gaaacaccta 360
ttgagcagaa taaaccattt tgagaaaatt cagatcatcc ccaaaagttc ttggtccagt 420
catgaagcct cattaggggt gagctcagca tgtccatacc agggaaagtc ctcctttttc 480
agaaatgtgg tatggcttat caaaaagaac agtacatacc caacaataaa gaggagctac 540
aataatacca accaagaaga tcttttggta ctgtgggggga ttcaccatcc taatgatgcg 600
gcagagcaga caaagctcta tcaaaaccca accacctata tttccgttgg gacatcaaca 660
ctaaaccaga gattggtacc aagaatagct actagatcca aagtaaacgg gcaaagtgga 720
aggatggagt tcttctggac aattttaaag ccgaatgatg caatcaactt cgagagtaat 780
ggaaatttca ttgctccaga atatgcatac aaaattgtca agaaagggga ctcaacaatt 840
atgaaaagtg aattggaata tggtaactgc aacaccaagt gtcaaactcc aatgggggcg 900
ataaactcta gcatgccatt ccacaatata caccctctca ccattgggga atgccccaaa 960
tatgtgaaat caaacagatt agtccttgcg actgggctca gaaatagccc tcaaagagag 1020
agaagaagaa aaaagagagg attatttgga gctatagcag gttttataga gggaggatgg 1080
cagggaatgg tagatggttg gtatgggtac caccatagca atgagcaggg gagtgggtac 1140
gctgcagaca aagaatccac tcaaaaggca atagatggag tcaccaataa ggtcaactcg 1200
atcattgaca aaatgaacac tcagtttgag gccgttggaa gggaatttaa caacttagaa 1260
aggagaatag agaatttaaa caagaagatg gaagacgggt tcctagatgt ctggacttat 1320
aatgctgaac ttctggttct catggaaaat gagagaactc tagactttca tgactcaaat 1380
gtcaagaacc tttacgacaa ggtccgacta cagcttaggg ataatgcaaa ggagctgggt 1440
aacggttgtt tcgagttcta tcataaatgt gataatgaat gtatggaaag tgtaagaaat 1500
ggaacgtatg actacccgca gtattcagaa gaagcgagac taaaaagaga ggaaataagt 1560
ggagtaaaat tggaatcaat aggaatttac caaatactgt caatttattc tacagtggcg 1620
agttccctag cactggcaat catggtagct ggtctatcct tatggatgtg ctccaatggg 1680
tcgttacaat gcagaatttg catttaa 1707

<210> SEQ ID NO 21
<211> LENGTH: 1707
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HA Influenza A virus
A-VietNam-1203-2004 (H5N1) - GenArt

<400> SEQUENCE: 21
atggaaaaga tcgtgctgct gttcgccatc gtgtccctcg tgaagtccga ccagatctgc 60
atcggctacc acgccaacaa cagcaccgaa caggtggaca ccatcatgga aaaaaacgtg 120
accgtgaccc acgcccagga catcctggaa aagaagcaca acggcaagct gtgcgacctg 180
gacggcgtga agcccctgat cctgagagat tgctctgtgg ccggctggct gctgggcaac 240
cccatgtgcg acgagttcat caacgtgccc gagtggtcct atatcgtgga aaaggccaac 300
cccgtgaacg acctgtgcta ccccggcgac ttcaacgact acgaggaact gaaacatctg 360
ctgagccgga tcaaccactt cgagaagatc cagatcatcc ccaagagcag ctggtccagc 420
cacgaagctt ctctgggcgt gtccagcgca tgcccatacc agggcaagtc cagcttcttc 480
cggaacgtcg tgtggctgat caagaagaac agcacctacc ccaccatcaa gcggagctac 540
aacaacacca accaggaaga tctgctggtg ctgtggggca tccaccaccc caatgatgcc 600
gccgagcaga ccaagctgta ccagaacccc accacctaca tcagcgtggg caccagcacc 660
ctgaaccagc ggctggtgcc tcggatcgcc acccggtcta aagtgaatgg ccagagcggc 720
cggatggaat tcttctggac catcctgaag cccaacgacg ccatcaactt cgagagcaac 780
ggcaacttta tcgcccccga gtacgcctac aagatcgtga agaagggcga cagcacaatc 840
atgaagtctg agctggaata cggcaactgc aacaccaagt gccagacccc catgggcgcc 900
atcaatagca gcatgccctt ccacaacatc cacccccctga ccatcggcga gtgccccaaa 960
tacgtgaagt ctaacagact ggtgctggcc accggcctga gaaacagccc tcagagagag 1020
cggcggagaa agaagcgggg cctgtttgga gccattgccg gctttatcga gggcggctgg 1080
cagggcatgg tggatgggtg gtacggctat caccacagca acgagcaggg cagcggatac 1140
gccgccgaca aagagagcac ccagaaagcc atcgacggcg tgaccaacaa agtgaacagc 1200
atcatcgaca agatgaacac ccagttcgag gccgtgggca gagagttcaa caacctggaa 1260
cggcggatcg agaacctgaa caagaaaatg gaagatggct tcctggacgt gtggacctac 1320
aacgccgagc tgctggtgct gatggaaaac gagcggaccc tggacttcca cgacagcaac 1380
gtgaagaacc tgtacgacaa agtgcggctg cagctgcggg acaacgccaa agaactgggc 1440
aacggctgct tcgagttcta ccacaagtgc gacaacgagt gcatggaaag cgtgcggaac 1500
ggcacctacg actacccccca gtacagcgag gaagcccggc tgaagcggga agagatcagc 1560
ggagtgaagc tggaatccat cggcatctac cagatcctga gcatctacag caccgtggcc 1620
agctcactgg ccctggccat tatggtggcc ggcctgtccc tgtggatgtg cagcaatggc 1680
agcctgcagt gcagaatctg catctga 1707

<210> SEQ ID NO 22
<211> LENGTH: 1707
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HA Influenza A virus
A-VietNam-1203-2004 (H5N1) - Blue Heron

<400> SEQUENCE: 22
atggaaaaaa tcgttttgtt gtttgctatc gtctcactcg ttaaaagcga tcaaatctgc 60
attggctatc acgctaacaa ctcaaccgaa caggtcgata caatcatgga gaaaaacgtc 120
actgtgaccc atgcccaaga cattctggag aaaaagcaca atggcaagct ctgcgatctc 180
gatggcgtta agcctttgat tctccgcgac tgttcagtgg caggatggct cctcggtaat 240
ccaatgtgcg acgaatttat taatgtacct gaatggagtt acatcgtcga aaaggctaac 300
cctgtcaacg acctgtgtta ccccggcgat ttcaacgact atgaagagct caagcacctc 360
ctcagccgca taaatcattt tgaaaagatc caaatcatac caaagtcttc ctggagctca 420
cacgaagcta gcctgggtgt ttcaagcgct tgcccctatc agggaaagtc tagttttttt 480
cggaacgtgg tctggcttat taaaaagaac tcaacttacc caaccatcaa aaggagttac 540
aacaacacaa atcaggaaga tctcctcgtg ctgtggggga tacatcaccc aaacgacgcc 600
gctgagcaga caaaactcta ccagaatccc accacgtata ttagtgtcgg caccagcacc 660
ttgaaccaac gacttgttcc taggatcgca acacggagca aggttaatgg ccaatcaggt 720
aggatggagt tcttctggac aatccttaag cccaatgatg caattaattt tgagagcaat 780
gggaacttca tcgctccgga gtacgcctac aagatagtga aaaaggggga cagcacgata 840
atgaaatctg aactggagta cgggaattgc aacacaaaat gtcagacccc aatgggcgca 900
ataaattcat caatgccctt tcacaatata cacccgttga ccataggtga atgccccaag 960
tatgtcaaga gtaaccggtt ggtccttgcg acgggcctca gaaatagccc acagcgggag 1020
cgcagacgca aaaagagagg acttttcggg gctattgccg ggttcatcga aggcggatgg 1080
caggggatgg tggacggatg gtatgggtac caccactcta atgagcaagg ctccggctac 1140
gcggcagaca aagaatccac acagaaggcg attgatggag ttacaaataa agtgaatagc 1200
atcattgaca agatgaacac acagtttgag gcagtgggac gcgaattcaa caacctggag 1260
aggagaattg aaaatcttaa caagaaaatg gaggatggct tccttgatgt gtggacctac 1320
aacgccgaac ttctggtcct tatggagaat gaacggactc tggactttca cgattctaat 1380
gtgaaaaacc tgtatgacaa ggttcgcctt caactgcgcg acaacgcaaa agagctggga 1440
aatggatgtt ttgagttcta ccataaatgc gacaatgaat gtatggaatc agttaggaat 1500
ggcacctatg actaccccca atatagtgaa gaggctcggc tcaaacgaga agaaatatcc 1560
ggcgttaagc tcgaatcaat cggtatctat cagattctct ccatctattc aacggtcgct 1620
agcagcctcg cattggctat catggtggct ggattgtccc tctggatgtg cagtaacggg 1680
tctctgcaat gccgaatatg tatatga 1707

<210> SEQ ID NO 23
<211> LENGTH: 1707
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HA Influenza A virus
A-VietNam-1203-2004 (H5N1) - DNA 2.0

<400> SEQUENCE: 23
atggagaaaa tcgtcctgct gttcgcaatt gtcagcctcg tgaagtccga ccagatttgc 60
atcggatacc acgcaaacaa ttccactgaa caagtggata ctatcatgga aaagaacgtg 120
accgtgaccc acgcccagga catcctggaa aagaagcaca acgggaaact gtgcgacctc 180
gacggagtga agcctctgat tctgcgggat tgcagcgtgg ccggctggct cctcggaaac 240
cctatgtgtg acgaattcat caacgtgccc gagtggagct acattgtcga gaaagccaac 300
cccgtgaacg acctgtgtta tccgggagac tttaacgact acgaggagct caagcatctg 360
ttgagccgga ttaatcattt cgagaagatc cagattatcc cgaaatcctc ttggagcagc 420
cacgaggcat ccctgggcgt gtcatctgcg tgcccctacc aagggaagtc gtcgttcttc 480
cgcaatgtcg tgtggctgat caagaagaac tccacctacc ccaccattaa gaggtcgtac 540
aacaacacta accaggaaga tctcctggtg ctctggggca tccaccaccc taatgacgcc 600
gctgaacaga ccaagctcta ccagaacccg accacctaca tctccgtggg cacctccacc 660
ctgaaccagc ggcttgtgcc gaggatcgcg actagatcca aggtcaacgg ccagtccggt 720
cgcatggagt tcttttggac catcctgaag ccgaacgatg ccatcaattt cgaatcaaac 780
gggaacttca ttgcccccga atacgcttac aagattgtca agaaggggga ctcgaccatc 840
atgaagtccg agctggaata cggaaactgt aacactaagt gccaaacccc aatgggcgcc 900
attaacagct ccatgccgtt ccacaacatt cacccgctga ctatcggaga gtgccctaaa 960
tacgtgaagt ccaaccgcct ggtgttggcg accggtttgc gcaactcccc ccaacgcgaa 1020
cggcggagaa agaagcgggg actgtttgga gccattgccg ggttcatcga gggcggttgg 1080
cagggaatgg tggacggttg gtacggttat caccactcca acgaacaggg atccggatac 1140
gccgctgaca aggagtcgac ccagaaagcg atcgatggcg tgaccaacaa ggtcaacagc 1200
atcatcgata agatgaacac tcagttcgag gccgtgggaa gggaattcaa caatcttgag 1260
cggagaatag agaatctcaa caagaagatg gaagatgggt ttcttgacgt gtggacctac 1320
aacgccgaac tgctggtgct catggagaac gagcgaacgc tggacttcca tgactcgaac 1380
gtgaagaacc tgtacgataa ggtccgcctg caactgcggg acaacgctaa ggaattggga 1440
aacggttgtt tcgaattcta ccataagtgc gacaacgagt gcatggagtc agtgcgcaac 1500
ggaacatacg actatccaca gtactcagag gaagcccggc tgaagagaga agagatctcg 1560
ggcgtgaagc tggaatcgat cgggatctac cagattctgt ccatctactc cacggtggcg 1620
tcgtccctgg ccctggccat catggtggcc ggcctcagcc tgtggatgtg cagcaacgga 1680
tcacttcagt gccgcatctg catctga 1707

<210> SEQ ID NO 24
<211> LENGTH: 729
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: EGFP

<400> SEQUENCE: 24
atgggaagag ccggcgtgag caagggcgag gagctgttca ccggggtggt gcccatcctg 60
gtcgagctgg acggcgacgt aaacggccac aagttcagcg tgtccggcga gggcgagggc 120
gatgccacct acggcaagct gaccctgaag ctgatctgca ccaccggcaa gctgcccgtg 180
ccctggccca ccctcgtgac caccctgggc tacggcctgc agtgcttcgc ccgctacccc 240
gaccacatga agcagcacga cttcttcaag tccgccatgc ccgaaggcta cgtccaggag 300
cgcaccatct tcttcaagga cgacggcaac tacaagaccc gcgccgaggt gaagttcgag 360
ggcgacaccc tggtgaaccg catcgagctg aagggcatcg acttcaagga ggacggcaac 420
atcctggggc acaagctgga gtacaactac aacagccaca acgtctatat caccgccgac 480
aagcagaaga acggcatcaa ggccaacttc aagatccgcc acaacatcga ggacggcggc 540
gtgcagctcg ccgaccacta ccagcagaac acccccatcg gcgacggccc cgtgctgctg 600
cccgacaacc actacctgag ctaccagtcc gccctgagca aagaccccaa cgagaagcgc 660
gatcacatgg tcctgctgga gttcgtgacc gccgccggga tcactctcgg catggacgag 720
ctgtacaag 729

<210> SEQ ID NO 25
<211> LENGTH: 4203
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Cas9-codon optimized 1

<400> SEQUENCE: 25
atggccccaa agaagaagcg gaaggtcggt atccacggag tcccagcagc cgacaagaag 60
tacagcatcg gcctggacat cggcaccaac tctgtgggct gggccgtgat caccgacgag 120
tacaaggtgc ccagcaagaa attcaaggtg ctgggcaaca ccgaccggca cagcatcaag 180
aagaacctga tcggagccct gctgttcgac agcggcgaaa cagccgaggc cacccggctg 240
aagagaaccg ccagaagaag atacaccaga cggaagaacc ggatctgcta tctgcaagag 300
atcttcagca acgagatggc caaggtggac gacagcttct tccacagact ggaagagtcc 360
ttcctggtgg aagaggataa gaagcacgag cggcacccca tcttcggcaa catcgtggac 420
gaggtggcct accacgagaa gtaccccacc atctaccacc tgagaaagaa actggtggac 480

-continued

```
agcaccgaca aggccgacct gcggctgatc tatctggccc tggcccacat gatcaagttc    540
cggggccact tcctgatcga gggcgacctg aaccccgaca acagcgacgt ggacaagctg    600
ttcatccagc tggtgcagac ctacaaccag ctgttcgagg aaaaccccat caacgccagc    660
ggcgtggacg ccaaggccat cctgtctgcc agactgagca agagcagacg gctggaaaat    720
ctgatcgccc agctgcccgg cgagaagaag aatggcctgt tcggaaacct gattgccctg    780
agcctgggcc tgacccccaa cttcaagagc aacttcgacc tggccgagga tgccaaactg    840
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gccccctga gcgcctctat gatcaagaga   1020
tacgacgagc accaccagga cctgaccctg ctgaaagctc tcgtgcggca gcagctgcct   1080
gagaagtaca aagagatttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcggaa gcagcggacc   1260
ttcgacaacg gcagcatccc ccaccagatc cacctgggag agctgcacgc cattctgcgg   1320
cggcaggaag atttttaccc attcctgaag gacaaccggg aaaagatcga gaagatcctg   1380
accttccgca tcccctacta cgtgggccct ctggccaggg gaaacagcag attcgcctgg   1440
atgaccagaa agagcgagga aaccatcacc ccctggaact tcgaggaagt ggtggacaag   1500
ggcgcttccg cccagagctt catcgagcgg atgaccaact tcgataagaa cctgcccaac   1560
gagaaggtgc tgcccaagca cagcctgctg tacgagtact tcaccgtgta taacgagctg   1620
accaaagtga aatacgtgac cgagggaatg agaaagcccg ccttcctgag cggcgagcag   1680
aaaaaggcca tcgtggacct gctgttcaag accaaccgga aagtgaccgt gaagcagctg   1740
aaagaggact acttcaagaa aatcgagtgc ttcgactccg tggaaatctc cggcgtggaa   1800
gatcggttca acgcctccct gggcacatac cacgatctgc tgaaaattat caaggacaag   1860
gacttcctgg acaatgagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg gctggggcag gctgagccgg   2040
aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagaggaca tccagaaagc ccaggtgtcc ggccagggcg atagcctgca cgagcacatt   2220
gccaatctgg ccggcagccc cgccattaag aagggcatcc tgcagacagt gaaggtggtg   2280
gacgagctcg tgaaagtgat gggccggcac aagcccgaga acatcgtgat cgaaatggcc   2340
agagagaacc agaccaccca gaagggacag aagaacagcc gcgagagaat gaagcggatc   2400
gaagagggca tcaaagagct gggcagccag atcctgaaag aacaccccgt ggaaaacacc   2460
cagctgcaga acgagaagct gtacctgtac tacctgcaga atgggcggga tatgtacgtg   2520
gaccaggaac tggacatcaa ccggctgtcc gactacgatg tggaccatat cgtgcctcag   2580
agctttctga aggacgactc catcgacaac aaggtgctga ccagaagcga caagaaccgg   2640
ggcaagagcg acaacgtgcc ctccgaagag gtcgtgaaga agatgaagaa ctactggcgg   2700
cagctgctga acgccaagct gattacccag agaaagttcg acaatctgac caaggccgag   2760
agaggcggcc tgagcgaact ggataaggcc ggcttcatca agagacagct ggtggaaacc   2820
cggcagatca caaagcacgt ggcacagatc ctggactccc ggatgaacac taagtacgac   2880
```

```
gagaatgaca agctgatccg ggaagtgaaa gtgatcaccc tgaagtccaa gctggtgtcc   2940

gatttccgga aggatttcca gttttacaaa gtgcgcgaga tcaacaacta ccaccacgcc   3000

cacgacgcct acctgaacgc cgtcgtggga accgccctga tcaaaaagta ccctaagctg   3060

gaaagcgagt tcgtgtacgg cgactacaag gtgtacgacg tgcggaagat gatcgccaag   3120

agcgagcagg aaatcggcaa ggctaccgcc aagtacttct tctacagcaa catcatgaac   3180

tttttcaaga ccgagattac cctggccaac ggcgagatcc ggaagcggcc tctgatcgag   3240

acaaacggcg aaaccgggga gatcgtgtgg gataagggcc gggattttgc caccgtgcgg   3300

aaagtgctga gcatgcccca agtgaatatc gtgaaaaaga ccgaggtgca gacaggcggc   3360

ttcagcaaag agtctatcct gcccaagagg aacagcgata agctgatcgc cagaaagaag   3420

gactgggacc ctaagaagta cggcggcttc gacagcccca ccgtggccta ttctgtgctg   3480

gtggtggcca aagtggaaaa gggcaagtcc aagaaactga agagtgtgaa agagctgctg   3540

gggatcacca tcatggaaag aagcagcttc gagaagaatc ccatcgactt tctggaagcc   3600

aagggctaca aagaagtgaa aaaggacctg atcatcaagc tgcctaagta ctccctgttc   3660

gagctggaaa acggccggaa gagaatgctg gcctctgccg gcgaactgca gaagggaaac   3720

gaactggccc tgccctccaa atatgtgaac ttcctgtacc tggccagcca ctatgagaag   3780

ctgaagggct cccccgagga taatgagcag aaacagctgt ttgtggaaca gcacaagcac   3840

tacctggacg agatcatcga gcagatcagc gagttctcca agagagtgat cctggccgac   3900

gctaatctgg acaaagtgct gtccgcctac aacaagcacc gggataagcc catcagagag   3960

caggccgaga atatcatcca cctgtttacc ctgaccaatc tgggagcccc tgccgccttc   4020

aagtactttg acaccaccat cgaccggaag aggtacacca gcaccaaaga ggtgctggac   4080

gccaccctga tccaccagag catcaccggc ctgtacgaga cacggatcga cctgtctcag   4140

ctgggaggcg acaaaaggcc ggcggccacg aaaaaggccg gccaggcaaa aaagaaaaag   4200

taa                                                                 4203
```

<210> SEQ ID NO 26
<211> LENGTH: 4251
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Cas9-codon optimized 2

<400> SEQUENCE: 26

```
atgcccaaga aaaagcggaa ggtcggcgac tacaaggatg acgatgacaa gttggagcct     60

ggagagaagc cctacaaatg ccctgagtgc ggaaagagct tcagccaatc tggagccttg    120

acccggcatc aacgaacgca tacacgagac aagaagtact ccatcgggct ggacatcggg    180

acgaactccg tgggatgggc cgtgatcaca gacgaataca aggtgccttc caagaagttc    240

aaggtgctgg ggaacacgga cagacactcc atcaagaaga acctcatcgg ggccttgctc    300

ttcgactccg gagaaaccgc cgaagcaacg cgattgaaaa gaaccgccag aagacgatac    360

acacgacgga agaaccgcat ctgctacctc caggagatct tcagcaacga gatggccaag    420

gtggacgact cgttctttca tcgcctggag gagagcttcc tggtggagga agacaagaaa    480

catgagcgcc acccgatctt cgggaacatc gtggacgaag tggcctacca cgagaaatac    540

cccacgatct accacttgcg caagaaactc gtggactcca cggacaaagc ggacttgcgg    600
```

-continued

```
ttgatctact tggccttggc ccacatgatc aaatttcggg gccacttcct gatcgagggc    660
gacttgaatc ccgacaattc cgacgtggac aagctcttca tccagctggt gcagacctac    720
aaccagctct tcgaggagaa ccccatcaat gcctccggag tggacgccaa agccatcttg    780
tccgcccgat tgtccaaatc cagacgcttg gagaacttga tcgcacaact tcctggcgag    840
aagaagaacg gcctcttcgg caacttgatc gcgctgtcgc tgggattgac gcctaacttc    900
aagtccaact tcgacttggc cgaggacgcc aagttgcaac tgtccaagga cacctacgac    960
gacgacctcg acaacctgct ggcccaaatt ggcgaccaat acgcggactt gtttttggcg   1020
gccaagaact tgagcgacgc catcttgttg agcgacatct tgcgcgtgaa tacggagatc   1080
accaaagccc ctttgtccgc ctctatgatc aagcggtacg acgagcacca ccaagacttg   1140
accctgttga aagccctcgt gcggcaacaa ttgcccgaga agtacaagga gatcttcttc   1200
gaccagtcca agaacgggta cgccggctac atcgacggag gagcctccca agaagagttc   1260
tacaagttca tcaagcccat cctggagaag atggacggca ccgaggagtt gctcgtgaag   1320
ctgaaccgcg aagacttgtt gcgaaaacag cggacgttcg acaatggcag catcccccac   1380
caaatccatt tgggagagtt gcacgccatc ttgcgacggc aagaggactt ctacccgttc   1440
ctgaaggaca accgcgagaa aatcgagaag atcctgacgt tcagaatccc ctactacgtg   1500
ggacccttgg cccgaggcaa ttcccggttt gcatggatga cgcgcaaaag cgaagagacg   1560
atcacccccct ggaacttcga agaagtggtc gacaaaggag catccgcaca gagcttcatc   1620
gagcgaatga cgaacttcga caagaacctg cccaacgaga aggtgttgcc caagcattcg   1680
ctgctgtacg agtacttcac ggtgtacaac gagctgacca aggtgaagta cgtgaccgag   1740
ggcatgcgca aacccgcgtt cctgtcggga gagcaaaaga aggccattgt ggacctgctg   1800
ttcaagacca accggaaggt gaccgtgaaa cagctgaaag aggactactt caagaagatc   1860
gagtgcttcg actccgtgga gatctccggc gtggaggacc gattcaatgc ctccttggga   1920
acctaccatg acctcctgaa gatcatcaag gacaaggact tcctggacaa cgaggagaac   1980
gaggacatcc tggaggacat cgtgctgacc ctgaccctgt tcgaggaccg agagatgatc   2040
gaggaacggt tgaaaacgta cgcccacttg ttcgacgaca aggtgatgaa gcagctgaaa   2100
cgccgccgct acaccggatg ggacgattg agccgcaaac tgattaatgg aattcgcgac   2160
aagcaatccg gaaagaccat cctggacttc ctgaagtccg acgggttcgc caaccgcaac   2220
ttcatgcagc tcatccacga cgactccttg accttcaagg aggacatcca gaaggcccaa   2280
gtgtccggac aaggagactc cttgcacgag cacatcgcca atttggccgg atcccccgca   2340
atcaaaaaag gcatcttgca aaccgtgaaa gtggtcgacg aactggtgaa ggtgatggga   2400
cggcacaagc ccgagaacat cgtgatcgaa atggcccgcg agaaccaaac cacccaaaaa   2460
ggacagaaga actcccgaga gcgcatgaag cggatcgaag agggcatcaa ggagttgggc   2520
tcccagatcc tgaaggagca tcccgtggag aatacccaat tgcaaaacga gaagctctac   2580
ctctactacc tccagaacgg gcgggacatg tacgtcgacc aagagctgga catcaaccgc   2640
ctctccgact acgatgtgga tcatattgtg ccccagagct tcctcaagga cgacagcatc   2700
gacaacaagg tcctgacgcg cagcgacaag aaccggggca agtctgacaa tgtgccttcc   2760
gaagaagtcg tgaagaagat gaagaactac tggcggcagc tgctcaacgc caagctcatc   2820
acccaacgga agttcgacaa cctgaccaag gccgagagag gaggattgtc cgagttggac   2880
aaagccggct tcattaaacg ccaactcgtg gagacccgcc agatcacgaa gcacgtggcc   2940
```

caaatcttgg actcccggat gaacacgaaa tacgacgaga atgacaagct gatccgcgag 3000
gtgaaggtga tcacgctgaa gtccaagctg gtgagcgact tccggaagga cttccagttc 3060
tacaaggtgc gggagatcaa caactaccat cacgcccatg acgcctacct gaacgccgtg 3120
gtcggaaccg ccctgatcaa gaaatacccc aagctggagt ccgaattcgt gtacggagat 3180
tacaaggtct acgacgtgcg gaagatgatc gcgaagtccg agcaggagat cggcaaagcc 3240
accgccaagt acttctttta ctccaacatc atgaacttct tcaagaccga gatcacgctc 3300
gccaacggcg agatccgcaa gcgccccctg atcgagacca acggcgagac gggagagatt 3360
gtgtgggaca aaggaagaga ttttgccaca gtgcgcaagg tgctgtccat gcctcaggtg 3420
aacatcgtga agaagaccga ggtgcaaaca ggagggtttt ccaaagagtc cattttgcct 3480
aagaggaatt ccgacaagct catcgcccgc aagaaggact gggaccccaa gaagtacggg 3540
ggcttcgact cccccacggt ggcctactcc gtgttggtgg tggccaaagt ggagaaaggg 3600
aagagcaaga agctgaaatc cgtgaaggag ttgctcggaa tcacgatcat ggaacgatcg 3660
tcgttcgaga aaaaccccat cgacttcctc gaagccaaag ggtacaaaga ggtgaagaag 3720
gacctgatca tcaagctgcc caagtactcc ctgttcgagc tggagaacgg ccgcaagcgg 3780
atgctggcct ccgccgggga actgcagaaa gggaacgaat tggccttgcc ctccaaatac 3840
gtgaacttcc tctacttggc ctcccattac gaaaagctca aaggatcccc tgaggacaat 3900
gagcagaagc aactcttcgt ggaacaacac aagcactacc tggacgagat catcgagcag 3960
atcagcgagt tctccaagcg cgtgatcctc gccgacgcca acctggacaa ggtgctctcc 4020
gcctacaaca agcaccgcga caagcctatc cgcgagcaag ccgagaatat cattcacctg 4080
tttaccctga cgaatttggg agcccctgcc gcctttaaat actttgacac caccatcgac 4140
cgcaaaagat acacctccac caaggaagtc ttggacgcca ccctcatcca ccagtccatc 4200
acgggcctct acgagacgcg catcgacctc tcccaattgg gcggcgacta a 4251

<210> SEQ ID NO 27
<211> LENGTH: 532
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Csy4-HP

<400> SEQUENCE: 27
atgagcgtgc tcttcggcaa gctccaccag gccctggtgg cacagggcgg ggacaggatc 60
ggcgtgagct tccccgacct cgacgaaagc cgctcccggc tgggcgagcg cctgcgcatt 120
catgcctcgg cggacgacct tcgtgccctg ctcgcccggc cctggctgga agggttgcgg 180
gaccatctgc aattcggaga accggcagtc gtgcctcacc ccacaccgta ccgtcaggtc 240
agtcgggttc aggcgaaaag caatccggaa cgcctgcggc ggcggctcat gcgccggcac 300
gatctgagtg aggaggaggc tcggaaacgc attcccgata cggtcgcgag agccttggac 360
ctgcccttcg tcacgctacg cagccagagc accggacagc acttccgtct cttcatccgc 420
cacgggccgt tgcaggtgac ggcagaggaa ggaggattca cctgttacgg gttgagcaaa 480
ggaggtttcg ttccctggtt ctaagttcac tgccgtatag gcagctaaga aa 532

<210> SEQ ID NO 28
<211> LENGTH: 795
<212> TYPE: DNA

<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Neomycin resistance gene

<400> SEQUENCE: 28
atgattgaac aagatggatt gcacgcaggt tctccggccg cttgggtgga gaggctattc 60
ggctatgact gggcacaaca gacaatcggc tgctctgatg ccgccgtgtt ccggctgtca 120
gcgcaggggc gcccggttct ttttgtcaag accgacctgt ccggtgccct gaatgaactg 180
caggacgagg cagcgcggct atcgtggctg gccacgacgg gcgttccttg cgcagctgtg 240
ctcgacgttg tcactgaagc gggaagggac tggctgctat tgggcgaagt gccggggcag 300
gatctcctgt catctcacct tgctcctgcc gagaaagtat ccatcatggc tgatgcaatg 360
cggcggctgc atacgcttga tccggctacc tgcccattcg accaccaagc gaaacatcgc 420
atcgagcgag cacgtactcg gatggaagcc ggtcttgtcg atcaggatga tctggacgaa 480
gagcatcagg ggctcgcgcc agccgaactg ttcgccaggc tcaaggcgcg catgcccgac 540
ggcgaggatc tcgtcgtgac ccatggcgat gcctgcttgc cgaatatcat ggtggaaaat 600
ggccgctttt ctggattcat cgactgtggc cggctgggtg tggcggaccg ctatcaggac 660
atagcgttgg ctacccgtga tattgctgaa gagcttggcg gcgaatgggc tgaccgcttc 720
ctcgtgcttt acggtatcgc cgctcccgat tcgcagcgca tcgccttcta tcgccttctt 780
gacgagttct tctga 795

<210> SEQ ID NO 29
<211> LENGTH: 600
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Puromycin resistance gene

<400> SEQUENCE: 29
atgaccgagt acaagcccac ggtgcgcctc gccacccgcg acgacgtccc cagggccgta 60
cgcaccctcg ccgccgcgtt cgccgactac cccgccacgc gccacaccgt cgatccggac 120
cgccacatcg agcgggtcac cgagctgcaa gaactcttcc tcacgcgcgt cgggctcgac 180
atcggcaagg tgtgggtcgc ggacgacggc gccgcggtgg cggtctggac cacgccggag 240
agcgtcgaag cgggggcggt gttcgccgag atcggcccgc gcatggccga gttgagcggt 300
tcccggctgg ccgcgcagca acagatggaa ggcctcctgg cgccgcaccg gcccaaggag 360
cccgcgtggt tcctggccac cgtcggcgtc tcgcccgacc accagggcaa gggtctgggc 420
agcgccgtcg tgctccccgg agtggaggcg gccgagcgcg ccggggtgcc cgccttcctg 480
gagacatccg cgccccgcaa cctccccttc tacgagcggc tcggcttcac cgtcaccgcc 540
gacgtcgagg tgcccgaagg accgcgcacc tggtgcatga cccgcaagcc cggtgcctga 600

<210> SEQ ID NO 30
<211> LENGTH: 2319
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: B1-8 Light-EMCV-Heavy

<400> SEQUENCE: 30

```
atggcctgga tctcactcat tctctccctc cttgctcttt cctccggggc cattagccaa     60
gccgtggtca cccaagaatc cgctctgacc acctccccgg gagagactgt gactctgacc    120
tgtcggagct ccaccggagc agtgaccact tccaactatg cgaactgggt gcaggagaag    180
cccgatcacc tgttcactgg tctgatcggc ggtactaaca atagggctcc gggagtcccg    240
gcccgcttct ccgggagcct gatcggagac aaggccgccc tgaccatcac gggcgcacag    300
accgaggacg aggcgatcta cttctgcgcc ctgtggtact cgaaccattg ggtgtttggt    360
ggcggcacca aattgaccgt gctggggcag cctaagagct caccatcagt gactctcttc    420
cctccctcgt ctgaagaact cgaaactaac aaggccacct tggtctgcac tattaccgac    480
ttctacccgg gagtcgtgac cgtggattgg aaggtcgacg gcactcccgt gacccaggga    540
atggaaacaa cccagccatc caagcagagc aacaacaagt acatggcctc ctcgtacctg    600
accctgaccg cccgcgcctg ggagcggcac agctcctact catgccaagt gacccacgag    660
ggccataccg tggaaaagtc cctgtcaaga gctgactgct cgtgactaac gttactggcc    720
gaagccgctt ggaataaggc cggtgtgcgt ttgtctatat gttattttcc accatattgc    780
cgtcttttgg caatgtgagg gcccggaaac ctggccctgt cttcttgacg agcattccta    840
ggggtctttc ccctctcgcc aaaggaatgc aaggtctgtt gaatgtcgtg aaggaagcag    900
ttcctctgga agcttcttga agacaaacaa cgtctgtagc gaccctttgc aggcagcgga    960
acccccacc tggcgacagg tgcctctgcg gccaaaagcc acgtgtataa gatacacctg   1020
caaaggcggc acaaccccag tgccacgttg tgagttggat agttgtggaa agagtcaaat   1080
ggctctcctc aagcgtattc aacaaggggc tgaaggatgc ccagaaggta ccccattgta   1140
tgggatctga tctggggcct cggtgcacat gctttacatg tgtttagtcg aggttaaaaa   1200
aacgtctagg ccccccgaac cacggggacg tggttttcct ttgaaaaaca gatgggttgg   1260
tcctgtatta tgctgtttct cgccgccact gctaccggag tgcactccca agtgcagctg   1320
cagcaatccg gtgccgagct tgtgaaaccc ggagcctcgg tcaagctgtc ctgcaaagct   1380
tccggctaca ctttcacctc ctactggatg cattgggtca agcagcggcc gggccggggc   1440
ctggaatgga ttggccgcat cgaccctaac agcggaggaa cgaagtacaa cgaaaagttt   1500
aagtccaagg ccaccctgac cgtggataag ccctcctcca ccgcctacat gcagctgagc   1560
tccctcacat ccgaggactc ggccgtctat tactgcgcac gctacgacta ctacggatca   1620
tcctacttcg actactgggg ccagggaact accgtgacgg tgtcgtcaaa gactacccct   1680
ccgagcgtgt acccactggc cccgggatct gcggcccaaa ctaactcgat ggtcaccctc   1740
ggttgtctgg tcaagggata tttcccggaa cctgtgaccg tcacctggaa ttctgggtcc   1800
ctctcgagcg gcgtgcatac cttccccgcc gtgctgcagt cggatctcta caccctgagc   1860
agcagcgtga ccgtcccgtc ctccacctgg ccctcggaaa ccgtgacttg caacgtcgca   1920
caccctgcga gctcgactaa ggtcgacaag aagatcgtgc cgagggactg cgggtgcaag   1980
ccttgcatct gcactgtgcc cgaagtgtcc tccgtgttca tcttcccgcc caagcctaaa   2040
gacgtgctga ccattactct gaccccaaag gtcacttgcg tggtggtgga catcagcaag   2100
gacgacccgg aggtgcagtt ctcatggttc gtggatgatg tggaagtgca cactgcccag   2160
acccagccgc gggaggagca gttcaacagc accttccgct cggtgtccga attgcccatt   2220
atgcaccagg actggctgaa cgggaaggag ttcaaatgta gagtgaactc agccgccttc   2280
```

cctgcgccta tcgaaaagac tatcagcaag accaaatag 2319

<210> SEQ ID NO 31
<211> LENGTH: 2519
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: B1-8 Light-EV71-Heavy

<400> SEQUENCE: 31
atggcctgga tctcactcat tctctccctc cttgctcttt cctccggggc cattagccaa 60
gccgtggtca cccaagaatc cgctctgacc acctccccgg gagagactgt gactctgacc 120
tgtcggagct ccaccggagc agtgaccact tccaactatg cgaactgggt gcaggagaag 180
cccgatcacc tgttcactgg tctgatcggc ggtactaaca atagggctcc gggagtcccg 240
gcccgcttct ccgggagcct gatcggagac aaggccgccc tgaccatcac gggcgcacag 300
accgaggacg aggcgatcta cttctgcgcc ctgtggtact cgaaccattg ggtgtttggt 360
ggcggcacca aattgaccgt gctggggcag cctaagagct caccatcagt gactctcttc 420
cctccctcgt ctgaagaact cgaaactaac aaggccacct tggtctgcac tattaccgac 480
ttctacccgg gagtcgtgac cgtggattgg aaggtcgacg gcactcccgt gacccaggga 540
atggaaacaa cccagccatc caagcagagc aacaacaagt acatggcctc ctcgtacctg 600
accctgaccg cccgcgcctg ggagcggcac agctcctact catgccaagt gacccacgag 660
ggccataccg tggaaaagtc cctgtcaaga gctgactgct cgtgattaaa acagctgtgg 720
gttgttccca cccacagggc ccactgggcg ctagcactct gattttacga aatccttgtg 780
cgcctgttta tatcccttcc ctaattcgaa acgtagaagc aatgcgcacc actgatcaat 840
agtaggcgta acgcgccagt tacgtcatga tcaagcatat ctgttccccc ggactgagta 900
tcaatagact gcttacgcgg ttgaaggaga aaacgttcgt tatccggcta actacttcga 960
gaagcccagt aacaccatgg aagctgcagg gtgtttcgct cagcacttcc cccgtgtaga 1020
tcaggtcgat gagccactgc aatccccaca ggtgactgtg gcagtggctg cgttggcggc 1080
ctgcctatgg ggagacccat aggacgctct aatgtggaca tggtgcgaag agcctattga 1140
gctagttagt agtcctccgg cccctgaatg cggctaatcc taactgcgga gcacatgcct 1200
tcaacccaga gggtagtgtg tcgtaacggg caactctgca gcggaaccga ctactttggg 1260
tgtccgtgtt tctttttat tcttatattg gctgcttatg gtgacaatta cagaattgtt 1320
accatatagc tattggattg gccatccggt gtgtaataga gctgttatat acctatttgt 1380
tggctttgta ccactaactt taaaatctat aactaccctc aactttatat taaccctcaa 1440
tacagttgac catgggttgg tcctgtatta tgctgtttct cgccgccact gctaccggag 1500
tgcactccca agtgcagctg cagcaatccg gtgccgagct tgtgaaaccc ggagcctcgg 1560
tcaagctgtc ctgcaaagct tccggctaca ctttcacctc ctactggatg cattgggtca 1620
agcagcggcc gggccggggc ctggaatgga ttggccgcat cgaccctaac agcggaggaa 1680
cgaagtacaa cgaaaagttt aagtccaagg ccaccctgac cgtggataag ccctcctcca 1740
ccgcctacat gcagctgagc tccctcacat ccgaggactc ggccgtctat tactgcgcac 1800
gctacgacta ctacggatca tcctacttcg actactgggg ccagggaact accgtgacgg 1860
tgtcgtcaaa gactacccct ccgagcgtgt acccactggc cccgggatct gcggcccaaa 1920
ctaactcgat ggtcaccctc ggttgtctgg tcaagggata tttcccggaa cctgtgaccg 1980
tcacctggaa ttctgggtcc ctctcgagcg gcgtgcatac cttccccgcc gtgctgcagt 2040
cggatctcta caccctgagc agcagcgtga ccgtcccgtc ctccacctgg ccctcggaaa 2100
ccgtgacttg caacgtcgca caccctgcga gctcgactaa ggtcgacaag aagatcgtgc 2160
cgagggactg cgggtgcaag ccttgcatct gcactgtgcc cgaagtgtcc tccgtgttca 2220
tcttcccgcc caagcctaaa gacgtgctga ccattactct gaccccaaag gtcacttgcg 2280
tggtggtgga catcagcaag gacgacccgg aggtgcagtt ctcatggttc gtggatgatg 2340
tggaagtgca cactgcccag acccagccgc gggaggagca gttcaacagc accttccgct 2400
cggtgtccga attgcccatt atgcaccagg actggctgaa cgggaaggag ttcaaatgta 2460
gagtgaactc agccgccttc cctgcgccta tcgaaaagac tatcagcaag accaaatag 2519

<210> SEQ ID NO 32
<211> LENGTH: 2709
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Herceptin

<400> SEQUENCE: 32
atggacatga gagtacctgc acagcttctg ggattactgt tactgtggct gtctggagcc 60
agatgtgaca tccaaatgac ccaaagccct tcttctctgt ctgcttctgt gggagataga 120
gtgacaatca cctgtagagc cagccaggat gtgaatacag ctgttgcttg gtaccagcag 180
aagcctggaa aagctcctaa actgctgatc tactctgcct ctttcctgta ctctggagtg 240
ccttctaggt tttctggcag cagatctggc acagacttca cactgacaat cagctctctg 300
cagcctgagg attttgccac atactactgt cagcagcact acacaacccc tcctacattt 360
ggacagggca caaaagtgga gatcaagaga acagtggctg ccccttctgt gttcatcttt 420
cctccttctg acgagcagct gaagtctgga acagcttctg tggtttgtct gctgaacaac 480
ttctacccta gagaggctaa ggtgcagtgg aaagtggata atgctctgca gtctggcaac 540
tctcaggaat ctgtgacaga gcaggacagc aaggactcta catactctct gagcagcaca 600
ctgacactgt ctaaggccga ttacgagaag cacaaggtgt acgcttgtga ggtgacacat 660
caaggactgt cttctcctgt gaccaagagc ttcaatagag gcgagtgtta attaagcccc 720
tctccctccc ccccccctaa cgttactggc cgaagccgct tggaataagg ccggtgtgcg 780
tttgtctata tgttattttc caccatattg ccgtcttttg gcaatgtgag ggcccggaaa 840
cctggccctg tcttcttgac gagcattcct aggggtcttt cccctctcgc caaaggaatg 900
caaggtctgt tgaatgtcgt gaaggaagca gttcctctgg aagcttcttg aagacaaaca 960
acgtctgtag cgaccctttg caggcagcgg aaccccccac ctggcgacag gtgcctctgc 1020
ggccaaaagc cacgtgtata agatacacct gcaaaggcgg cacaacccca gtgccacgtt 1080
gtgagttgga tagttgtgga aagagtcaaa tggctctcct caagcgtatt caacaagggg 1140
ctgaaggatg cccagaaggt accccattgt atgggatctg atctggggcc tcggtgcaca 1200
tgctttacat gtgtttagtc gaggttaaaa aacgtctagg ccccccgaac cacggggacg 1260
tggttttcct ttgaaaaaca cgatgataat atggccacaa ccatggaact gggactgtca 1320
tggatcttct tgctggctat cctgaaggga gtgcagtgtg aagttcagct ggtggaatca 1380
ggaggaggat tagttcaacc aggcggatct ctgagactgt cttgtgctgc ttctggcttc 1440
aacatcaagg acacctacat ccattgggtg agacaagctc ctggaaaagg attggaatgg 1500
gtggctagga tctaccctac aaatggctac accagatacg ccgatagcgt gaaaggcaga 1560
ttcacaatca gcgccgatac ctctaagaac acagcttatc tgcagatgaa cagcctgaga 1620
gctgaggata cagctgtgta ctactgtagc agatggggag gagatggctt ttacgctatg 1680
gattactggg gacagggcac attagtgaca gtgtcttctg ccagcacaaa gggaccttct 1740
gtgtttcctc ttgccccttc ttctaagagc acatctggag gaacagctgc tttgggatgt 1800
ctggtgaagg actactttcc tgaacctgtg acagtgagct ggaattctgg agctctgaca 1860
tctggagtgc acacatttcc tgctgttctg cagtcttctg gcctgtattc tctgtcttct 1920
gtggtgacag tgccttctag ctctcttgga acacagacct acatctgcaa cgtgaaccac 1980
aagcctagca acacaaaggt ggacaagaag gtggagccta agagctgtga caagacacac 2040
acatgtcctc cttgtcctgc tcctgaatta cttggaggac cttctgtgtt cctgttccct 2100
cctaaaccta aggacaccct gatgatcagc agaacacctg aagtgacctg tgtggtggtt 2160
gatgtgtctc atgaggatcc tgaggtgaag ttcaactggt acgtggatgg agtggaggtg 2220
cataatgcca agacaaagcc tagagaggag cagtacaaca gcacctatag agtggtgtct 2280
gtgctgacag tgctgcatca agattggctg aatggcaagg agtacaagtg caaggtgagc 2340
aataaggctc tgcctgctcc tatcgagaag acaatctcta aggccaaggg acagcctaga 2400
gaacctcagg tttacacact tcctcctagc agagaggaga tgaccaagaa tcaggtgagc 2460
ctgacatgtc tggtgaaggg attttaccct agcgatatcg ctgtggaatg ggagtctaat 2520
ggacagcctg agaacaacta caagaccaca cctcctgtgc tggattctga tggctctttc 2580
ttcctgtaca gcaagctgac agtggacaag tctagatggc aacagggcaa tgtgttcagc 2640
tgttctgtga tgcatgaggc tctgcacaac cactataccc agaaaagcct gagcctgtct 2700
cctggataa 2709

<210> SEQ ID NO 33
<211> LENGTH: 2712
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Humira

<400> SEQUENCE: 33
atggacatga gagtacctgc acagcttctg ggattactgt tactgtggct gtctggagcc 60
agatgtgata ttcagatgac ccagagccct tctagccttt ctgcttctgt tggcgataga 120
gtgaccatca cctgtagagc ttctcaggga atccggaatt accttgcttg gtatcagcag 180
aagcccggaa aagctcctaa actgctgatc tatgccgcct ctacactgca atctggagtt 240
cctagcaggt tttctggctc tggatctgga acagacttca cactgaccat cagctctctt 300
cagcctgaag atgtggccac atactactgt cagcggtaca atagagcccc ttacacattt 360
ggacagggca caaaagtgga gatcaagaga acagtggctg ccccttctgt gttcatcttt 420
cctccttctg acgagcagct gaagtctgga acagcttctg tggtttgtct gctgaacaac 480
ttctacccta gagaggctaa ggtgcagtgg aaagtggata atgctctgca gtctggcaac 540
tctcaggaat ctgtgacaga gcaggacagc aaggactcta catactctct gagcagcaca 600

-continued

```
ctgacactgt ctaaggccga ttacgagaag cacaaggtgt acgcttgtga ggtgacacat    660
caaggactgt cttctcctgt gaccaagagc ttcaatagag gcgagtgtta attaagcccc    720
tctccctccc ccccccctaa cgttactggc cgaagccgct tggaataagg ccggtgtgcg    780
tttgtctata tgttattttc caccatattg ccgtcttttg gcaatgtgag ggcccggaaa    840
cctggccctg tcttcttgac gagcattcct aggggtcttt cccctctcgc caaaggaatg    900
caaggtctgt tgaatgtcgt gaaggaagca gttcctctgg aagcttcttg aagacaaaca    960
acgtctgtag cgaccctttg caggcagcgg aaccccccac ctggcgacag gtgcctctgc   1020
ggccaaaagc cacgtgtata agatacacct gcaaaggcgg cacaacccca gtgccacgtt   1080
gtgagttgga tagttgtgga aagagtcaaa tggctctcct caagcgtatt caacaagggg   1140
ctgaaggatg cccagaaggt accccattgt atgggatctg atctggggcc tcggtgcaca   1200
tgctttacat gtgtttagtc gaggttaaaa aacgtctagg ccccccgaac cacggggacg   1260
tggttttcct ttgaaaaaca cgatgataat atggccacaa ccatggaact gggactgtca   1320
tggatcttct tgctggctat cctgaaggga gtgcagtgtg aagtgcagtt agtggaatct   1380
ggaggaggat tagtgcagcc tggaagatct cttagactgt cttgtgctgc ctctggcttc   1440
acattcgacg attatgctat gcactgggtg agacaagctc ctggaaaagg attggaatgg   1500
gtgtctgcca tcacctggaa ttctggacac atcgattacg ccgactctgt tgaaggcaga   1560
ttcacaatca gccgggataa tgccaagaac agcctgtatc tgcagatgaa cagcctgaga   1620
gctgaggata cagctgtgta ctactgtgct aaggtgagct acctgtctac agcctcttct   1680
ctggattact ggggacaagg aacactggtt acagtgtctt ctgccagcac aaaaggccct   1740
tctgtgtttc ctcttgcccc ttcttctaag agcacatctg gaggaacagc tgctttggga   1800
tgtctggtga aggactactt tcctgaacct gtgacagtga gctggaattc tggagctctg   1860
acatctggag tgcacacatt tcctgctgtt ctgcagtctt ctggcctgta ttctctgtct   1920
tctgtggtga cagtgccttc tagctctctt ggaacacaga cctacatctg caacgtgaac   1980
cacaagccta gcaacacaaa ggtggacaag aaggtggagc ctaagagctg tgacaagaca   2040
cacacatgtc ctccttgtcc tgctcctgaa ttacttggag gaccttctgt gttcctgttc   2100
cctcctaaac ctaaggacac cctgatgatc agcagaacac ctgaagtgac ctgtgtggtg   2160
gttgatgtgt ctcatgagga tcctgaggtg aagttcaact ggtacgtgga tggagtggag   2220
gtgcataatg ccaagacaaa gcctagagag gagcagtatc agagcaccta tagagtggtg   2280
tctgtgctga cagtgctgca tcaagattgg ctgaatggca aggagtacaa gtgcaaggtg   2340
agcaataagg ctctgcctgc tcctatcgag aagacaatct ctaaggccaa gggacagcct   2400
agagaacctc aggtttacac acttcctcct agcagagatg agctgaccaa gaatcaggtg   2460
agcctgacat gtctggtgaa gggattttac cctagcgata tcgctgtgga atgggagtct   2520
aatggacagc ctgagaacaa ctacaagacc acacctcctg tgctggattc tgatggctct   2580
ttcttcctgt acagcaagct gacagtggac aagtctagat ggcaacaggg caatgtgttc   2640
agctgttctg tgatgcatga ggctctgcac aaccactata cccagaaaag cctgagcctg   2700
tctcctggat aa                                                       2712
```

<210> SEQ ID NO 34
<211> LENGTH: 1335
<212> TYPE: DNA
<213> ORGANISM: Artificial Sequence
<220> FEATURE:

-continued

<223> OTHER INFORMATION: Synthetic polynucleotide
<220> FEATURE:
<221> NAME/KEY: misc_feature
<223> OTHER INFORMATION: GFP-ApoAI fusion

<400> SEQUENCE: 34
atgggaagag ccggcgtgag caagggcgag gagctgttca ccggggtggt gcccatcctg 60
gtcgagctgg acggcgacgt aaacggccac aagttcagcg tgtccggcga gggcgagggc 120
gatgccacct acggcaagct gaccctgaag ctgatctgca ccaccggcaa gctgcccgtg 180
ccctggccca ccctcgtgac caccctgggc tacggcctgc agtgcttcgc ccgctacccc 240
gaccacatga agcagcacga cttcttcaag tccgccatgc ccgaaggcta cgtccaggag 300
cgcaccatct tcttcaagga cgacggcaac tacaagaccc gcgccgaggt gaagttcgag 360
ggcgacaccc tggtgaaccg catcgagctg aagggcatcg acttcaagga ggacggcaac 420
atcctggggc acaagctgga gtacaactac aacagccaca acgtctatat caccgccgac 480
aagcagaaga acggcatcaa ggccaacttc aagatccgcc acaacatcga ggacggcggc 540
gtgcagctcg ccgaccacta ccagcagaac acccccatcg gcgacggccc cgtgctgctg 600
cccgacaacc actacctgag ctaccagtcc gccctgagca aagaccccaa cgagaagcgc 660
gatcacatgg tcctgctgga gttcgtgacc gccgccggga tcactctcgg catggacgag 720
ctgtacaagc atatgctgaa cctgctggaa aactgggaca ccctgggttc taccgtttct 780
cagctgcagg aacgtctggg tccgctgacc cgtgacttct gggacaacct ggaaaaagaa 840
accgactggg ttcgtcagga aatgaacaaa gacctggaag aagttaaaca gaaagttcag 900
ccgtacctgg acgaattcca gaaaaaatgg aaagaagacg ttgaactgta ccgtcagaaa 960
gttgcgccgc tgggtgcgga actgcaggaa tctgcgcgtc agaaactgca ggaactgcag 1020
ggtcgtctgt ctccggttgc ggaagaattc cgtgaccgta tgcgtaccca cgttgactct 1080
ctgcgtaccc agctggcgcc gcactctgaa cagatgcgtg aatctctggc gcagcgtctg 1140
gcggaactga aatctaaccc gaccctgaac gaataccaca cccgtgcgaa aacccacctg 1200
aaaaccctgg gtgaaaaagc gcgtccggcg ctggaagacc tgcgtcactc tctgatgccg 1260
atgctggaaa ccctgaaaac caaagcgcag tctgttatcg acaaagcgtc tgaaaccctg 1320
accgcgcagg gatcc 1335

<210> SEQ ID NO 35
<211> LENGTH: 1632
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: IL-12

<400> SEQUENCE: 35
atgtgtcctc agaagctaac catctcctgg tttgccatcg ttttgctggt gtctccactc 60
atggccatgt gggagctgga gaaagacgtt tatgttgtag aggtggactg gactcccgat 120
gcccctggag aaacagtgaa cctcacctgt gacacgcctg aagaagatga catcacctgg 180
acctcagacc agagacatgg agtcataggc tctggaaaga ccctgaccat cactgtcaaa 240
gagtttctag atgctggcca gtacacctgc cacaaaggag gcgagactct gagccactca 300
catctgctgc tccacaagaa ggaaaatgga atttggtcca ctgaaatttt aaaaaatttc 360
aaaaacaaga ctttcctgaa gtgtgaagca ccaaattact ccggacggtt cacgtgctca 420
tggctggtgc aaagaaacat ggacttgaag ttcaacatca agagcagtag cagttcccct 480
gactctcggg cagtgacatg tggaatggcg tctctgtctg cagagaaggt cacactggac 540
caaagggact atgagaagta ttcagtgtcc tgccaggagg atgtcacctg cccaactgcc 600
gaggagaccc tgcccattga actggcgttg gaagcacggc agcagaataa atatgagaac 660
tacagcacca gcttcttcat cagggacatc atcaaaccag acccgcccaa gaacttgcag 720
atgaagcctt tgaagaactc acaggtggag gtcagctggg agtaccctga ctcctggagc 780
actccccatt cctacttctc cctcaagttc tttgttcgaa tccagcgcaa gaaagaaaag 840
atgaaggaga cagaggaggg gtgtaaccag aaaggtgcgt tcctcgtaga gaagacatct 900
accgaagtcc aatgcaaagg cgggaatgtc tgcgtgcaag ctcaggatcg ctattacaat 960
tcctcatgca gcaagtgggc atgtgttccc tgcagggtcc gatccggtgg cggtggctcg 1020
ggcggtggtg ggtcgggtgg cggcggatct agggtcattc cagtctctgg acctgccagg 1080
tgtcttagcc agtcccgaaa cctgctgaag accacagatg acatggtgaa gacggccaga 1140
gaaaaactga aacattattc ctgcactgct gaagacatcg atcatgaaga catcacacgg 1200
gaccaaacca gcacattgaa gacctgttta ccactggaac tacacaagaa cgagagttgc 1260
ctggctacta gagagacttc ttccacaaca agagggagct gcctgccccc acagaagacg 1320
tctttgatga tgaccctgtg ccttggtagc atctatgagg acttgaagat gtaccagaca 1380
gagttccagg ccatcaacgc agcacttcag aatcacaacc atcagcagat cattctagac 1440
aagggcatgc tggtggccat cgatgagctg atgcagtctc tgaatcataa tggcgagact 1500
ctgcgccaga aacctcctgt gggagaagca gacccttaca gagtgaaaat gaagctctgc 1560
atcctgcttc acgccttcag cacccgcgtc gtgaccatca acagggtgat gggctatctg 1620
agctccgcct ga 1632

<210> SEQ ID NO 36
<211> LENGTH: 948
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: EpCam

<400> SEQUENCE: 36
atggcgggtc cccaggccct cgcgttcggg ctcctgctcg cggtggtcac agcgacgctg 60
gccgcggctc agagagactg tgtctgtgac aactacaagc tggcaacaag ttgctctctg 120
aatgaatatg gtgaatgcca gtgtacttcc tatggtacac agaatactgt catttgctcc 180
aaactggcgt ctaaatgctt ggcgatgaaa gcagaaatga ctcacagcaa gtctgggagg 240
aggataaagc ccgaaggggc gatccagaac aacgatgggc tgtacgaccc cgactgcgac 300
gagcaggggc tcttcaaagc caagcagtgc aacggcaccg ccacgtgctg gtgtgtcaac 360
accgccggag tccgaagaac cgacaaggac acggagatca cgtgctccga gcgcgtgagg 420
acctactgga tcatcattga actaaaacac aaagaaagag aaagccccta cgaccatcag 480
agcttgcaga ctgcgcttca agaggcgttc acatctcgat ataagctgaa tcagaaattt 540
atcaaaaaca ttatgtatga gaataatgtt atcaccattg atctgatgca aaactcttct 600
cagaaaacac aagacgacgt ggacatagct gatgtggctt actattttga aaaagatgtg 660
aagggggagt ccctgttcca ttcttctaag agcatggacc tgagagtgaa cggagagccg 720
ctcgatctgg accccgggca gactctgatt tactacgttg atgaaaaggc acccgagttc 780
tccatgcagg gcctcacggc cgggatcatc gctgtcattg tggtggtgtc attagcagtc 840
atcgcgggga ttgttgtcct ggttatatct acaaggaaga aatcagcaaa atatgagaag 900
gctgagataa aggagatggg tgagatccac agagagctta atgcctag 948

<210> SEQ ID NO 37
<211> LENGTH: 1434
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: His6-CT26

<400> SEQUENCE: 37
atgcaccatc accatcacca tttgcactcc ggacagaacc acctgaaaga aatggccatc 60
tccgtgcttg aagccagagc ctgcgcagct gctggccaat cgggaggttc aggaggggga 120
ggaagcggtg gagatactct gtcagccatg agcaatcccc gcgctatgca agtcctgctc 180
caaatccaac aaggcctgca gactctggcg accggcggat ccggtggcgg aggttccgga 240
ggagatgggc agctcgaact gttggctcag ggagctctgg ataacgccct gtcctccatg 300
ggagccctgc acgcactgcg gcctggagga tcgggaggag gaggatcagg aggctggaag 360
gggggtcctg tgaaaattga ccccttggct ctgatgcagg ccatcgaaag atatctggtc 420
gtgcggggat acggtggagg gtccggaggg ggcggatcgg gcggacagga catcaacgac 480
aacaacccga gctttccaac cgggaagatg aagctggaaa tctcggaagc tctggcccct 540
ggaaccggcg gctccggtgg aggcggtagc gggggatccg acccgcgggc cgcgtatttc 600
agacaggccg aaaacgacat gtacatcaga atggccctgc tggctactgt gcttggcggt 660
ggatctggag gagggggatc cggaatggac ttgttggcat tcgaacggaa actggaccaa 720
accgtgatgc ggaagagact ggacatccag gaggctctta agaggggagg ttctggaggc 780
ggaggatctg gtggtattac cacttgcctc gccgtgggag ggctggatgt gaagttccag 840
gaggcggcac tgagggccgc ccctgatatt ctgatcgggg gatcaggcgg aggaggctcc 900
gggggaaagg cccggctgaa gtcaaaggat gtgaagctgg ctgaggcgca tcagcaggag 960
tgctgtcaga agttcgaaca gctctccgga ggctcgggcg gtggaggcag cggtggagga 1020
gaagtgccac ctcaaaaact tcaggccctg caacgcgcgc tgcagtcaga attctgcaac 1080
gccgtgcggg aggtgtacgg aggatccgga ggaggtggca gcggaggaca ggccattgtg 1140
cggggttgct cgatgccggg accctggcgg tccggccgcc tgctcgtgtc aagaagatgg 1200
agcgtggaag gaggctcagg gggtggaggg agcggaggag gttacatctc ccgcgtcacc 1260
gcgggaaagg actcctacat cgctctcgtg gataagaaca ttatgggata cattgcgtcc 1320
ggaggttcgg gtggcggtgg ctccggaggc ggagaggtgc caccgcagaa gctccaggcc 1380
ttgcaaagag cccttcagtc cgagttctgt aacgcagtca gggaggtcta ctag 1434

<210> SEQ ID NO 38
<211> LENGTH: 1446
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature -continued
<223> OTHER INFORMATION: myc-CT26

<400> SEQUENCE: 38

```
atggaacaaa aactcatctc agaagaggat ctgttgcact ccggacagaa ccacctgaaa      60
gaaatggcca tctccgtgct tgaagccaga gcctgcgcag ctgctggcca atcgggaggt     120
tcaggagggg gaggaagcgg tggagatact ctgtcagcca tgagcaatcc ccgcgctatg     180
caagtcctgc tccaaatcca acaaggcctg cagactctgg cgaccggcgg atccggtggc     240
ggaggttccg gaggagatgg gcagctcgaa ctgttggctc agggagctct ggataacgcc     300
ctgtcctcca tgggagccct gcacgcactg cggcctggag gatcgggagg aggaggatca     360
ggaggctgga aggggggtcc tgtgaaaatt gaccccttgg ctctgatgca ggccatcgaa     420
agatatctgg tcgtgcgggg atacggtgga gggtccggag ggggcggatc gggcggacag     480
gacatcaacg acaacaaccc gagctttcca accgggaaga tgaagctgga aatctcggaa     540
gctctggccc ctggaaccgg cggctccggt ggaggcggta gcgggggatc cgacccgcgg     600
gccgcgtatt tcagacaggc cgaaaacgac atgtacatca gaatggccct gctggctact     660
gtgcttggcg gtggatctgg aggaggggga tccggaatgg acttgttggc attcgaacgg     720
aaactggacc aaaccgtgat gcggaagaga ctggacatcc aggaggctct taagagggga     780
ggttctggag gcggaggatc tggtggtatt accacttgcc tcgccgtggg agggctggat     840
gtgaagttcc aggaggcggc actgagggcc gcccctgata ttctgatcgg gggatcaggc     900
ggaggaggct ccggggggaaa ggcccggctg aagtcaaagg atgtgaagct ggctgaggcg     960
catcagcagg agtgctgtca gaagttcgaa cagctctccg gaggctcggg cggtggaggc    1020
agcggtggag gagaagtgcc acctcaaaaa cttcaggccc tgcaacgcgc gctgcagtca    1080
gaattctgca acgccgtgcg ggaggtgtac ggaggatccg gaggaggtgg cagcggagga    1140
caggccattg tgcggggttg ctcgatgccg ggaccctggc ggtccggccg cctgctcgtg    1200
tcaagaagat ggagcgtgga aggaggctca gggggtggag ggagcggagg aggttacatc    1260
tcccgcgtca ccgcgggaaa ggactcctac atcgctctcg tggataagaa cattatggga    1320
tacattgcgt ccggaggttc gggtggcggt ggctccggag gcggagaggt gccaccgcag    1380
aagctccagg ccttgcaaag agcccttcag tccgagttct gtaacgcagt cagggaggtc    1440
tactag                                                               1446
```

<210> SEQ ID NO 39
<211> LENGTH: 732
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: codon-optimized EGFP

<400> SEQUENCE: 39

```
atgggcaggg caggagtttc taagggggaa gagcttttta cgggcgtcgt gccgatactt      60
gtcgagcttg acggagacgt aaacggccat aaattctcag tctctggtga aggagaaggc     120
gacgcgacat acggaaagtt gacgttgaag ttgatatgca ctactggaaa gctgcctgta     180
ccgtggccga ccctggtgac aactctcgga tatggtcttc aatgtttcgc gcgctatccc     240
gatcatatga aacaacatga ctttttttaag tctgcaatgc ccgaggggta cgtccaggag     300
cgcaccattt tctttaaaga tgacggtaac tacaagacaa gagccgaggt taagttcgag     360
```

ggggacacgc tcgttaaccg aatagaactg aaggggattg acttcaaaga ggacggtaac 420
atcctcggcc acaaactgga gtataactat aacagtcaca acgtatacat caccgctgat 480
aaacaaaaga atggtataaa agccaatttc aaaattagac acaatatcga ggacgggggg 540
gtgcagcttg cggaccacta tcagcaaaat acacccatag gagacggccc ggtcttgctt 600
cccgataacc attacttgtc atatcagtct gctctttcaa aagatccgaa cgagaaacgg 660
gaccacatgg ttcttcttga atttgtaact gctgcgggga ttacactggg tatggatgag 720
ttgtataagt ag 732

<210> SEQ ID NO 40
<211> LENGTH: 9752
<212> TYPE: DNA
<213> ORGANISM: Artificial Sequence
<220> FEATURE:
<223> OTHER INFORMATION: Synthetic polynucleotide

<400> SEQUENCE: 40
gctcgaagtg tgtatggtgc catatacggc tcaccaccat atacactgca agaattacta 60
ttcttgtggg cccctctcgg taaatcctag agggctttcc tctcgttatt gcgagattcg 120
tcgttagata acggcaagtt ccctttctta ctatcctatt ttcatcttgt ggcttgacgg 180
gtcactgcca tcgtcgtcga tctctatcaa ctacccttgc gactatggca accttctccg 240
ctactggatt tggagggagt tttgttaggg actggtccct ggacttaccc gacgcttgtg 300
agcatggcgc gggattgtgc tgcgaagtgg acggctccac cttatgcgcc gagtgttttc 360
gcggttgcga aggaatggag caatgtcctg gcttgttcat gggactgtta aaactggctt 420
cgccagttcc agtgggacat aagttcctga ttggttggta tcgagctgcc aaagtcaccg 480
ggcgttacaa tttccttgag ctgttgcaac accctgcttt cgcccagctg cgtgtggttg 540
atgctaggtt agccattgaa gaggcaagtg tgtttatttc cactgaccac gcgtctgcta 600
agcgtttccc tggcgctaga tttgcgctga caccggtgta tgctaacgct tgggttgtga 660
gcccggctgc taacagtttg atagtgacca ctgaccagga acaagatggg ttctgctggt 720
taaaactttt gccacctgac cgccgtgagg ctggtttgcg gttgtattac aaccattacc 780
gcgaacaaag gaccgggtgg ctgtctaaaa caggacttcg cttatggctt ggagacctgg 840
gtttgggcat caatgcgagc tctggagggc tgaaattcca cattatgagg ggttcgcctc 900
agcgagcttg gcatatcaca acacgcagct gcaagctgaa gagctactac gtttgtgaca 960
tctctgaagc agactggtcc tgtttgcctg ctggcaacta cggcggctac aatccaccag 1020
gggacggagc ttgcggttac aggtgcttgg ccttcatgaa tggcgccact gttgtgtcgg 1080
ctggttgcag ttctgacttg tggtgtgatg atgagttggc ttatcgagtc tttcaattgt 1140
cacccacgtt cacggttacc atcccaggtg ggcgagtttg tccgaatgcc aagtacgcaa 1200
tgatttgtga caagcagcac tggcgcgtca aacgtgcaaa gggcgtcggc ctgtgtctcg 1260
atgaaagctg tttcaggggc atctgcaatt gccaacgcat gagtggacca ccacctgcac 1320
ccgtgtcagc cgccgtgtta gatcacatac tggaggcggc gacgtttggc aacgttcgcg 1380
tggttacacc tgaagggcag ccacgccccg taccagcgcc gcgagttcgt cccagcgcca 1440
actcttctgg agatgtcaaa gatccggcgc ccgttccgcc agtaccaaaa ccaaggacca 1500
agcttgccac accgaaccca actcaggcgc ccatcccagc accgcgcacg cgacttcaag 1560
gggcctcaac acaggagcca ctggcgagtg caggagttgc ttctgactcg gcacctaaat 1620
ggcgtgtggc caaaactgtg tacagctccg cggagcgctt tcggaccgaa ctggtacaac 1680
gtgctcggtc cgttggggac gttcttgttc aagcgctacc gctcaaaacc ccagcagtgc 1740
agcggtatac catgactctg aagatgatgc gttcacgctt cagttggcac tgcgacgtgt 1800
ggtacccttt ggctgtaatc gcttgtttgc tccctatatg gccatctctt gctttgctcc 1860
ttagctttgc cattgggttg atacccagtg tgggcaataa tgttgttctg acagcgcttc 1920
tggtttcatc agctaattat gttgcgtcaa tggaccatca atgtgaaggt gcggcttgct 1980
tagccttgct ggaagaagaa cactattata gagcggtccg ttggcgcccg attacaggcg 2040
cgctgtcgct tgtgctcaat ttactggggc aggtaggcta tgtagctcgt tccacctttg 2100
atgcagctta tgttccttgc actgtgttcg atctttgcag ctttgctatt ctgtacctct 2160
gccgcaatcg ttgctggaga tgcttcggac gctgtgtgcg agttgggcct gccacgcatg 2220
ttttgggctc caccgggcaa cgagtttcca aactggcgct cattgatttg tgtgaccact 2280
tttcaaagcc caccatcgat gttgtgggca tggcaactgg ttggagcgga tgttacacag 2340
gaaccgccgc aatggagcgt cagtgtgcct ctacggtgga ccctcactcg ttcgaccaga 2400
agaaggcagg agcgactgtt tacctcaccc cccctgtcaa cagcgggtca gcgctgcagt 2460
gcctcaatgt catgtggaag cgaccaattg ggtccactgt ccttggggaa caaacaggag 2520
ctgttgtgac ggcggtcaag agtatctctt tctcacctcc ctgctgcgtc tctaccactt 2580
tgcccacccg acccggtgtg accgttgtcg accatgctct ttacaaccgg ttgactgctt 2640
caggggtcga tcccgcttta ttgcgtgttg ggcaaggtga ttttctaaaa cttaatccgg 2700
ggttccggct gataggtgga tggatttatg ggatatgcta ttttgtgttg gtggttgtgt 2760
caacttttac ctgcttacct atcaaatgtg gcattggcac ccgcgaccct ttctgccgca 2820
gagtgttttc tgtacccgtc accaagaccc aagagcactg ccatgctgga atgtgtgcta 2880
gcgctgaagg catctctctg gactctctgg ggttaactca gttacaaagt tactggatcg 2940
cagccgtcac tagcggatta gtgatcttgt tggtctgcca ccgcctggcc atcagcgcct 3000
tggacttgtt gactctagct tccccttag tgttgcttgt gttcccttgg gcatctgtgg 3060
ggcttttact tgcttgcagt ctcgctggtg ctgctgtgaa aatacagttg ttggcgacgc 3120
tttttgtgaa tctattcttt ccccaagcta cccttgtcac tatgggatac tgggcgtgcg 3180
tggcggcttt ggccgtttac agtttgatgg gcttgcgagt gaaagtgaat gtgcccatgt 3240
gtgtgacacc tgcccatttt ctgctgctgg cgaggtcagc tggacagtca agagagcaga 3300
tgctccgggt cagcgctgct gcccccacca attcactgct tggagtggct cgtgattgtt 3360
atgtcacagg cacaactcgg ctgtacatac ccaaggaagg cgggatggtg tttgaagggc 3420
tattcaggtc accgaaggcg cgcggcaacg tcggcttcgt ggctggtagc agctacggca 3480
cagggtcagt gtggaccagg aacaacgagg tcgtcgtact gacagcgtca cacgtggttg 3540
gccgcgctaa catggccact ctgaagatcg gtgacgcaat gctgactctg actttcaaaa 3600
agaatggcga cttcgccgag gcagtgacga cacagtccga gctcccaggc aattggccac 3660
agttgcattt cgcccaacca acaaccgggc ccgcttcatg gtgcactgcc acaggagatg 3720
aagaaggctt gctcagtggc gaggtttgtc tggcgtggac tactagtggc gactctggat 3780
ctgcagtggt tcagggtgac gctgtggtag gggtccacac cggttcgaac acaagtggtg 3840
ttgcctacgt gaccacccca agcggaaaac tccttggcgc cgacaccgtg actttgtcat 3900
cactgtcaaa gcatttcaca ggccctttga catcaatccc gaaggacatc cctgacaaca 3960
ttattgccga tgttgatgct gttcctcgtt ctctggccat gctgattgat ggcttatcca 4020

-continued

```
atagagagag cagcctttct ggacctcagt tgttgttaat tgcttgtttt atgtggtctt   4080
atcttaacca acctgcttac ttgccttatg tgctgggctt ctttgccgct aacttcttcc   4140
tgccaaaaag tgttggccgc cctgtggtca ctgggcttct atggttgtgc tgcctcttca   4200
caccgctttc catgcgcttg tgcttgttcc atctggtctg tgctaccgtc acgggaaacg   4260
tgatatcttt gtggttctac atcactgccg ctggcacgtc ttacctttct gagatgtggt   4320
tcggaggcta tcccaccatg ttgtttgtgc cacggttcct agtgtaccag ttccccggct   4380
gggctattgg cacagtacta gcggtatgca gcatcaccat gctggctgct gccctcggtc   4440
acaccctgtt actggatgtg ttctccgcct caggtcgctt tgacaggact ttcatgatga   4500
aatacttcct ggagggagga gtgaaagaga gtgtcaccgc ctcagtcacc cgcgcttatg   4560
gcaaaccaat tacccaggag agtctcactg caacattagc tgccctcact gatgatgact   4620
tccaattcct ctctgatgtg cttgactgtc gggccgtccg atcggcaatg aatctgcgtg   4680
ccgctctcac aagttttcaa gtggcgcagt atcgtaacat ccttaatgca tccttgcaag   4740
tcgatcgtga cgctgctcgt agtcgcagac taatggcaaa actggctgat tttgcggttg   4800
aacaagaagt aacagctgga gaccgtgttg tggttatcga cggtctggac cgcatggctc   4860
acttcaaaga cgatttggtg ctggttcctt tgaccaccaa agtagtaggc ggttctaggt   4920
gcaccatttg tgacgtcgtt aaggaagaag ccaatgacac cccagttaag ccaatgccca   4980
gcaggagacg ccgcaagggc ctgcctaaag gtgctcagtt ggagtgggac cgtcaccagg   5040
aagagaagag gaacgccggt gatgatgatt ttgcggtctc gaatgattat gtcaagagag   5100
tgccaaagta ctgggatccc agcgacaccc gaggcacgac agtgaaaatc gccggcacta   5160
cctatcagaa agtggttgac tattcaggca atgtgcatta cgtggagcat caggaagatc   5220
tgctagacta cgtgctgggc aaggggagct atgaaggcct agatcaggac aaagtgttgg   5280
acctcacaaa catgcttaaa gtggacccca cggagctctc ctccaaagac aaagccaagg   5340
cgcgtcagct tgctcatctg ctgttggatc tggctaaccc agttgaggca gtgaatcagt   5400
taaactgaga gcgccccaca tctttcccgg cgatgtgggg cgtcggacct ttgctgactc   5460
taaagacaag ggtttcgtgg ctctacacag tcgcacaatg tttttagctg cccgggactt   5520
tttatttaac atcaaatttg tgtgcgacga agagttcaca aagaccccaa aagacacact   5580
gcttgggtac gtacgcgcct gccctggtta ctggtttatt ttccgtcgta cgcaccggtc   5640
gctgattgat gcatactggg acagtatgga gtgcgtttac gcgcttccca ccatatctga   5700
ttttgatgtg agcccaggtg acgtcgcagt gacgggcgag cgatgggatt ttgaatctcc   5760
cggaggaggc cgtgcaaaac gtctcacagc tgatctggtg cacgcttttc aagggttcca   5820
cggagcctct tattcctatg atgacaaggt ggcagctgct gtcagtggtg acccgtatcg   5880
gtcggacggc gtcttgtata acacccgttg gggcaacatt ccatattctg tcccaaccaa   5940
tgctttggaa gccacagctt gctaccgtgc tggatgtgag gccgttaccg acgggaccaa   6000
cgtcatcgca acaattgggc ccttcccgga gcaacaaccc ataccggaca tcccaaagag   6060
cgtgcttgac aactgcgctg acatcagctg tgacgctttc atagcgcccg ctgcagagac   6120
agccctgtgt ggagatttag agaaatacaa cctatccacg cagggttttg tgttgcctag   6180
tgttttctcc atggtgcggg cgtacttaaa agaggagatt ggagacgctc caccactcta   6240
cttgccatct actgtaccat ctaaaaattc acaagccgga attaacggcg ctgagtttcc   6300
tacaaagtct ttacagagct actgtttgat tgatgacatg gtgtcacagt ccatgaaaag   6360
caatctacaa accgccacca tggcgacttg taaacggcaa tactgttcca aatacaagat   6420
```

taggagcatt ctgggcacca acaattacat tggcctaggt ttgcgtgcct gcctttcggg 6480
ggttacggcc gcattccaaa aagctggaaa ggatgggtca ccgatttatt tgggcaagtc 6540
aaaattcgac ccgataccag ctcctgacaa gtactgcctt gaaacagacc tggagagttg 6600
tgatcgctcc accccggctt tggtgcgttg gttcgctact aatcttattt ttgagctagc 6660
tggccagccc gagttggtgc acagctacgt gttgaattgc tgtcacgatc tagttgtggc 6720
gggtagtgta gcattcacca aacgcggggg tttgtcatct ggagacccta tcacttccat 6780
ttccaatacc atctattcat tggtgctgta cacccagcac atgttgctat gtggacttga 6840
aggctatttc ccagagattg cagaaaaata tcttgatggc agcctggagc tgcgggacat 6900
gttcaagtac gttcgagtgt acatctactc ggacgatgtg gttctaacca cacccaacca 6960
gcattacgcg gccagctttg accgctgggt cccccacctg caggcgctgc taggtttcaa 7020
ggttgaccca aagaaaactg tgaacaccag ctccccttcc tttttgggct gccggttcaa 7080
gcaagtggac ggcaagtgtt atctagccag tcttcaggac cgcgttacac gctctctgtt 7140
ataccacatt ggtgcaaaga atccctcaga gtactatgaa gctgctgttt ccatctttaa 7200
ggactccatt atctgctgtg atgaagactg gtggacggac ctccatcgac gtatcagtgg 7260
cgctgcgcgt accgacggag ttgagttccc caccattgaa atgttaacat ccttccgcac 7320
caagcagtat gagagtgccg tgtgcacagt ttgtggggcc gcccccgtgg ccaagtctgc 7380
ttgtggaggg tggttctgtg gcaattgtgt cccgtaccac gcgggtcatt gtcacacaac 7440
ctcgctcttc gccaactgcg ggcacgacat catgtaccgc tccacttact gcacaatgtg 7500
tgagggttcc ccaaaacaga tggtaccaaa agtgcctcac ccgatcctgg atcatttgct 7560
gtgccacatt gattacggca gtaaagagga actaactctg gtagtggcgg atggtcgaac 7620
aacatcaccg cccgggcgct acaaagtggg tcacaaggta gtcgccgtgg ttgcagatgt 7680
gggaggcaac attgtgtttg ggtgcggtcc tggatcacac atcgcagtac cacttcagga 7740
tacgctcaag ggcgtggtgg tgaataaagc tctgaagaac gccgccgcct ctgagtacgt 7800
ggaaggaccc cctgggagtg ggaagacttt tcacctggtc aaagatgtgc tagccgtggt 7860
cggtagcgcg accttggttg tgcccaccca cgcgtccatg ctggactgca tcaacaagct 7920
caaacaagcg ggcgccgatc catactttgt ggtgcccaag tatacagttc ttgactttcc 7980
ccggcctggc agtggaaaca tcacagtgcg actgccacag gtcggaacca gtgagggaga 8040
aacctttgtg gatgaggtgg cctacttctc accagtggat ctggcgcgca ttttaaccca 8100
gggtcgagtc aagggttacg gtgatttaaa tcagctcggg tgcgtcggac ccgcgagcgt 8160
gccacgtaac ctttggctcc gacattttgt cagcctggag cccttgcgag tgtgccatcg 8220
attcggcgct gctgtgtgtg atttgatcaa gggcatttat ccttattatg agccagctcc 8280
acataccact aaagtggtgt ttgtgccaaa tccagacttt gagaaaggtg tagtcatcac 8340
cgcctaccac aaagatcgcg gtcttggtca ccgcacaatt gattcaattc aaggctgtac 8400
attccctgtt gtgactcttc gactgcccac accccaatca ctgacgcgcc cgcgcgcagt 8460
tgtggcggtt actagggcgt ctcaggaatt atacatctac gaccccttg atcagcttag 8520
cgggttgttg aagttcacca aggaagcaga ggcgcaggac ttgatccatg gcccacctac 8580
agcatgccac ctgggccaag aaattgacct ttggtccaat gagggcctcg aatattacaa 8640
ggaagtcaac ctgctgtaca cacacgtccc catcaaggat ggtgtaatac acagttaccc 8700
taattgtggc cctgcctgtg gctgggaaaa gcaatccaac aaaatttcgt gcctcccgag 8760

-continued

```
agtggcacaa aatttgggct accactattc cccagactta ccaggatttt gccccatacc   8820

aaaagaactc gctgagcatt ggcccgtagt gtccaatgat agatacccga attgcttgca   8880

aattacctta cagcaagtat gtgaactcag taaaccgtgc tcagcgggct atatggttgg   8940

acaatcggtt ttcgtgcaga cgcctggtgt gacatcttac tggcttactg aatgggtcga   9000

cggcaaagcg cgtgctctac cagattcctt attctcgtcc ggtaggttcg agactaacag   9060

ccgcgctttc ctcgatgaag ccgaggaaaa gtttgccgcc gctcaccctc atgcctgttt   9120

gggagaaatt aataagtcca ccgtgggagg atcccacttc atcttttccc aatatttacc   9180

accattgcta cccgcagacg ctgttgccct ggtaggtgct tcattggctg ggaaagctgc   9240

taaagctgct tgcagcgttg ttgatgtcta tgctccatca tttgaacctt atctacaccc   9300

tgagacactg agtcgcgtgt acaagattat gatcgatttc aagccgtgta ggcttatggt   9360

gtggagaaac gcgacctttt atgtccaaga gggtgttgat gcagttacat cagcactagc   9420

agctgtgtcc aaactcatca aagtgccggc caatgagcct gtttcattcc atgtggcatc   9480

agggtacaga accaacgcgc tggtagcgcc ccaggctaaa atttcaattg gagcctacgc   9540

cgccgagtgg gcactgtcaa ctgaaccgcc acctgctggt tatgcgatcg tgcggcgata   9600

tattgtaaag aggctcctca gctcaacaga agtgttcttg tgccgcaggg gtgttgtgtc   9660

ttccacctca gtgcagacca tttgtgcact agagggatgt aaacctctgt tcaacttctt   9720

acaaattggt tcagtcattg ggcccgtgtg ac                                 9752
```

<210> SEQ ID NO 41
<211> LENGTH: 801
<212> TYPE: DNA
<213> ORGANISM: Artificial Sequence
<220> FEATURE:
<223> OTHER INFORMATION: Synthetic polynucleotide

<400> SEQUENCE: 41

```
ggagccatag attcattttg tggtgacggg attttaggtg agtatctaga ttactttatt     60

ctgtccgtcc cactcttgct gttgcttact aggtatgtag catctgggtt agtgtatgtt    120

ttgactgcct tgttctattc ctttgtatta gcagcttata tttggtttgt tatagttgga    180

agagcctttt ctactgctta tgcttttgtg cttttggctg cttttctgtt attagtaatg    240

aggatgattg tgggtatgat gcctcgtctt cggtccattt tcaaccatcg ccaactggtg    300

gtagctgatt ttgtggacac acctagtgga cctgttccca tcccccgccc aaccactcag    360

gtagtggttc gcggcaacgg gtacaccgca gttggtaaca agcttgtcga tggcgtcaag    420

acgatcacgt ccgcaggccg cctcttttcg aaacggacgg cggcgacagc ctacaagcta    480

caatgaccta ctgcgcatgt ttggtcagat gcgggtccgc aaaccgcccg cgcaacccac    540

tcaggctatt attgcagagc ctggagacct taggcatgat ttaaatcaac aggagcgcgc    600

cacccttttcg tcgaacgtac aacggttctt catgattggg catggttcac tcactgcaga   660

tgccggagga ctcacgtaca ccgtcagttg ggttcctacc aaacaaatcc agcgcaaagt    720

tgcgcctcca gcagggccgt aagacgtgga tattctcctg tgtggcgtca tgttgaagta    780

gttattagcc acccaggaac c                                              801
```

<210> SEQ ID NO 42
<211> LENGTH: 10565
<212> TYPE: DNA
<213> ORGANISM: Artificial Sequence
<220> FEATURE:
<223> OTHER INFORMATION: Synthetic polynucleotide

<400> SEQUENCE: 42
gctcgaagtg tgtatggtgc catatacggc tcaccaccat atacactgca agaattacta 60
ttcttgtggg cccctctcgg taaatcctag agggctttcc tctcgttatt gcgagattcg 120
tcgttagata acggcaagtt ccctttctta ctatcctatt ttcatcttgt ggcttgacgg 180
gtcactgcca tcgtcgtcga tctctatcaa ctacccttgc gactatggca accttctccg 240
ctactggatt tggagggagt tttgttaggg actggtccct ggacttaccc gacgcttgtg 300
agcatggcgc gggattgtgc tgcgaagtgg acggctccac cttatgcgcc gagtgttttc 360
gcggttgcga aggaatggag caatgtcctg gcttgttcat gggactgtta aaactggctt 420
cgccagttcc agtgggacat aagttcctga ttggttggta tcgagctgcc aaagtcaccg 480
ggcgttacaa tttccttgag ctgttgcaac accctgcttt cgcccagctg cgtgtggttg 540
atgctaggtt agccattgaa gaggcaagtg tgtttatttc cactgaccac gcgtctgcta 600
agcgtttccc tggcgctaga tttgcgctga caccggtgta tgctaacgct tgggttgtga 660
gcccggctgc taacagtttg atagtgacca ctgaccagga acaagatggg ttctgctggt 720
taaaactttt gccacctgac cgccgtgagg ctggtttgcg gttgtattac aaccattacc 780
gcgaacaaag gaccgggtgg ctgtctaaaa caggacttcg cttatggctt ggagacctgg 840
gtttgggcat caatgcgagc tctggagggc tgaaattcca cattatgagg ggttcgcctc 900
agcgagcttg gcatatcaca acacgcagct gcaagctgaa gagctactac gtttgtgaca 960
tctctgaagc agactggtcc tgtttgcctg ctggcaacta cggcggctac aatccaccag 1020
gggacggagc ttgcggttac aggtgcttgg ccttcatgaa tggcgccact gttgtgtcgg 1080
ctggttgcag ttctgacttg tggtgtgatg atgagttggc ttatcgagtc tttcaattgt 1140
cacccacgtt cacggttacc atcccaggtg ggcgagtttg tccgaatgcc aagtacgcaa 1200
tgatttgtga caagcagcac tggcgcgtca aacgtgcaaa gggcgtcggc ctgtgtctcg 1260
atgaaagctg tttcaggggc atctgcaatt gccaacgcat gagtggacca ccacctgcac 1320
ccgtgtcagc cgccgtgtta gatcacatac tggaggcggc gacgtttggc aacgttcgcg 1380
tggttacacc tgaagggcag ccacgccccg taccagcgcc gcgagttcgt cccagcgcca 1440
actcttctgg agatgtcaaa gatccggcgc ccgttccgcc agtaccaaaa ccaaggacca 1500
agcttgccac accgaaccca actcaggcgc ccatcccagc accgcgcacg cgacttcaag 1560
gggcctcaac acaggagcca ctggcgagtg caggagttgc ttctgactcg gcacctaaat 1620
ggcgtgtggc caaaactgtg tacagctccg cggagcgctt tcggaccgaa ctggtacaac 1680
gtgctcggtc cgttggggac gttcttgttc aagcgctacc gctcaaaacc ccagcagtgc 1740
agcggtatac catgactctg aagatgatgc gttcacgctt cagttggcac tgcgacgtgt 1800
ggtacccttt ggctgtaatc gcttgtttgc tccctatatg gccatctctt gctttgctcc 1860
ttagctttgc cattgggttg atacccagtg tgggcaataa tgttgttctg acagcgcttc 1920
tggtttcatc agctaattat gttgcgtcaa tggaccatca atgtgaaggt gcggcttgct 1980
tagccttgct ggaagaagaa cactattata gagcggtccg ttggcgcccg attacaggcg 2040
cgctgtcgct tgtgctcaat ttactggggc aggtaggcta tgtagctcgt tccacctttg 2100
atgcagctta tgttccttgc actgtgttcg atctttgcag ctttgctatt ctgtacctct 2160
gccgcaatcg ttgctggaga tgcttcggac gctgtgtgcg agttgggcct gccacgcatg 2220
ttttgggctc caccgggcaa cgagtttcca aactggcgct cattgatttg tgtgaccact 2280

-continued

```
tttcaaagcc caccatcgat gttgtgggca tggcaactgg ttggagcgga tgttacacag   2340
gaaccgccgc aatggagcgt cagtgtgcct ctacggtgga ccctcactcg ttcgaccaga   2400
agaaggcagg agcgactgtt tacctcaccc cccctgtcaa cagcgggtca gcgctgcagt   2460
gcctcaatgt catgtggaag cgaccaattg ggtccactgt ccttggggaa caaacaggag   2520
ctgttgtgac ggcggtcaag agtatctctt tctcacctcc ctgctgcgtc tctaccactt   2580
tgcccacccg acccggtgtg accgttgtcg accatgctct ttacaaccgg ttgactgctt   2640
caggggtcga tcccgcttta ttgcgtgttg ggcaaggtga ttttctaaaa cttaatccgg   2700
ggttccggct gataggtgga tggatttatg ggatatgcta ttttgtgttg gtggttgtgt   2760
caacttttac ctgcttacct atcaaatgtg gcattggcac ccgcgaccct ttctgccgca   2820
gagtgttttc tgtacccgtc accaagaccc aagagcactg ccatgctgga atgtgtgcta   2880
gcgctgaagg catctctctg gactctctgg ggttaactca gttacaaagt tactggatcg   2940
cagccgtcac tagcggatta gtgatcttgt tggtctgcca ccgcctggcc atcagcgcct   3000
tggacttgtt gactctagct tcccctttag tgttgcttgt gttcccttgg gcatctgtgg   3060
ggcttttact tgcttgcagt ctcgctggtg ctgctgtgaa aatacagttg ttggcgacgc   3120
tttttgtgaa tctattcttt ccccaagcta cccttgtcac tatgggatac tgggcgtgcg   3180
tggcggcttt ggccgtttac agtttgatgg gcttgcgagt gaaagtgaat gtgcccatgt   3240
gtgtgacacc tgcccatttt ctgctgctgg cgaggtcagc tggacagtca agagagcaga   3300
tgctccgggt cagcgctgct gcccccacca attcactgct tggagtggct cgtgattgtt   3360
atgtcacagg cacaactcgg ctgtacatac ccaaggaagg cgggatggtg tttgaagggc   3420
tattcaggtc accgaaggcg cgcggcaacg tcggcttcgt ggctggtagc agctacggca   3480
cagggtcagt gtggaccagg aacaacgagg tcgtcgtact gacagcgtca cacgtggttg   3540
gccgcgctaa catggccact ctgaagatcg gtgacgcaat gctgactctg actttcaaaa   3600
agaatggcga cttcgccgag gcagtgacga cacagtccga gctcccaggc aattggccac   3660
agttgcattt cgcccaacca acaaccgggc ccgcttcatg gtgcactgcc acaggagatg   3720
aagaaggctt gctcagtggc gaggtttgtc tggcgtggac tactagtggc gactctggat   3780
ctgcagtggt tcagggtgac gctgtggtag ggtccacac cggttcgaac acaagtggtg    3840
ttgcctacgt gaccacccca agcggaaaac tccttggcgc cgacaccgtg actttgtcat   3900
cactgtcaaa gcatttcaca ggccctttga catcaatccc gaaggacatc cctgacaaca   3960
ttattgccga tgttgatgct gttcctcgtt ctctggccat gctgattgat ggcttatcca   4020
atagagagag cagcctttct ggacctcagt tgttgttaat tgcttgtttt atgtggtctt   4080
atcttaacca acctgcttac ttgccttatg tgctgggctt ctttgccgct aacttcttcc   4140
tgccaaaaag tgttggccgc cctgtggtca ctgggcttct atggttgtgc tgcctcttca   4200
caccgctttc catgcgcttg tgcttgttcc atctggtctg tgctaccgtc acgggaaacg   4260
tgatatcttt gtggttctac atcactgccg ctggcacgtc ttacctttct gagatgtggt   4320
tcggaggcta tcccaccatg ttgtttgtgc cacggttcct agtgtaccag ttccccggct   4380
gggctattgg cacagtacta gcggtatgca gcatcaccat gctggctgct gccctcggtc   4440
acaccctgtt actggatgtg ttctccgcct caggtcgctt tgacaggact ttcatgatga   4500
aatacttcct ggagggagga gtgaaagaga gtgtcaccgc ctcagtcacc cgcgcttatg   4560
gcaaaccaat tacccaggag agtctcactg caacattagc tgccctcact gatgatgact   4620
tccaattcct ctctgatgtg cttgactgtc gggccgtccg atcggcaatg aatctgcgtg   4680
```

```
ccgctctcac aagttttcaa gtggcgcagt atcgtaacat ccttaatgca tccttgcaag   4740
tcgatcgtga cgctgctcgt agtcgcagac taatggcaaa actggctgat tttgcggttg   4800
aacaagaagt aacagctgga gaccgtgttg tggttatcga cggtctggac cgcatggctc   4860
acttcaaaga cgatttggtg ctggttcctt tgaccaccaa agtagtaggc ggttctaggt   4920
gcaccatttg tgacgtcgtt aaggaagaag ccaatgacac cccagttaag ccaatgccca   4980
gcaggagacg ccgcaagggc ctgcctaaag gtgctcagtt ggagtgggac cgtcaccagg   5040
aagagaagag gaacgccggt gatgatgatt ttgcggtctc gaatgattat gtcaagagag   5100
tgccaaagta ctgggatccc agcgacaccc gaggcacgac agtgaaaatc gccggcacta   5160
cctatcagaa agtggttgac tattcaggca atgtgcatta cgtggagcat caggaagatc   5220
tgctagacta cgtgctgggc aaggggagct atgaaggcct agatcaggac aaagtgttgg   5280
acctcacaaa catgcttaaa gtggacccca cggagctctc ctccaaagac aaagccaagg   5340
cgcgtcagct tgctcatctg ctgttggatc tggctaaccc agttgaggca gtgaatcagt   5400
taaactgaga gcgccccaca tctttcccgg cgatgtgggg cgtcggacct ttgctgactc   5460
taaagacaag ggtttcgtgg ctctacacag tcgcacaatg tttttagctg cccgggactt   5520
tttatttaac atcaaatttg tgtgcgacga agagttcaca aagaccccaa aagacacact   5580
gcttgggtac gtacgcgcct gccctggtta ctggtttatt ttccgtcgta cgcaccggtc   5640
gctgattgat gcatactggg acagtatgga gtgcgtttac gcgcttccca ccatatctga   5700
ttttgatgtg agcccaggtg acgtcgcagt gacgggcgag cgatgggatt ttgaatctcc   5760
cggaggaggc cgtgcaaaac gtctcacagc tgatctggtg cacgcttttc aagggttcca   5820
cggagcctct tattcctatg atgacaaggt ggcagctgct gtcagtggtg acccgtatcg   5880
gtcggacggc gtcttgtata acacccgttg gggcaacatt ccatattctg tcccaaccaa   5940
tgctttggaa gccacagctt gctaccgtgc tggatgtgag gccgttaccg acgggaccaa   6000
cgtcatcgca acaattgggc ccttcccgga gcaacaaccc ataccggaca tcccaaagag   6060
cgtgcttgac aactgcgctg acatcagctg tgacgctttc atagcgcccg ctgcagagac   6120
agccctgtgt ggagatttag agaaatacaa cctatccacg cagggttttg tgttgcctag   6180
tgttttctcc atggtgcggg cgtacttaaa agaggagatt ggagacgctc caccactcta   6240
cttgccatct actgtaccat ctaaaaattc acaagccgga attaacggcg ctgagtttcc   6300
tacaaagtct ttacagagct actgtttgat tgatgacatg gtgtcacagt ccatgaaaag   6360
caatctacaa accgccacca tggcgacttg taaacggcaa tactgttcca aatacaagat   6420
taggagcatt ctgggcacca acaattacat tggcctaggt ttgcgtgcct gcctttcggg   6480
ggttacggcc gcattccaaa aagctggaaa ggatgggtca ccgatttatt tgggcaagtc   6540
aaaattcgac ccgataccag ctcctgacaa gtactgcctt gaaacagacc tggagagttg   6600
tgatcgctcc accccggctt tggtgcgttg gttcgctact aatcttattt ttgagctagc   6660
tggccagccc gagttggtgc acagctacgt gttgaattgc tgtcacgatc tagttgtggc   6720
gggtagtgta gcattcacca aacgcggggg tttgtcatct ggagacccta tcacttccat   6780
ttccaatacc atctattcat tggtgctgta cacccagcac atgttgctat gtggacttga   6840
aggctatttc ccagagattg cagaaaaata tcttgatggc agcctggagc tgcgggacat   6900
gttcaagtac gttcgagtgt acatctactc ggacgatgtg gttctaacca cacccaacca   6960
gcattacgcg gccagctttg accgctgggt cccccacctg caggcgctgc taggtttcaa   7020
```

-continued

```
ggttgaccca aagaaaactg tgaacaccag ctccccttcc tttttgggct gccggttcaa   7080
gcaagtggac ggcaagtgtt atctagccag tcttcaggac cgcgttacac gctctctgtt   7140
ataccacatt ggtgcaaaga atccctcaga gtactatgaa gctgctgttt ccatctttaa   7200
ggactccatt atctgctgtg atgaagactg gtggacggac ctccatcgac gtatcagtgg   7260
cgctgcgcgt accgacggag ttgagttccc caccattgaa atgttaacat ccttccgcac   7320
caagcagtat gagagtgccg tgtgcacagt ttgtggggcc gcccccgtgg ccaagtctgc   7380
ttgtggaggg tggttctgtg gcaattgtgt cccgtaccac gcgggtcatt gtcacacaac   7440
ctcgctcttc gccaactgcg ggcacgacat catgtaccgc tccacttact gcacaatgtg   7500
tgagggttcc cccaaaacaga tggtaccaaa agtgcctcac ccgatcctgg atcatttgct   7560
gtgccacatt gattacggca gtaaagagga actaactctg gtagtggcgg atggtcgaac   7620
aacatcaccg cccgggcgct acaaagtggg tcacaaggta gtcgccgtgg ttgcagatgt   7680
gggaggcaac attgtgtttg ggtgcggtcc tggatcacac atcgcagtac cacttcagga   7740
tacgctcaag ggcgtggtgg tgaataaagc tctgaagaac gccgccgcct ctgagtacgt   7800
ggaaggaccc cctgggagtg ggaagacttt tcacctggtc aaagatgtgc tagccgtggt   7860
cggtagcgcg accttggttg tgcccaccca cgcgtccatg ctggactgca tcaacaagct   7920
caaacaagcg ggcgccgatc catactttgt ggtgcccaag tatacagttc ttgactttcc   7980
ccggcctggc agtggaaaca tcacagtgcg actgccacag gtcggaacca gtgagggaga   8040
aacctttgtg gatgaggtgg cctacttctc accagtggat ctggcgcgca ttttaaccca   8100
gggtcgagtc aagggttacg gtgatttaaa tcagctcggg tgcgtcggac ccgcgagcgt   8160
gccacgtaac ctttggctcc gacattttgt cagcctggag cccttgcgag tgtgccatcg   8220
attcggcgct gctgtgtgtg atttgatcaa gggcatttat ccttattatg agccagctcc   8280
acataccact aaagtggtgt ttgtgccaaa tccagacttt gagaaaggtg tagtcatcac   8340
cgcctaccac aaagatcgcg gtcttggtca ccgcacaatt gattcaattc aaggctgtac   8400
attccctgtt gtgactcttc gactgcccac accccaatca ctgacgcgcc cgcgcgcagt   8460
tgtggcggtt actagggcgt ctcaggaatt atacatctac gacccctttg atcagcttag   8520
cgggttgttg aagttcacca aggaagcaga ggcgcaggac ttgatccatg gcccacctac   8580
agcatgccac ctgggccaag aaattgacct ttggtccaat gagggcctcg aatattacaa   8640
ggaagtcaac ctgctgtaca cacacgtccc catcaaggat ggtgtaatac acagttaccc   8700
taattgtggc cctgcctgtg gctgggaaaa gcaatccaac aaaatttcgt gcctcccgag   8760
agtggcacaa aatttgggct accactattc cccagactta ccaggatttt gccccatacc   8820
aaaagaactc gctgagcatt ggcccgtagt gtccaatgat agatacccga attgcttgca   8880
aattacctta cagcaagtat gtgaactcag taaaccgtgc tcagcgggct atatggttgg   8940
acaatcggtt ttcgtgcaga cgcctggtgt gacatcttac tggcttactg aatgggtcga   9000
cggcaaagcg cgtgctctac cagattcctt attctcgtcc ggtaggttcg agactaacag   9060
ccgcgctttc ctcgatgaag ccgaggaaaa gtttgccgcc gctcaccctc atgcctgttt   9120
gggagaaatt aataagtcca ccgtgggagg atcccacttc atcttttccc aatatttacc   9180
accattgcta cccgcagacg ctgttgccct ggtaggtgct tcattggctg ggaaagctgc   9240
taaagctgct tgcagcgttg ttgatgtcta tgctccatca tttgaacctt atctacaccc   9300
tgagacactg agtcgcgtgt acaagattat gatcgatttc aagccgtgta ggcttatggt   9360
gtggagaaac gcgacctttt atgtccaaga gggtgttgat gcagttacat cagcactagc   9420
```

agctgtgtcc aaactcatca aagtgccggc caatgagcct gtttcattcc atgtggcatc 9480
agggtacaga accaacgcgc tggtagcgcc ccaggctaaa atttcaattg gagcctacgc 9540
cgccgagtgg gcactgtcaa ctgaaccgcc acctgctggt tatgcgatcg tgcggcgata 9600
tattgtaaag aggctcctca gctcaacaga agtgttcttg tgccgcaggg gtgttgtgtc 9660
ttccacctca gtgcagacca tttgtgcact agagggatgt aaacctctgt tcaacttctt 9720
acaaattggt tcagtcattg ggcccgtgtg acttataact cgagggagcc atagattcat 9780
tttgtggtga cgggatttta ggtgagtatc tagattactt tattctgtcc gtcccactct 9840
tgctgttgct tactaggtat gtagcatctg ggttagtgta tgttttgact gccttgttct 9900
attcctttgt attagcagct tatatttggt ttgttatagt tggaagagcc ttttctactg 9960
cttatgcttt tgtgcttttg gctgcttttc tgttattagt aatgaggatg attgtgggta 10020
tgatgcctcg tcttcggtcc attttcaacc atcgccaact ggtggtagct gattttgtgg 10080
acacacctag tggacctgtt cccatccccc gcccaaccac tcaggtagtg gttcgcggca 10140
acgggtacac cgcagttggt aacaagcttg tcgatggcgt caagacgatc acgtccgcag 10200
gccgcctctt ttcgaaacgg acggcggcga cagcctacaa gctacaatga cctactgcgc 10260
atgtttggtc agatgcgggt ccgcaaaccg cccgcgcaac ccactcaggc tattattgca 10320
gagcctggag accttaggca tgatttaaat caacaggagc gcgccaccct ttcgtcgaac 10380
gtacaacggt tcttcatgat tggccatggt tcactcactg cagatgccgg aggactcacg 10440
tacaccgtca gttgggttcc taccaaacaa atccagcgca aagttgcgcc tccagcaggg 10500
ccgtaagacg tggatattct cctgtgtggc gtcatgttga agtagttatt agccacccag 10560
gaacc 10565

<210> SEQ ID NO 43
<211> LENGTH: 711
<212> TYPE: DNA
<213> ORGANISM: Artificial Sequence
<220> FEATURE:
<223> OTHER INFORMATION: Archetype_Herceptin_LC

<400> SEQUENCE: 43
atggacatga gagtacctgc acagcttctg ggattactgt tactgtggct gtctggagcc 60
agatgtgaca tccaaatgac ccaaagccct tcttctctgt ctgcttctgt gggagataga 120
gtgacaatca cctgtagagc cagccaggat gtgaatacag ctgttgcttg gtaccagcag 180
aagcctggaa aagctcctaa actgctgatc tactctgcct ctttcctgta ctctggagtg 240
ccttctaggt tttctggcag cagatctggc acagacttca cactgacaat cagctctctg 300
cagcctgagg attttgccac atactactgt cagcagcact acacaacccc tcctacattt 360
ggacagggca caaaagtgga gatcaagaga acagtggctg ccccttctgt gttcatcttt 420
cctccttctg acgagcagct gaagtctgga acagcttctg tggtttgtct gctgaacaac 480
ttctacccta gagaggctaa ggtgcagtgg aaagtggata atgctctgca gtctggcaac 540
tctcaggaat ctgtgacaga gcaggacagc aaggactcta catactctct gagcagcaca 600
ctgacactgt ctaaggccga ttacgagaag cacaaggtgt acgcttgtga ggtgacacat 660
caaggactgt cttctcctgt gaccaagagc ttcaatagag gcgagtgtta a 711

<210> SEQ ID NO 44
<211> LENGTH: 1407
<212> TYPE: DNA

<213> ORGANISM: Artificial Sequence
<220> FEATURE:
<223> OTHER INFORMATION: Archetype_Herceptin_HC

<400> SEQUENCE: 44
atggaactgg gactgtcatg gatcttcttg ctggctatcc tgaagggagt gcagtgtgaa 60
gttcagctgg tggaatcagg aggaggatta gttcaaccag gcggatctct gagactgtct 120
tgtgctgctt ctggcttcaa catcaaggac acctacatcc attgggtgag acaagctcct 180
ggaaaaggat tggaatgggt ggctaggatc taccctacaa atggctacac cagatacgcc 240
gatagcgtga aaggcagatt cacaatcagc gccgatacct ctaagaacac agcttatctg 300
cagatgaaca gcctgagagc tgaggataca gctgtgtact actgtagcag atggggagga 360
gatggctttt acgctatgga ttactgggga cagggcacat tagtgacagt gtcttctgcc 420
agcacaaagg gaccttctgt gtttcctctt gccccttctt ctaagagcac atctggagga 480
acagctgctt tgggatgtct ggtgaaggac tactttcctg aacctgtgac agtgagctgg 540
aattctggag ctctgacatc tggagtgcac acatttcctg ctgttctgca gtcttctggc 600
ctgtattctc tgtcttctgt ggtgacagtg ccttctagct ctcttggaac acagacctac 660
atctgcaacg tgaaccacaa gcctagcaac acaaaggtgg acaagaaggt ggagcctaag 720
agctgtgaca agacacacac atgtcctcct tgtcctgctc ctgaattact tggaggacct 780
tctgtgttcc tgttccctcc taaacctaag gacaccctga tgatcagcag aacacctgaa 840
gtgacctgtg tggtggttga tgtgtctcat gaggatcctg aggtgaagtt taattggtac 900
gtggatggag tggaggtgca taatgccaag acaaagccta gagaggagca gtacaacagc 960
acctatagag tggtgtctgt gctgacagtg ctgcatcaag attggctgaa tggcaaggag 1020
tacaagtgca aggtgagcaa taaggctctg cctgctccta tcgagaagac aatctctaag 1080
gccaagggac agcctagaga acctcaggtt tacacacttc ctcctagcag agaggagatg 1140
accaagaatc aggtgagcct gacatgtctg gtgaagggat tttaccctag cgatatcgct 1200
gtggaatggg agtctaatgg acagcctgag aacaactaca agaccacacc tcctgtgctg 1260
gattctgatg gctctttctt cctgtacagc aagctgacag tggacaagtc tagatggcaa 1320
cagggcaatg tgttcagctg ttctgtgatg catgaggctc tgcacaacca ctatacccag 1380
aaaagcctga gcctgtctcc tggataa 1407

<210> SEQ ID NO 45
<211> LENGTH: 12836
<212> TYPE: DNA
<213> ORGANISM: Artificial Sequence
<220> FEATURE:
<223> OTHER INFORMATION: EAV_HERCEPTIN_LC_HC

<400> SEQUENCE: 45
taatacgact cactatagct cgaagtgtgt atggtgccat atacggctca ccaccatata 60
cactgcaaga attactattc ttgtgggccc ctctcggtaa atcctagagg gctttcctct 120
cgttattgcg agattcgtcg ttagataacg gcaagttccc tttcttacta tcctattttc 180
atcttgtggc ttgacgggtc actgccatcg tcgtcgatct ctatcaacta cccttgcgac 240
tatggcaacc ttctccgcta ctggatttgg agggagtttt gttagggact ggtccctgga 300
cttacccgac gcttgtgagc atggcgcggg attgtgctgc gaagtggacg gctccacctt 360
atgcgccgag tgttttcgcg gttgcgaagg aatggagcaa tgtcctggct tgttcatggg 420
actgttaaaa ctggcttcgc cagttccagt gggacataag ttcctgattg gttggtatcg 480

-continued

```
agctgccaaa gtcaccgggc gttacaattt ccttgagctg ttgcaacacc ctgctttcgc    540
ccagctgcgt gtggttgatg ctaggttagc cattgaagag gcaagtgtgt ttatttccac    600
tgaccacgcg tctgctaagc gtttccctgg cgctagattt gcgctgacac cggtgtatgc    660
taacgcttgg gttgtgagcc cggctgctaa cagtttgata gtgaccactg accaggaaca    720
agatgggttc tgctggttaa aacttttgcc acctgaccgc cgtgaggctg gtttgcggtt    780
gtattacaac cattaccgcg aacaaaggac cgggtggctg tctaaaacag gacttcgctt    840
atggcttgga gacctgggtt tggcatcaa tgcgagctct ggagggctga aattccacat    900
tatgaggggt tcgcctcagc gagcttggca tatcacaaca cgcagctgca agctgaagag    960
ctactacgtt tgtgacatct ctgaagcaga ctggtcctgt ttgcctgctg gcaactacgg   1020
cggctacaat ccaccagggg acggagcttg cggttacagg tgcttggcct tcatgaatgg   1080
cgccactgtt gtgtcggctg gttgcagttc tgacttgtgg tgtgatgatg agttggctta   1140
tcgagtcttt caattgtcac ccacgttcac ggttaccatc ccaggtgggc gagtttgtcc   1200
gaatgccaag tacgcaatga tttgtgacaa gcagcactgg cgcgtcaaac gtgcaaaggg   1260
cgtcggcctg tgtctcgatg aaagctgttt caggggcatc tgcaattgcc aacgcatgag   1320
tggaccacca cctgcacccg tgtcagccgc cgtgttagat cacatactgg aggcggcgac   1380
gtttggcaac gttcgcgtgg ttacacctga agggcagcca cgccccgtac cagcgccgcg   1440
agttcgtccc agcgccaact cttctggaga tgtcaaagat ccggcgcccg ttccgccagt   1500
accaaaacca aggaccaagc ttgccacacc gaacccaact caggcgccca tcccagcacc   1560
gcgcacgcga cttcaagggg cctcaacaca ggagccactg gcgagtgcag gagttgcttc   1620
tgactcggca cctaaatggc gtgtggccaa aactgtgtac agctccgcgg agcgctttcg   1680
gaccgaactg gtacaacgtg ctcggtccgt tggggacgtt cttgttcaag cgctaccgct   1740
caaaacccca gcagtgcagc ggtataccat gactctgaag atgatgcgtt cacgcttcag   1800
ttggcactgc gacgtgtggt accctttggc tgtaatcgct tgtttgctcc ctatatggcc   1860
atctcttgct ttgctcctta gctttgccat tgggttgata cccagtgtgg gcaataatgt   1920
tgttctgaca gcgcttctgg tttcatcagc taattatgtt gcgtcaatgg accatcaatg   1980
tgaaggtgcg gcttgcttag ccttgctgga agaagaacac tattatagag cggtccgttg   2040
gcgcccgatt acaggcgcgc tgtcgcttgt gctcaattta ctggggcagg taggctatgt   2100
agctcgttcc acctttgatg cagcttatgt tccttgcact gtgttcgatc tttgcagctt   2160
tgctattctg tacctctgcc gcaatcgttg ctggagatgc ttcggacgct gtgtgcgagt   2220
tgggcctgcc acgcatgttt tgggctccac cgggcaacga gtttccaaac tggcgctcat   2280
tgatttgtgt gaccactttt caaagcccac catcgatgtt gtgggcatgg caactggttg   2340
gagcggatgt tacacaggaa ccgccgcaat ggagcgtcag tgtgcctcta cggtggaccc   2400
tcactcgttc gaccagaaga aggcaggagc gactgtttac ctcacccccc ctgtcaacag   2460
cgggtcagcg ctgcagtgcc tcaatgtcat gtggaagcga ccaattgggt ccactgtcct   2520
tggggaacaa acaggagctg ttgtgacggc ggtcaagagt atctctttct cacctccctg   2580
ctgcgtctct accactttgc ccacccgacc cggtgtgacc gttgtcgacc atgctcttta   2640
caaccggttg actgcttcag ggtcgatcc cgctttattg cgtgttgggc aaggtgattt   2700
tctaaaactt aatccggggt tccggctgat aggtggatgg atttatggga tatgctattt   2760
tgtgttggtg gttgtgtcaa cttttacctg cttacctatc aaatgtggca ttggcacccg   2820
```

-continued

```
cgaccctttc tgccgcagag tgttttctgt acccgtcacc aagacccaag agcactgcca   2880
tgctggaatg tgtgctagcg ctgaaggcat ctctctggac tctctggggt taactcagtt   2940
acaaagttac tggatcgcag ccgtcactag cggattagtg atcttgttgg tctgccaccg   3000
cctggccatc agcgccttgg acttgttgac tctagcttcc cctttagtgt tgcttgtgtt   3060
cccttgggca tctgtggggc ttttacttgc ttgcagtctc gctggtgctg ctgtgaaaat   3120
acagttgttg gcgacgcttt ttgtgaatct attctttccc caagctaccc ttgtcactat   3180
gggatactgg gcgtgcgtgg cggctttggc cgtttacagt ttgatgggct tgcgagtgaa   3240
agtgaatgtg cccatgtgtg tgacacctgc ccattttctg ctgctggcga ggtcagctgg   3300
acagtcaaga gagcagatgc tccgggtcag cgctgctgcc cccaccaatt cactgcttgg   3360
agtggctcgt gattgttatg tcacaggcac aactcggctg tacataccca aggaaggcgg   3420
gatggtgttt gaagggctat tcaggtcacc gaaggcgcgc ggcaacgtcg gcttcgtggc   3480
tggtagcagc tacggcacag ggtcagtgtg gaccaggaac aacgaggtcg tcgtactgac   3540
agcgtcacac gtggttggcc gcgctaacat ggccactctg aagatcggtg acgcaatgct   3600
gactctgact ttcaaaaaga atggcgactt cgccgaggca gtgacgacac agtccgagct   3660
cccaggcaat tggccacagt tgcatttcgc ccaaccaaca accgggcccg cttcatggtg   3720
cactgccaca ggagatgaag aaggcttgct cagtggcgag gtttgtctgg cgtggactac   3780
tagtggcgac tctggatctg cagtggttca gggtgacgct gtggtagggg tccacaccgg   3840
ttcgaacaca agtggtgttg cctacgtgac caccccaagc ggaaaactcc ttggcgccga   3900
caccgtgact ttgtcatcac tgtcaaagca tttcacaggc cctttgacat caatcccgaa   3960
ggacatccct gacaacatta ttgccgatgt tgatgctgtt cctcgttctc tggccatgct   4020
gattgatggc ttatccaata gagagagcag cctttctgga cctcagttgt tgttaattgc   4080
ttgttttatg tggtcttatc ttaaccaacc tgcttacttg ccttatgtgc tgggcttctt   4140
tgccgctaac ttcttcctgc caaaaagtgt tggccgccct gtggtcactg ggcttctatg   4200
gttgtgctgc ctcttcacac cgctttccat gcgcttgtgc ttgttccatc tggtctgtgc   4260
taccgtcacg ggaaacgtga tatctttgtg gttctacatc actgccgctg gcacgtctta   4320
cctttctgag atgtggttcg gaggctatcc caccatgttg tttgtgccac ggttcctagt   4380
gtaccagttc cccggctggg ctattggcac agtactagcg gtatgcagca tcaccatgct   4440
ggctgctgcc ctcggtcaca ccctgttact ggatgtgttc tccgcctcag gtcgctttga   4500
caggactttc atgatgaaat acttcctgga gggaggagtg aaagagagtg tcaccgcctc   4560
agtcacccgc gcttatggca aaccaattac ccaggagagt ctcactgcaa cattagctgc   4620
cctcactgat gatgacttcc aattcctctc tgatgtgctt gactgtcggg ccgtccgatc   4680
ggcaatgaat ctgcgtgccg ctctcacaag ttttcaagtg gcgcagtatc gtaacatcct   4740
taatgcatcc ttgcaagtcg atcgtgacgc tgctcgtagt cgcagactaa tggcaaaact   4800
ggctgatttt gcggttgaac aagaagtaac agctggagac cgtgttgtgg ttatcgacgg   4860
tctggaccgc atggctcact tcaaagacga tttggtgctg gttcctttga ccaccaaagt   4920
agtaggcggt tctaggtgca ccatttgtga cgtcgttaag gaagaagcca atgacacccc   4980
agttaagcca atgcccagca ggagacgccg caagggcctg cctaaaggtg ctcagttgga   5040
gtgggaccgt caccaggaag agaagaggaa cgccggtgat gatgattttg cggtctcgaa   5100
tgattatgtc aagagagtgc caaagtactg ggatcccagc gacacccgag gcacgacagt   5160
gaaaatcgcc ggcactacct atcagaaagt ggttgactat tcaggcaatg tgcattacgt   5220
```

ggagcatcag gaagatctgc tagactacgt gctgggcaag gggagctatg aaggcctaga 5280
tcaggacaaa gtgttggacc tcacaaacat gcttaaagtg gaccccacgg agctctcctc 5340
caaagacaaa gccaaggcgc gtcagcttgc tcatctgctg ttggatctgg ctaacccagt 5400
tgaggcagtg aatcagttaa actgagagcg ccccacatct ttcccggcga tgtggggcgt 5460
cggacctttg ctgactctaa agacaagggt ttcgtggctc tacacagtcg cacaatgttt 5520
ttagctgccc gggacttttt atttaacatc aaatttgtgt gcgacgaaga gttcacaaag 5580
accccaaaag acacactgct tggtacgta cgcgcctgcc ctggttactg gtttattttc 5640
cgtcgtacgc accggtcgct gattgatgca tactgggaca gtatggagtg cgtttacgcg 5700
cttcccacca tatctgattt tgatgtgagc ccaggtgacg tcgcagtgac gggcgagcga 5760
tgggattttg aatctcccgg aggaggccgt gcaaaacgtc tcacagctga tctggtgcac 5820
gcttttcaag ggttccacgg agcctcttat tcctatgatg acaaggtggc agctgctgtc 5880
agtggtgacc cgtatcggtc ggacggcgtc ttgtataaca cccgttgggg caacattcca 5940
tattctgtcc caaccaatgc tttggaagcc acagcttgct accgtgctgg atgtgaggcc 6000
gttaccgacg ggaccaacgt catcgcaaca attgggccct tcccggagca acaacccata 6060
ccggacatcc caaagagcgt gcttgacaac tgcgctgaca tcagctgtga cgctttcata 6120
gcgcccgctg cagagacagc cctgtgtgga gatttagaga aatacaacct atccacgcag 6180
ggttttgtgt tgcctagtgt tttctccatg gtgcgggcgt acttaaaaga ggagattgga 6240
gacgctccac cactctactt gccatctact gtaccatcta aaaattcaca agccggaatt 6300
aacggcgctg agtttcctac aaagtcttta cagagctact gtttgattga tgacatggtg 6360
tcacagtcca tgaaaagcaa tctacaaacc gccaccatgg cgacttgtaa acggcaatac 6420
tgttccaaat acaagattag gagcattctg ggcaccaaca attacattgg cctaggtttg 6480
cgtgcctgcc tttcgggggt tacggccgca ttccaaaaag ctggaaagga tgggtcaccg 6540
atttatttgg gcaagtcaaa attcgacccg ataccagctc ctgacaagta ctgccttgaa 6600
acagacctgg agagttgtga tcgctccacc ccggctttgg tgcgttggtt cgctactaat 6660
cttattttg agctagctgg ccagcccgag ttggtgcaca gctacgtgtt gaattgctgt 6720
cacgatctag ttgtggcggg tagtgtagca ttcaccaaac gcgggggttt gtcatctgga 6780
gaccctatca cttccatttc caataccatc tattcattgg tgctgtacac ccagcacatg 6840
ttgctatgtg gacttgaagg ctatttccca gagattgcag aaaaatatct tgatggcagc 6900
ctggagctgc gggacatgtt caagtacgtt cgagtgtaca tctactcgga cgatgtggtt 6960
ctaaccacac ccaaccagca ttacgcggcc agctttgacc gctgggtccc ccacctgcag 7020
gcgctgctag gtttcaaggt tgacccaaag aaaactgtga acaccagctc cccttccttt 7080
ttgggctgcc ggttcaagca agtggacggc aagtgttatc tagccagtct tcaggaccgc 7140
gttacacgct ctctgttata ccacattggt gcaaagaatc cctcagagta ctatgaagct 7200
gctgtttcca tctttaagga ctccattatc tgctgtgatg aagactggtg gacggacctc 7260
catcgacgta tcagtggcgc tgcgcgtacc gacggagttg agttccccac cattgaaatg 7320
ttaacatcct tccgcaccaa gcagtatgag agtgccgtgt gcacagtttg tggggccgcc 7380
cccgtggcca agtctgcttg tggagggtgg ttctgtggca attgtgtccc gtaccacgcg 7440
ggtcattgtc acacaacctc gctcttcgcc aactgcgggc acgacatcat gtaccgctcc 7500
acttactgca caatgtgtga gggttcccca aaacagatgg taccaaaagt gcctcacccg 7560
atcctggatc atttgctgtg ccacattgat tacggcagta aagaggaact aactctggta 7620
gtggcggatg gtcgaacaac atcaccgccc gggcgctaca aagtgggtca caaggtagtc 7680
gccgtggttg cagatgtggg aggcaacatt gtgtttgggt gcggtcctgg atcacacatc 7740
gcagtaccac ttcaggatac gctcaagggc gtggtggtga ataaagctct gaagaacgcc 7800
gccgcctctg agtacgtgga aggaccccct gggagtggga agacttttca cctggtcaaa 7860
gatgtgctag ccgtggtcgg tagcgcgacc ttggttgtgc ccacccacgc gtccatgctg 7920
gactgcatca acaagctcaa acaagcgggc gccgatccat actttgtggt gcccaagtat 7980
acagttcttg actttccccg gcctggcagt ggaaacatca cagtgcgact gccacaggtc 8040
ggaaccagtg agggagaaac ctttgtggat gaggtggcct acttctcacc agtggatctg 8100
gcgcgcattt taacccaggg tcgagtcaag ggttacggtg atttaaatca gctcgggtgc 8160
gtcggacccg cgagcgtgcc acgtaacctt tggctccgac attttgtcag cctggagccc 8220
ttgcgagtgt gccatcgatt cggcgctgct gtgtgtgatt tgatcaaggg catttatcct 8280
tattatgagc cagctccaca taccactaaa gtggtgtttg tgccaaatcc agactttgag 8340
aaaggtgtag tcatcaccgc ctaccacaaa gatcgcggtc ttggtcaccg cacaattgat 8400
tcaattcaag gctgtacatt ccctgttgtg actcttcgac tgcccacacc ccaatcactg 8460
acgcgcccgc gcgcagttgt ggcggttact agggcgtctc aggaattata catctacgac 8520
ccctttgatc agcttagcgg gttgttgaag ttcaccaagg aagcagaggc gcaggacttg 8580
atccatggcc cacctacagc atgccacctg ggccaagaaa ttgacctttg gtccaatgag 8640
ggcctcgaat attacaagga agtcaacctg ctgtacacac acgtccccat caaggatggt 8700
gtaatacaca gttaccctaa ttgtggccct gcctgtggct gggaaaagca atccaacaaa 8760
atttcgtgcc tcccgagagt ggcacaaaat ttgggctacc actattcccc agacttacca 8820
ggattttgcc ccataccaaa agaactcgct gagcattggc ccgtagtgtc caatgataga 8880
tacccgaatt gcttgcaaat taccttacag caagtatgtg aactcagtaa accgtgctca 8940
gcgggctata tggttggaca atcggttttc gtgcagacgc ctggtgtgac atcttactgg 9000
cttactgaat gggtcgacgg caaagcgcgt gctctaccag attccttatt ctcgtccggt 9060
aggttcgaga ctaacagccg cgctttcctc gatgaagccg aggaaaagtt tgccgccgct 9120
caccctcatg cctgtttggg agaaattaat aagtccaccg tgggaggatc ccacttcatc 9180
ttttcccaat atttaccacc attgctaccc gcagacgctg ttgccctggt aggtgcttca 9240
ttggctggga aagctgctaa agctgcttgc agcgttgttg atgtctatgc tccatcattt 9300
gaaccttatc tacaccctga gacactgagt cgcgtgtaca agattatgat cgatttcaag 9360
ccgtgtaggc ttatggtgtg gagaaacgcg accttttatg tccaagaggg tgttgatgca 9420
gttacatcag cactagcagc tgtgtccaaa ctcatcaaag tgccggccaa tgagcctgtt 9480
tcattccatg tggcatcagg gtacagaacc aacgcgctgg tagcgcccca ggctaaaatt 9540
tcaattggag cctacgccgc cgagtgggca ctgtcaactg aaccgccacc tgctggttat 9600
gcgatcgtgc ggcgatatat tgtaaagagg ctcctcagct caacagaagt gttcttgtgc 9660
cgcaggggtg ttgtgtcttc cacctcagtg cagaccattt gtgcactaga gggatgtaaa 9720
cctctgttca acttcttaca aattggttca gtcattgggc ccgtgtgaat ggacatgaga 9780
gtacctgcac agcttctggg attactgtta ctgtggctgt ctggagccag atgtgacatc 9840
caaatgaccc aaagcccttc ttctctgtct gcttctgtgg gagatagagt gacaatcacc 9900
tgtagagcca gccaggatgt gaatacagct gttgcttggt accagcagaa gcctggaaaa 9960
gctcctaaac tgctgatcta ctctgcctct ttcctgtact ctggagtgcc ttctaggttt 10020
tctggcagca gatctggcac agacttcaca ctgacaatca gctctctgca gcctgaggat 10080
tttgccacat actactgtca gcagcactac acaacccctc ctacatttgg acagggcaca 10140
aaagtggaga tcaagagaac agtggctgcc ccttctgtgt tcatctttcc tccttctgac 10200
gagcagctga agtctggaac agcttctgtg gtttgtctgc tgaacaactt ctaccctaga 10260
gaggctaagg tgcagtggaa agtggataat gctctgcagt ctggcaactc tcaggaatct 10320
gtgacagagc aggacagcaa ggactctaca tactctctga gcagcacact gacactgtct 10380
aaggccgatt acgagaagca caaggtgtac gcttgtgagg tgacacatca aggactgtct 10440
tctcctgtga ccaagagctt caatagaggc gagtgttaag tggacctgtt cccatccccc 10500
gctcaactac tcaggtagtg gttcgcggca acgggtacac cgcagttggt aacaagcttg 10560
tcgatggaac tgggactgtc atggatcttc ttgctggcta tcctgaaggg agtgcagtgt 10620
gaagttcagc tggtggaatc aggaggagga ttagttcaac caggcggatc tctgagactg 10680
tcttgtgctg cttctggctt caacatcaag gacacctaca tccattgggt gagacaagct 10740
cctggaaaag gattggaatg ggtggctagg atctacccta caaatggcta caccagatac 10800
gccgatagcg tgaaaggcag attcacaatc agcgccgata cctctaagaa cacagcttat 10860
ctgcagatga acagcctgag agctgaggat acagctgtgt actactgtag cagatgggga 10920
ggagatggct tttacgctat ggattactgg ggacagggca cattagtgac agtgtcttct 10980
gccagcacaa agggaccttc tgtgtttcct cttgcccctt cttctaagag cacatctgga 11040
ggaacagctg ctttgggatg tctggtgaag gactactttc ctgaacctgt gacagtgagc 11100
tggaattctg gagctctgac atctggagtg cacacatttc ctgctgttct gcagtcttct 11160
ggcctgtatt ctctgtcttc tgtggtgaca gtgccttcta gctctcttgg aacacagacc 11220
tacatctgca acgtgaacca caagcctagc aacacaaagg tggacaagaa ggtggagcct 11280
aagagctgtg acaagacaca cacatgtcct ccttgtcctg ctcctgaatt acttggagga 11340
ccttctgtgt tcctgttccc tcctaaacct aaggacaccc tgatgatcag cagaacacct 11400
gaagtgacct gtgtggtggt tgatgtgtct catgaggatc ctgaggtgaa gttcaactgg 11460
tacgtggatg gagtggaggt gcataatgcc aagacaaagc ctagagagga gcagtacaac 11520
agcacctata gagtggtgtc tgtgctgaca gtgctgcatc aagattggct gaatggcaag 11580
gagtacaagt gcaaggtgag caataaggct ctgcctgctc ctatcgagaa gacaatctct 11640
aaggccaagg gacagcctag agaacctcag gtttacacac ttcctcctag cagagaggag 11700
atgaccaaga atcaggtgag cctgacatgt ctggtgaagg gattttaccc tagcgatatc 11760
gctgtggaat gggagtctaa tggacagcct gagaacaact acaagaccac acctcctgtg 11820
ctggattctg atggctcttt cttcctgtac agcaagctga cagtggacaa gtctagatgg 11880
caacagggca atgtgttcag ctgttctgtg atgcatgagg ctctgcacaa ccactatacc 11940
cagaaaagcc tgagcctgtc tcctggataa ggagccatag attcattttg tggtgacggg 12000
attttaggtg agtatctaga ttactttatt ctgtccgtcc cactcttgct gttgcttact 12060
aggtatgtag catctgggtt agtgtatgtt ttgactgcct tgttctattc ctttgtatta 12120
gcagcttata tttggtttgt tatagttgga agagcctttt ctactgctta tgcttttgtg 12180
cttttggctg cttttctgtt attagtaatg aggatgattg tgggtatgat gcctcgtctt 12240
cggtccattt tcaaccatcg ccaactggtg gtagctgatt ttgtggacac acctagtgga 12300

-continued

```
cctgttccca tcccccgccc aaccactcag gtagtggttc gcggcaacgg gtacaccgca  12360

gttggtaaca agcttgtcga tggcgtcaag acgatcacgt ccgcaggccg cctcttttcg  12420

aaacggacgg cggcgacagc ctacaagcta caatgaccta ctgcgcatgt ttggtcagat  12480

gcgggtccgc aaaccgcccg cgcaacccac tcaggctatt attgcagagc ctggagacct  12540

taggcatgat ttaaatcaac aggagcgcgc caccctttcg tcgaacgtac aacggttctt  12600

catgattggg catggttcac tcactgcaga tgccggagga ctcacgtaca ccgtcagttg  12660

ggttcctacc aaacaaatcc agcgcaaagt tgcgcctcca gcagggccgt aagacgtgga  12720

tattctcctg tgtggcgtca tgttgaagta gttattagcc acccaggaac caaaaaaaaa  12780

aaaaaaaaaa aaaaaaaaaa aaaaaaaaaa aaaaaaaaaa aaaaaaaaaa aaaaaa      12836
```

```
<210> SEQ ID NO 46
<211> LENGTH: 11581
<212> TYPE: DNA
<213> ORGANISM: Artificial Sequence
<220> FEATURE:
<223> OTHER INFORMATION: VBS-R-Egfp
<220> FEATURE:
<221> NAME/KEY: misc_feature
<222> LOCATION: (1)..(60)
<223> OTHER INFORMATION: overlap regions to pW70
<220> FEATURE:
<221> NAME/KEY: misc_feature
<222> LOCATION: (69)..(85)
<223> OTHER INFORMATION: T7 promoter
<220> FEATURE:
<221> NAME/KEY: misc_feature
<222> LOCATION: (11397)..(11521)
<223> OTHER INFORMATION: Poly A

<400> SEQUENCE: 46

gtcgatcaga ctatcagcgt gagactacga ttccatcaat gcctgtcaag ggcaagtatt     60

gcgatcgcta atacgactca ctatagctcg aagtgtgtat ggtgccatat acggctcacc    120

accatataca ctgcaagaat tactattctt gtgggcccct ctcggtaaat cctagagggc    180

tttcctctcg ttattgcgag attcgtcgtt agataacggc aagttccctt tcttactatc    240

ctattttcat cttgtggctt gacgggtcac tgccatcgtc gtcgatctct atcaactacc    300

cttgcgacta tggcaacctt ctccgctact ggatttggag ggagttttgt tagggactgg    360

tccctggact tacccgacgc ttgtgagcat ggcgcgggat tgtgctgtga agtggacggc    420

tccaccttat gcgccgagtg ttttcgcggt tgcgaaggag tggagcaatg tcctggcttg    480

ttcatgggac tgttaaaact ggcttcgcca gttccagtgg gacataagtt cctgattggt    540

tggtatcgag ctgccaaagt caccgggcgt tacaatttcc ttgagctgtt gcaacaccct    600

gctttcgccc agctgcgtgt ggttgatgct aggttagcca ttgaagaggc aagtgtgttt    660

atttccactg accacgcgtc tgctaagcgt ttccctggcg ctagatttgc gctgacaccg    720

gtgtatgcta gcgcttgggt tgcgagcccg gctgctaaca gtttgatagt gaccattgac    780

caggaacaag atgggttctg ctggttaaaa cttttgccac ctgaccgccg tgaggctggt    840

ttgcggttgt attacaacca ttaccgcgaa caaaggaccg ggtggctgtc taaaacagga    900

cttcgcttat ggcttggaga cctgggtttg ggcatcaatg cgagctctgg agggctgaaa    960

ttccacatta tgaggggttc gcctcagcga gcttggcata tcacaacacg cagctgcaag   1020

ctgaagagct actacgtttg tgacatctct gaagcagact ggtcctgttt gcctgctggc   1080

aactacggcg gctacaatcc accaggggac ggagcttgcg gttacaggtg cttggccttc   1140

atgaatggcg ccactgttgt gtcggctggt tgcagttctg acttgtggtg tgatgatgag   1200
```

-continued

```
ttggcttatc gagtctttca attgtcaccc acgttcacgg ttaccatccc aggtgggcga   1260
gtttgtccga atgccaagta cgcaatgatt tgtgacaagc agcactggcg cgtcaaacgt   1320
gcaaagggcg tcggcctgtg tctcgatgaa agctgtttca ggggcacctg caattgccaa   1380
cgcatgagtg gaccaccacc tgcacccgtg tcagccgccg tgttagatca catactggag   1440
gcggcgacgt ttgacaacgt tcgcgtggtt acacctgaag ggcagccacg ccccgtacca   1500
gcgccgcgag ttcgtcccag cgccaactct tctggagatg tcaaagatcc ggcgcccgtt   1560
ccgccagtac caaaaccaag gaccaagctt gccaaaccga acccaactca ggcgcccatc   1620
ccagcaccgc gcacgcgact tcaaggggcc tcaacacagg agccactggc gagtgcagga   1680
gttgcttctg actcggcacc taaatggcgt gtggccaaaa ctgtgtacag ctccgcggag   1740
cgctttcgga ccgaactggt acaacgtgct cggtccgttg ggacgttct tgttcaagcg    1800
ctaccgctca aaaccccagc agtgcagcgg tataccatga ctctgaagat gatgcgttca   1860
cgcttcagtt ggcactgcga cgtgtggtac cctttggctg taatcgcttg tttgctccct   1920
atatggccat ctcttgcttt gctccttagc tttgccattg ggttgatacc cagtgtgggc   1980
aatagtgttg ttctgacagc gcttctggtt tcatcagcta attatgttgc gtcaatggac   2040
catcaatgtg aaggtgcggc ttgcttagcc ttgctggaag aagaacacta ttatagagcg   2100
gtccgttggc gcccgattac aggcgcgctg tcgcttgtgc tcaatttact ggggcaggta   2160
ggctatgtag ctcgttccac ctttgatgca gcttatgttc cttgcactgt gttcgatctt   2220
tgcagctttg ctattctgta cctctgccgc aatcgttgct ggagatgctt cggacgctgt   2280
gtgcgagttg ggcctgccac gcatgttttg ggttccaccg ggcaacgagt ttccaaactg   2340
gcgctcattg atttgtgtga ccacttttca aagcccacca tcgatgttgt gggcatggca   2400
actggttgga gcggatgtta cacaggaacc gccgcaatgg agcgtcagtg tgcctctacg   2460
gtggaccctc actcgttcga ccagaagaag gcaggagcga ttgtttacct caccccccct   2520
gtcaacagcg ggtcagcgct gcagtgcctc aatgtcatgt ggaagcgacc aattgggtcc   2580
actgtccttg gggaacaaac aggagctgtt gtgacggcgg tcaagagtat ctctttctca   2640
cctccctgct gcgtctctac cactttgccc acgcgacccg gtgtgaccgt tgtcgaccat   2700
gctctttaca accggttgac tgcttcaggg gtcgatcccg ctttattgcg tgttgggcaa   2760
ggtgattttc taaaacttaa tccggggttc cggctgatag gtggatggat ttatgggata   2820
tgctattttg tgttggtggt tgtgtcaact tttacctgct tacctatcaa atgtggcatt   2880
ggcacccgcg accctttctg ccgcagagtg ttttctgtac ccgtcaccaa gacccaagag   2940
cactgccatg ctggaatgtg tgctagcgct gaaggcatct ctctggactc tctggggtta   3000
actcagttac aaagttactg gatcgctgcc gtcactagcg gattagtgat cttgttggtc   3060
tgccaccgcc tggccatcag cgccttggac ttgttgactc tagcttcccc tttagtgttg   3120
cttgtgttcc cttgggcatc tgtggggctt ttacttgctt gcagtctcgc tggtgctgct   3180
gtgaaaatac agttgttggc gacgcttttt gtgaatctgt tctttcccca agctaccctt   3240
gtcactatgg gatactgggc gtgcgtggcg gctttggccg tttacagttt gatgggcttg   3300
cgagtgaaag tgaatgtgcc catgtgtgtg acacctgccc attttctgct gctggcgagg   3360
tcagctggac agtcaagaga gcagatgctc cgggtcagcg ctgctgcccc caccaattca   3420
ctgcttggag tggctcgtga ttgttatgtc acaggcacaa ctcggctgta catacccaag   3480
gagggcggga tggtgtttga agggctattc aggtcaccga aggcgcgcgg caacgtcggc   3540
```

-continued

```
ttcgtggctg gtagcagcta cggcacaggg tcagtgtgga ccaggaacaa cgaggtcgtc   3600
gtactgacag cgtcacacgt ggttggccgc gctaacatgg ccactctgaa gatcggtgac   3660
gcaatgctga ctctgacttt caaaaagaat ggcgacttcg ccgaggcagt gacgacacag   3720
tccgagctcc caggcaattg gccacagttg catttcgccc aaccaacaac cgggcccgct   3780
tcatggtgca ccgccacagg agatgaagaa ggcttgctca gtggcgaggt ttgtctggcg   3840
tggactacta gtggcgactc tggatcagca gtggttcagg gtgacgctgt ggtaggggtc   3900
cacaccggtt cgaacacaag tggtgttgcc tacgtgacca ccccaagcgg aaaactcctt   3960
ggcgccgaca ccgtgacttt gtcatcactg tcaaagcatt tcacaggccc tttgacatca   4020
atcccgaagg acatccctga caacatcatt gccgatgttg atgctgttcc tcgttctctg   4080
gccatgctga ttgatggctt atccaataga gagagcagcc tttctggacc tcagttgttg   4140
ttaattgctt gttttatgtg gtcttatctt aaccaacctg cttacttgcc ttatgtgctg   4200
ggcttctttg ccgctaactt cttcctgcca aaaagtgttg gccgccctgt ggtcactggg   4260
cttctatggt tgtgctgcct cttcacaccg ctttccatgc gcttgtgctt gttccatctg   4320
gtctgtgcta ccgtcacggg aaacgtgata tctttgtggt tctacatcac tgccgctggc   4380
acgtcttacc tttctgagat gtggttcgga ggctatccca ccatgttgtt tgtgccacgg   4440
ttcctagtgt accagttccc cggctgggct attggcacag tactagcggt atgcagcatc   4500
accatgctgg ctgctgccct cggtcacacc ctgttactgg atgtgttctc cgcctcaggt   4560
cgctttgaca ggactttcat gatgaaatac ttcctggagg gaggagtgaa agagagtgtc   4620
accgcctcag tcacccgcgc ttatggcaaa ccaattaccc aggagagtct cactgcaaca   4680
ttagctgccc tcactgatga tgacttccaa ttcctctctg atgtgcttga ctgtcgggcc   4740
gtccgatcgg caatgaatct gcgtgccgct ctcacaagtt ttcaagtggc gcagtatcgt   4800
aacatcctta atgcatcctt gcaagtcgat cgtgacgctg ctcgttctag aagactaatg   4860
gcaaaactgg ctgattttgc ggttgaacaa gaagtaacag ctggagaccg tgttgtggtt   4920
atcgacggtc tggaccgcat ggctcacttc aaagacgatt tggtgctggt tcctttgacc   4980
accaaagtag taggcggttc taggtgcacc atttgtgacg tcgttaagga agaagccaat   5040
gacaccccag ttaagccaat gcccagcagg agacgccgca agggcctgcc taaaggtgct   5100
cagttggagt gggaccgtca ccaggaagag aagaggaacg ccggtgatga tgattttgcg   5160
gtctcgaatg attatgtcaa gagagtgcca aagtactggg accccagcga cacccgaggc   5220
acgacagtga aaatcgccgg cactacctat cagaaagtgg ttgactattc aggcaatgtg   5280
cattacgtgg agcatcagga agatctgcta gactacgtgc tgggcaaggg gagctatgaa   5340
ggcctagatc aggacaaagt gttggacctc acaaacatgc ttaaagtgga ccccacggag   5400
ctctcctcca aagacaaagc caaggcgcgt cagcttgctc atctgctgtt ggatctggct   5460
aacccagttg aggcagtgaa tcagttaaac tgagagcgcc ccacatcttt cccggcgatg   5520
tggggcgtcg gacctttgct gactctaaag acaagggttt cgtggctcta cacagtcgca   5580
caatgttttt agctgcccgg gactttttat ttaacatcaa atttgtgtgc gacgaagagt   5640
tcacaaagac cccaaaagac acactgcttg ggtacgtacg cgcctgccct ggttactggt   5700
ttattttccg tcgtacgcac cggtcgctga ttgatgcata ctgggacagt atggagtgcg   5760
tttacgcgct tcccaccata tctgattttg atgtgagccc aggtgacgtc gcagtgacgg   5820
gcgagcgatg ggattttgaa tctcccggag gaggccgtgc aaaacgtctc acagctgatc   5880
tggtgcacgc ttttcaaggg ttccacggag cctcttattc ctatgatgac aaggtggcag   5940
```

```
ctgctgtcag tggtgacccg tatcggtcgg acggcgtctt gtataacacc cgttggggca   6000
acattccata ttctgtccca accaatgctt tggaagccac agcttgctac cgtgctggat   6060
gtgaggccgt taccgacggg accaacgtca tcgcaacaat tgggcccttc ccggagcaac   6120
aacccatacc ggacatccca aagagcgtgc ttgacaactg cgctgacatc agctgtgacg   6180
ctttcatagc gcccgctgca gagacagccc tgtgtggaga tttagagaaa tacaacctat   6240
ccacgcaggg ttttgtgttg cctagtgttt tctccatggt gcgggcgtac ttaaaagagg   6300
agattggaga cgctccacca ctctacttgc catctactgt accatctaaa aattcacaag   6360
ccggaattaa cggcgctgag tttcctacaa agtctttaca gagctactgt ttgattgatg   6420
acatggtgtc acagtccatg aaaagcaatc tacaaaccgc caccatggcg acttgtaaac   6480
ggcaatactg ttccaaatac aagattagga gcattctggg caccaacaat tacattggcc   6540
taggtttgcg tgcctgcctt tcgggggtta cggccgcatt ccaaaaagct ggaaaggatg   6600
ggtcaccgat ttatttgggc aagtcaaaat tcgacccgat accagctcct gacaagtact   6660
gccttgaaac agacctggag agttgtgatc gctccacccc ggctttggtg cgttggttcg   6720
ctactaatct tatttttgag ctagctggcc agcccgagtt ggtgcacagc tacgtgttga   6780
attgctgtca cgatctagtt gtggcgggta gtgtagcatt caccaaacgc gggggtttgt   6840
catctggaga ccctatcact tccatttcca ataccatcta ttcattggtg ctgtacaccc   6900
agcacatgtt gctatgtgga cttgaaggct atttcccaga gattgcagaa aaatatcttg   6960
atggcagcct ggagctgcgg gacatgttca agtacgttcg agtgtacatc tactcggacg   7020
atgtggttct aaccacaccc aaccagcatt acgcggccag ctttgaccgc tgggtccccc   7080
acctgcaggc gctgctaggt ttcaaggttg acccaaagaa aactgtgaac accagctccc   7140
cttccttttt gggctgccgg ttcaagcaag tggacggcaa gtgttatcta gccagtcttc   7200
aggaccgcgt tacacgctct ctgttatacc acattggtgc aaagaatccc tcagagtact   7260
atgaagctgc tgtttccatc tttaaggact ccattatctg ctgtgatgaa gactggtgga   7320
cggacctcca tcgacgtatc agtggcgctg cgcgtaccga cggagttgag ttccccacca   7380
ttgaaatgtt aacatccttc cgcaccaagc agtatgagag tgccgtgtgc acagtttgtg   7440
gggccgcccc cgtggccaag tctgcttgtg gagggtggtt ctgtggcaat tgtgtcccgt   7500
accacgcggg tcattgtcac acaacctcgc tcttcgccaa ctgcgggcac gacatcatgt   7560
accgctccac ttactgcaca atgtgtgagg gttccccaaa acagatggta ccaaaagtgc   7620
ctcacccgat cctggatcat ttgctgtgcc acattgatta cggcagtaaa gaggaactaa   7680
ctctggtagt ggcggatggt cgaacaacat caccgcccgg gcgctacaaa gtgggtcaca   7740
aggtagtcgc cgtggttgca gatgtgggag gcaacattgt gtttgggtgc ggtcctggat   7800
cacacatcgc agtaccactt caggatacgc tcaagggcgt ggtggtgaat aaagctctga   7860
agaacgccgc cgcctctgag tacgtggaag gacccccctgg gagtgggaag actttttcacc   7920
tggtcaaaga tgtgctagcc gtggtcggta gcgcgacctt ggttgtgccc acccacgcgt   7980
ccatgctgga ctgcatcaac aagctcaaac aagcgggcgc cgatccatac tttgtggtgc   8040
ccaagtatac agttcttgac tttccccggc ctggcagtgg aaacatcaca gtgcgactgc   8100
cacaggtcgg aaccagtgag ggagaaacct ttgtggatga ggtggcctac ttctcaccag   8160
tggatctggc gcgcatttta acccagggtc gagtcaaggg ttacggtgat ttaaatcagc   8220
tcgggtgcgt cggacccgcg agcgtgccac gtaacctttg gctccgacat tttgtctgcc   8280
```

-continued

```
tggagccctt gcgagtgtgc catcgattcg gcgctgctgt gtgtgatttg atcaagggca   8340
tttatcctta ttatgagcca gctccacata ccactaaagt ggtgtttgtg ccaaatccag   8400
actttgagaa aggtgtagtc atcaccgcct accacaaaga tcgcggtctt ggtcaccgca   8460
caattgattc aattcaaggc tgtacattcc ctgttgtgac tcttcgactg cccacacccc   8520
aatcactgac gcgcccgcgc gcagttgtgg cggttactag ggcgtctcag gaattataca   8580
tctacgaccc ctttgatcag cttagcgggt tgttgaagtt caccaaggaa gcagaggcgc   8640
aggacttgat ccatggccca cctacagcat gccacctggg ccaagaaatt gacctttggt   8700
ccaatgaggg cctcgaatat tacaaggaag tcaacctgct gtacacacac gtccccatca   8760
aggatggtgt aatacacagt taccctaatt gtggccctgc ctgtggctgg gaaaagcaat   8820
ccaacaaaat ttcgtgcctc ccgagagtgg cacaaaattt gggctaccac tattccccag   8880
acttaccagg attttgcccc ataccaaaag aactcgctga gcattggccc gtagtgtcca   8940
atgatagata cccgaattgc ttgcaaatta ccttacagca agtatgtgaa ctcagtaaac   9000
cgtgctcagc gggctatatg gttggccaaa gcgtcttcgt ccagacgcct ggtgtgacat   9060
cttactggct tactgaatgg gtcgacggca aagcgcgtgc tctaccagat tccttattct   9120
cgtccggtag gttcgagact aacagccgcg ctttcctcga tgaagccgag gaaaagtttg   9180
ccgccgctca ccctcatgcc tgtttgggag aaattaataa gtccaccgtg ggaggatccc   9240
acttcatctt ttcccaatat ttaccaccat tgctacccgc agacgctgtt gccctggtag   9300
gtgcttcatt ggctgggaaa gctgctaaag ctgcttgcag cgtcgttgac gtctatgctc   9360
catcatttga accttatctg caccctgaga cactgagtcg cgtgtacaag attatgatcg   9420
atttcaagcc gtgtaggctt atggtgtgga gaaacgcgac cttttatgtc caagagggtg   9480
ttgatgcagt tacatcagca ctagcagctg tgtccaaact catcaaagtg ccggccaatg   9540
agcctgtttc attccatgtg gcatcagggt acagaaccaa cgcgctggta gcgccccagg   9600
ctaaaatttc gattggagcc tacgccgccg agtgggcact gtcaactgaa ccgccaccgg   9660
ctggttatgc gatcgtgcgg cgatatattg taaagaggct cctcagctca acagaagtgt   9720
tcttgtgccg caggggtgtt gtgtcttcca cctcagtgca gaccatttgt gcactagagg   9780
gatgtaaacc tctgttcaac ttcttacaaa ttggttcagt cattgggccc gtgtgagttt   9840
aaacatggga agagccggcg tgagcaaggg cgaggagctg ttcaccgggg tggtgcccat   9900
cctggtcgag ctggacggcg acgtaaacgg ccacaagttc agcgtgtccg gcgagggcga   9960
gggcgatgcc acctacggca agctgaccct gaagctgatc tgcaccaccg gcaagctgcc  10020
cgtgccctgg cccaccctcg tgaccaccct gggctacggc ctgcagtgct tcgcccgcta  10080
ccccgaccac atgaagcagc acgacttctt caagtccgcc atgcccgaag gctacgtcca  10140
ggagcgcacc atcttcttca aggacgacgg caactacaag acccgcgccg aggtgaagtt  10200
cgagggcgac accctggtga accgcatcga gctgaagggc atcgacttca aggaggacgg  10260
caacatcctg gggcacaagc tggagtacaa ctacaacagc cacaacgtct atatcaccgc  10320
cgacaagcag aagaacggca tcaaggccaa cttcaagatc cgccacaaca tcgaggacgg  10380
cggcgtgcag ctcgccgacc actaccagca gaacaccccc atcggcgacg gccccgtgct  10440
gctgcccgac aaccactacc tgagctacca gtccgccctg agcaaagacc ccaacgagaa  10500
gcgcgatcac atggtcctgc tggagttcgt gaccgccgcc gggatcactc tcggcatgga  10560
cgagctgtac aagtaggctc ttcgtaaggc gcgccggagc catagattca ttttgtggtg  10620
acgggatttt aggtgagtat ctagattact ttattctgtc cgtcccactc ttgctgttgc  10680
```

ttaccaggta tgtagcatct gggttagtgt atgttttgac tgccttgttc tattcctttg 10740
tattagcagc ttatatttgg tttgttatag ttggaagagc cttttctact gcttatgctt 10800
ttgtgctttt ggctgctttt ctgttattag taatgaggat gattgtaggt atgatgcctc 10860
gtcttcggtc cattttcaac catcgccaac tggtggtagc tgattttgtg gacacaccta 10920
gtggacctgt tcccatcccc cgcccaacca ctcagatagt ggttcgcggc aacgggtaca 10980
ccgcagttgg taacaagctt gtcgatggcg tcaagacgat cacgtccgca ggccgcctct 11040
tttcgaaacg ggcggcggcg acagcctaca agctacaatg acctactgcg tatgtttggt 11100
cagatgcggg tccgcaaacc gcccgcgcaa cccactcagg ctatcattgc agagcctgga 11160
gaccttaggc atgatttaaa tcaacaggag cgcgccaccc tttcgtcgaa cgtacaacgg 11220
ttcttcatga ttgggcatgg ttcactcact gcagatgccg gaggactcac gtacaccgtc 11280
agttgggttc ctaccaaaca aatccagcgc aaagttgcgc ctccagcagg gccgtaagac 11340
gtggatattc tcctgtgtgg cgtcatgttg aagtagttat tagccaccca ggaaccaaaa 11400
aaaaaaaaaa aaaaaaaaaa aaaaaaaaaa aaaaaaaaaa aaaaaaaaaa aaaaaaaaaa 11460
aaaaaaaaaa aaaaaaaaaa aaaaaaaaaa aaaaaaaaaa aaaaaaaaaa aaaaaaaaaa 11520
agcggccgcc cgggccgtcg accaattctc atgtttgaca gcttatcatc gaatttctgc 11580
c 11581

<210> SEQ ID NO 47
<211> LENGTH: 12974
<212> TYPE: DNA
<213> ORGANISM: Artificial Sequence
<220> FEATURE:
<223> OTHER INFORMATION: VBS-IC
<220> FEATURE:
<221> NAME/KEY: misc_feature
<222> LOCATION: (1)..(60)
<223> OTHER INFORMATION: overlap regions to pW70
<220> FEATURE:
<221> NAME/KEY: misc_feature
<222> LOCATION: (69)..(85)
<223> OTHER INFORMATION: T7 promoter
<220> FEATURE:
<221> NAME/KEY: misc_feature
<222> LOCATION: (12790)..(12914)
<223> OTHER INFORMATION: Poly A

<400> SEQUENCE: 47
gtcgatcaga ctatcagcgt gagactacga ttccatcaat gcctgtcaag ggcaagtatt 60
gcgatcgcta atacgactca ctatagctcg aagtgtgtat ggtgccatat acggctcacc 120
accatataca ctgcaagaat tactattctt gtgggcccct ctcggtaaat cctagagggc 180
tttcctctcg ttattgcgag attcgtcgtt agataacggc aagttccctt tcttactatc 240
ctattttcat cttgtggctt gacgggtcac tgccatcgtc gtcgatctct atcaactacc 300
cttgcgacta tggcaacctt ctccgctact ggatttggag ggagttttgt tagggactgg 360
tccctggact tacccgacgc ttgtgagcat ggcgcgggat tgtgctgtga agtggacggc 420
tccaccttat gcgccgagtg ttttcgcggt tgcgaaggag tggagcaatg tcctggcttg 480
ttcatgggac tgttaaaact ggcttcgcca gttccagtgg gacataagtt cctgattggt 540
tggtatcgag ctgccaaagt caccgggcgt tacaatttcc ttgagctgtt gcaacaccct 600
gctttcgccc agctgcgtgt ggttgatgct aggttagcca ttgaagaggc aagtgtgttt 660
atttccactg accacgcgtc tgctaagcgt ttccctggcg ctagatttgc gctgacaccg 720

-continued

```
gtgtatgcta gcgcttgggt tgcgagcccg gctgctaaca gtttgatagt gaccattgac    780
caggaacaag atgggttctg ctggttaaaa cttttgccac ctgaccgccg tgaggctggt    840
ttgcggttgt attacaacca ttaccgcgaa caaaggaccg ggtggctgtc taaaacagga    900
cttcgcttat ggcttggaga cctgggtttg ggcatcaatg cgagctctgg agggctgaaa    960
ttccacatta tgaggggttc gcctcagcga gcttggcata tcacaacacg cagctgcaag   1020
ctgaagagct actacgtttg tgacatctct gaagcagact ggtcctgttt gcctgctggc   1080
aactacggcg gctacaatcc accaggggac ggagcttgcg gttacaggtg cttggccttc   1140
atgaatggcg ccactgttgt gtcggctggt tgcagttctg acttgtggtg tgatgatgag   1200
ttggcttatc gagtctttca attgtcaccc acgttcacgg ttaccatccc aggtgggcga   1260
gtttgtccga atgccaagta cgcaatgatt tgtgacaagc agcactggcg cgtcaaacgt   1320
gcaaagggcg tcggcctgtg tctcgatgaa agctgtttca ggggcacctg caattgccaa   1380
cgcatgagtg gaccaccacc tgcacccgtg tcagccgccg tgttagatca catactggag   1440
gcggcgacgt ttgacaacgt tcgcgtggtt acacctgaag ggcagccacg ccccgtacca   1500
gcgccgcgag ttcgtcccag cgccaactct tctggagatg tcaaagatcc ggcgcccgtt   1560
ccgccagtac caaaaccaag gaccaagctt gccaaaccga acccaactca ggcgcccatc   1620
ccagcaccgc gcacgcgact tcaaggggcc tcaacacagg agccactggc gagtgcagga   1680
gttgcttctg actcggcacc taaatggcgt gtggccaaaa ctgtgtacag ctccgcggag   1740
cgctttcgga ccgaactggt acaacgtgct cggtccgttg ggacgttctt tgttcaagcg   1800
ctaccgctca aaaccccagc agtgcagcgg tataccatga ctctgaagat gatgcgttca   1860
cgcttcagtt ggcactgcga cgtgtggtac cctttggctg taatcgcttg tttgctccct   1920
atatggccat ctcttgcttt gctccttagc tttgccattg ggttgatacc cagtgtgggc   1980
aatagtgttg ttctgacagc gcttctggtt tcatcagcta attatgttgc gtcaatggac   2040
catcaatgtg aaggtgcggc ttgcttagcc ttgctggaag aagaacacta ttatagagcg   2100
gtccgttggc gcccgattac aggcgcgctg tcgcttgtgc tcaatttact ggggcaggta   2160
ggctatgtag ctcgttccac ctttgatgca gcttatgttc cttgcactgt gttcgatctt   2220
tgcagctttg ctattctgta cctctgccgc aatcgttgct ggagatgctt cggacgctgt   2280
gtgcgagttg ggcctgccac gcatgttttg ggttccaccg ggcaacgagt ttccaaactg   2340
gcgctcattg atttgtgtga ccacttttca aagcccacca tcgatgttgt gggcatggca   2400
actggttgga gcggatgtta cacaggaacc gccgcaatgg agcgtcagtg tgcctctacg   2460
gtggaccctc actcgttcga ccagaagaag gcaggagcga ttgtttacct caccccccct   2520
gtcaacagcg ggtcagcgct gcagtgcctc aatgtcatgt ggaagcgacc aattgggtcc   2580
actgtccttg gggaacaaac aggagctgtt gtgacggcgg tcaagagtat ctctttctca   2640
cctccctgct gcgtctctac cactttgccc acgcgacccg gtgtgaccgt tgtcgaccat   2700
gctctttaca accggttgac tgcttcaggg gtcgatcccg ctttattgcg tgttgggcaa   2760
ggtgattttc taaaacttaa tccggggttc cggctgatag gtggatggat ttatgggata   2820
tgctattttg tgttggtggt tgtgtcaact tttacctgct tacctatcaa atgtggcatt   2880
ggcacccgcg accctttctg ccgcagagtg ttttctgtac ccgtcaccaa gacccaagag   2940
cactgccatg ctggaatgtg tgctagcgct gaaggcatct ctctggactc tctggggtta   3000
actcagttac aaagttactg gatcgctgcc gtcactagcg gattagtgat cttgttggtc   3060
tgccaccgcc tggccatcag cgccttggac ttgttgactc tagcttcccc tttagtgttg   3120
```

```
cttgtgttcc cttgggcatc tgtggggctt ttacttgctt gcagtctcgc tggtgctgct   3180
gtgaaaatac agttgttggc gacgcttttt gtgaatctgt tctttcccca agctaccctt   3240
gtcactatgg gatactgggc gtgcgtggcg gctttggccg tttacagttt gatgggcttg   3300
cgagtgaaag tgaatgtgcc catgtgtgtg acacctgccc attttctgct gctggcgagg   3360
tcagctggac agtcaagaga gcagatgctc cgggtcagcg ctgctgcccc caccaattca   3420
ctgcttggag tggctcgtga ttgttatgtc acaggcacaa ctcggctgta catacccaag   3480
gagggcggga tggtgtttga agggctattc aggtcaccga aggcgcgcgg caacgtcggc   3540
ttcgtggctg gtagcagcta cggcacaggg tcagtgtgga ccaggaacaa cgaggtcgtc   3600
gtactgacag cgtcacacgt ggttggccgc gctaacatgg ccactctgaa gatcggtgac   3660
gcaatgctga ctctgacttt caaaaagaat ggcgacttcg ccgaggcagt gacgacacag   3720
tccgagctcc caggcaattg gccacagttg catttcgccc aaccaacaac cgggcccgct   3780
tcatggtgca ccgccacagg agatgaagaa ggcttgctca gtggcgaggt ttgtctggcg   3840
tggactacta gtggcgactc tggatcagca gtggttcagg gtgacgctgt ggtagggtc    3900
cacaccggtt cgaacacaag tggtgttgcc tacgtgacca ccccaagcgg aaaactcctt   3960
ggcgccgaca ccgtgacttt gtcatcactg tcaaagcatt tcacaggccc tttgacatca   4020
atcccgaagg acatccctga caacatcatt gccgatgttg atgctgttcc tcgttctctg   4080
gccatgctga ttgatggctt atccaataga gagagcagcc tttctggacc tcagttgttg   4140
ttaattgctt gttttatgtg gtcttatctt aaccaacctg cttacttgcc ttatgtgctg   4200
ggcttctttg ccgctaactt cttcctgcca aaaagtgttg gccgccctgt ggtcactggg   4260
cttctatggt tgtgctgcct cttcacaccg ctttccatgc gcttgtgctt gttccatctg   4320
gtctgtgcta ccgtcacggg aaacgtgata tctttgtggt tctacatcac tgccgctggc   4380
acgtcttacc tttctgagat gtggttcgga ggctatccca ccatgttgtt tgtgccacgg   4440
ttcctagtgt accagttccc cggctgggct attggcacag tactagcggt atgcagcatc   4500
accatgctgg ctgctgccct cggtcacacc ctgttactgg atgtgttctc cgcctcaggt   4560
cgctttgaca ggactttcat gatgaaatac ttcctggagg gaggagtgaa agagagtgtc   4620
accgcctcag tcacccgcgc ttatggcaaa ccaattaccc aggagagtct cactgcaaca   4680
ttagctgccc tcactgatga tgacttccaa ttcctctctg atgtgcttga ctgtcgggcc   4740
gtccgatcgg caatgaatct gcgtgccgct ctcacaagtt ttcaagtggc gcagtatcgt   4800
aacatcctta atgcatcctt gcaagtcgat cgtgacgctg ctcgttctag aagactaatg   4860
gcaaaactgg ctgattttgc ggttgaacaa gaagtaacag ctggagaccg tgttgtggtt   4920
atcgacggtc tggaccgcat ggctcacttc aaagacgatt tggtgctggt tcctttgacc   4980
accaaagtag taggcggttc taggtgcacc atttgtgacg tcgttaagga agaagccaat   5040
gacaccccag ttaagccaat gcccagcagg agacgccgca agggcctgcc taaaggtgct   5100
cagttggagt gggaccgtca ccaggaagag aagaggaacg ccggtgatga tgattttgcg   5160
gtctcgaatg attatgtcaa gagagtgcca aagtactggg accccagcga cacccgaggc   5220
acgacagtga aaatcgccgg cactacctat cagaaagtgg ttgactattc aggcaatgtg   5280
cattacgtgg agcatcagga agatctgcta gactacgtgc tgggcaaggg gagctatgaa   5340
ggcctagatc aggacaaagt gttggacctc acaaacatgc ttaaagtgga ccccacggag   5400
ctctcctcca aagacaaagc caaggcgcgt cagcttgctc atctgctgtt ggatctggct   5460
```

aacccagttg aggcagtgaa tcagttaaac tgagagcgcc ccacatcttt cccggcgatg 5520
tggggcgtcg gacctttgct gactctaaag acaagggttt cgtggctcta cacagtcgca 5580
caatgttttt agctgcccgg gactttttat ttaacatcaa atttgtgtgc gacgaagagt 5640
tcacaaagac cccaaaagac acactgcttg ggtacgtacg cgcctgccct ggttactggt 5700
ttattttccg tcgtacgcac cggtcgctga ttgatgcata ctgggacagt atggagtgcg 5760
tttacgcgct tcccaccata tctgattttg atgtgagccc aggtgacgtc gcagtgacgg 5820
gcgagcgatg ggattttgaa tctcccggag gaggccgtgc aaaacgtctc acagctgatc 5880
tggtgcacgc ttttcaaggg ttccacggag cctcttattc ctatgatgac aaggtggcag 5940
ctgctgtcag tggtgacccg tatcggtcgg acggcgtctt gtataacacc cgttggggca 6000
acattccata ttctgtccca accaatgctt tggaagccac agcttgctac cgtgctggat 6060
gtgaggccgt taccgacggg accaacgtca tcgcaacaat tgggcccttc ccggagcaac 6120
aacccatacc ggacatccca aagagcgtgc ttgacaactg cgctgacatc agctgtgacg 6180
ctttcatagc gcccgctgca gagacagccc tgtgtggaga tttagagaaa tacaacctat 6240
ccacgcaggg ttttgtgttg cctagtgttt tctccatggt gcgggcgtac ttaaaagagg 6300
agattggaga cgctccacca ctctacttgc catctactgt accatctaaa aattcacaag 6360
ccggaattaa cggcgctgag tttcctacaa agtctttaca gagctactgt ttgattgatg 6420
acatggtgtc acagtccatg aaaagcaatc tacaaaccgc caccatggcg acttgtaaac 6480
ggcaatactg ttccaaatac aagattagga gcattctggg caccaacaat tacattggcc 6540
taggtttgcg tgcctgcctt tcgggggtta cggccgcatt ccaaaaagct ggaaaggatg 6600
ggtcaccgat ttatttgggc aagtcaaaat tcgacccgat accagctcct gacaagtact 6660
gccttgaaac agacctggag agttgtgatc gctccacccc ggctttggtg cgttggttcg 6720
ctactaatct tatttttgag ctagctggcc agcccgagtt ggtgcacagc tacgtgttga 6780
attgctgtca cgatctagtt gtggcgggta gtgtagcatt caccaaacgc gggggtttgt 6840
catctggaga ccctatcact tccatttcca ataccatcta ttcattggtg ctgtacaccc 6900
agcacatgtt gctatgtgga cttgaaggct atttcccaga gattgcagaa aaatatcttg 6960
atggcagcct ggagctgcgg gacatgttca agtacgttcg agtgtacatc tactcggacg 7020
atgtggttct aaccacaccc aaccagcatt acgcggccag ctttgaccgc tgggtccccc 7080
acctgcaggc gctgctaggt ttcaaggttg acccaaagaa aactgtgaac accagctccc 7140
cttccttttt gggctgccgg ttcaagcaag tggacggcaa gtgttatcta gccagtcttc 7200
aggaccgcgt tacacgctct ctgttatacc acattggtgc aaagaatccc tcagagtact 7260
atgaagctgc tgtttccatc tttaaggact ccattatctg ctgtgatgaa gactggtgga 7320
cggacctcca tcgacgtatc agtggcgctg cgcgtaccga cggagttgag ttccccacca 7380
ttgaaatgtt aacatccttc cgcaccaagc agtatgagag tgccgtgtgc acagtttgtg 7440
gggccgcccc cgtggccaag tctgcttgtg gagggtggtt ctgtggcaat tgtgtcccgt 7500
accacgcggg tcattgtcac acaacctcgc tcttcgccaa ctgcgggcac gacatcatgt 7560
accgctccac ttactgcaca atgtgtgagg gttccccaaa acagatggta ccaaaagtgc 7620
ctcacccgat cctggatcat ttgctgtgcc acattgatta cggcagtaaa gaggaactaa 7680
ctctggtagt ggcggatggt cgaacaacat caccgcccgg gcgctacaaa gtgggtcaca 7740
aggtagtcgc cgtggttgca gatgtgggag gcaacattgt gtttgggtgc ggtcctggat 7800
cacacatcgc agtaccactt caggatacgc tcaagggcgt ggtggtgaat aaagctctga 7860

-continued

```
agaacgccgc cgcctctgag tacgtggaag gaccccctgg gagtgggaag acttttcacc   7920
tggtcaaaga tgtgctagcc gtggtcggta gcgcgacctt ggttgtgccc acccacgcgt   7980
ccatgctgga ctgcatcaac aagctcaaac aagcgggcgc cgatccatac tttgtggtgc   8040
ccaagtatac agttcttgac tttccccggc ctggcagtgg aaacatcaca gtgcgactgc   8100
cacaggtcgg aaccagtgag ggagaaacct ttgtggatga ggtggcctac ttctcaccag   8160
tggatctggc gcgcatttta acccagggtc gagtcaaggg ttacggtgat ttaaatcagc   8220
tcgggtgcgt cggacccgcg agcgtgccac gtaacctttg gctccgacat tttgtctgcc   8280
tggagccctt gcgagtgtgc catcgattcg gcgctgctgt gtgtgatttg atcaagggca   8340
tttatcctta ttatgagcca gctccacata ccactaaagt ggtgtttgtg ccaaatccag   8400
actttgagaa aggtgtagtc atcaccgcct accacaaaga tcgcggtctt ggtcaccgca   8460
caattgattc aattcaaggc tgtacattcc ctgttgtgac tcttcgactg cccacacccc   8520
aatcactgac gcgcccgcgc gcagttgtgg cggttactag ggcgtctcag gaattataca   8580
tctacgaccc ctttgatcag cttagcgggt tgttgaagtt caccaaggaa gcagaggcgc   8640
aggacttgat ccatggccca cctacagcat gccacctggg ccaagaaatt gacctttggt   8700
ccaatgaggg cctcgaatat tacaaggaag tcaacctgct gtacacacac gtccccatca   8760
aggatggtgt aatacacagt taccctaatt gtggccctgc ctgtggctgg gaaaagcaat   8820
ccaacaaaat ttcgtgcctc ccgagagtgg cacaaaattt gggctaccac tattccccag   8880
acttaccagg attttgcccc ataccaaaag aactcgctga gcattggccc gtagtgtcca   8940
atgatagata cccgaattgc ttgcaaatta ccttacagca agtatgtgaa ctcagtaaac   9000
cgtgctcagc gggctatatg gttggccaaa gcgtcttcgt ccagacgcct ggtgtgacat   9060
cttactggct tactgaatgg gtcgacggca aagcgcgtgc tctaccagat tccttattct   9120
cgtccggtag gttcgagact aacagccgcg ctttcctcga tgaagccgag gaaaagtttg   9180
ccgccgctca ccctcatgcc tgtttgggag aaattaataa gtccaccgtg ggaggatccc   9240
acttcatctt ttcccaatat ttaccaccat tgctacccgc agacgctgtt gccctggtag   9300
gtgcttcatt ggctgggaaa gctgctaaag ctgcttgcag cgtcgttgac gtctatgctc   9360
catcatttga accttatctg caccctgaga cactgagtcg cgtgtacaag attatgatcg   9420
atttcaagcc gtgtaggctt atggtgtgga gaaacgcgac cttttatgtc caagagggtg   9480
ttgatgcagt tacatcagca ctagcagctg tgtccaaact catcaaagtg ccggccaatg   9540
agcctgtttc attccatgtg gcatcagggt acagaaccaa cgcgctggta gcgccccagg   9600
ctaaaatttc gattggagcc tacgccgccg agtgggcact gtcaactgaa ccgccaccgg   9660
ctggttatgc gatcgtgcgg cgatatattg taaagaggct cctcagctca acagaagtgt   9720
tcttgtgccg caggggtgtt gtgtcttcca cctcagtgca gaccatttgt gcactagagg   9780
gatgtaaacc tctgttcaac ttcttacaaa ttggttcagt cattgggccc gtgtgatggg   9840
cttagtgtgg tcactgattt caaattctat tcagactatt attgctgatt ttgctatttc   9900
tgtgattgat gcagcgcttt tctttctcat gctacttgca ttggctgttg ttactgtgtt   9960
tcttttctgg ctcattgttg ccatcggccg cagcttggtg gcgcggtgtt cacgaggtgc  10020
gcgttacaga cctgtttaag gatttgcagt gcgacaacct gcgcgcgaaa gatgccttcc  10080
cgagtctggg atatgctctg tcgattggcc agtcgaggct atcgtatatg ctgcaggatt  10140
ggttgcttgc tgcgcaccgc aaggaagtta tgccctccaa tatcatgcct atgcccggtc  10200
```

-continued

```
ttactcctga ttgctttgac catctggagt cttctagcta tgctccattt atcaatgcct  10260
atcggcaggc aatcttgagt caatactcac aagagctcct gctcgaagcc atcaactgta  10320
aattgcttgc tgtggttgca ccggcattgt atcataatta ccatctagcc aatttgaccg  10380
gaccggccac atgggtcgtg cctacagtgg gccagttgca ctattatgct tcttcctcta  10440
tttttgcttc atctgtggaa gtgttggcag caataatact actatttgca tgcataccac  10500
tagtgacacg agtgtacatc tcttttacgc ggctaatgtc accttcccgt cgcacttcca  10560
gcggcacttt gccgcggcgc aagattttgt agtgcacacg ggttatgaat atgccggggt  10620
cactatgtta gtgcacttgt ttgccaactt ggttctgaca tttccgagct tagttaattg  10680
ttcccgccct gtgaatgtct ttgctaatgc ttcttgcgtg caagtggttt gtagtcatac  10740
caactcaact actggcttgg gtcaactttc tttttccttt gtagatgaag atctacggct  10800
gcatattagg cctactctta tttgttggtt tgccttgttg ttggtgcact ttctacccat  10860
gccacgctgc agaggctcgt aattttactt acattagtca tggattgggc cacgtgcacg  10920
gtcatgaggg gtgtaggaat tttattaatg tcactcattc tgcatttctt tatcttaatc  10980
ccaccactct cactgcgccg gctataactc attgtttact tctggttctg gcagccaaaa  11040
tggaacaccc aaacgctact atctggctgc agctgcagcc gtttgggtat catgtggctg  11100
gcgatgtcat tgtcaacttg gaagagaata agaggcatcc ttactttaaa cttttgagag  11160
cgccggcttt accgcttggt tttgtggcta tagtttatgt tcttttacga ctggtacgtt  11220
gggctcaaca atgttatcta tgattgtatt gctattcttg ctttggggtg cgccatcaca  11280
tgcttacttc tcatactaca ccgctcagcg cttcacagac ttcaccttgt gtatgctgac  11340
ggatcgcggc gttattgcca atttgctgcg atatgatgag cacactgctt tgtacaattg  11400
ttccgccagt aaaacctgtt ggtattgcac attcctggac gaacagatta tcacgtttgg  11460
aaccgattgt aatgacacct acgcggtccc agttgctgag gtcctggaac aggcgcatgg  11520
accgtacagt gtgctgttta atgacatgcc cccttttatt tactatggcc gtgaattcgg  11580
catagttgtg ttggatgtgt ttatgttcta tcccgtttta gttctgtttt tcttatcagt  11640
actaccctat gctacgctta ttcttgaaat gtgtgtatct attctgttta taatctatgg  11700
catttacagc ggggcctact tggccatggg catatttgcg gccacgcttg ctatacattc  11760
aattgtggtc ctccgccaat tactgtggtt atgcctggct tggcgatacc gctgtacgct  11820
tcacgcgtcc tttatatcag ctgaggggaa agtgtacccc gtagaccccg gactcccggt  11880
tgccgccgcg ggcaatcggt tgttagtccc aggtaggccc actatcgatt atgcagtggc  11940
ctacggcagc aaagtcaacc ttgtgaggtt gggggcagct gaggtatggg agccatagat  12000
tcattttgtg gtgacgggat tttaggtgag tatctagatt actttattct gtccgtccca  12060
ctcttgctgt tgcttaccag gtatgtagca tctgggttag tgtatgtttt gactgccttg  12120
ttctattcct ttgtattagc agcttatatt tggtttgtta tagttggaag agccttttct  12180
actgcttatg cttttgtgct tttggctgct ttttctgttat tagtaatgag gatgattgta  12240
ggtatgatgc ctcgtcttcg gtccattttc aaccatcgcc aactggtggt agctgatttt  12300
gtggacacac ctagtggacc tgttcccatc cccgctcaa ctactcagat agtggttcgc  12360
ggcaacgggt acaccgcagt tggtaacaag cttgtcgatg gcgtcaagac gatcacgtcc  12420
gcaggccgcc tcttttcgaa acgggcggcg gcgacagcct acaagctaca atgacctact  12480
gcgtatgttt ggtcagatgc gggtccgcaa accgcccgcg caacccactc aggctatcat  12540
tgcagagcct ggagacctta ggcatgattt aaatcaacag gagcgcgcca ccctttcgtc  12600
```

```
gaacgtacaa cggttcttca tgattgggca tggttcactc actgcagatg ccggaggact  12660

cacgtacacc gtcagttggg ttcctaccaa acaaatccag cgcaaagttg cgcctccagc  12720

agggccgtaa gacgtggata ttctcctgtg tggcgtcatg ttgaagtagt tattagccac  12780

ccaggaacca aaaaaaaaaa aaaaaaaaaa aaaaaaaaaa aaaaaaaaaa aaaaaaaaaa  12840

aaaaaaaaaa aaaaaaaaaa aaaaaaaaaa aaaaaaaaaa aaaaaaaaaa aaaaaaaaaa  12900

aaaaaaaaaa aaaagcggcc gcccgggccg tcgaccaatt ctcatgtttg acagcttatc  12960

atcgaatttc tgcc                                                    12974
```

<210> SEQ ID NO 48
<211> LENGTH: 12358
<212> TYPE: DNA
<213> ORGANISM: Artificial Sequence
<220> FEATURE:
<223> OTHER INFORMATION: VBS-R-rFF
<220> FEATURE:
<221> NAME/KEY: misc_feature
<222> LOCATION: (1)..(17)
<223> OTHER INFORMATION: T7 promoter
<220> FEATURE:
<221> NAME/KEY: misc_feature
<222> LOCATION: (12233)..(12358)
<223> OTHER INFORMATION: Poly A

<400> SEQUENCE: 48

```
taatacgact cactatagct cgaagtgtgt atggtgccat atacggctca ccaccatata    60

cactgcaaga attactattc ttgtgggccc ctctcggtaa atcctagagg gctttcctct   120

cgttattgcg agattcgtcg ttagataacg gcaagttccc tttcttacta tcctattttc   180

atcttgtggc ttgacgggtc actgccatcg tcgtcgatct ctatcaacta cccttgcgac   240

tatggcaacc ttctccgcta ctggatttgg agggagtttt gttagggact ggtccctgga   300

cttacccgac gcttgtgagc atggcgcggg attgtgctgt gaagtggacg gctccacctt   360

atgcgccgag tgttttcgcg gttgcgaagg agtggagcaa tgtcctggct tgttcatggg   420

actgttaaaa ctggcttcgc cagttccagt gggacataag ttcctgattg gttggtatcg   480

agctgccaaa gtcaccgggc gttacaattt ccttgagctg ttgcaacacc ctgctttcgc   540

ccagctgcgt gtggttgatg ctaggttagc cattgaagag gcaagtgtgt ttatttccac   600

tgaccacgcg tctgctaagc gtttccctgg cgctagattt gcgctgacac cggtgtatgc   660

tagcgcttgg gttgcgagcc cggctgctaa cagtttgata gtgaccattg accaggaaca   720

agatgggttc tgctggttaa aacttttgcc acctgaccgc cgtgaggctg gtttgcggtt   780

gtattacaac cattaccgcg aacaaaggac cgggtggctg tctaaaacag gacttcgctt   840

atggcttgga gacctgggtt tgggcatcaa tgcgagctct ggagggctga aattccacat   900

tatgaggggt tcgcctcagc gagcttggca tatcacaaca cgcagctgca agctgaagag   960

ctactacgtt tgtgacatct ctgaagcaga ctggtcctgt ttgcctgctg gcaactacgg  1020

cggctacaat ccaccagggg acggagcttg cggttacagg tgcttggcct tcatgaatgg  1080

cgccactgtt gtgtcggctg gttgcagttc tgacttgtgg tgtgatgatg agttggctta  1140

tcgagtcttt caattgtcac ccacgttcac ggttaccatc ccaggtgggc gagtttgtcc  1200

gaatgccaag tacgcaatga tttgtgacaa gcagcactgg cgcgtcaaac gtgcaaaggg  1260

cgtcggcctg tgtctcgatg aaagctgttt caggggcacc tgcaattgcc aacgcatgag  1320

tggaccacca cctgcacccg tgtcagccgc cgtgttagat cacatactgg aggcggcgac  1380
```

-continued

```
gtttgacaac gttcgcgtgg ttacacctga agggcagcca cgccccgtac cagcgccgcg   1440
agttcgtccc agcgccaact cttctggaga tgtcaaagat ccggcgcccg ttccgccagt   1500
accaaaacca aggaccaagc ttgccaaacc gaacccaact caggcgccca tcccagcacc   1560
gcgcacgcga cttcaagggg cctcaacaca ggagccactg gcgagtgcag gagttgcttc   1620
tgactcggca cctaaatggc gtgtggccaa aactgtgtac agctccgcgg agcgctttcg   1680
gaccgaactg gtacaacgtg ctcggtccgt tggggacgtt cttgttcaag cgctaccgct   1740
caaaacccca gcagtgcagc ggtataccat gactctgaag atgatgcgtt cacgcttcag   1800
ttggcactgc gacgtgtggt accctttggc tgtaatcgct tgtttgctcc ctatatggcc   1860
atctcttgct ttgctcctta gctttgccat tgggttgata cccagtgtgg gcaatagtgt   1920
tgttctgaca gcgcttctgg tttcatcagc taattatgtt gcgtcaatgg accatcaatg   1980
tgaaggtgcg gcttgcttag ccttgctgga agaagaacac tattatagag cggtccgttg   2040
gcgcccgatt acaggcgcgc tgtcgcttgt gctcaattta ctggggcagg taggctatgt   2100
agctcgttcc acctttgatg cagcttatgt tccttgcact gtgttcgatc tttgcagctt   2160
tgctattctg tacctctgcc gcaatcgttg ctggagatgc ttcggacgct gtgtgcgagt   2220
tgggcctgcc acgcatgttt tgggttccac cgggcaacga gtttccaaac tggcgctcat   2280
tgatttgtgt gaccactttt caaagcccac catcgatgtt gtgggcatgg caactggttg   2340
gagcggatgt tacacaggaa ccgccgcaat ggagcgtcag tgtgcctcta cggtggaccc   2400
tcactcgttc gaccagaaga aggcaggagc gattgtttac ctcacccccc ctgtcaacag   2460
cgggtcagcg ctgcagtgcc tcaatgtcat gtggaagcga ccaattgggt ccactgtcct   2520
tggggaacaa acaggagctg ttgtgacggc ggtcaagagt atctctttct cacctccctg   2580
ctgcgtctct accactttgc ccacgcgacc cggtgtgacc gttgtcgacc atgctcttta   2640
caaccggttg actgcttcag ggtcgatcc cgctttattg cgtgttgggc aaggtgattt   2700
tctaaaactt aatccggggt tccggctgat aggtggatgg atttatggga tatgctattt   2760
tgtgttggtg gttgtgtcaa cttttacctg cttacctatc aaatgtggca ttggcacccg   2820
cgaccctttc tgccgcagag tgttttctgt acccgtcacc aagacccaag agcactgcca   2880
tgctggaatg tgtgctagcg ctgaaggcat ctctctggac tctctggggt taactcagtt   2940
acaaagttac tggatcgctg ccgtcactag cggattagtg atcttgttgg tctgccaccg   3000
cctggccatc agcgccttgg acttgttgac tctagcttcc cctttagtgt tgcttgtgtt   3060
cccttgggca tctgtggggc ttttacttgc ttgcagtctc gctggtgctg ctgtgaaaat   3120
acagttgttg gcgacgcttt ttgtgaatct gttctttccc caagctaccc ttgtcactat   3180
gggatactgg gcgtgcgtgg cggctttggc cgtttacagt ttgatgggct tgcgagtgaa   3240
agtgaatgtg cccatgtgtg tgacacctgc ccattttctg ctgctggcga ggtcagctgg   3300
acagtcaaga gagcagatgc tccgggtcag cgctgctgcc cccaccaatt cactgcttgg   3360
agtggctcgt gattgttatg tcacaggcac aactcggctg tacataccca aggagggcgg   3420
gatggtgttt gaagggctat tcaggtcacc gaaggcgcgc ggcaacgtcg gcttcgtggc   3480
tggtagcagc tacggcacag ggtcagtgtg gaccaggaac aacgaggtcg tcgtactgac   3540
agcgtcacac gtggttggcc gcgctaacat ggccactctg aagatcggtg acgcaatgct   3600
gactctgact ttcaaaaaga atggcgactt cgccgaggca gtgacgacac agtccgagct   3660
cccaggcaat tggccacagt tgcatttcgc ccaaccaaca accgggcccg cttcatggtg   3720
caccgccaca ggagatgaag aaggcttgct cagtggcgag gtttgtctgg cgtggactac   3780
```

```
tagtggcgac tctggatcag cagtggttca gggtgacgct gtggtagggg tccacaccgg   3840
ttcgaacaca agtggtgttg cctacgtgac caccccaagc ggaaaactcc ttggcgccga   3900
caccgtgact ttgtcatcac tgtcaaagca tttcacaggc cctttgacat caatcccgaa   3960
ggacatccct gacaacatca ttgccgatgt tgatgctgtt cctcgttctc tggccatgct   4020
gattgatggc ttatccaata gagagagcag cctttctgga cctcagttgt tgttaattgc   4080
ttgttttatg tggtcttatc ttaaccaacc tgcttacttg ccttatgtgc tgggcttctt   4140
tgccgctaac ttcttcctgc caaaaagtgt tggccgccct gtggtcactg ggcttctatg   4200
gttgtgctgc ctcttcacac cgctttccat gcgcttgtgc ttgttccatc tggtctgtgc   4260
taccgtcacg ggaaacgtga tatctttgtg gttctacatc actgccgctg gcacgtctta   4320
cctttctgag atgtggttcg gaggctatcc caccatgttg tttgtgccac ggttcctagt   4380
gtaccagttc cccggctggg ctattggcac agtactagcg gtatgcagca tcaccatgct   4440
ggctgctgcc ctcggtcaca ccctgttact ggatgtgttc tccgcctcag gtcgctttga   4500
caggactttc atgatgaaat acttcctgga gggaggagtg aaagagagtg tcaccgcctc   4560
agtcacccgc gcttatggca aaccaattac ccaggagagt ctcactgcaa cattagctgc   4620
cctcactgat gatgacttcc aattcctctc tgatgtgctt gactgtcggg ccgtccgatc   4680
ggcaatgaat ctgcgtgccg ctctcacaag ttttcaagtg gcgcagtatc gtaacatcct   4740
taatgcatcc ttgcaagtcg atcgtgacgc tgctcgttct agaagactaa tggcaaaact   4800
ggctgatttt gcggttgaac aagaagtaac agctggagac cgtgttgtgg ttatcgacgg   4860
tctggaccgc atggctcact tcaaagacga tttggtgctg gttcctttga ccaccaaagt   4920
agtaggcggt tctaggtgca ccatttgtga cgtcgttaag gaagaagcca atgacacccc   4980
agttaagcca atgcccagca ggagacgccg caagggcctg cctaaaggtg ctcagttgga   5040
gtgggaccgt caccaggaag agaagaggaa cgccggtgat gatgattttg cggtctcgaa   5100
tgattatgtc aagagagtgc caaagtactg ggaccccagc gacacccgag gcacgacagt   5160
gaaaatcgcc ggcactacct atcagaaagt ggttgactat tcaggcaatg tgcattacgt   5220
ggagcatcag gaagatctgc tagactacgt gctgggcaag ggagctatg aaggcctaga   5280
tcaggacaaa gtgttggacc tcacaaacat gcttaaagtg gaccccacgg agctctcctc   5340
caaagacaaa gccaaggcgc gtcagcttgc tcatctgctg ttggatctgg ctaacccagt   5400
tgaggcagtg aatcagttaa actgagagcg ccccacatct ttcccggcga tgtggggcgt   5460
cggacctttg ctgactctaa agacaagggt ttcgtggctc tacacagtcg cacaatgttt   5520
ttagctgccc gggacttttt atttaacatc aaatttgtgt gcgacgaaga gttcacaaag   5580
accccaaaag acacactgct tgggtacgta cgcgcctgcc ctggttactg gtttattttc   5640
cgtcgtacgc accggtcgct gattgatgca tactgggaca gtatggagtg cgtttacgcg   5700
cttcccacca tatctgattt tgatgtgagc ccaggtgacg tcgcagtgac gggcgagcga   5760
tgggattttg aatctcccgg aggaggccgt gcaaaacgtc tcacagctga tctggtgcac   5820
gcttttcaag ggttccacgg agcctcttat tcctatgatg acaaggtggc agctgctgtc   5880
agtggtgacc cgtatcggtc ggacggcgtc ttgtataaca cccgttgggg caacattcca   5940
tattctgtcc caaccaatgc tttggaagcc acagcttgct accgtgctgg atgtgaggcc   6000
gttaccgacg ggaccaacgt catcgcaaca attgggccct tcccggagca acaaccccata   6060
ccggacatcc caaagagcgt gcttgacaac tgcgctgaca tcagctgtga cgctttcata   6120
```

gcgcccgctg cagagacagc cctgtgtgga gatttagaga aatacaacct atccacgcag 6180
ggttttgtgt tgcctagtgt tttctccatg gtgcgggcgt acttaaaaga ggagattgga 6240
gacgctccac cactctactt gccatctact gtaccatcta aaaattcaca agccggaatt 6300
aacggcgctg agtttcctac aaagtcttta cagagctact gtttgattga tgacatggtg 6360
tcacagtcca tgaaaagcaa tctacaaacc gccaccatgg cgacttgtaa acggcaatac 6420
tgttccaaat acaagattag gagcattctg ggcaccaaca attacattgg cctaggtttg 6480
cgtgcctgcc tttcgggggt tacggccgca ttccaaaaag ctggaaagga tgggtcaccg 6540
atttatttgg gcaagtcaaa attcgacccg ataccagctc ctgacaagta ctgccttgaa 6600
acagacctgg agagttgtga tcgctccacc ccggctttgg tgcgttggtt cgctactaat 6660
cttatttttg agctagctgg ccagcccgag ttggtgcaca gctacgtgtt gaattgctgt 6720
cacgatctag ttgtggcggg tagtgtagca ttcaccaaac gcgggggttt gtcatctgga 6780
gaccctatca cttccatttc caataccatc tattcattgg tgctgtacac ccagcacatg 6840
ttgctatgtg gacttgaagg ctatttccca gagattgcag aaaaatatct tgatggcagc 6900
ctggagctgc gggacatgtt caagtacgtt cgagtgtaca tctactcgga cgatgtggtt 6960
ctaaccacac ccaaccagca ttacgcggcc agctttgacc gctgggtccc ccacctgcag 7020
gcgctgctag gtttcaaggt tgacccaaag aaaactgtga acaccagctc cccttccttt 7080
ttgggctgcc ggttcaagca agtggacggc aagtgttatc tagccagtct tcaggaccgc 7140
gttacacgct ctctgttata ccacattggt gcaaagaatc cctcagagta ctatgaagct 7200
gctgtttcca tctttaagga ctccattatc tgctgtgatg aagactggtg gacggacctc 7260
catcgacgta tcagtggcgc tgcgcgtacc gacggagttg agttccccac cattgaaatg 7320
ttaacatcct tccgcaccaa gcagtatgag agtgccgtgt gcacagtttg tggggccgcc 7380
cccgtggcca agtctgcttg tggagggtgg ttctgtggca attgtgtccc gtaccacgcg 7440
ggtcattgtc acacaacctc gctcttcgcc aactgcgggc acgacatcat gtaccgctcc 7500
acttactgca caatgtgtga gggttcccca aaacagatgg taccaaaagt gcctcacccg 7560
atcctggatc atttgctgtg ccacattgat tacggcagta aagaggaact aactctggta 7620
gtggcggatg gtcgaacaac atcaccgccc gggcgctaca aagtgggtca caaggtagtc 7680
gccgtggttg cagatgtggg aggcaacatt gtgtttgggt gcggtcctgg atcacacatc 7740
gcagtaccac ttcaggatac gctcaagggc gtggtggtga ataaagctct gaagaacgcc 7800
gccgcctctg agtacgtgga aggacccccct gggagtggga agacttttca cctggtcaaa 7860
gatgtgctag ccgtggtcgg tagcgcgacc ttggttgtgc ccacccacgc gtccatgctg 7920
gactgcatca acaagctcaa acaagcgggc gccgatccat actttgtggt gcccaagtat 7980
acagttcttg actttccccg gcctggcagt ggaaacatca cagtgcgact gccacaggtc 8040
ggaaccagtg agggagaaac ctttgtggat gaggtggcct acttctcacc agtggatctg 8100
gcgcgcattt taacccaggg tcgagtcaag ggttacggtg atttaaatca gctcgggtgc 8160
gtcggacccg cgagcgtgcc acgtaacctt tggctccgac attttgtctg cctggagccc 8220
ttgcgagtgt gccatcgatt cggcgctgct gtgtgtgatt tgatcaaggg catttatcct 8280
tattatgagc cagctccaca taccactaaa gtggtgtttg tgccaaatcc agactttgag 8340
aaaggtgtag tcatcaccgc ctaccacaaa gatcgcggtc ttggtcaccg cacaattgat 8400
tcaattcaag gctgtacatt ccctgttgtg actcttcgac tgcccacacc ccaatcactg 8460
acgcgcccgc gcgcagttgt ggcggttact agggcgtctc aggaattata catctacgac 8520

-continued

```
ccctttgatc agcttagcgg gttgttgaag ttcaccaagg aagcagaggc gcaggacttg   8580
atccatggcc cacctacagc atgccacctg ggccaagaaa ttgacctttg gtccaatgag   8640
ggcctcgaat attacaagga agtcaacctg ctgtacacac acgtccccat caaggatggt   8700
gtaatacaca gttaccctaa ttgtggccct gcctgtggct gggaaaagca atccaacaaa   8760
atttcgtgcc tcccgagagt ggcacaaaat ttgggctacc actattcccc agacttacca   8820
ggattttgcc ccataccaaa agaactcgct gagcattggc ccgtagtgtc caatgataga   8880
tacccgaatt gcttgcaaat taccttacag caagtatgtg aactcagtaa accgtgctca   8940
gcgggctata tggttggcca aagcgtcttc gtccagacgc ctggtgtgac atcttactgg   9000
cttactgaat gggtcgacgg caaagcgcgt gctctaccag attccttatt ctcgtccggt   9060
aggttcgaga ctaacagccg cgctttcctc gatgaagccg aggaaaagtt tgccgccgct   9120
caccctcatg cctgtttggg agaaattaat aagtccaccg tgggaggatc ccacttcatc   9180
ttttcccaat atttaccacc attgctaccc gcagacgctg ttgccctggt aggtgcttca   9240
ttggctggga aagctgctaa agctgcttgc agcgtcgttg acgtctatgc tccatcattt   9300
gaaccttatc tgcaccctga gacactgagt cgcgtgtaca agattatgat cgatttcaag   9360
ccgtgtaggc ttatggtgtg gagaaacgcg accttttatg tccaagaggg tgttgatgca   9420
gttacatcag cactagcagc tgtgtccaaa ctcatcaaag tgccggccaa tgagcctgtt   9480
tcattccatg tggcatcagg gtacagaacc aacgcgctgg tagcgcccca ggctaaaatt   9540
tcgattggag cctacgccgc cgagtgggca ctgtcaactg aaccgccacc ggctggttat   9600
gcgatcgtgc ggcgatatat tgtaaagagg ctcctcagct caacagaagt gttcttgtgc   9660
cgcaggggtg ttgtgtcttc cacctcagtg cagaccattt gtgcactaga gggatgtaaa   9720
cctctgttca acttcttaca aattggttca gtcattgggc ccgtgtgagt ttaaacatgg   9780
aaaatatgga aaacgacgag aacatcgtgg tgggccccaa gcccttctac cccatcgagg   9840
aaggcagcgc cggcacccag ctgcggaagt acatggaaag atacgccaag ctgggcgcca   9900
ttgccttcac caacgccgtg accggcgtgg actacagcta cgccgagtac ctggaaaaga   9960
gctgctgcct gggcaaggct ctgcagaact acggcctggt ggtggacggc cggatcgccc  10020
tgtgcagcga gaactgcgag gaattcttca tccccgtgat cgccggcctg ttcatcggcg  10080
tgggcgtggc tcccaccaac gagatctaca ccctgcggga gctggtgcac agcctgggca  10140
tcagcaagcc caccatcgtg ttcagcagca agaagggcct ggacaaagtc atcaccgtgc  10200
agaaaaccgt gaccaccatc aagaccatcg tgatcctgga cagcaaggtg gactaccggg  10260
gctaccagtg cctggacacc ttcatcaagc ggaacacccc ccctggcttc caggccagca  10320
gcttcaagac cgtggaggtg gaccggaaag aacaggtggc cctgatcatg aacagcagcg  10380
gcagcaccgg cctgcccaag ggcgtgcagc tgacccacga gaacaccgtg acccggttca  10440
gccacgccag ggaccccatc tacggcaacc aggtgtcccc cggcaccgcc gtgctgaccg  10500
tggtgccctt ccaccacggc ttcggcatgt tcaccaccct gggctacctg atctgcggct  10560
tccgggtggt gatgctgacc aagttcgacg aggaaacctt cctgaaaacc ctgcaggact  10620
acaagtgcac ctacgtgatt ctggtgccca ccctgttcgc catcctgaac aagagcgagc  10680
tgctgaacaa gtacgacctg agcaacctgg tggagatcgc cagcggcgga gcccccctga  10740
gcaaagaagt gggagaggcc gtcgccaggc ggttcaatct gcccggcgtg cggcagggct  10800
acggcctgac cgagacaacc agcgccatca tcatcacccc cgagggcgac gacaagcctg  10860
```

-continued gagccagcgg caaggtggtg cccctgttca aggccaaagt gatcgacctg gacaccaaga 10920
agagcctggg ccccaacaga cggggcgaag tgtgcgtgaa gggccccatg ctgatgaagg 10980
gctacgtgaa caaccccgag gccaccaaag agctgatcga cgaagagggc tggctgcaca 11040
ccggcgacat cggctactac gacgaagaga agcacttctt catcgtggac cggctgaaga 11100
gcctgatcaa gtacaagggc tatcaggtgc cccctgccga gctggaaagc gtcctgctgc 11160
agcaccccag catcttcgac gccggcgtgg ccggggtgcc agatcctgtg gccggcgagc 11220
tgcctggcgc cgtggtggtg ctggaatccg gcaagaacat gaccgagaaa gaagtgatgg 11280
actacgtcgc cagccaggtg tccaacgcca agcggctgag aggcggcgtg agattcgtgg 11340
acgaagtgcc aaagggcctg accggcaaga tcgacggcag ggccatccgg gagatcctga 11400
agaaacccgt ggccaagatg tgaggcgcgc cggagccata gattcatttt gtggtgacgg 11460
gattttaggt gagtatctag attactttat tctgtccgtc ccactcttgc tgttgcttac 11520
caggtatgta gcatctgggt tagtgtatgt tttgactgcc ttgttctatt cctttgtatt 11580
agcagcttat atttggtttg ttatagttgg aagagccttt tctactgctt atgcttttgt 11640
gcttttggct gcttttctgt tattagtaat gaggatgatt gtaggtatga tgcctcgtct 11700
tcggtccatt ttcaaccatc gccaactggt ggtagctgat tttgtggaca cacctagtgg 11760
acctgttccc atcccccgcc caaccactca gatagtggtt cgcggcaacg ggtacaccgc 11820
agttggtaac aagcttgtcg atggcgtcaa gacgatcacg tccgcaggcc gcctcttttc 11880
gaaacgggcg gcggcgacag cctacaagct acaatgacct actgcgtatg tttggtcaga 11940
tgcgggtccg caaaccgccc gcgcaaccca ctcaggctat cattgcagag cctggagacc 12000
ttaggcatga tttaaatcaa caggagcgcg ccaccctttc gtcgaacgta caacggttct 12060
tcatgattgg gcatggttca ctcactgcag atgccggagg actcacgtac accgtcagtt 12120
gggttcctac caaacaaatc cagcgcaaag ttgcgcctcc agcagggccg taagacgtgg 12180
atattctcct gtgtggcgtc atgttgaagt agttattagc cacccaggaa ccaaaaaaaa 12240
aaaaaaaaaa aaaaaaaaaa aaaaaaaaaa aaaaaaaaaa aaaaaaaaaa aaaaaaaaaa 12300
aaaaaaaaaa aaaaaaaaaa aaaaaaaaaa aaaaaaaaaa aaaaaaaaaa aaaaaaaa 12358

<210> SEQ ID NO 49
<211> LENGTH: 435
<212> TYPE: DNA
<213> ORGANISM: Artificial Sequence
<220> FEATURE:
<223> OTHER INFORMATION: g-block for construction of pBR322+VBS-R-TRS7-rFF

<400> SEQUENCE: 49
ttcttacaaa ttggttcagt cattgggccc gtgtgagttt aaactggacc tgttcccatc 60
ccccgctcaa ctactcagat agtggttcgc ggcaacgggt acaccgcagt tggtaacaag 120
cttgtcgatg gaaaatatgg aaaacgacga gaacatcgtg gtgggcccca agcccttcta 180
ccccatcgag gaaggcagcg ccggcaccca gctgcggaag tacatggaaa gatacgccaa 240
gctgggcgcc attgccttca ccaacgccgt gaccggcgtg gactacagct acgccgagta 300
cctggaaaag agctgctgcc tgggcaaggc tctgcagaac tacggcctgg tggtggacgg 360
ccggatcgcc ctgtgcagcg agaactgcga ggaattcttc atccccgtga tcgccggcct 420
gttcatcggc gtggg 435

<210> SEQ ID NO 50

-continued

<211> LENGTH: 12441
<212> TYPE: DNA
<213> ORGANISM: Artificial Sequence
<220> FEATURE:
<223> OTHER INFORMATION: VBS-R-TRS7-rFF
<220> FEATURE:
<221> NAME/KEY: misc_feature
<222> LOCATION: (1)..(17)
<223> OTHER INFORMATION: T7 promoter
<220> FEATURE:
<221> NAME/KEY: misc_feature
<222> LOCATION: (12316)..(12441)
<223> OTHER INFORMATION: Poly A

<400> SEQUENCE: 50
taatacgact cactatagct cgaagtgtgt atggtgccat atacggctca ccaccatata 60
cactgcaaga attactattc ttgtgggccc ctctcggtaa atcctagagg gctttcctct 120
cgttattgcg agattcgtcg ttagataacg gcaagttccc tttcttacta tcctattttc 180
atcttgtggc ttgacgggtc actgccatcg tcgtcgatct ctatcaacta cccttgcgac 240
tatggcaacc ttctccgcta ctggatttgg agggagtttt gttagggact ggtccctgga 300
cttacccgac gcttgtgagc atggcgcggg attgtgctgt gaagtggacg gctccacctt 360
atgcgccgag tgttttcgcg gttgcgaagg agtggagcaa tgtcctggct tgttcatggg 420
actgttaaaa ctggcttcgc cagttccagt gggacataag ttcctgattg gttggtatcg 480
agctgccaaa gtcaccgggc gttacaattt ccttgagctg ttgcaacacc ctgctttcgc 540
ccagctgcgt gtggttgatg ctaggttagc cattgaagag gcaagtgtgt ttatttccac 600
tgaccacgcg tctgctaagc gtttccctgg cgctagattt gcgctgacac cggtgtatgc 660
tagcgcttgg gttgcgagcc cggctgctaa cagtttgata gtgaccattg accaggaaca 720
agatgggttc tgctggttaa aacttttgcc acctgaccgc cgtgaggctg gtttgcggtt 780
gtattacaac cattaccgcg aacaaaggac cgggtggctg tctaaaacag gacttcgctt 840
atggcttgga gacctgggtt tgggcatcaa tgcgagctct ggagggctga aattccacat 900
tatgaggggt tcgcctcagc gagcttggca tatcacaaca cgcagctgca agctgaagag 960
ctactacgtt tgtgacatct ctgaagcaga ctggtcctgt ttgcctgctg gcaactacgg 1020
cggctacaat ccaccagggg acggagcttg cggttacagg tgcttggcct tcatgaatgg 1080
cgccactgtt gtgtcggctg gttgcagttc tgacttgtgg tgtgatgatg agttggctta 1140
tcgagtcttt caattgtcac ccacgttcac ggttaccatc ccaggtgggc gagtttgtcc 1200
gaatgccaag tacgcaatga tttgtgacaa gcagcactgg cgcgtcaaac gtgcaaaggg 1260
cgtcggcctg tgtctcgatg aaagctgttt caggggcacc tgcaattgcc aacgcatgag 1320
tggaccacca cctgcacccg tgtcagccgc cgtgttagat cacatactgg aggcggcgac 1380
gtttgacaac gttcgcgtgg ttacacctga agggcagcca cgccccgtac cagcgccgcg 1440
agttcgtccc agcgccaact cttctggaga tgtcaaagat ccggcgcccg ttccgccagt 1500
accaaaacca aggaccaagc ttgccaaacc gaacccaact caggcgccca tcccagcacc 1560
gcgcacgcga cttcaagggg cctcaacaca ggagccactg gcgagtgcag gagttgcttc 1620
tgactcggca cctaaatggc gtgtggccaa aactgtgtac agctccgcgg agcgctttcg 1680
gaccgaactg gtacaacgtg ctcggtccgt tggggacgtt cttgttcaag cgctaccgct 1740
caaaacccca gcagtgcagc ggtataccat gactctgaag atgatgcgtt cacgcttcag 1800
ttggcactgc gacgtgtggt acccctttggc tgtaatcgct tgtttgctcc ctatatggcc 1860
atctcttgct ttgctcctta gctttgccat tgggttgata cccagtgtgg gcaatagtgt 1920

-continued

```
tgttctgaca gcgcttctgg tttcatcagc taattatgtt gcgtcaatgg accatcaatg   1980
tgaaggtgcg gcttgcttag ccttgctgga agaagaacac tattatagag cggtccgttg   2040
gcgcccgatt acaggcgcgc tgtcgcttgt gctcaattta ctggggcagg taggctatgt   2100
agctcgttcc acctttgatg cagcttatgt tccttgcact gtgttcgatc tttgcagctt   2160
tgctattctg tacctctgcc gcaatcgttg ctggagatgc ttcggacgct gtgtgcgagt   2220
tgggcctgcc acgcatgttt tgggttccac cgggcaacga gtttccaaac tggcgctcat   2280
tgatttgtgt gaccactttt caaagcccac catcgatgtt gtgggcatgg caactggttg   2340
gagcggatgt tacacaggaa ccgccgcaat ggagcgtcag tgtgcctcta cggtggaccc   2400
tcactcgttc gaccagaaga aggcaggagc gattgtttac ctcacccccc ctgtcaacag   2460
cgggtcagcg ctgcagtgcc tcaatgtcat gtggaagcga ccaattgggt ccactgtcct   2520
tggggaacaa acaggagctg ttgtgacggc ggtcaagagt atctctttct cacctccctg   2580
ctgcgtctct accactttgc ccacgcgacc cggtgtgacc gttgtcgacc atgctcttta   2640
caaccggttg actgcttcag gggtcgatcc cgctttattg cgtgttgggc aaggtgattt   2700
tctaaaactt aatccggggt tccggctgat aggtggatgg atttatggga tatgctattt   2760
tgtgttggtg gttgtgtcaa cttttacctg cttacctatc aaatgtggca ttggcacccg   2820
cgaccctttc tgccgcagag tgttttctgt acccgtcacc aagacccaag agcactgcca   2880
tgctggaatg tgtgctagcg ctgaaggcat ctctctggac tctctggggt taactcagtt   2940
acaaagttac tggatcgctg ccgtcactag cggattagtg atcttgttgg tctgccaccg   3000
cctggccatc agcgccttgg acttgttgac tctagcttcc cctttagtgt tgcttgtgtt   3060
cccttgggca tctgtggggc ttttacttgc ttgcagtctc gctggtgctg ctgtgaaaat   3120
acagttgttg gcgacgcttt ttgtgaatct gttctttccc caagctaccc ttgtcactat   3180
gggatactgg gcgtgcgtgg cggctttggc cgtttacagt ttgatgggct tgcgagtgaa   3240
agtgaatgtg cccatgtgtg tgacacctgc ccattttctg ctgctggcga ggtcagctgg   3300
acagtcaaga gagcagatgc tccgggtcag cgctgctgcc cccaccaatt cactgcttgg   3360
agtggctcgt gattgttatg tcacaggcac aactcggctg tacataccca aggagggcgg   3420
gatggtgttt gaagggctat tcaggtcacc gaaggcgcgc ggcaacgtcg gcttcgtggc   3480
tggtagcagc tacggcacag ggtcagtgtg gaccaggaac aacgaggtcg tcgtactgac   3540
agcgtcacac gtggttggcc gcgctaacat ggccactctg aagatcggtg acgcaatgct   3600
gactctgact ttcaaaaaga atggcgactt cgccgaggca gtgacgacac agtccgagct   3660
cccaggcaat tggccacagt tgcatttcgc ccaaccaaca accgggcccg cttcatggtg   3720
caccgccaca ggagatgaag aaggcttgct cagtggcgag gtttgtctgg cgtggactac   3780
tagtggcgac tctggatcag cagtggttca gggtgacgct gtggtagggg tccacaccgg   3840
ttcgaacaca agtggtgttg cctacgtgac caccccaagc ggaaaactcc ttggcgccga   3900
caccgtgact ttgtcatcac tgtcaaagca tttcacaggc cctttgacat caatcccgaa   3960
ggacatccct gacaacatca ttgccgatgt tgatgctgtt cctcgttctc tggccatgct   4020
gattgatggc ttatccaata gagagagcag cctttctgga cctcagttgt tgttaattgc   4080
ttgttttatg tggtcttatc ttaaccaacc tgcttacttg ccttatgtgc tgggcttctt   4140
tgccgctaac ttcttcctgc caaaaagtgt tggccgccct gtggtcactg ggcttctatg   4200
gttgtgctgc ctcttcacac cgctttccat gcgcttgtgc ttgttccatc tggtctgtgc   4260
```

-continued

```
taccgtcacg ggaaacgtga tatctttgtg gttctacatc actgccgctg gcacgtctta   4320
cctttctgag atgtggttcg gaggctatcc caccatgttg tttgtgccac ggttcctagt   4380
gtaccagttc cccggctggg ctattggcac agtactagcg gtatgcagca tcaccatgct   4440
ggctgctgcc ctcggtcaca ccctgttact ggatgtgttc tccgcctcag gtcgctttga   4500
caggactttc atgatgaaat acttcctgga gggaggagtg aaagagagtg tcaccgcctc   4560
agtcacccgc gcttatggca aaccaattac ccaggagagt ctcactgcaa cattagctgc   4620
cctcactgat gatgacttcc aattcctctc tgatgtgctt gactgtcggg ccgtccgatc   4680
ggcaatgaat ctgcgtgccg ctctcacaag ttttcaagtg gcgcagtatc gtaacatcct   4740
taatgcatcc ttgcaagtcg atcgtgacgc tgctcgttct agaagactaa tggcaaaact   4800
ggctgatttt gcggttgaac aagaagtaac agctggagac cgtgttgtgg ttatcgacgg   4860
tctggaccgc atggctcact tcaaagacga tttggtgctg gttcctttga ccaccaaagt   4920
agtaggcggt tctaggtgca ccatttgtga cgtcgttaag gaagaagcca atgacacccc   4980
agttaagcca atgcccagca ggagacgccg caagggcctg cctaaaggtg ctcagttgga   5040
gtgggaccgt caccaggaag agaagaggaa cgccggtgat gatgattttg cggtctcgaa   5100
tgattatgtc aagagagtgc caaagtactg ggaccccagc gacacccgag gcacgacagt   5160
gaaaatcgcc ggcactacct atcagaaagt ggttgactat tcaggcaatg tgcattacgt   5220
ggagcatcag gaagatctgc tagactacgt gctgggcaag gggagctatg aaggcctaga   5280
tcaggacaaa gtgttggacc tcacaaacat gcttaaagtg gaccccacgg agctctcctc   5340
caaagacaaa gccaaggcgc gtcagcttgc tcatctgctg ttggatctgg ctaacccagt   5400
tgaggcagtg aatcagttaa actgagagcg ccccacatct ttcccggcga tgtggggcgt   5460
cggacctttg ctgactctaa agacaagggt ttcgtggctc tacacagtcg cacaatgttt   5520
ttagctgccc gggacttttt atttaacatc aaatttgtgt gcgacgaaga gttcacaaag   5580
accccaaaag acacactgct tgggtacgta cgcgcctgcc ctggttactg gtttattttc   5640
cgtcgtacgc accggtcgct gattgatgca tactgggaca gtatggagtg cgtttacgcg   5700
cttcccacca tatctgattt tgatgtgagc ccaggtgacg tcgcagtgac gggcgagcga   5760
tgggattttg aatctcccgg aggaggccgt gcaaaacgtc tcacagctga tctggtgcac   5820
gcttttcaag ggttccacgg agcctcttat tcctatgatg acaaggtggc agctgctgtc   5880
agtggtgacc cgtatcggtc ggacggcgtc ttgtataaca cccgttgggg caacattcca   5940
tattctgtcc caaccaatgc tttggaagcc acagcttgct accgtgctgg atgtgaggcc   6000
gttaccgacg ggaccaacgt catcgcaaca attgggccct tcccggagca acaaccccata   6060
ccggacatcc caaagagcgt gcttgacaac tgcgctgaca tcagctgtga cgctttcata   6120
gcgcccgctg cagagacagc cctgtgtgga gatttagaga aatacaacct atccacgcag   6180
ggttttgtgt tgcctagtgt tttctccatg gtgcgggcgt acttaaaaga ggagattgga   6240
gacgctccac cactctactt gccatctact gtaccatcta aaaattcaca agccggaatt   6300
aacggcgctg agtttcctac aaagtcttta cagagctact gtttgattga tgacatggtg   6360
tcacagtcca tgaaaagcaa tctacaaacc gccaccatgg cgacttgtaa acggcaatac   6420
tgttccaaat acaagattag gagcattctg ggcaccaaca attacattgg cctaggtttg   6480
cgtgcctgcc tttcgggggt tacggccgca ttccaaaaag ctggaaagga tgggtcaccg   6540
atttatttgg gcaagtcaaa attcgacccg ataccagctc ctgacaagta ctgccttgaa   6600
acagacctgg agagttgtga tcgctccacc ccggctttgg tgcgttggtt cgctactaat   6660
```

cttatttttg agctagctgg ccagcccgag ttggtgcaca gctacgtgtt gaattgctgt 6720
cacgatctag ttgtggcggg tagtgtagca ttcaccaaac gcgggggttt gtcatctgga 6780
gaccctatca cttccatttc caataccatc tattcattgg tgctgtacac ccagcacatg 6840
ttgctatgtg gacttgaagg ctatttccca gagattgcag aaaaatatct tgatggcagc 6900
ctggagctgc gggacatgtt caagtacgtt cgagtgtaca tctactcgga cgatgtggtt 6960
ctaaccacac ccaaccagca ttacgcggcc agctttgacc gctgggtccc ccacctgcag 7020
gcgctgctag gtttcaaggt tgacccaaag aaaactgtga acaccagctc cccttccttt 7080
ttgggctgcc ggttcaagca agtggacggc aagtgttatc tagccagtct tcaggaccgc 7140
gttacacgct ctctgttata ccacattggt gcaaagaatc cctcagagta ctatgaagct 7200
gctgtttcca tctttaagga ctccattatc tgctgtgatg aagactggtg gacggacctc 7260
catcgacgta tcagtggcgc tgcgcgtacc gacggagttg agttccccac cattgaaatg 7320
ttaacatcct tccgcaccaa gcagtatgag agtgccgtgt gcacagtttg tggggccgcc 7380
cccgtggcca agtctgcttg tggagggtgg ttctgtggca attgtgtccc gtaccacgcg 7440
ggtcattgtc acacaacctc gctcttcgcc aactgcgggc acgacatcat gtaccgctcc 7500
acttactgca caatgtgtga gggttcccca aaacagatgg taccaaaagt gcctcacccg 7560
atcctggatc atttgctgtg ccacattgat tacggcagta aagaggaact aactctggta 7620
gtggcggatg gtcgaacaac atcaccgccc gggcgctaca aagtgggtca caaggtagtc 7680
gccgtggttg cagatgtggg aggcaacatt gtgtttgggt gcggtcctgg atcacacatc 7740
gcagtaccac ttcaggatac gctcaagggc gtggtggtga ataaagctct gaagaacgcc 7800
gccgcctctg agtacgtgga aggaccccct gggagtggga agacttttca cctggtcaaa 7860
gatgtgctag ccgtggtcgg tagcgcgacc ttggttgtgc ccacccacgc gtccatgctg 7920
gactgcatca acaagctcaa acaagcgggc gccgatccat actttgtggt gcccaagtat 7980
acagttcttg actttccccg gcctggcagt ggaaacatca cagtgcgact gccacaggtc 8040
ggaaccagtg agggagaaac ctttgtggat gaggtggcct acttctcacc agtggatctg 8100
gcgcgcattt taacccaggg tcgagtcaag ggttacggtg atttaaatca gctcgggtgc 8160
gtcggacccg cgagcgtgcc acgtaacctt tggctccgac attttgtctg cctggagccc 8220
ttgcgagtgt gccatcgatt cggcgctgct gtgtgtgatt tgatcaaggg catttatcct 8280
tattatgagc cagctccaca taccactaaa gtggtgtttg tgccaaatcc agactttgag 8340
aaaggtgtag tcatcaccgc ctaccacaaa gatcgcggtc ttggtcaccg cacaattgat 8400
tcaattcaag gctgtacatt ccctgttgtg actcttcgac tgcccacacc ccaatcactg 8460
acgcgcccgc gcgcagttgt ggcggttact agggcgtctc aggaattata catctacgac 8520
ccctttgatc agcttagcgg gttgttgaag ttcaccaagg aagcagaggc gcaggacttg 8580
atccatggcc cacctacagc atgccacctg ggccaagaaa ttgacctttg gtccaatgag 8640
ggcctcgaat attacaagga agtcaacctg ctgtacacac acgtccccat caaggatggt 8700
gtaatacaca gttaccctaa ttgtggccct gcctgtggct gggaaaagca atccaacaaa 8760
atttcgtgcc tcccgagagt ggcacaaaat ttgggctacc actattcccc agacttacca 8820
ggattttgcc ccataccaaa agaactcgct gagcattggc ccgtagtgtc caatgataga 8880
tacccgaatt gcttgcaaat taccttacag caagtatgtg aactcagtaa accgtgctca 8940
gcgggctata tggttggcca aagcgtcttc gtccagacgc ctggtgtgac atcttactgg 9000

```
cttactgaat gggtcgacgg caaagcgcgt gctctaccag attccttatt ctcgtccggt   9060
aggttcgaga ctaacagccg cgctttcctc gatgaagccg aggaaaagtt tgccgccgct   9120
caccctcatg cctgtttggg agaaattaat aagtccaccg tgggaggatc ccacttcatc   9180
ttttcccaat atttaccacc attgctaccc gcagacgctg ttgccctggt aggtgcttca   9240
ttggctggga aagctgctaa agctgcttgc agcgtcgttg acgtctatgc tccatcattt   9300
gaaccttatc tgcaccctga gacactgagt cgcgtgtaca agattatgat cgatttcaag   9360
ccgtgtaggc ttatggtgtg gagaaacgcg accttttatg tccaagaggg tgttgatgca   9420
gttacatcag cactagcagc tgtgtccaaa ctcatcaaag tgccggccaa tgagcctgtt   9480
tcattccatg tggcatcagg gtacagaacc aacgcgctgg tagcgcccca ggctaaaatt   9540
tcgattggag cctacgccgc cgagtgggca ctgtcaactg aaccgccacc ggctggttat   9600
gcgatcgtgc ggcgatatat tgtaaagagg ctcctcagct caacagaagt gttcttgtgc   9660
cgcaggggtg ttgtgtcttc cacctcagtg cagaccattt gtgcactaga gggatgtaaa   9720
cctctgttca acttcttaca aattggttca gtcattgggc ccgtgtgagt ttaaactgga   9780
cctgttccca tcccccgctc aactactcag atagtggttc gcggcaacgg gtacaccgca   9840
gttggtaaca agcttgtcga tggaaaatat ggaaaacgac gagaacatcg tggtgggccc   9900
caagcccttc taccccatcg aggaaggcag cgccggcacc cagctgcgga agtacatgga   9960
aagatacgcc aagctgggcg ccattgcctt caccaacgcc gtgaccggcg tggactacag  10020
ctacgccgag tacctggaaa agagctgctg cctgggcaag gctctgcaga actacggcct  10080
ggtggtggac ggccggatcg ccctgtgcag cgagaactgc gaggaattct tcatccccgt  10140
gatcgccggc ctgttcatcg gcgtgggcgt ggctcccacc aacgagatct acaccctgcg  10200
ggagctggtg cacagcctgg gcatcagcaa gcccaccatc gtgttcagca gcaagaaggg  10260
cctggacaaa gtcatcaccg tgcagaaaac cgtgaccacc atcaagacca tcgtgatcct  10320
ggacagcaag gtggactacc ggggctacca gtgcctggac accttcatca agcggaacac  10380
ccccccctggc ttccaggcca gcagcttcaa gaccgtggag gtggaccgga aagaacaggt  10440
ggccctgatc atgaacagca gcggcagcac cggcctgccc aagggcgtgc agctgaccca  10500
cgagaacacc gtgacccggt tcagccacgc cagggacccc atctacggca accaggtgtc  10560
ccccggcacc gccgtgctga ccgtggtgcc cttccaccac ggcttcggca tgttcaccac  10620
cctgggctac ctgatctgcg gcttccgggt ggtgatgctg accaagttcg acgaggaaac  10680
cttcctgaaa accctgcagg actacaagtg cacctacgtg attctggtgc ccaccctgtt  10740
cgccatcctg aacaagagcg agctgctgaa caagtacgac ctgagcaacc tggtggagat  10800
cgccagcggc ggagcccccc tgagcaaaga agtgggagag gccgtcgcca ggcggttcaa  10860
tctgcccggc gtgcggcagg gctacggcct gaccgagaca accagcgcca tcatcatcac  10920
ccccgagggc gacgacaagc ctggagccag cggcaaggtg gtgcccctgt tcaaggccaa  10980
agtgatcgac ctggacacca agaagagcct gggccccaac agacggggcg aagtgtgcgt  11040
gaagggcccc atgctgatga agggctacgt gaacaacccc gaggccacca aagagctgat  11100
cgacgaagag ggctggctgc acaccggcga catcggctac tacgacgaag agaagcactt  11160
cttcatcgtg gaccggctga agagcctgat caagtacaag ggctatcagg tgccccctgc  11220
cgagctggaa agcgtcctgc tgcagcaccc cagcatcttc gacgccggcg tggccggggt  11280
gccagatcct gtggccggcg agctgcctgg cgccgtggtg gtgctggaat ccggcaagaa  11340
catgaccgag aaagaagtga tggactacgt cgccagccag gtgtccaacg ccaagcggct  11400
```

gagaggcggc gtgagattcg tggacgaagt gccaaagggc ctgaccggca agatcgacgg 11460
cagggccatc cgggagatcc tgaagaaacc cgtggccaag atgtgaggcg cgccggagcc 11520
atagattcat tttgtggtga cgggatttta ggtgagtatc tagattactt tattctgtcc 11580
gtcccactct tgctgttgct taccaggtat gtagcatctg ggttagtgta tgttttgact 11640
gccttgttct attcctttgt attagcagct tatatttggt ttgttatagt tggaagagcc 11700
ttttctactg cttatgcttt tgtgcttttg gctgcttttc tgttattagt aatgaggatg 11760
attgtaggta tgatgcctcg tcttcggtcc attttcaacc atcgccaact ggtggtagct 11820
gattttgtgg acacacctag tggacctgtt cccatccccc gcccaaccac tcagatagtg 11880
gttcgcggca acgggtacac cgcagttggt aacaagcttg tcgatggcgt caagacgatc 11940
acgtccgcag gccgcctctt ttcgaaacgg gcggcggcga cagcctacaa gctacaatga 12000
cctactgcgt atgtttggtc agatgcgggt ccgcaaaccg cccgcgcaac ccactcaggc 12060
tatcattgca gagcctggag accttaggca tgatttaaat caacaggagc gcgccaccct 12120
ttcgtcgaac gtacaacggt tcttcatgat tgggcatggt tcactcactg cagatgccgg 12180
aggactcacg tacaccgtca gttgggttcc taccaaacaa atccagcgca aagttgcgcc 12240
tccagcaggg ccgtaagacg tggatattct cctgtgtggc gtcatgttga agtagttatt 12300
agccacccag gaaccaaaaa aaaaaaaaaa aaaaaaaaaa aaaaaaaaaa aaaaaaaaaa 12360
aaaaaaaaaa aaaaaaaaaa aaaaaaaaaa aaaaaaaaaa aaaaaaaaaa aaaaaaaaaa 12420
aaaaaaaaaa aaaaaaaaaa a 12441

<210> SEQ ID NO 51
<211> LENGTH: 13740
<212> TYPE: DNA
<213> ORGANISM: Artificial Sequence
<220> FEATURE:
<223> OTHER INFORMATION: SHFV-R-TRS7-rFF
<220> FEATURE:
<221> NAME/KEY: misc_feature
<222> LOCATION: (1)..(39)
<223> OTHER INFORMATION: overlap regions to pW70
<220> FEATURE:
<221> NAME/KEY: misc_feature
<222> LOCATION: (17)..(34)
<223> OTHER INFORMATION: T7 promoter
<220> FEATURE:
<221> NAME/KEY: misc_feature
<222> LOCATION: (13581)..(13706)
<223> OTHER INFORMATION: Poly A

<400> SEQUENCE: 51
ttgaccatgt tggtatgtaa tacgactcac tatagattaa aataaaagtg tgaagctccc 60
tgtgctttca tgccaggaca gcaatccaat accctagccc ggattggata agcttagtcc 120
aggagttgtg aggtctacag acacctcgca gcaacctaca cctctctatc cccgagagca 180
gcgtaggctc cttttatttt gatttgccac tggtggcttg ggatttgcag accctcctta 240
accatgttct gtgagtgccc tcgttcaaac cttgtggtaa tgtgctctgg cgccttctgt 300
tgcgtgctct gcggccaccg ccgtcggcca cgacccgctt cagaatccga ccgtgctaag 360
tatggaccca tcgtgcaata cgtggaagcc cgcgttgcac atgtgtattc tggattggaa 420
gggcgctatt gcgctcttga gatgataccc attacttacg gtaacaagtt cccttactgt 480
aagccactgc cggtttcctt cgtgatcaaa accttagccg gagtccaagg agacctgacc 540
cgtctggaag aaacaccgct cccgggtgga tacggcgtaa tcccctgctg gggaccgcat 600

-continued

```
cttgcagctg tggggtatct atctcccgct catgtgggcc gcgattggtt tgagggtgct    660
actcatgcta ttgtgcacat tggctcatat ggcggacatg aacgtcccac caccattcca    720
ttcaacacga ctggaggtga cgtttatcag ttaggaacct gcactatcgt tgagaccata    780
gatcatgtcg agtggcatgc aggtgttaag cctggaaccg ctatctgtcc tcttgatcga    840
atcgactttg cgcagaaagt gataacggcg tttcccgagg gcttcttggc taacaaggcc    900
tggctcggag ataagcgcgg cactctgaag gtcgaagcag acccggagac tgctgcactc    960
tcctttgagc atggccgctg ctggctgaag ttgttcccgg atcccgcctg tgaactcacc   1020
actgcaagca ctttcggtta tcaattgaac tgtggcgttc aaggaaaata cattgcacgt   1080
cgcttacaga ccaatggatt gaaactggtg cagaaccagg aaggcaagtt catcgcctac   1140
accttccacc gaggatcttg gctcgggcac atcggtcatg ccgatgagtc tgtaccgccc   1200
gattgccaga tcattgcacg ttttgacgtg ctcccctaca acgagtggtc tccactcccc   1260
ctccttaagt tgccagggaa gacttatttc ggtggaaatg ccagttcggt tagctggcct   1320
gaatggaagt acgatgagca gcttctgtat gccgactccc tcactgctgg gttctgttgg   1380
ttgcagctat ttccccctct ctcccgcaag tctgaggccc agcgcgctat cctcgcgcaa   1440
caggtcaaca actacggagt gaccgggact tatctcgaat acagacttag acagtatggc   1500
attgtccttg cagaatgcga ctacggtgag cattacatct atgctgccgc tagtgattct   1560
tccatcagac acatttctcc cgtccctata cacgaccgac atcacgtgtt tgtaacgcgt   1620
ctcacggccc gattcggcgc ctttgacgag ggttcgatt taggattcgg aacgcgttac   1680
ggtcgccgtc gaggaggcgg caagaagtca ggccaatcga gtggtgtgag agcacccgga   1740
agaacgaccc ctgacttggc tggggactgg gggaaggccg ttgatgatca ggagaaaacg   1800
gcctccaaag tcactacaga caaggctatg tccaccagtg agcctgctgt tgtgcaagta   1860
ggatgtgaaa caaagcctgt cgctgatgca gctgcggtac ccgcctctgt caacagtacc   1920
ggatgtgcgc tattgcccgt gcaagccgac ccatgctgta ctgccggtgt ggctgccaaa   1980
gagagtgaac ctaaggctgt agctgcccct tccataccga tcacgtttgg agctcctgca   2040
ggagagaccc tgccagtggc tgcctcacct ctggtcgtga agaaggataa gagatgcatc   2100
agtgtaaaac ttactgcaaa aaaggctttg ccaaaggaga cattcatccc gcctccggac   2160
ggaggttgtg gagtccatgc gtttgctgcc atccagtatc acatcaatac tggacattgg   2220
ccagagcaaa agccggttgt gaactgggct tatgaagcat ggacaacaaa tgaggatatt   2280
gggcacatga tttgctccac cgagacacct gccgctcttg agccttgcct gcacgcccgc   2340
tacgttgtgc gccttgactc tgaccattgg gtggttgatc actatccaaa tcgcccgatg   2400
tgttttgtcg aggcctgcgc gcatggctgg tgctctagct tgctcagcga gccaactggt   2460
gaagaaggtg agcatctcgt tgattgctca gctctttatg actgtcttgg caagtttcgg   2520
aatggcactg agtttgccga tacggtgctg ggtttatcca agaccgcgca ctgctgcaac   2580
aagcgcgtcc ccacaccgcg caagcaggcc atcatgtcac tcctgaacag accaaactgt   2640
gtgccttgca ttgccccacc atcgcaggtc cgtaccgttg atccatcaca gcccgcggca   2700
cctcttccac cagtgccacg tccacggaaa cgcaaggctg cagcccaaca agtctcaaaa   2760
gtgccgagtg agcaggatcc ctctttggct cacgatccgc cagagaagcc tgactccgtt   2820
cggccgccaa agttaggcta tttagatagg gcctggaata acatgttagc taggactcac   2880
aagctccata acctgcagca gcgggttttt ggcttgtacc cccagctcct ttccatgctg   2940
ctcccatctg gtgctcgccc ttctacccct cgcctgctgg gctgctactt ctctatggct   3000
```

gtcgctatgt tctttctatt tttgggttca cccctcttca tcctatgtgc agtacttgct 3060
ggagttatcg ccccaagcgc caggtacccc aaaattttat gctgttgcct ggtcgttgtc 3120
tacatatgta ctctgtttgc tgatgcgata tcctctgtct gcgacaatga tgacgctgac 3180
tgtcgtgctt tcctcagtga tttgggtgat aggtactcca ctaatcagcc tgtttatatc 3240
acgcccggac ccgcaacatt cttccttgct gtatctcgca attttttgt tgtctcggtg 3300
gccctgtttc ctttacacct gcttctcctt atggttgatg ttttacttgt cattggtgta 3360
ctgtgcatgg atggctattg tttcaggtgc ttctccagat gtgttaggaa ggctccagag 3420
gaggtatccc tccttacgat accccagtct cgtgtgtcgc gccgctttct actggatata 3480
tgtgatttct actccgctcc acccgttgat atcattcgcc tggcgactgg actcaacggt 3540
tgttttcgag gagactactc ccctattgga tcaagtacca gtgtgatcac tgctgacaag 3600
atcgacgtca agaaagtctc ttgtcgcacg gtttgctcct ttccttcctg cccaagtgag 3660
gctgtcaagg tcctgcacgt cttgtctgtt cgcggtcaga tgtgtgccca caacgagcaa 3720
aaggttgaga aggtcgacgc actcccgtgc aagaacccct tgtttccata cgatctctcc 3780
tcaaagaaaa ttgttccagt agactcaggt acctatgaga ttttgagcag catcggctgc 3840
gacatgtctc accttgtcat cggcgatgga gacttcttca aagttatggg cgtccccaga 3900
ccatcccctt tcactgtaat gcggttgagg gcctgtcggg tcgtcggtgg tggtaggatc 3960
ttcagaactg ctcttgctgc agcttgggtt ctcttctttg tatgtgctgg ctattgggtc 4020
cagatgagca ctccctgcgg gatcgggacc aatgacccct tctgcaagtc ctctttcggc 4080
gttcctactt atgtcaatca gggtgtctgc catggacaat attgtgcatc ctcaaaaggc 4140
gtctcacgcg ccacatccat actcactgtt agaaatcccg ccgttgctcc atacattgtt 4200
cttgcagcat gtctcgtgta tcttgcttct gtctatgtac caggtattat tgaggtgtct 4260
ctgttggtcc taaatgcact gttacctgct ggcccggcaa tttccgctct gcggaccctt 4320
gtcatgatca ttgccgcgcc ccacctttcc atgaagtata ttgctttctt ctgctgcacc 4380
accgcctttg ttgactttac cagtgtcgtt gttgttctca cagcactcct ggtgggttgg 4440
atccttgcac gctacactgg cattggagga ttcgtcaccc cctacgacat tcatgacgtt 4500
gttaagagcc aacgtgatgg agttgctgtt gcgaatgccc cacccaacac ctaccttggg 4560
gccgttcggc gagccgcgct gactggaaag ccagcgttct tcgtggctaa caacactggt 4620
attgtgcttg agggactcct ccgggaaaag accagagcca gcaactctgt gtcagtttac 4680
ggcgttacct gtgggtctgg tggtttgttt tccgatggca acaatactgt ctgcttgacc 4740
gcgacgcacg tctgcggcaa caacaaagcc gtcgttgatt accaaggtac ccgctatgaa 4800
gcggtgttca ccaccaaagg agactatgct tcagctgttg tgccgatccc cggcgcattc 4860
cctccactga agtttgcccc acagtcttac actggccgtg cttattggta tgccaacacc 4920
ggagttgaga caggatttgt agggactaca ggttgcttgg tgttctcagg ccccggcgat 4980
tccggatcgc ccatcatcac ccctgatggc ctgattgtcg gagtccacac aggcagcgac 5040
tccaaaggaa gcggtgctta cacaaccccc aacgggctca ctgtgtctgg tcccctatca 5100
ctgaaggaaa tgggggcgca ctatgagggc cctattgttg atgtaccgac ccgcttgcct 5160
agaaatgtcc acaacgacac caagtctgtg cctcagccac tggcacgcct gttagagagt 5220
agcataaatc tggagggtgg tctgggtacc atccagctca tcattgttgc agtggtcttg 5280
tggaagtatg ctgttgaccc actctctatc ccatttgttg tcgctttctt tctgttgaat 5340
gagatccttc caaaatgcct aattcgttgt ttctacaact actcgctatt ttgcttggct 5400
gccttctcac ctcttgcatc tcgcatcttt tttattcgcc tactcactgc agccctcaac 5460
agaaacccca cagctctcat ctgccatgct tgctttgccg gcattgctgt gctgaatgac 5520
ttcatcattc ttggcgacat taggcttgct ctgcgtttca cttctttcta cgttgtgggt 5580
gtaaatcatg atgctattgc tattgcagtt attggagctc ttgtttgtgt tgccgcttgc 5640
tgtcttgaac ttttcgggtt gccacagatg gcctctgtga tcggttgtca tggttctttc 5700
gacccaacct tcctctctcg ctatgttcac gagggcatac gccagggagt aagctcagga 5760
ttcggaacag aatcactgtc caccgcttta gcgtgcgcct tgtctgagga cgaactcaac 5820
ttccttgctc aggctgttga tcacaaggct atcgtgtcgg caattcacgt gcacaagact 5880
cttcaggact acatcctttc caagaacgca aagattcttc gtgcttcact tgcgtctgtc 5940
cacgctaatc acaatgctag taaagccttg gcctcattgg acaaatttct gcaaggcacc 6000
agcacacaac tcaaaccagg cgaccccgtg atcctcttgg gtagcacctc tgctgagctc 6060
gtttccgtct ttagtggcga ttccgagtac atcgcagaac ccataaggtc ccacccagtt 6120
gccggtacca tctgtacact gtgtgttgtc caggccaagt gcgaaggagg tttggtgacc 6180
caagtcaatg gcaaattttc tcccgcaaaa taccttgcag ttgctgggaa agttctcgct 6240
gaccaccctg actacaaact ggaaaatgat ggtcgtttcc cccgcactcg ggaggataga 6300
gtgaaggact cagttcaggt tgacaccgtt gacataggtt cacacacttt caagaagatg 6360
tggaataaga ccaccgggga tgtctggtac gacatcatca tgccagaatc tgcggccaac 6420
cctttggccg tgcatgactt ggactctgcc gttgctgcca tcggcatgtc caaagaaatc 6480
cccgaaaagg acatgaatcg cttgcgcgct atcatctcta agctccaagg ccttgtttca 6540
tctgaagctt taaactgcta accgctgcgg gatgtaccag tgctgaccgt agcggactgg 6600
tgattacact ggattatgcc aagatcatca ctcatcatgc gcggactcgc gccttctcca 6660
gtatagattt taaagttgtc tcacctgacg aggcgatgag gactgctcgt ctttctccat 6720
ctcctcagcc aattattgct tccttctctg atgataagtt cttgctcctg cggcgtcacc 6780
cgccgtctct ccttgacgtt ctcacaaagg ggttggatgc cacttgccgc gagcccctcc 6840
actcacctgg ggatcaaggc atcgatggct atctttggga ttttgaagca cctcactcta 6900
aggaggcaat ttggcttagc aaccagatta tcagcgcctg tgcagcgcga cgaggagatg 6960
ctcccggctg ctacccctat aagctgcacc ccgtcagagg agatccatac agagttggaa 7020
atgttctcaa gaacacgaga tttggcgatg ttacctatac tgctgtttct gattcagatt 7080
ccccttggct aaaagttgca tcaattaata gtggaggttg ccctgtagtc acggacaggg 7140
tgttagggag tactattcca gttgggtctg aaatttatct ccccacattg cctgaatcag 7200
tgctagatta tttggattca cgccctgact gcccaaccta ctacacacag catggttgcg 7260
aggcggcggc tctacaagac cttaaaaagt ttaatctcag cacccaagga ttcattcttc 7320
cagaggtcct caacatcgta aggaactacc tccttggtac aattggatac agacctgcca 7380
tttacaaacc ctccacagtc ccttccaacg actctcacgc tggtatcaat ggcttgtctt 7440
tctctactaa aactcttcag gcactcccgg acatagatga gctctgcgag aaagctatcg 7500
cagaagtatg gcaaaccgtg accccagtca cgttgaaaaa gcaattctgc tccaaggcca 7560
aaactaggac catcttagga actaatgcca tggcctcctt agctcttaga gcattgctga 7620
gtggtgttac tcaaggcttt caattggctg gcaagaactc accgatttgc ttaggcaagt 7680
ccaaatttga cccctgcact ttcgaagtga aggggcgatg ccttgaaact gatttggcct 7740
cgtgtgacag atccacacct gccattgtga gacacttcgc cactaagctg ctctttgaga 7800
tggcttgtgc tgagcgcgct ttgccattgt atgttgtgaa ttgctgccat gacctgattg 7860
tcactcaaac gtccgccgcg accaagcgcg gtggtctctc ctcaggtgat ccagtgacat 7920
caattgccaa taccatctat tcattggttc tctatgtcca gcacatggtt ctgactctcc 7980
tagaaaatgg gcacccccctc agtctcaaat ttctgtctgg caagctcaac ttccaggacc 8040
tctacaaatt acaggctttt attgtttatt ctgatgacct gatcctcctt aatgagtcag 8100
atgatcttcc aaattttgaa agatgggtcc cccatctgga gcttgcatta ggtttcaaag 8160
ttgaccccaa gaagacagtc atcacctcca acccaggctt cttaggttgt gaatacaggc 8220
atggctggct agttccccaa aagcagcgag ttctcgccgc actagcctac cacgtaaatg 8280
ccaaagatgt ccacacctac tacattaatg ccacggcgat tctcaacgac gcctcggcac 8340
tctcagcctt cgagcctgac tggtttgatg acttggtcat agggcttgct gactgtgccc 8400
gcaaagacgg gtactctttc cctggacctg ccgctttcag ggaattcttc agtagggtct 8460
caggttacca gtttgagggt aaggaagttc aagtttgttc catctgctgc agtactgccc 8520
gtaccacatc cctgtgcggt atggctctct gtgatttctg tgctcataga cattaccatc 8580
ctgggtgcca tgtcttatct tctttctgca agcatgtaat tggctccaat acttgtaaaa 8640
tgtgctccat ccctatcctc aaagacagaa caaaatttgc tgagctcctc gcatctgatc 8700
aatataggtc tgtttgcacc gttgaggtga cagttgttga tggttacacc gatgctgccc 8760
cgggtcgata ctcataccag aagaagcagt atatgctccg taaagagcgt agaggctgcc 8820
cccttgactt gcctgacggt aagtacagta tgaagctgtt gcccaacagc tgctctggta 8880
tttgtgtccc caaggcccag gagaacgcca ctctgtctaa ctttgtggtg ggaccccctg 8940
gctctggcaa gactaccttt attagcaact tgttagacga cgatgcagtt gtctactgtc 9000
ctactcatgt ttctctcatt gcctactcca aatctttgcc tgctgctagg tttagcgtgc 9060
ctcgaggtca ggatcctgct gaatatggaa cacctgcatt gtctggacca acactccagc 9120
tcctttccgc cggctacgtc cccggcgcca agcattacct cgatgaggcc tgttacgcta 9180
accccttga tgtcttcaag cttctgtcta agactcccat cacagcaatt ggtgaccccg 9240
ctcagttgac tcctgtaggc tttgacacac ctctgtatgt atttgagctc atgaagaaga 9300
atgcgctgca tgcaatttac agatttggcc agaacatctg caacgcaatt cagccctgtt 9360
acagcactaa attggtttcc cagaggcaag gtgatactga ggtcatcttc cagaccaaat 9420
ttgctccacg aggcaaagta ctcaccccat atcacaggga cagagttggt gcagcggtca 9480
caattgactc ctctcaaggg tcgacctacg acgtggtcac tctgtacctg cctaccaaag 9540
gcagtctgac actggctcgt ggtttagtag gaatcactag agcccgagag aggttgtatg 9600
tttatgaccc gcatcatcag ctcgcaaagt actttaatct tcagccgtcc agcaccacaa 9660
ttcggcctca tgctgtagtc atcgatggca aggcgcgagt catgctgtct gacaagtgct 9720
acgctgcccc agaggacttc ccgggcatgc tctgcactgc gaggcccgct accgcggctg 9780
acaggaagat tttggaagag acttgcctca aattagattt tcttgaatct ggctcactgt 9840
cccctcttcc ccgtgtgtgc tataatctag ggttctatta ctcaccagac attaccaaat 9900
tgctccccat tccatctgaa ttggcaaaac actggcccgt cgcgactaac cggaataatc 9960
cagagtggcc caatcgtcta gtggtttcag ccacccggct gtcacctcta tcacatccgg 10020
ccgtgtgcgc aggttactac gtgggggact cactctttgt tggtactcca aacgtgacct 10080

-continued

```
cgtactggtt gacgaagttt ctagatggtc gggctgttcc tatggaagat tctgtttact  10140
ccactggccg gtttgaaatg gatatcaggg attatttgga ttcagctgaa agggatttcg  10200
ctgctaagca cccacatgct ttcatcggcg atacgaaggg cacgactgtt ggtggttgcc  10260
atcatatcac ctcacagtac ttgccccatg tgctacctgc cgacagtgtt gtcaaggttg  10320
gtgtcagcaa gcctggggtc gctcacaaag cactctgtac ggtaactgat atctacctcc  10380
cgatgctggg ctcgtacaca tcacctccca ctcagtctaa agtctacaaa gtaaatgttg  10440
accacaaggc gtgcaaactc atggtctggc gtgaccagac aatgtacttc caagagggtt  10500
ttgattatca cacgctcgtg gatgcactcc ggttcgtccg cttgagcagt gatggggtct  10560
atcgcgtcgc ccctgagctg acgcccatga ttggcaatag gaggttggac ctgggcgcta  10620
aacctctgag acccgttgat ttggctatca ccccttggga tgaccccaaa tgtgagtttc  10680
tggtgacaca cgcctcccca tttgacatgt ctgatgagtt tcttctagtc aatgcttttg  10740
atttcatcaa ggaggatctg ctaggcaaat ctgtcacacc tgtgtatttc tataagaggc  10800
tttctgaacc cttgcatttt gaccaaaatc tgccgcctca tgttggagct atcctgtcca  10860
aagcaccccg ctttatatct ctagccaagg tctttaactt ctgtttcaca cctacagcct  10920
gtcactgtaa ggtgtcagtt aagaccgcca caggtgacca catgtgtaaa tgctccctct  10980
cctctgatga gtttctgtcc aggtttaatc ctactgttgg tactccttaa gccaaaaggg  11040
gtcttgttaa cctgaggaag tatggaaaat atggaaaacg acgagaacat cgtggtgggc  11100
cccaagccct tctaccccat cgaggaaggc agcgccggca cccagctgcg gaagtacatg  11160
gaaagatacg ccaagctggg cgccattgcc ttcaccaacg ccgtgaccgg cgtggactac  11220
agctacgccg agtacctgga aaagagctgc tgcctgggca aggctctgca gaactacggc  11280
ctggtggtgg acggccggat cgccctgtgc agcgagaact gcgaggaatt cttcatcccc  11340
gtgatcgccg gcctgttcat cggcgtgggc gtggctccca ccaacgagat ctacaccctg  11400
cgggagctgg tgcacagcct gggcatcagc aagcccacca tcgtgttcag cagcaagaag  11460
ggcctggaca aagtcatcac cgtgcagaaa accgtgacca ccatcaagac catcgtgatc  11520
ctggacagca aggtggacta ccggggctac cagtgcctgg acaccttcat caagcggaac  11580
acccccccg gcttccaggc cagcagcttc aagaccgtgg aggtggaccg gaaagaacag  11640
gtggccctga tcatgaacag cagcggcagc accggcctgc ccaagggcgt gcagctgacc  11700
cacgagaaca ccgtgacccg gttcagccac gccagggacc ccatctacgg caaccaggtg  11760
tcccccggca ccgccgtgct gaccgtggtg cccttccacc acggcttcgg catgttcacc  11820
accctgggct acctgatctg cggcttccgg gtggtgatgc tgaccaagtt cgacgaggaa  11880
accttcctga aaaccctgca ggactacaag tgcacctacg tgattctggt gcccaccctg  11940
ttcgccatcc tgaacaagag cgagctgctg aacaagtacg acctgagcaa cctggtggag  12000
atcgccagcg gcggagcccc cctgagcaaa gaagtgggag aggccgtcgc caggcggttc  12060
aatctgcccg gcgtgcggca gggctacggc ctgaccgaga caaccagcgc catcatcatc  12120
acccccgagg gcgacgacaa gcctggagcc agcggcaagg tggtgcccct gttcaaggcc  12180
aaagtgatcg acctggacac caagaagagc ctgggcccca acagacgggg cgaagtgtgc  12240
gtgaagggcc ccatgctgat gaagggctac gtgaacaacc ccgaggccac caaagagctg  12300
atcgacgaag agggctggct gcacaccggc gacatcggct actacgacga agagaagcac  12360
ttcttcatcg tggaccggct gaagagcctg atcaagtaca agggctatca ggtgcccccct  12420
gccgagctgg aaagcgtcct gctgcagcac cccagcatct tcgacgccgg cgtggccggg  12480
```

-continued

```
gtgccagatc ctgtggccgg cgagctgcct ggcgccgtgg tggtgctgga atccggcaag  12540

aacatgaccg agaaagaagt gatggactac gtcgccagcc aggtgtccaa cgccaagcgg  12600

ctgagaggcg gcgtgagatt cgtggacgaa gtgccaaagg gcctgaccgg caagatcgac  12660

ggcagggcca tccgggagat cctgaagaaa cccgtggcca agatgtgagt agtatccctt  12720

tgcagtgacc cggggtacac caccttggct tttactattg ctcctgcatt aatagccttt  12780

ttaagatatt tccgcccatc cgtgcgcggt ttcatatgct tggtatgcat tgctacactt  12840

gcttatgctg caactgcttt caatgaacat tcccttgcaa cattactaac aattgggttc  12900

agtctggtat acttgaccta taaattcatc acgtggacca ttctacgtgt gcggatgtgt  12960

tggctcggcc ggcaatacat aaccgcccct tccagtatgg ttgagtcatc ccttggccgt  13020

ttagcgatca acgcgactgg ttctaccgca gtcgtaactc gccgatctgg catgacagca  13080

gtcaatggta gtctcatgcc ggatgtgaaa aggatcatac tcaatggaag ggttgccgcc  13140

aaaaggggtc ttgttaacct gaggaagtat cgctggcaaa ccaaaaacaa ataacaaggg  13200

aaaatcccag tccagaggag ggaataggct tccccaacga cctcgccgca gcactcaaca  13260

acgtagagct gctcctgtcc acaagcctct aaatgagaca cattatgttt tcgccgaacc  13320

cggcgacctc cgagttgttc tacctggtcc cacctcagca cacatcaaac agctgctgat  13380

caggtactac gacaacggag gcggaaatct ttcatatgac ggacagagaa tcaattttgc  13440

tgctatcatc acaccaccac acaacatgct gaagcagctg gcgaaggtca cctcctccac  13500

ctaggccaga cactgattat atggttcata tgggtaatta ccttccctag gctaaggact  13560

aactggtata taccataatt aaaaaaaaaa aaaaaaaaaa aaaaaaaaaa aaaaaaaaaa  13620

aaaaaaaaaa aaaaaaaaaa aaaaaaaaaa aaaaaaaaaa aaaaaaaaaa aaaaaaaaaa  13680

aaaaaaaaaa aaaaaaaaaa aaaaacccct ctctaaacgg aggggttttt ttcagcgtaa  13740
```

<210> SEQ ID NO 52
<211> LENGTH: 139
<212> TYPE: DNA
<213> ORGANISM: Artificial Sequence
<220> FEATURE:
<223> OTHER INFORMATION: Synthetic Oligonucleotide

<400> SEQUENCE: 52

```
tcaacttctt acaaattggt tcagtcattg ggcccgtgtg actctagagt ggacctgttc     60

ccatcccccg ctcaactact caggtagtgg ttcgcggcaa cgggtacacc gcagttggta    120

acaagcttgt cgatgactt                                                 139
```

<210> SEQ ID NO 53
<211> LENGTH: 180
<212> TYPE: DNA
<213> ORGANISM: Artificial Sequence
<220> FEATURE:
<223> OTHER INFORMATION: Subgenomic Promoter TRS

<400> SEQUENCE: 53

```
cattttcaac catcgccaac tggtggtagc tgattttgtg gacacaccta gtggacctgt     60

tcccatcccc cgctcaacta ctcaggtagt ggttcgcggc aacgggtaca ccgcagttgg    120

taacaagctt gtcgatggcg tcaagacgat cacgtccgca ggccgcctct tttcgaaacg    180
```